US008932557B2

(12) United States Patent
Chen et al.

(10) Patent No.: US 8,932,557 B2
(45) Date of Patent: *Jan. 13, 2015

(54) IMAGING AGENTS FOR DETECTING NEUROLOGICAL DYSFUNCTION

(75) Inventors: Gang Chen, Redondo Beach, CA (US); Umesh B. Gangadharmath, Los Angeles, CA (US); Dhanalakshmi Kasi, Los Angeles, CA (US); Anjana Sinha, San Diego, CA (US); Wei Zhang, Los Angeles, CA (US); Kai Chen, San Gabriel, CA (US); Vani P. Mocharla, Los Angeles, CA (US)

(73) Assignee: Eli Lilly and Company, Indianapolis, IN (US)

( * ) Notice: Subject to any disclaimer, the term of this patent is extended or adjusted under 35 U.S.C. 154(b) by 110 days.

This patent is subject to a terminal disclaimer.

(21) Appl. No.: 13/477,095

(22) Filed: May 22, 2012

(65) Prior Publication Data
US 2012/0302755 A1   Nov. 29, 2012

Related U.S. Application Data

(63) Continuation-in-part of application No. 12/372,717, filed on Feb. 17, 2009, now Pat. No. 8,318,132.

(60) Provisional application No. 61/489,284, filed on May 24, 2011, provisional application No. 61/066,101, filed on Feb. 14, 2008.

(51) Int. Cl.
A61K 51/00 (2006.01)
A61M 36/14 (2006.01)
C07B 59/00 (2006.01)
C07D 471/04 (2006.01)
C07D 471/14 (2006.01)

(52) U.S. Cl.
CPC ............ C07B 59/002 (2013.01); C07D 471/04 (2013.01); C07D 471/14 (2013.01)
USPC ................ 424/1.65; 546/82; 546/86; 546/87; 546/85

(58) Field of Classification Search
None
See application file for complete search history.

(56) References Cited

U.S. PATENT DOCUMENTS

| 5,871,934 | A | 2/1999 | Lee et al. |
| 2003/0149250 | A1 | 8/2003 | Kung et al. |
| 2006/0110787 | A1 | 5/2006 | Walker |
| 2007/0060618 | A1 | 3/2007 | Cosford et al. |
| 2007/0258887 | A1 | 11/2007 | Tamagnan et al. |
| 2010/0239496 | A1 | 9/2010 | Gangadharmath et al. |
| 2011/0091382 | A1 | 4/2011 | Kolb et al. |
| 2011/0182812 | A1 | 7/2011 | Szardenings et al. |
| 2012/0283490 | A1 | 11/2012 | Gangadharmath et al. |

FOREIGN PATENT DOCUMENTS

| DE | 102006062203 A1 | 6/2008 |
| EP | 1655287 | 5/2006 |
| EP | 1815872 | 8/2007 |
| EP | 1815872 A1 | 8/2007 |
| EP | 1944281 | 7/2008 |
| EP | 2218464 | 8/2010 |
| EP | 2511006 | 10/2012 |
| JP | 9165378 | 6/1997 |
| JP | 0148786 | 2/2001 |
| JP | 2006100537 | 4/2006 |
| JP | 2007223952 | 9/2007 |
| JP | 2012089777 A | 5/2012 |
| WO | 9414477 | 7/1994 |
| WO | 9714679 | 4/1997 |
| WO | 99/18794 | 4/1999 |
| WO | 02085903 | 10/2002 |
| WO | 2004043496 | 5/2004 |
| WO | 2004056399 | 7/2004 |
| WO | 2006005063 A2 | 1/2006 |
| WO | 2006066104 | 6/2006 |
| WO | 2006125887 A1 | 11/2006 |
| WO | 2007002540 A2 | 1/2007 |
| WO | 2007014467 | 2/2007 |
| WO | 2007057705 | 5/2007 |
| WO | 2007063946 | 6/2007 |
| WO | 2007094718 | 8/2007 |
| WO | 2008073350 | 6/2008 |
| WO | 2008083454 | 7/2008 |
| WO | 2008124812 | 10/2008 |
| WO | 2008131148 | 10/2008 |
| WO | 2008132454 | 11/2008 |
| WO | 2009004914 | 4/2009 |

(Continued)

OTHER PUBLICATIONS

Chen et al. Synlett, 2008, 77-82.*
Franck et al. Tetrahedron 62 (2008) 6030-6037.*
Bergstrom, Mats et al.: "Synthesis of some 11C-labeled MAO-A inhibitors and their in vivo uptake kinetics in rhesus monkey brain", Nuclear Medicine and Biology, 24(5), 381-388 Coden: Nimbieo; ISSN: 0883-2897, 1997.
Sintas, Jose A. et al.: "Iodination, radioiodination and spectroscopic identification of beta.-carboline derivatives", Journal of Labelled Compounds & Radiopharmaceuticals, 42(5), 409-413 Coden: JLCRD4; ISSN: 0362-4803, 1999.

(Continued)

*Primary Examiner* — Michael G Hartley
*Assistant Examiner* — Sean R Donohue
(74) *Attorney, Agent, or Firm* — Zhigang Rao; Kyle W. Grimshaw

(57) ABSTRACT

Disclosed here in are compounds and methods of diagnosing Alzheimer's Disease or a predisposition thereto in a mammal, the method comprising administering to the mammal a diagnostically effective amount of a radiolabeled compound, wherein the compound is selected from the group consisting of radiolabeled carbazoles and derivatives thereof and triazoles derivatives, allowing the compound to distribute into the brain tissue, and imaging the brain tissue, wherein an increase in binding of the compound to the brain tissue compared to a normal control level of binding indicates that the mammal is suffering from or is at risk of developing Alzheimer's Disease.

5 Claims, 14 Drawing Sheets

(56) References Cited

FOREIGN PATENT DOCUMENTS

| | | |
|---|---|---|
| WO | 2009045535 A2 | 4/2009 |
| WO | 2009055401 | 4/2009 |
| WO | 2009102498 A1 | 8/2009 |
| WO | 2010011964 | 1/2010 |
| WO | 2010073719 | 7/2010 |
| WO | 2010073719 A1 | 7/2010 |
| WO | 2010095042 A2 | 8/2010 |
| WO | 2010111303 | 9/2010 |
| WO | 2011119565 | 9/2011 |

OTHER PUBLICATIONS

Karimi, Farhad et al.: "Synthesis of 11c-labelled amides by palladium-mediated carboxamination using [11C]carbon monoxide, in situ activated amines and 1,2,2,6,6-pentamethylpiperidine", European Journal of Organic Chemistry, (11), 2132-2137 Coden: Ejocfk; ISSN: 1434-193X, 2003.

Baranowska-Kortylewicz J et al.: "Radioiodination of 7-Methoxy- and 6,7-Dimethoxy-4-Bromomethylcoumarins", Journal of Labelled Compounds and Radiopharmaceuticals, John Wiley, Chichester, DB, vol. 29, No. 12, Jan. 1, 1991, pp. 1301-1307, ISSN: 0362-4803.

Heike Radeke et al.: "Synthesis and biological evaluation of the mitochondrial complex 1 inhibitor 2-[4-(4-fluorobutyl) benzylsulfanyl]-3-meth ylchromene-4-one as a potential cardiac positron emission tomography tracer", J. Med. Chem., vol. 50, 2007, pp. 4304-4315.

Maria Graciela Barolli et al.: "Synthesis of [131I]-iodinated quercetin", J. Label. Compds. Radiopharm., vol. 32, No. 11, 1997, pp. 297-933.

Hollie I. Swanson et al.: "Use of [125I]4'-iodoflavone as a tool to characterize ligand-dependent differences in Ah receptor behavior", J. Biochem. Molecular Toxicology, vol. 16, No. 6, 2002, pp. 298-310.

Takahashi K et al.: "Imaging of aromatase distribution in rat and rhesus monkey brains with [<11>C]vorozole"Nuclear Medicine and Biology, Elsevier, NY, US, vol. 33, No. 5, Jul. 1, 2006, pp. 599-605, XP025103506 ISSN: 0969-8051.

Wenchao Qu et al.: "Quick Assembly of 2,24-diphenyltriazoles as probes targeting beta-amyloid aggregates in alzheimer's disease", J. Med. Chem., vol. 50, 2007, pp. 3380-3387.

Glaser M et al.: "Click Labeling with 2-[18F]Fluoroethylazide for Positron Emission Tomography" Bioconjugate Chemistry, ACS, Washington, DC, US, vol. 18, Apr. 13, 2007, pp. 989-993, ISSN: 1043-1802.

Sirion et al.: "An efficient F-18 labeling method for PET study: Huisgen 1,3-dipolar cycloaddition of bioactive substances and F-18-labeled compounds" Tetrahenron Letters, Elsevier, Amsterdam, vol. 48, No. 23, Jun. 4, 2007, pp. 3953-3957, ISSN: 0040-4039.

Mathias C. J. et al.: "Radiolebeled hypoxic cell sensitizers: Tracers for assessment of ischemia" Life Sciences, Pergamon Press, Oxford, GB, vol. 41, No. 2, Jul. 13, 1987, pp. 199-206, ISSN: 0024-3205.

Jerabek P.A. et al.: "Synthesis and biodistrubtion of <18>F-labeled fluoronitroimidazoles: Potential in vivo markers of hypoxic tissue", Applied Radiation and Isotopes, International Journal of Radiation Applications and Instrumentation, Part A, Pergamon Press, Ltd., GB, vol. 37, No. 7, Jan. 1, 1986, pp. 599-605, ISSN: 0883-2889.

Visser G.W. M. et al.: "THe preparation and stability of <211>Atastato-imidazoles" International Journal of Applied Radiation and Isotops, Pergamon Press, New York, NY, US, vol. 31, No. 5, May 1, 1980, pp. 275-278, ISSN: 0020-708X.

Miriko Tanaka et al.: "radiosynthesis and evaluation of 11C-labeled diaryl-substituted imidazole and indole derivatives for mapping cyclooxygenase-2" Biological & Pharmaceutical Bulletin (Of Japan)., vol. 29, No. 10, 2006, pp. 2087-2094, Pharmaceutical Society of Japan, Tokyo.

Gareth Getvoldsen et al.: Microwave-assisted cyclocondensation of 1,2-diaminobenzene with [4-18F]fluorobenzoic acid: microwave synthesis of 2-([4-18F]fluorophenyl) benzimidazole, Journal of Labelled Compounds and Radiopharmaceuticals, research article, J. Label Compd Radiopharm 2004; 47: 139-145.

Piotr Garnuszek et al.: "Synthesis and characterisation of platinum(II) complexes with histamine and iodohistamine", Inorganica Chimica Acta, vol. 338 (2002) 119-126.

Fumihiko Yamamoto et al.: "Synthesis and Evaluation of 4-Bromo-1-(3-[18F]fluoropropyl)-2-nitroimidazole with a Low Entergy LUMO Orbital Designed as Brain Hypoxia-Targeting Imaging Agent", Biol.Pharm. Bull. 25(5) 616-621 (2002), vol. 25, No. 5.

Fumihiko Yamamoto et al.: "Synthesis and Characterization of Lipohilic 1-[18F]Fluoralkyl-2lnitroimidazoles for Imaging Hypoxia", Biol. Pharm. Bull. 22(6) 590-597 (1999), vol. 22, No. 6.

International Search Report of Application No. PCT/US2009/000961 dated Jul. 10, 2009.

Blom, Elisabeth et al.: "Synthesis and in vitro evaluation of 18F-.beta.-carboline alkaloids as PET ligands" Journal of Labelled Compounds and Radiophaarmaceuticlas, 51(6), 277-282 Coden: JLCRD4, May 2008.

Dumont F. et al.: "Synthesis and in Vivo Evaluation of 7-chloro-5-[<123>I]iodo-4-oxo-1,4 dihydroquinoline-2-carboxylic Acid" Applied Radiation and Isotopes, Elsevier, Oxford, GB, vol. 48, No. 9, Sep. 1, 1997, pp. 1173-1177.

Livni E. et al.: "Synthesis and biodistribution of <18>F-labeled Fleroxacin" Nuclear Medicine and Biology, Elsevier, NY, US, vol. 20, No. 1, Jan. 1, 1993, pp. 81-87.

Zijlstra S et al.: "Synthesis and evaluation of fluorine-18 labelled compounds for imaging of bacterial infections with pet" Applied Radiation and Isotopes, Elsevier, Oxford, GB, vol. 64, No. 7, Jul. 1, 2006, pp. 802-807.

Chemical Abstracts Service, Columbus, Ohio, US: Choi, Osaku Wataru et al.: "Preparatoin of F-18 labeling benzyl N-containing heterocyclyl compounds as PET diagnostic remedies", Database accession No. 127:65770 abstract & JP 09 165378 A, Jun. 24, 1997.

Aoyama, et al., "Polymethylated .gamma.-carbolines with potent anti-bovine viral diarrhea virus (BVDV) activity", Heterocycles (2009), 77(2), 779-785.

Sako, et al., "Gamma-carboline derivatives with anti-bovine viral diarrhea virus (BVDV) activity", Bioorg Med Chem Apr. 1, 2008 , 16(7), 3780-3790.

Chen, et al., "Microwave-enhanced Fischer reaction: an efficient one-pot synthesis of y-carbolines", Synlett (2008), (1), 77-82.

Engler, et al., "Lewis Acid-Directed Cyclocondensation of Piperidone Enol Ethers with 2-Methoxy-4-(N-phenylsulfonyl)-1,4-benzoquinoneimine: A New Regioselective Synthesis of Oxygenated Carbolines", Journal of Organic Chemistry (2000), 65(8), 2444-2457.

Mehta, et al., "The elimination of an alkoxy group in the photo-Graebe—Ullmann conversion of 1-(2,5-dialkoxyphenyl) triazolopyridines into carbolines, and the preparation of α-, γ- and δ-carboline quinones", J. Chem. Soc., Perkin Trans. 1, 1993, 1261-1267.

Parrick, et al., "Some carbazole and carboline quinones and an unexpected demethoxylation reaction", Journal of Chemical Research, Synopses (1990), 1.

Molina, et al., "Novel DNA Intercalators Based on the Pyridazino [1',6':1,2] pyrido [4,3-b] indol-5-inium System", J. Org. Chem, 1999, 64, 3907-3915.

Liu, J., et al., High-Yield, Automated Radiosynthesis of 2-(1-{6-[(2-[18F]Fluoroethyl)(methyl)amino]-2-naphthyl} ethylidene)malonitrile ([18F]FDDNP) Ready for Animal or Human Administration, Molecular Imaging and Biology, 2007. 9: p. 6-16.

Hardy, J. and D. Selkoe, The Amyloid Hypothesis of Alzheimer's Disease: Progress and Problems on the Road to Therapeutics, Science, 2002. 297: p. 353-356.

Talaga, P., Inhibitors of beta-amyloid aggregation: still an issue of structure and function? Drug Discovery Today: Therapeutic Strategies, 2004. 1: p. 7-12.

Jewett, D.M. (1992) A Simple Synthesis of [11C]Methyl Triflate, Appl. Radiat. Isot. 43, 1383-1385.

Wilson, A.A. (1990) Radiochemistry of Tracers for Neurotransmitter Receptor Studies. In: Quantitative Imaging: Neuroreceptors, Neurotransmitters, and Enzymes. (Edited by Frost, J.J. Wagner Jr., H.N. pp. 19-35, Raven Press, New York.

(56) References Cited

OTHER PUBLICATIONS

Watkins, G., Jewett, D., Mulholland, G., Kitbourn, M., and Toorongian, S. (1988) A Captive Solvent Method for Rapid N-[11C]Methylation of Secondary Amides: Application to the Benzodiazepine, 4'-Chlorodiazepam (RO5-4864) Appl. Radiat. Isot. 39, 441-444.
PCT/US2010/028360 Search Report issued Nov. 22, 2010.
Kruglenko, et al.; "Condensed Imidazo-1,2,4-azines. 31. Synthesis and Chemical Transformations of Substituted 1,2,4-Triazepino[2,3-a]benzimidaloses"; Chemistry of Heterocyclic Compounds, vol. 38, No. 5, 2002—pp. 598-606.
Tseng, et al., "A Simple Regioselective Synthesis of Pyrimido[1,2-a]benzimidazoles"; vol. 24, May 1, 1987; Jun. 1, 1987, pp. 837-843.
Yousefi, et al., "Synthesis and Evaluation of 11C-Labeled Imidazo [2,1-b] benzothiazoles (IBTs) as PET Tracers for Imaging β-Amyloid Plaques in Alzheimer's Disease", J. Med. Chem., Article ASAP, DOI: 10.1021/jm101129a Publication Date (Web): Jan. 28, 2011.
Nordberg, A., "PET imaging of amyloid in Alzheimer's disease", Lancet Neurology, Lancet Publ. Group, London, GB, vol. 3, No. 9, Sep. 1, 2004, pp. 519-527.
Okamura, et al., "Quinoline and Benzimidazole Derivatives: Candidate Probes for in Vivo Imaging of Tau Pathology in Alzheimer's Disease.", Journal of Neuroscience, Nov. 23, 2005, 25(47):10857-10862.
Zheng, et al., "Biological Characters of [18F]0-FEt-PIB In A Rat Model of Alzheimer's Disease Using Micro-PET Imaging", Published in Acta Pharmacologica Sinica, vol. 29, No. 5, May 1, 2008 (pp. 548-554).
Wang, et al., "PET Imaging and Optical Imaging With D-Luciferin [<11>C]methyl Ester and D-Luciferin [11C]methyl Ether of Luciferase Gene Expression in Tumor Xenografts of Living Mice", Published in Bioorganic & Medicinal Chemistry Letters, vol. 16, No. 2, Jan. 15, 2006 (pp. 331-337).
Solbach, et al., "Efficient Radiosynthesis of Carbon-11 Labelled Uncharged Thioflavin T Derivatives Using [11C]methyl Triflate for Beta-Amyloid Imaging in Alzheimer's Disease With PET", Published in Applied Radiation and Isotopes, vol. 62, No. 4, Apr. 1, 2005 (pp. 591-595).
Mathis, et al., "Synthesis and Evaluation of 11C-Labeled 6-Substituted 2-Arylbenzothiazoles As Amyloid Imaging Agents", Published in Journal of Medicinal Chemistry, American Chemical Society, vol. 46, Jun. 19, 2003 (pp. 2740-2754).
Serdons, et al., "Synthesis and Evaluation of 18F-Labeled 2-Phenylbenzothiazoles As Positron Emission Tomography Imaging Agents for Amyloid Plaques in Alzheimer's Disease", Published in Journal of Medicinal Chemistry, American Cancer Society, vol. 52, Feb. 13, 2009 (pp. 1428-1437).
Johnson, et al., "AZD2184: A Radioligand for Sensitive Detection of Beta-Amyloid Deposits", Published in Journal of Neurochemistry, vol. 108, Mar. 1, 2009 (pp. 1177-1186).
Seneca, et al., "Brain and Whole-Body Imaging in Nonhuman Primates With [11C]MeS-IMPY, a Candidate Radioligand for Beta-Amyloid Plaques", Published in Nuclear Medicine and Biology, vol. 34, Aug. 6, 2007 (pp. 681-689).
Vasdev, et al., "Synthesis and Ex Vivo Evaluation of Carbon-11 Labelled N-(4-methoxybenzyl)-N'-(5-nitro-1,3-thiazol-2-yl)urea([11C]AR-A014418): A Radiolabelled Glycogen Synthase Kinase-3beta Specific Inhibitor for PET Studies", Published in Bioorganic & Medicinal Chemistry Letters, vol. 15, No. 23, Dec. 1, 2005 (pp. 5270-5273).
Qu, et al., Radioiodinated Aza-Diphenylacetylenes As Potential SPECT Imaging Agents for Beta-Amyloid Plaque Detection, Published in Bioorganic & Medicinal Chemistry Letters, vol. 17, No. 13, Jul. 2007 (pp. 3581-3584). Science Direct, Elsevier.
Gao, et al., "Derivatives of (−)-7-Methyl-2-(5-(pyridinyl)pyridin-3-yl)-7-azabicyclo[2.2.1]heptane Are Potential Ligands for Positron Emission Tomography Imaging of Extrathalamic Nicotinic Acetylcholine Receptors", J. Med. Chem., 2007, 50 (16), pp. 3814-3824.
Naya, et al., "Myocardial B-Adrenergic Receptor Density Assessed by 11C-CGP12177 PET Predicts Improvement of Cardiac Function After Carvedilol Treatment in Patients With Idiopathic Dilated Cardiomyopathy", In The Journal of Nuclear Medicine, vol. 50, No. 2, Feb. 2009, pp. 220-225.
Doze, et al., "Synthesis and Evaluation of (S)-[18F]-Fluoroethylcarazolol for In Vivo B-Adrenoceptor Imaging in the Brain", In Neurochemistry International, vol. 41, No. 1, Jul. 1, 2002, pp. 17-27.
Bart, et al., "New Positron Emission Tomography Tracer [11C] Carvedilol Reveals P-Glycoprotein Modulation Kinetics", In British Journal of Pharmacology, vol. 145, No. 8, Aug. 1, 2005 pp. 1045-1051.
Elder, et al., "Esters of 6-(4'-Fluorobenzylamino)-B-Carboline-3-Carboxylic Acid As Potential Benzodiazepine Imaging Agents for P.E.T.", In Journal of Labelled Compounds and Radiopharmaceutical, vol. 36, No. 3, Jan. 1, 1995 pp. 205-211.
Database Caplus [Online], 9-Azafluorene (XP-002688209), Chemical Abstracts Service, Nov. 16, 1984. Retrieved from STN Database accession No. 86-74-8 (1 Page).
Crossfire Beilstein, 2-Fluoro-7-lodo-9H-Carbazole (XP-002234312),1994 (1 Page).
Crossfire Beilstein,2-Methoxy-7-Methyl-9H-Carbazole, 1984 (2 Pages).
Nakamura, et al, "[18]O Incorporation From H2 18O2 In The Oxidation of N-Methylcarbazole and Sulfides Catalyzed by Microperoxidase-11", In Tetrahedron Letters, Elsevier, Amsterdam, NL, vol. 33, No. 37, Sep. 8, 1992 pp. 5409-5412.
Invitation to Pay Additional Fees in PCT/US2012/061912 dated Dec. 20, 2012, 14 pages.
Crouzel, C. Langstrom, B., Pike, V.W., and Coenen, H.H., "Recommendations for a Practical Production of [11C] methyl Iodide", Appl. Radiat. Isot., vol. 38, No. 8, pp. 601-603, (1987) Int. J. Radial. Appl. Instrum. Part A.
Jewett, D.M., Manger, T.J., and Watkins, G.L., "Captive Solvent Methods for Fast Simple Carbon-11 Radioalkylations", In: New Trends in Radiopharmaceutical Synthesis, Quality Assurance and Regulatory Control (Edited by Emran, A.M.) (1991) pp. 387-391. Plenum Press, New York.
Marazano, C., Maziere, M., Berger, G., and Comar, D., "Synthesis of Methyl Iodide-11C and Formaldehyde-11C", International Journal of Applied Radiation and Isotopes, vol. 28, pp. 49-52, 1977.
Wilson, A. A., DaSilva, J.N., and Houle, S., "In Vivo Evaluation of [11C] and [18F]-Labelled Cocaine Analogues as Potential Dopamine Transporter Ligands for Positron Emission Tomography" Nucl. Med. Biol. 23, 141-146, 1996.
Moura, D.J., et al., "Effects of β-carboline alkaloids in the object recognition task in mice", Life Sciences 79, (2006) 2099-2104.
Narlawar, R., et al., "N-Substituted carbazolyloxyacetic acids modulate Alzheimer associated g-secretas", Bioorganic & Medicinal Chemistry Letters, (2007) 17, 176-182.
Howlett, D.R., et al., "Common Structural Features Determine the Effectiveness of Carvedilol, Daunomycin and Rotiletracycline as Inhibitors of Alzheimer β-Amyloid Fibril Formation", Biochemical Journal (1999) 343, 419-423.
Saengkhae, C., et al., "Ability of Carbazole Salts, Inhibitors of Alzheimer β-Amyloid Fibril Formation, to Cross Cellular Membranes", European Journal of Pharmacology, (2007) 559, 124-131.
Molina, et al., "Synthesis and DNA Binding Properties of y-Carbolinium Derivatives and Benzologues", J. Org. Chem, (1996) 61, 5587-5599.
Hyatt, John A., Photochemistry in the Tetrazole-Azidoazomethine System. A Facile Synthesis of 9H-Pyrimido[4,5-b]indoles, J. Org. Chem., 1972, pp. 3216-3220, vol. 37, No. 21.
Shigeo Manabe et al., Carcinogenic tryptophan pyrolysis products in human lens, Experimental Eye Research, Mar. 1, 1989, vol. 48 No. 3, pp. 351-363.
Easter John A., Synthesis of Isotopically Labeled, 1-(2,4-DI-1-Pyrrolidinyl-9H-Pyrimidio[4,5-B]indol-9-yl)-Acetyl) pyrrolidine monohydrochloride, PNU-142731A, An Orally Active Antiasthma Agent, Isotope Production and Applications in the 21st Century, Proceedings of the International Conference on Isotopes, 3rd, Vancouver, BC, Canada, Sep. 6-10, 1999 (2000), pp. 345-346.

(56) References Cited

OTHER PUBLICATIONS

Stolle W.T. et al., The Preparation of Isotopically Labeled 2,4,6-Tri-Substituted Pyrimidines. Synthesis and Applications of Isotopically Labelled Compounds, Proceedings of the International Symposium, 7th, Dresden, Germany, Jun. 18-22, 2000 (2001), pp. 272-275.

Easter John A. et al., Synthesis of several isotopically labeled pyrrolo[1,3-d]pyrimidine analogs, Journal of Labelled Compounds and Radiopharmaceuticals, 2001, pp. 797-810, vol. 44, No. 11.

Chemical Abstracts Service 5H-Pyrido[4,3-b]indol-3-amine-3-14C, 1,4-dimethyl-, monoacetate (9CI) CAS Registry No. 210049-08-4 XP002695120.

Chemical Abstracts Service 5H-Pyrido[4,3-b]indol-3-amine-3-14C, 1-methyl-, monoacetate (9Cl) CAS Registry No. 210049-15-3 XP002695121.

Chemical Abstracts Service 5H-Pyrido[4,3-b]indol-3-amine-3-14C, 1-methyl-(9Cl) CAS Registry No. 210049-14-2 XP002695118.

Chemical Abstracts Service 5H-Pyrido[4,3-b]indol-3-amine-3-14C, 1,4-dimethyl-(9Cl) CAS Registry No. 210049-07-3 XP002695119.

Invitation to Pay Additional Fees in PCT/US2010/028360, Date Mar. 23, 2010.

Canadian Office Action for Canadian application No. 2,715,390 dated Sep. 18, 2012.

Canadian Office Action for Canadian application No. 2,715,390 dated Jul. 4, 2013.

Canadian Office Action for Canadian application No. 2,715,390 dated Mar. 6, 2014.

European Office Action for European application No. 13157487.3-1451/2599763 dated Jun. 10, 2013, including European Search Report.

European Office Action for European application No. 13157487.3-1451/2599763 dated Dec. 16, 2013.

European Office Action for European application No. 13157487.3-1451/2599763 dated Jan. 22, 2014.

Hyun-Seok Hong et al. "Combining the rapid MTT formazan exocytosis assay and the MC65 protection assat led to the discovery of carbazole analogs as small molecule inhibitors of Abeta oligomer-induced cytotocity," Published Dec. 8, 2006 in Brain Research.

Mei-Ping Kung et al. "Binding of two potential imaging agents targeting amyloid plaques in postmortem brain tissues of patients with Alzheimer's disease," Published Sep. 11, 2004 in Brain Research.

Maria Graciela Barolli et a. Synthesis of [131-I]-Iodinated Quercetin, XP-002536476, Journal of Labelled compounds and Radiopharmacueticals (1997), 39(11), 927-933.

Japanese Office Action dated Oct. 15, 2013 (including English translation) for Japanese Patent Application No. 2010-546795.

European Office Action for European application no. 09711194.Feb. 1451, dated 14 Jul.. 2014.

European Office Action and Search Report for European application no. 09711194.2-1451dated Jun 14 2013.

\* cited by examiner

IMAGING AGENTS FOR DETECTING NEUROLOGICAL DYSFUNCTION

CROSS-REFERENCE TO RELATED APPLICATIONS

This application claims priority to provisional patent application No. 61/489,284, filed on May 24, 2011; the entire contents of which are incorporated by reference. This application is a continuation-in-part of U.S. application Ser. No. 12/372,717, filed Feb. 17, 2009; the entire contents of which are incorporated by reference. U.S. Ser. No. 12/372,717 claims priority to 60/066,101, filed Feb. 14, 2008, which is also incorporated herein by reference.

BACKGROUND

Alzheimer's disease (AD), a leading cause of dementia, develops in one percent of the population between the ages 65 and 69, and increasing to 40-50% in those 95 years and older. AD patients exhibit telltale clinical symptoms that include cognitive impairment and deficits in memory function. In these patients, heavy senile plaque burden found in the cerebral cortex, verified by post mortem histopathological examination, confirms the presence of AD. The mature senile plaques consist of intracellular neurofibrillary tangles (NFT) derived from filaments of hyperphosphorylated tau proteins, and extracellular β-amyloid peptides derived from enzymatic processing of amyloid precursor protein. Interestingly, despite the development and presence of senile plaques in elderly persons with normal cognitive function, the severity of NFT and senile plaque deposition purportedly correlates with a loss of cognitive function and neuronal circuitry deterioration.

Neurological imaging of AD has seen the emergence of imaging tracers that appear to confirm the presence of AD based on plaque and fibril mediated tracer uptake and, subsequently, are currently undergoing extensive clinical examination. Many of these tracers contain chemotypes that derive from fluorescent dyes (Table 1).

The current array of AD imaging agents can only confirm the well-established manifestation of AD and this late stage diagnosis offers little defense against further disease progression past 36 months. Secondly, the detection of senile plaques and tangles may not correlate to development of the early stages of AD. Recent data suggests that the amyloid cascade model [Hardy, J. and D. Selkoe, *The Amyloid Hypothesis of Alzheimer's Disease: Progress and Problems on the Road to Therapeutics*. Science, 2002. 297: p. 353-356] does not accurately depict the primary factors leading to cognitive decline in AD patients and that other contributing factors, such as neuorotoxic soluble oligomers and aggregates may play a contributory role in neurodegeneration. [Talaga, P., *Inhibitors of beta-amyloid aggregation: still an issue of structure and function*? Drug Discovery Today: Therapeutic Strategies, 2004. 1: p. 7-12]. To date, FDDNP and PIB are not known to bind to neurotoxic soluble oligomers and aggregates and thus are not expected to differentiate accurately between the early stages of AD from the advanced stages of AD in patients.

A number of medical diagnostic procedures, including PET and SPECT utilize radiolabeled compounds. PET and SPECT are very sensitive techniques and require small quantities of radiolabeled compounds, called tracers. The labeled compounds are transported, accumulated and converted in vivo in exactly the same way as the corresponding non-radioactively compound. Tracers, or probes, can be radiolabeled with a radionuclide useful for PET imaging, such as $^{11}$C, $^{13}$N, $^{15}$O, $^{18}$F, $^{64}$Cu and $^{124}$I, or with a radionuclide useful for SPECT imaging, such as $^{99}$Tc, $^{77}$Br, $^{61}$Cu, $^{153}$Gd, $^{123}$I, $^{125}$I, $^{131}$I and $^{32}$P.

PET creates images based on the distribution of molecular imaging tracers carrying positron-emitting isotopes in the tissue of the patient. The PET method has the potential to detect malfunction on a cellular level in the investigated tissues or organs. PET has been used in clinical oncology, such as for the imaging of tumors and metastases, and has been used for diagnosis of certain brain diseases, as well as mapping brain and heart function. Similarly, SPECT can be used to complement any gamma imaging study, where a true 3D representation can be helpful, for example, imaging tumor, infection (leukocyte), thyroid or bones.

SUMMARY

Figure 1:
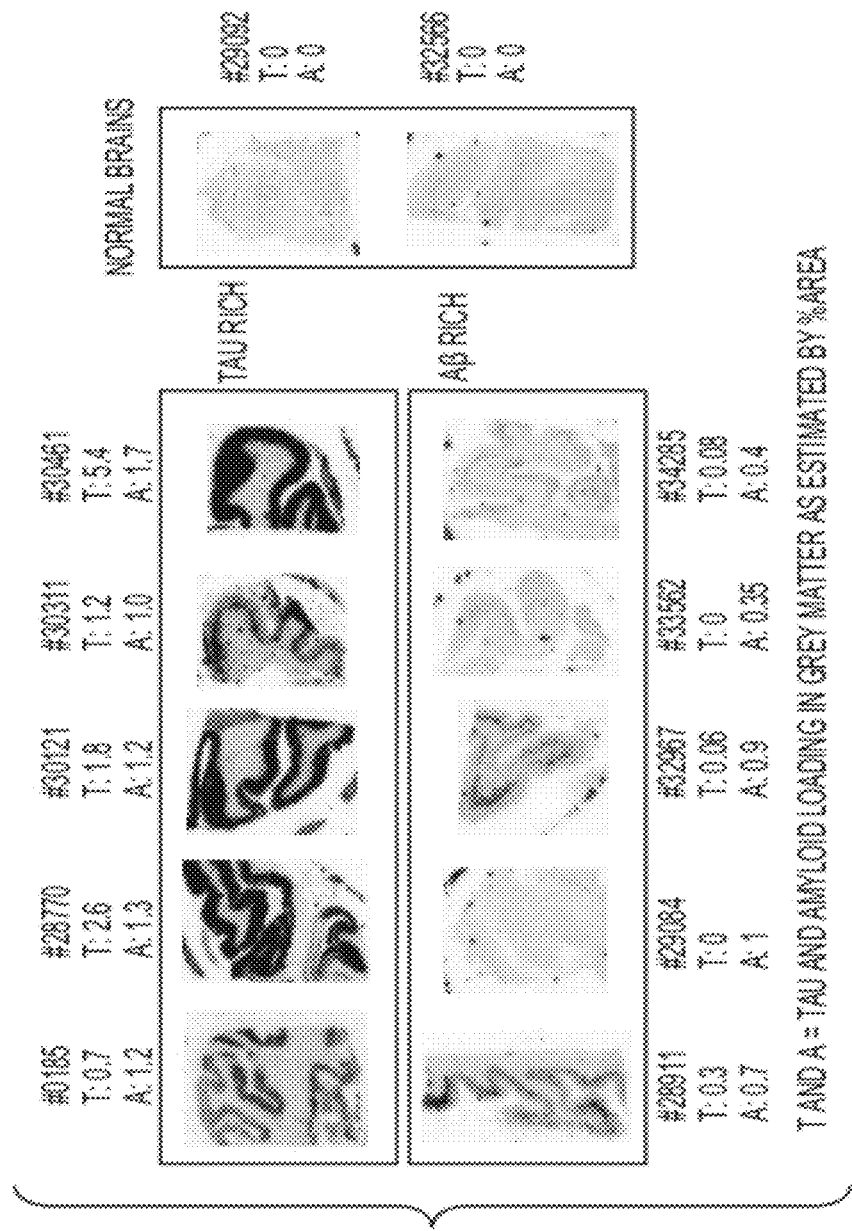
FIG. 1 shows Audoradiography of [18F]-T794.
Figure 2:
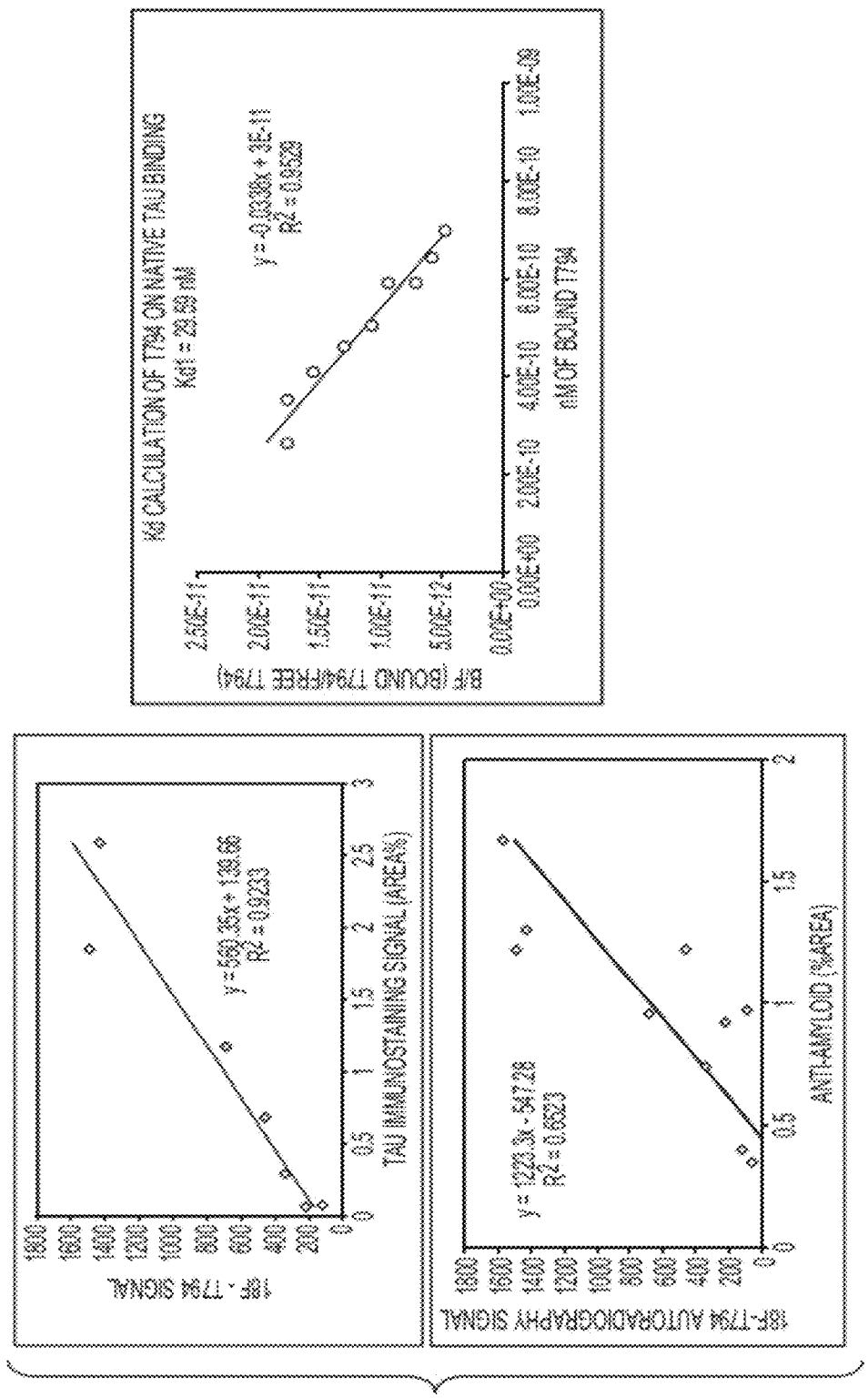
FIG. 2 shows the correlation of [18F]-T794 with Tau and Amyloid loads and KD (30 nM).

In one embodiment, there is provided a radiolabeled compound of the Formula 7:

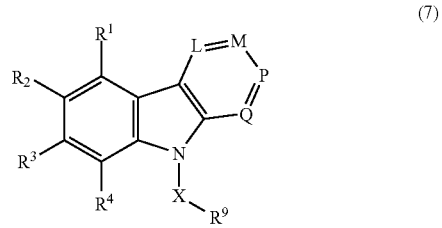

(7)

and pharmaceutically acceptable salts and stereoisomers thereof,
wherein:
L is N or CR$^5$;
M is N or CR$^6$;
P is N or CR$^7$; and
Q is N or CR$^8$;
X is a bond or is C$_{1-14}$alkyl, wherein at least one carbon is optionally replaced by C(O), O, S, SO$_2$, or NH, NH—C$_{1-8}$alkyl, and wherein at least one H of C$_{1-8}$alkyl is optionally replaced by halo, OH, C$_{1-6}$alkyl;
R$^9$ is H, a protecting group, a leaving group, an azide, an alkyne, OH, halo, NH$_2$, N(C$_{1-8}$alkyl)$_2$, aryl or heteroaryl, wherein at least one H of the aryl or heteroaryl is optionally replaced by halo, $SO_2$, $NH_2$, or $C_{1-6}$ alkyl, wherein at least one H of the $C_{1-6}$ alkyl is optionally replaced by halo, or $C_{3-8}$cycloalkyl, wherein at least one H of the $C_{3-8}$cycloalkyl is optionally replaced by halo and wherein at least one $CH_2$ of the $C_{3-8}$cycloalkyl is optionally replaced with O, OH, S, SH, NH, N—$C_{1-8}$alkyl;

$R^1$-$R^8$ are independently H, OH, halo, $NH_2$, $CH_3$, $SO_2$, $NO_2$, a leaving group, a protecting group, aryl, heteroaryl, $NHR^{12}$, $N(R^{12})_2 C_{3-8}$cycloalkyl, $(-CH_2)_{1-12}-R^{12}$, wherein $R^{12}$ is $CH_3$, aryl, H or heteroaryl, wherein at least one H of $(-CH_2)_{1-12}-R^{12}$, $C_{3-8}$cycloalkyl, aryl, or heteroaryl, is optionally replaced by halo, OH, $NH_2$, a leaving group, a protecting group and $C_{1-8}$alkyl, wherein at least one H of the $C_{1-8}$alkyl is optionally replaced by halo, OH, $NH_2$, a leaving group, a protecting group, and wherein at least one $CH_2$ of $(-CH_2)_{1-12}-R^{12}$ is optionally replaced with C(O), O, S, $SO_2$, or NH, NH—$C_{1-8}$alkyl, $N(C_{1-8}alkyl)_2$, wherein at least one H of the $C_{1-8}$alkyl is optionally replaced by halo, OH, $NH_2$, a leaving group, a protecting group, and wherein at least one $CH_2$ of the $C_{3-8}$cycloalkyl is optionally replaced by C(O), O, S or NH, N—$C_{1-8}$alkyl, wherein at least one H of the $C_{1-8}$alkyl is optionally replaced by halo, OH, a leaving group, a protecting group, wherein at least one halo is optionally replaced with a radionuclide or a fluorescent tag.

In another embodiment, the invention is a compound of the Formula 7a:

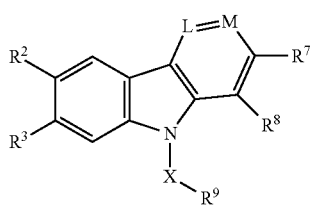

(7a)

and pharmaceutically acceptable salts and stereoisomers thereof,
wherein:
L is N or $CR^5$;
M is N or $CR^6$;
X is a bond or is $C_{1-14}$alkyl, wherein at least one carbon is optionally replaced by C(O), O, S, $SO_2$, or NH, NH—$C_{1-8}$alkyl, and wherein at least one H of $C_{1-8}$alkyl is optionally replaced by halo, OH, $C_{1-6}$alkyl;

$R^9$ is H, a protecting group, a leaving group, an azide, an alkyne, OH, halo, $NH_2$, $N(C_{1-8}alkyl)_2$, aryl or heteroaryl, wherein at least one H of the aryl or heteroaryl is optionally replaced by halo, $SO_2$, $NH_2$, or $C_{1-6}$ alkyl or $C_{1-6}$ alkyl, wherein at least one H of the $C_{1-6}$ alkyl is optionally replaced by halo, or $C_{3-8}$cycloalkyl, wherein at least one H of the $C_{3-8}$cycloalkyl is optionally replaced by halo and wherein at least one $CH_2$ of the $C_{3-8}$cycloalkyl is optionally replaced with O, OH, S, SH, NH, N—$C_{1-8}$alkyl;

$R^2$, $R^3$, $R^7$ and $R^8$ are independently H, OH, halo, $NH_2$, $CH_3$, $SO_2$, $NO_2$, a leaving group, a protecting group, aryl, heteroaryl, $NHR^{12}$, $N(R^{12})_2 C_{3-8}$cycloalkyl, $(-CH_2)_{1-12}-R^{12}$, wherein $R^{12}$ is $CH_3$, aryl, H or heteroaryl, wherein at least one H of $(-CH_2)_{1-12}-R^{12}$, $C_{3-8}$cycloalkyl, aryl, or heteroaryl, is optionally replaced by halo, OH, $NH_2$, a leaving group, a protecting group and $C_{1-8}$alkyl, wherein at least one H of the $C_{1-8}$alkyl is optionally replaced by halo, OH, $NH_2$, a leaving group, a protecting group, and wherein at least one $CH_2$ of $(-CH_2)_{1-12}-R^{12}$ is optionally replaced with C(O), O, S, $SO_2$, or NH, NH—$C_{1-8}$alkyl, $N(C_{1-8}alkyl)_2$, wherein at least one H of the $C_{1-8}$alkyl is optionally replaced by halo, OH, $NH_2$, a leaving group, a protecting group, and wherein at least one $CH_2$ of the $C_{3-8}$cycloalkyl is optionally replaced by C(O), O, S or NH, N—$C_{1-8}$alkyl, wherein at least one H of the $C_{1-8}$alkyl is optionally replaced by halo, OH, a leaving group, a protecting group, wherein at least one halo is optionally replaced with a radionuclide or a fluorescent tag.

In another embodiment, the invention is a compound of the Formula 8:

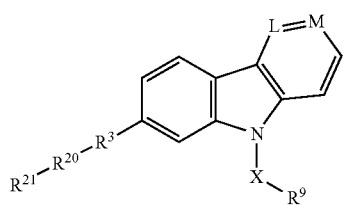

(8)

and pharmaceutically acceptable salts and stereoisomers thereof,
wherein:
L is N or $CR^5$;
M is N or $CR^6$;
X is a bond or is $C_{1-14}$alkyl, wherein at least one carbon is optionally replaced by C(O), O, S, $SO_2$, or NH, NH—$C_{1-8}$alkyl, and wherein at least one H of $C_{1-8}$alkyl is optionally replaced by halo, OH, $C_{1-6}$alkyl;

$R^9$ is H, a protecting group, a leaving group, an azide, an alkyne, OH, halo, $NH_2$, $N(C_{1-8}alkyl)_2$, aryl or heteroaryl, wherein at least one H of the aryl or heteroaryl is optionally replaced by halo, $SO_2$, $NH_2$, or $C_{1-6}$ alkyl or $C_{1-6}$ alkyl, wherein at least one H of the $C_{1-6}$ alkyl is optionally replaced by halo, or $C_{3-8}$cycloalkyl, wherein at least one H of the $C_{3-8}$cycloalkyl is optionally replaced by halo and wherein at least one $CH_2$ of the $C_{3-8}$cycloalkyl is optionally replaced with O, OH, S, SH, NH, N—$C_{1-8}$alkyl;

$R^3$ is a bond or is at least one of O, S, C(O), $SO_2$, NH, N—$C_{1-8}$alkyl, $(CH_2)_{1-12}$, wherein at least one C of $(CH_2)_{1-12}$ is optionally replaced by C(O), O, S, $SO_2$, NH, N—$C_{1-8}$alkyl and wherein at least one H is optionally replaced by $C_{1-8}$alkyl or halo, $R^{20}$ is aryl or heteroaryl;
$R^{21}$ is H, OH, halo, $NH_2$, $CH_3$, $SO_2$, $NO_2$, a leaving group, a protecting group, $(-CH_2)_{1-12}-CH_3$, $C_{3-8}$cycloalkyl, wherein at least one H of the $(-CH_2)_{1-12}-CH_3$ or the $C_{3-8}$cycloalkyl is optionally replaced by halo, OH, $NH_2$, a leaving group, a protecting group and $C_{1-8}$alkyl, wherein at least one H of the $C_{1-8}$alkyl is optionally replaced by halo, OH, a leaving group, a protecting group, and wherein at least one $CH_2$ of the $(-CH_2)_{1-12}-CH_3$ is optionally replaced with C(O), O, S, $SO_2$, or NH, NH—$C_{1-8}$alkyl, $N(C_{1-8}alkyl)_2$, wherein at least one H of the $C_{1-8}$alkyl is optionally replaced by halo, OH, $NH_2$, a leaving group, a protecting group, and wherein at least one $CH_2$ of the $C_{3-8}$cycloalkyl is optionally replaced by C(O), O, S, $SO_2$, or NH, N—$C_{1-8}$alkyl, wherein at least one H of the $C_{1-8}$alkyl is optionally replaced by halo, OH, $NH_2$, a leaving group, a protecting group,
wherein at least one halo is optionally replaced with a radionuclide or a fluorescent tag.

In another embodiment, the invention is a compound of the Formula 7b:

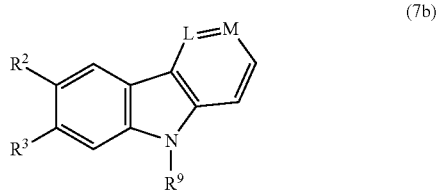

(7b)

and pharmaceutically acceptable salts and stereoisomers thereof,
wherein:
L is N or $CR^5$;
M is N or $CR^6$;
$R^9$ is H, a protecting group, a leaving group, halo, or $CH_3$;
$R^2$, $R^3$, $R^5$ and $R^6$ are independently H, OH, halo, $NH_2$, $CH_3$, $SO_2$, $NO_2$, a leaving group, a protecting group, aryl, heteroaryl, $NHR^{12}$, $N(R^{12})_2 C_{3-8}$cycloalkyl, (—$CH_2$)$_{1-12}$—$R^{12}$, wherein $R^{12}$ is $CH_3$, aryl, H or heteroaryl,
wherein at least one H of (—$CH_2$)$_{1-12}$—$R^{12}$, $C_{3-8}$cycloalkyl, aryl, or heteroaryl, is optionally replaced by halo, OH, $NH_2$, a leaving group, a protecting group and $C_{1-8}$alkyl, wherein at least one H of the $C_{1-8}$alkyl is optionally replaced by halo, OH, $NH_2$, a leaving group, a protecting group, and
wherein at least one $CH_2$ of (—$CH_2$)$_{1-12}$—$R^{12}$ is optionally replaced with C(O), O, S, $SO_2$, or NH, NH—$C_{1-8}$alkyl, $N(C_{1-8}alkyl)_2$, wherein at least one H of the $C_{1-8}$alkyl is optionally replaced by halo, OH, $NH_2$, a leaving group, a protecting group,
and wherein at least one $CH_2$ of the $C_{3-8}$cycloalkyl is optionally replaced by C(O), O, S or NH, N—$C_{1-8}$alkyl, wherein at least one H of the $C_{1-8}$alkyl is optionally replaced by halo, OH, a leaving group, a protecting group,
wherein at least one halo is optionally replaced with a radionuclide or a fluorescent tag.

In another embodiment, the invention is a compound of the Formula 7c:

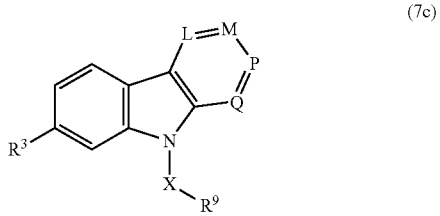

(7c)

and pharmaceutically acceptable salts and stereoisomers thereof,
wherein:
L is N or $CR^5$;
M is N or $CR^6$;
P is N or $CR^7$; and
Q is N or $CR^8$;
X is a bond or is $C_{1-14}$alkyl, wherein at least one carbon is optionally replaced by C(O), O, S, $SO_2$, or NH, NH—$C_{1-8}$alkyl, and wherein at least one H of $C_{1-8}$alkyl is optionally replaced by halo, OH, $C_{1-6}$alkyl;
$R^9$ is H, a protecting group, a leaving group, OH, $NH_2$, $N(C_{1-8}alkyl)_2$, aryl or heteroaryl, wherein at least one H of the aryl or heteroaryl is optionally replaced by $SO_2$, $NH_2$, or $C_{1-6}$alkyl, wherein at least one H of the $C_{1-6}$ alkyl is optionally replaced by $C_{3-8}$cycloalkyl, wherein at least one $CH_2$ of the $C_{3-8}$cycloalkyl is optionally replaced with O, OH, S, SH, NH, N—$C_{1-8}$alkyl;
$R^3$ and $R^5$-$R^8$ are independently H or (—$CH_2$)$_{1-12}$—$R^{13}$, wherein $R^{13}$ is an azide or an alkyne,
wherein at least one H of (—$CH_2$)$_{1-12}$—$R^{13}$ is optionally replaced by OH, $NH_2$, and $C_{1-8}$alkyl, wherein at least one H of the $C_{1-8}$alkyl is optionally replaced by OH, $NH_2$, and
wherein at least one $CH_2$ of (—$CH_2$)$_{1-12}$—$R^{13}$ is optionally replaced with C(O), O, S, $SO_2$, or NH, NH—$C_{1-8}$alkyl, $N(C_{1-8}alkyl)_2$, wherein at least one H of the $C_{1-8}$alkyl is optionally replaced by OH, $NH_2$.

In another embodiment, the invention is a pharmaceutical composition for in vivo imaging of amyloid deposits and tau tangles, comprising (a) the compound of any of the Formulas herein and/or shown in claims 1-43 and (b) a pharmaceutically acceptable carrier.

In another embodiment, the invention is a method of diagnosing Alzheimer's Disease or a predisposition thereto in a mammal, the method comprising: a) administering to the mammal a diagnostically effective amount of a radiolabeled compound of any of the Formulas herein, wherein the compound passes the blood-brain barrier and preferentially binds to amyloid plaques and/or tau tangles in a brain tissue and wherein the compound is selected from the group consisting of radiolabeled compounds of formula 7, for example; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, the invention is a method of diagnosing Alzheimer's Disease or a predisposition thereto in a mammal, the method comprising: a) administering to the mammal a diagnostically effective amount of a radiolabeled compound of any of claims 1-43, wherein the compound passes the blood-brain barrier and preferentially binds to amyloid plaques and/or tau tangles in a brain tissue and wherein the compound is selected from the group consisting of radiolabeled compounds of formula I; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

DETAILED DESCRIPTION

"Halogen" or "halo" means F, Cl, Br and I.

"Alkyl" means a saturated monovalent hydrocarbon radical having straight or branched moieties. Examples of alkyl groups include, but are not limited to, methyl, ethyl, n-propyl, isopropyl and t-butyl.

"Alkenyl" means an alkyl moieties having at least one carbon-carbon double bond wherein alkyl is as defined above. Examples of alkenyl include, but are not limited to, ethenyl and propenyl.

"Alkynyl" means alkyl moieties having at least one carbon-carbon triple bond wherein alkyl is as defined above. Examples of alkynyl groups include, but are not limited to, ethynyl and 2-propynyl.

"Alkylene" or "alkenylenyl" means a saturated, divalent hydrocarbon radicals i.e., generally present as a bridging or linking group between two other groups, having straight or branched moieties. Examples of alkylene groups include —CH$_2$— (methylene); —CH$_2$CH$_2$— (ethylene); —CH$_2$CH$_2$CH$_2$— (propylene), —CH(CH$_3$)CH$_2$-(isopropylene) etc.

"Amino" means a nitrogen moiety having two further substituents where a hydrogen or carbon atom is attached to the nitrogen. For example, representative amino groups include —NH$_2$, —NHCH$_3$, —N(CH$_3$)$_2$, —NHC$_{2-3}$-alkyl, —N(C$_{2-3}$-alkyl)$_2$ and the like. Unless indicated otherwise, the compounds of the invention containing amino moieties may include protected derivatives thereof. Suitable protecting groups for amino moieties include acetyl, tert-butoxycarbonyl, benzyloxycarbonyl and the like.

"Aryl" means an organic radical derived from an aromatic hydrocarbon by removal of one hydrogen, such as phenyl, naphthyl, indenyl, indanyl and fluorenyl. "Aryl" encompasses fused ring groups wherein at least one ring is aromatic.

"Cycloalkyl" means non-aromatic saturated cyclic alkyl moieties consisting of one or more rings, wherein said rings (if more than one) share at least one carbon atom, wherein alkyl is as defined above. Examples of cycloalkyl include, but are not limited to, cyclopropyl, cyclobutyl, cyclopentyl, cyclohexyl, cycloheptyl, bicyclo-[3.1.0]-hexyl, bicyclo-[2.2.1]-hept-1-yl, norbornyl, spiro[4.5]decyl, spiro[4.4]nonyl, spiro[4.3]octyl, spiro[4.2]heptyl and adamantanyl.

"HaloC$_1$-6alkyl" means a C$_1$-6alkyl group that is substituted with at least one halogen atom on a carbon atom of the alkyl group. Non-exclusive, representative examples of such haloC$_{1-6}$alkyl include F—CH$_2$—, F—CH$_2$CH$_2$—, F—CH$_2$CH$_2$CH$_2$—, CHF$_2$—, CHF$_2$CH$_2$—, CHF$_2$CH$_2$CH$_2$—, Br—CH$_2$—, Br—CH$_2$CH$_2$—, Br—CH$_2$CH$_2$CH$_2$—, CHBr$_2$—, CHBr$_2$CH$_2$—, CHBr$_2$CH$_2$CH$_2$— and the like.

"Heterocyclic" or "heterocycloalkyl" means a non-aromatic cyclic groups consisting of one or more rings, wherein the rings (if more than one) share one or two atoms and each ring contains up to four heteroatoms (i.e. from zero to four heteroatoms, provided that at least one ring contains at least one heteroatom). The heterocyclic groups of this invention can also include ring systems substituted with one or more O, S(O)$_{0-2}$, and/or N—R$^{10}$ as heteroatoms, wherein R$^{10}$ is as defined herein, and wherein the subscript "0-2" of S(O)$_{0-2}$ represents an integer of 0, 1 or 2. Thus, S(O)$_2$ represents the group consisting of S, S(=O), and S(O)$_2$. Examples of non-aromatic heterocyclic groups are aziridinyl, azetidinyl, pyrrolidinyl, piperidinyl, azepinyl, piperazinyl, 1,2,3,6-tetrahydropyridinyl, oxiranyl, oxetanyl, tetrahydrofuranyl, tetrahydrothienyl, tetrahydropyranyl, tetrahydrothiopyranyl, morpholino, thiomorpholino, thioxanyl, pyrrolinyl, indolinyl, 2H-pyranyl, 4H-pyranyl, dioxanyl, 1,3-dioxolanyl, pyrazolinyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, quinolizinyl, quinuclidinyl, 1,4-dioxaspiro[4.5]decyl, 1,4-dioxaspiro[4.4]nonyl, 1,4-dioxaspiro[4.3]octyl and 1,4-dioxaspiro[4.2]heptyl.

"Heteroaryl" means an aromatic group containing one or more heteroatoms (O, S, or N), preferably from one to four heteroatoms. A heteroaryl may be a monocyclic or a polycyclic group. Examples of heteroaryl groups are pyridinyl, pyridazinyl, imidazolyl, pyrimidinyl, pyrazolyl, triazolyl, pyrazinyl, quinolyl, isoquinolyl, 1,2,3,4-tetrahydroquinolyl, tetrazolyl, furyl, thienyl, isoxazolyl, thiazolyl, oxazolyl, isothiazolyl, pyrrolyl, indolyl, benzimidazolyl, benzofuranyl, indazolyl, indolizinyl, phthalazinyl, triazinyl, 1,3,5-triazinyl, isoindolyl, purinyl, oxadiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl and azaindolyl. In certain aspects of the present application, the heteroaryl is a 4-substituted-1H-1,2,3-triazol-1-yl.

As used herein, where a divalent group, such as a linker for example, is represented by a structure -A-B—, as shown below, it is intended to also represent a group that may be attached in both possible permutations, as noted in the two structures below.

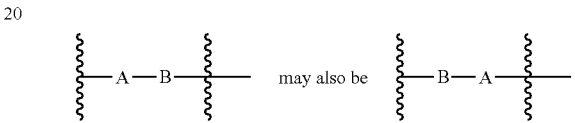

For example, when a divalent group such as the group "—N(R$^{10}$)C(O)-" is provided, for example, the group is intended to also include both the divalent group —N(R$^{10}$)C(O)— and also the divalent group —C(O)N(R$^{10}$)—.

The substituents or the groups C$_{1-6}$alkyl, C$_{3-6}$cycloalkyl, C$_{3-12}$cycloalkylC$_{1-5}$alkyl, C$_{6-14}$aryl, C$_{6-14}$aryloxy, C$_{6-10}$arylC$_{1-4}$alkyl, heteroaryl, heteroaryloxy etc. . . . of the variables R$^1$, R$^2$, R$^3$, R$^4$, R$^5$, R$^6$, R$^7$, R$^8$, R$^9$ and R$^{10}$ are also optionally further substituted by substituents selected from the group consisting of amino, halo, cyano, nitro, hydroxyl, —SH, —SC$_{1-6}$alkyl, —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl.

For example, in certain aspect of the present application, the heteroaryl substituent is a 4-substituted-1H-1,2,3-triazol-1-yl. In the radiolabeled compounds of the present application, a radionuclide may be attached to an aryl group of the compound of Formula I, as in a 2-$^{18}$F-'carbazole derivative such as the compound represented as:

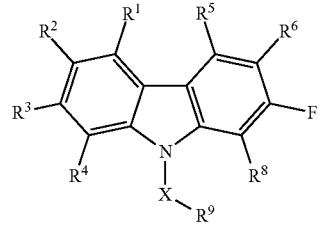

or a 2-($^{18}$F-fluoroethyl)-'carbazole, 2-($^{18}$F-fluoromethyl)-'carbazole, a $^{11}$C-methoxy-group, for example, and/or the radionuclide may be attached to any one or more of the variables R$^1$, R$^2$, R$^3$, R$^4$, R$^5$, R$^6$, R$^7$, R$^8$, R$^9$ and R$^{10}$ by way of a $^{18}$F-fluoroethyl-group, a $^{18}$F-fluoromethyl-group, a $^{11}$C-methoxy-group, 4-[($^{18}$F-fluoroethyl)-1H-1,2,3-triazol-1-yl]-ethoxy-group, 4-[($^{18}$F-fluoroethyl)-1H-1,2,3-triazol-1-yl]-propyloxy-group, a $^{123}$I, a $^{124}$I, a $^{125}$I or a $^{131}$I group, and the like. Unless otherwise noted, a compound represented as being substituted by an atom, such as the generic representation by the atom fluorine in F—CH$_2$CH$_2$-('carbazole) or F—CH$_2$CH$_2$O-('carbazole), for example, is intended to cover both the naturally occurring element $^{19}$F (fluorine-19) as well as the $^{18}$F (fluorine-18) isotope(s) of the element itself.

The term "optionally substituted" or "substituted" refers to the specific substituents or groups wherein one to four hydrogen atoms in the group may be replaced by one to four substituents, for example, independently selected from the substituents amino, halo, cyano, nitro, hydroxyl, —SH, —SC$_{1-6}$alkyl, —C(O)NH$_2$, —C(S)NH$_2$, haloC$_{1-6}$alkyl, perhaloC$_{1-6}$alkyl, C$_{1-6}$alkyl, C$_{3-6}$cycloalkyl, C$_{3-12}$cycloalkyl, C$_{6-14}$aryl and heteroaryl, or as specifically disclosed herein. In addition, the substituents may also include alkyl, aryl, alkylene-aryl, hydroxy, alkoxy, aryloxy, perhaloalkoxy, heterocyclyl, azido, amino, guanidino, amidino, halo, alkylthio, oxo, acylalkyl, carboxy esters, carboxyl, carboxamido, acyloxy, aminoalkyl, alkylaminoaryl, alkylaminoalkyl, alkoxyaryl, arylamino, phosphono, sulfonyl, carboxamidoaryl, hydroxyalkyl, haloalkyl, alkoxyalkyl and perhaloalkyl. In addition, the term "optionally substituted" or "substituted" in reference to the variables R$^1$, R$^2$, R$^3$, R$^4$, R$^5$, R$^6$, R$^7$, R$^8$, R$^9$ and R$^{10}$, includes groups substituted by one to four substituents, as identified above, that further comprise a positron or gamma emitter. Such positron emitters include, but are not limited to, and $^{11}$C, $^{13}$N, $^{15}$O, $^{18}$F, $^{123}$I, $^{124}$I, $^{125}$I, $^{131}$I and $^{77}$Br.

The term "radiolabeled compound" as used herein refers to compounds having an atom or group that may provide a radiolabel or may be converted to a radiolabel, such as from a non-radioactive atom to a radionuclide that is active, such as for example, $^{11}$C, $^{13}$N, $^{15}$O, $^{18}$F, $^{123}$I, $^{124}$I, $^{125}$I, $^{131}$I and $^{77}$Br. In addition, for the purpose of the present application, such "radiolabeled compound" may also refer to an atom or a group, that comprises a non-active nuclide, such as a halogen, such as $^{19}$F for example, wherein the compound may be used and administered in a therapeutically effective amount.

Compounds of the Formulas disclosed herein may have optical centers and therefore may occur in different enantiomeric and diastereomeric configurations. The present invention includes all enantiomers, diastereomers, and other stereoisomers of such compounds of the Formulas disclosed herein, as well as racemic compounds and racemic mixtures and other mixtures of stereoisomers thereof. Pharmaceutically acceptable salts of the compounds of the Formulas disclosed herein include the acid addition and base salts thereof. Suitable acid addition salts are formed from acids which form non-toxic salts. Examples include, but are not limited to, the acetate, adipate, aspartate, benzoate, besylate, bicarbonate/carbonate, bisulphate/sulphate, borate, citrate, formate, fumarate, gluconate, glucuronate, hydrochloride/chloride, hydrobromide/bromide, hydroiodide/iodide, lactate, malate, maleate, malonate, mesylate, methylsulphate, naphthylate, oxalate, palmitate, phosphate/hydrogen phosphate/dihydrogen phosphate, pyroglutamate, salicylate, stearate, succinate, sulfonate, tartrate, tosylate and trifluoroacetate salts. Suitable base salts are formed from bases which form non-toxic salts. Examples include, but are not limited to, the aluminum, arginine, benzathine, calcium, choline, diethylamine, diolamine, glycine, lysine, magnesium, potassium, sodium, tromethamine and zinc salts. Hemisalts of acids and bases may also be formed, for example, hemisulphate and hemicalcium salts. For a review on suitable salts, see Handbook of Pharmaceutical Salts: Properties, Selection, and Use by Stahl and Wermuth (Wiley-VCH, 2002). Pharmaceutically acceptable salts of compounds of the Formulas disclosed herein may be prepared by one or more of three methods: (i) by reacting the compound of the Formulas disclosed herein with the desired acid or base; (ii) by removing an acid- or base-labile protecting group from a suitable precursor of the compound of the Formulas disclosed herein; or (iii) by converting one salt of the compound of the Formulas disclosed herein to another salt by the reaction with an appropriate acid or base or by means of a suitable ion exchange column.

In another embodiment, the imaging is by employing a fluorescence imaging technique or a nuclear imaging technique selected from the group consisting of positron emission tomography (PET) and single photon emission computed tomography (SPECT), the fluorescence imaging technique and/or nuclear imaging technique for monitoring or visualizing a distribution of the radiolabeled or tagged compound within the brain or within a portion thereof.

In another embodiment, the invention is a method for treating a disease or condition, in a mammal in need thereof, selected from the group consisting of anxiety, depression, schizophrenia, Alzheimer's Disease, stress-related disease, panic, a phobia, obsessive compulsive disorder, obesity, post-traumatic stress syndrome, or epilepsy comprising administering to the mammal a therapeutically effective amount of the compound of formulas 7-8.

In one embodiment, there is provided a radiolabeled compound of the formula:

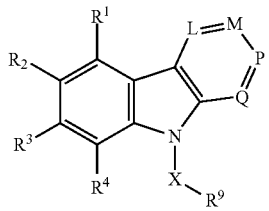

and pharmaceutically acceptable salts and stereoisomers thereof, wherein:

L is N or CR$^5$;

M is N or CR$^6$;

P is N or CR$^7$; and

Q is N or CR$^8$;

X is a bond or is C$_{1-14}$alkyl, wherein at least one carbon is optionally replaced by C(O), O, S, SO$_2$, or NH, NH—C$_{1-8}$alkyl, and wherein at least one H of C$_{1-8}$alkyl is optionally replaced by halo, OH, C$_{1-6}$alkyl;

R$^9$ is H, a protecting group, a leaving group, an azide, an alkyne, OH, halo, NH$_2$, N(C$_{1-8}$alkyl)$_2$, aryl or heteroaryl, wherein at least one H of the aryl or heteroaryl is optionally replaced by halo, SO$_2$, NH$_2$, or C$_{1-6}$ alkyl, wherein at least one H of the C$_{1-6}$ alkyl is optionally replaced by halo, or C$_{3-8}$cycloalkyl, wherein at least one H of the C$_{3-8}$cycloalkyl is optionally replaced by halo and wherein at least one CH$_2$ of the C$_{3-8}$cycloalkyl is optionally replaced with O, OH, S, SH, NH, N—C$_{1-8}$alkyl;

R$^1$-R$^8$ are independently H, OH, halo, NH$_2$, CH$_3$, SO$_2$, a leaving group, a protecting group, aryl, heteroaryl, NHR$^{12}$, N(R$^{12}$)$_2$C$_{3-8}$cycloalkyl, (—CH$_2$)$_{1-12}$—R$^{12}$, wherein R$^{12}$ is CH$_3$, aryl, H or heteroaryl, wherein at least one H of (—CH$_2$)$_{1-12}$—R$^{12}$, C$_{3-8}$cycloalkyl, aryl, or heteroaryl, is optionally replaced by halo, OH, NH$_2$, a leaving group, a protecting group and C$_{1-8}$alkyl, wherein at least one H of the C$_{1-8}$alkyl is optionally replaced by halo, OH, NH$_2$, a leaving group, a protecting group, and wherein at least one CH$_2$ of (—CH$_2$)$_{1-12}$—R$^{12}$ is optionally replaced with C(O), O, S, SO$_2$, or NH, NH—C$_{1-8}$alkyl, N(C$_{1-8}$alkyl)$_2$, wherein at least one H of the C$_{1-8}$alkyl is optionally replaced by halo, OH, NH$_2$, a leaving group, a protecting group, and wherein at least one CH$_2$ of the C$_{3-8}$cycloalkyl is optionally replaced by C(O), O, S or NH, N—C$_{1-8}$alkyl, wherein at least one H of the C$_{1-8}$alkyl is optionally replaced by halo, OH, a leaving group, a protecting group, wherein at least one halo is optionally replaced with a radionuclide or a fluorescent tag.

In another embodiment, the invention is a compound of the formula:

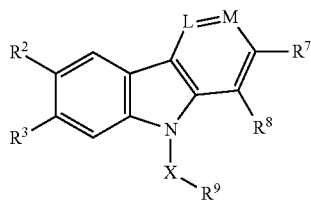

and pharmaceutically acceptable salts and stereoisomers thereof,
wherein:
L is N or CR$^5$;
M is N or CR$^6$;
X is a bond or is C$_{1-14}$ alkyl, wherein at least one carbon is optionally replaced by C(O), O, S, SO$_2$, or NH, NH—C$_{1-8}$ alkyl, and wherein at least one H of C$_{1-8}$alkyl is optionally replaced by halo, OH, C$_{1-6}$alkyl;
R$^9$ is H, a protecting group, a leaving group, an azide, an alkyne, OH, halo, NH$_2$, N(C$_{1-8}$alkyl)$_2$, aryl or heteroaryl, wherein at least one H of the aryl or heteroaryl is optionally replaced by halo, SO$_2$, NH$_2$, or C$_{1-6}$ alkyl or C$_{1-6}$ alkyl, wherein at least one H of the C$_{1-6}$ alkyl is optionally replaced by halo, or C$_{3-8}$cycloalkyl, wherein at least one H of the C$_{3-8}$cycloalkyl is optionally replaced by halo and wherein at least one CH$_2$ of the C$_{3-8}$cycloalkyl is optionally replaced with O, OH, S, SH, NH, N—C$_{1-8}$alkyl;
R$^2$, R$^3$, R$^7$ and R$^8$ are independently H, OH, halo, NH$_2$, CH$_3$, SO$_2$, a leaving group, a protecting group, aryl, heteroaryl, NHR$^{12}$, N(R$^{12}$)$_2$C$_{3-8}$cycloalkyl, (—CH$_2$)$_{1-12}$—R$^{12}$, wherein R$^{12}$ is CH$_3$, aryl, H or heteroaryl,
wherein at least one H of (—CH$_2$)$_{1-12}$—R$^{12}$, C$_{3-8}$cycloalkyl, aryl, or heteroaryl, is optionally replaced by halo, OH, NH$_2$, a leaving group, a protecting group and C$_{1-8}$alkyl, wherein at least one H of the C$_{1-8}$alkyl is optionally replaced by halo, OH, NH$_2$, a leaving group, a protecting group, and
wherein at least one CH$_2$ of (—CH$_2$)$_{1-12}$—R$^{12}$ is optionally replaced with C(O), O, S, SO$_2$, or NH, NH—C$_{1-8}$alkyl, N(C$_{1-8}$alkyl)$_2$, wherein at least one H of the C$_{1-8}$alkyl is optionally replaced by halo, OH, NH$_2$, a leaving group, a protecting group,
and wherein at least one CH$_2$ of the C$_{3-8}$cycloalkyl is optionally replaced by C(O), O, S or NH, N—C$_{1-8}$alkyl, wherein at least one H of the C$_{1-8}$alkyl is optionally replaced by halo, OH, a leaving group, a protecting group,
wherein at least one halo is optionally replaced with a radionuclide or a fluorescent tag.

In another embodiment, the invention is a compound of the formula:

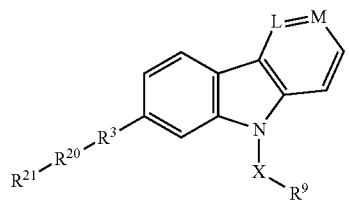

and pharmaceutically acceptable salts and stereoisomers thereof,
wherein:
L is N or CR$^5$;
M is N or CR$^6$;
X is a bond or is C$_{1-14}$alkyl, wherein at least one carbon is optionally replaced by C(O), O, S, SO$_2$, or NH, NH—C$_{1-8}$alkyl, and wherein at least one H of C$_{1-8}$alkyl is optionally replaced by halo, OH, C$_{1-6}$alkyl;
R$^9$ is H, a protecting group, a leaving group, an azide, an alkyne, OH, halo, NH$_2$, N(C$_{1-8}$alkyl)$_2$, aryl or heteroaryl, wherein at least one H of the aryl or heteroaryl is optionally replaced by halo, SO$_2$, NH$_2$, or C$_{1-6}$ alkyl or C$_{1-6}$ alkyl, wherein at least one H of the C$_{1-6}$ alkyl is optionally replaced by halo, or C$_{3-8}$cycloalkyl, wherein at least one H of the C$_{3-8}$cycloalkyl is optionally replaced by halo and wherein at least one CH$_2$ of the C$_{3-8}$cycloalkyl is optionally replaced with O, OH, S, SH, NH, N—C$_{1-8}$alkyl;
R$^3$ is a bond or is at least one of O, S, C(O), SO$_2$, NH, N—C$_{1-8}$alkyl, (CH$_2$)$_{1-12}$, wherein at least one C of (CH$_2$)$_{1-12}$ is optionally replaced by C(O), O, S, SO$_2$, NH, N—C$_{1-8}$alkyl and wherein at least one H is optionally replaced by C$_{1-8}$alkyl or halo,
R$^{20}$ is aryl or heteroaryl;
R$^{21}$ is H, OH, halo, NH$_2$, CH$_3$, SO$_2$, a leaving group, a protecting group, (—CH$_2$)$_{1-12}$—CH$_3$, C$_{3-8}$cycloalkyl,
wherein at least one H of the (—CH$_2$)$_{1-12}$—CH$_3$ or the C$_{3-8}$cycloalkyl is optionally replaced by halo, OH, NH$_2$, a leaving group, a protecting group and C$_{1-8}$alkyl, wherein at least one H of the C$_{1-8}$alkyl is optionally replaced by halo, OH, a leaving group, a protecting group,
and wherein at least one CH$_2$ of the (—CH$_2$)$_{1-12}$—CH$_3$ is optionally replaced with C(O), O, S, SO$_2$, or NH, NH—C$_{1-8}$alkyl, N(C$_{1-8}$alkyl)$_2$, wherein at least one H of the C$_{1-8}$alkyl is optionally replaced by halo, OH, NH$_2$, a leaving group, a protecting group,
and wherein at least one CH$_2$ of the C$_{3-8}$cycloalkyl is optionally replaced by C(O), O, S, SO$_2$, or NH, N—C$_{1-8}$alkyl, wherein at least one H of the C$_{1-8}$alkyl is optionally replaced by halo, OH, NH$_2$, a leaving group, a protecting group,
wherein at least one halo is optionally replaced with a radionuclide or a fluorescent tag.

In another embodiment, the invention is a compound of the formula:

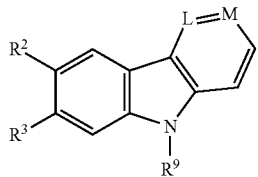

and pharmaceutically acceptable salts and stereoisomers thereof,
wherein:
L is N or $CR^5$;
M is N or $CR^6$;
$R^9$ is H, a protecting group, a leaving group, halo, or $CH_3$;
$R^2$, $R^3$, $R^5$ and $R^6$ are independently H, OH, halo, $NH_2$, $CH_3$, $SO_2$, a leaving group, a protecting group, aryl, heteroaryl, $NHR^{12}$, $N(R^{12})_2$ $C_{3-8}$cycloalkyl, $(-CH_2)_{1-12}-R^{12}$, wherein $R^{12}$ is $CH_3$, aryl, H or heteroaryl,
wherein at least one H of $(-CH_2)_{1-12}-R^{12}$, $C_{3-8}$cycloalkyl, aryl, or heteroaryl, is optionally replaced by halo, OH, $NH_2$, a leaving group, a protecting group and $C_{1-8}$alkyl, wherein at least one H of the $C_{1-8}$alkyl is optionally replaced by halo, OH, $NH_2$, a leaving group, a protecting group, and
wherein at least one $CH_2$ of $(-CH_2)_{1-12}-R^{12}$ is optionally replaced with C(O), O, S, $SO_2$, or NH, $NH-C_{1-8}$alkyl, $N(C_{1-8}alkyl)_2$, wherein at least one H of the $C_{1-8}$alkyl is optionally replaced by halo, OH, $NH_2$, a leaving group, a protecting group,
and wherein at least one $CH_2$ of the $C_{3-8}$cycloalkyl is optionally replaced by C(O), O, S or NH, $N-C_{1-8}$alkyl, wherein at least one H of the $C_{1-8}$alkyl is optionally replaced by halo, OH, a leaving group, a protecting group,
wherein at least one halo is optionally replaced with a radionuclide or a fluorescent tag.

In another embodiment, the invention is a compound of the formula:

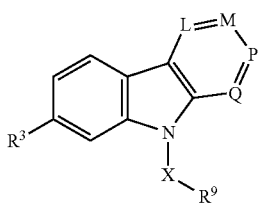

and pharmaceutically acceptable salts and stereoisomers thereof,
wherein:
L is N or $CR^5$;
M is N or $CR^6$;
P is N or $CR^7$; and
Q is N or $CR^8$;
X is a bond or is $C_{1-14}$alkyl, wherein at least one carbon is optionally replaced by C(O), O, S, $SO_2$, or NH, $NH-C_{1-8}$ alkyl, and wherein at least one H of $C_{1-8}$alkyl is optionally replaced by halo, OH, $C_{1-6}$alkyl;
$R^9$ is H, a protecting group, a leaving group, OH, $NH_2$, $N(C_{1-8}alkyl)_2$, aryl or heteroaryl, wherein at least one H of the aryl or heteroaryl is optionally replaced by $SO_2$, $NH_2$, or $C_{1-6}$ alkyl, wherein at least one H of the $C_{1-6}$ alkyl is optionally replaced by $C_{3-8}$cycloalkyl, wherein at least one $CH_2$ of the $C_{3-8}$cycloalkyl is optionally replaced with O, OH, S, SH, NH, $N-C_{1-8}$alkyl;
$R^3$ and $R^5$-$R^8$ are independently H or $(-CH_2)_{1-12}-R^{13}$, wherein $R^{13}$ is an azide or an alkyne,
wherein at least one H of $(-CH_2)_{1-12}-R^{13}$ is optionally replaced by OH, $NH_2$, and $C_{1-8}$alkyl, wherein at least one H of the $C_{1-8}$alkyl is optionally replaced by OH, $NH_2$, and
wherein at least one $CH_2$ of $(-CH_2)_{1-12}-R^{13}$ is optionally replaced with C(O), O, S, $SO_2$, or NH, $NH-C_{1-8}$alkyl, $N(C_{1-8}alkyl)_2$, wherein at least one H of the $C_{1-8}$alkyl is optionally replaced by OH, $NH_2$.

In another embodiment, the invention is a pharmaceutical composition for in vivo imaging of amyloid deposits and tau tangles, comprising (a) the compound of any of the Formulas above or shown in claims 1-43 and (b) a pharmaceutically acceptable carrier.

In another embodiment, the invention is a method of diagnosing Alzheimer's Disease or a predisposition thereto in a mammal, the method comprising: a) administering to the mammal a diagnostically effective amount of a radiolabeled compound, wherein the compound passes the blood-brain barrier and preferentially binds to amyloid plaques and/or tau tangles in a brain tissue and wherein the compound is selected from the group consisting of radiolabeled compounds of formula 7, for example; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, the invention is a method of diagnosing Alzheimer's Disease or a predisposition thereto in a mammal, the method comprising: a) administering to the mammal a diagnostically effective amount of a radiolabeled compound of any of claims 1-43, provided below, wherein the compound passes the blood-brain barrier and preferentially binds to amyloid plaques and/or tau tangles in a brain tissue and wherein the compound is selected from the group consisting of radiolabeled compounds of formula 7, for example; b) allowing the compound to distribute into the brain tissue; and c) imaging the brain tissue, wherein an increase in binding of the compound to the brain tissue compared to a normal control level of binding indicates that the mammal is suffering from or is at risk of developing Alzheimer's Disease.

In another embodiment, the present invention is a method for imaging and detection of senile plaques and/or neurofibrillary tangles in a brain tissue, the method comprising treating the tissue with a compound of formulas 7-8 for detection of neurological disorders.

The neurological disorder may be detected by measuring the affinity of compounds of formulas 7-8 for tau aggrerates.

In one embodiment, the detection may be by gamma imaging with PET or SPECT.

TABLE 1

Known AD positive fluorescent dyes and imaging agents

| Name | Compound and Reference | Target | Binding Affinity |
|---|---|---|---|
| Congo Red | 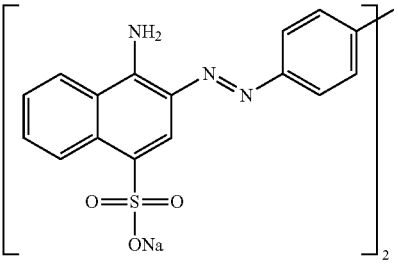<br>*Anal. Biochem.* 2006, 356, 265-272; *J. Biol. Chem.* 2005, 280, 5892-5901 | Aβ monomer | $IC_{50}$: 2-10 uM |
| Curcumin | 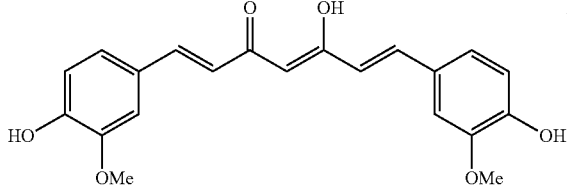<br>*Anal. Biochem.* 2006, 356, 265-272; *J. Biol. Chem.* 2005, 280, 5892-5901 | Aβ monomer | $IC_{50}$: 10-20 uM |
| ANS | 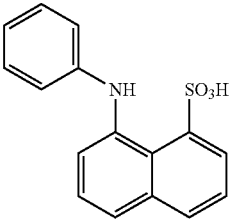<br>*Anal. Biochem.* 2006, 356, 265-272 | Aβ monomer | $IC_{50}$: >100 uM |
| Thioflavin T | 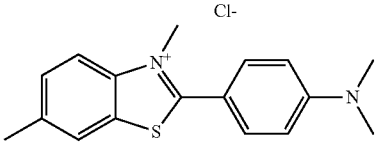<br>*Anal. Biochem.* 2006, 356, 265-272 | Aβ monomer | $IC_{50}$: >500 uM |
| Iodinated Flavone | 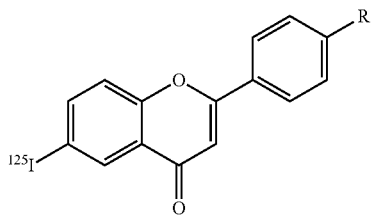<br>R = NHMe, $NMe_2$, OMe, OH<br>*J. Med. Chem.* 2005, 48, 7253-7260 | Aβ40 aggregates | $K_i$ = 13 nM (—$NMe_2$) to 72 nM (—OH) |

TABLE 1-continued

Known AD positive fluorescent dyes and imaging agents

| Name | Compound and Reference | Target | Binding Affinity |
|---|---|---|---|
| Pyridyl Styrene | R = NHMe, NMe$_2$<br>*J. Med. Chem.* 2007, 50, 2157-2165 | Aβ fibrils | Kd = 7.5-9 nM |
| Diaryl acetylenes | R = —OH, —OCH$_2$CH$_2$—O—CH$_2$CH$_2$F<br>*Bioorg. Med. Chem.* 2007, 17, 3581-3584 | Aβ plaques | Kd = ~10 nM |
| Thiophene chalcones | R, R' = H, Me<br>*Bioorg. Med. Chem.* 2007, 15, 6802-6809 | Aβ 1-42 aggregates | Ki = 3.9-14 nM |
| Aurones | *Biochem. Biophys. Res. Commun.* 2007, 361, 116-121 | Aβ 1-42 aggregates | Ki = 1.24 nM |
| Benzofuran | *J. Med. Chem.* 2006, 49, 2725-2730 | Aβ fibrils | Ki = 2.8 nM |

TABLE 2

Examples of compounds useful for detecting AD biomarkers in vivo. These compounds may be radiolabeled or be "cold".

| Name | Structure | Chemical Formula | MW | Code |
| --- | --- | --- | --- | --- |
| 2-(2-fluoroethoxy)-9H-carbazole | 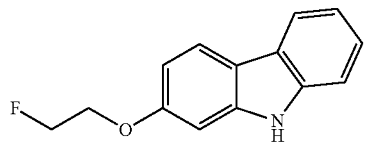 [SMILES: FCCOc1ccc2c(c1)[nH]c1ccccc12] | $C_{14}H_{12}FNO$ | 229.25 | CB-001 |
| 9-(2-fluoroethyl)-9H-carbazol-2-ol | 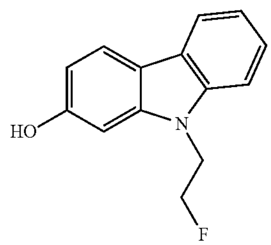 [SMILES: Oc1ccc2c3ccccc3n(CCF)c2c1] | $C_{14}H_{12}FNO$ | 229.25 | |
| N-(2-fluoroethyl)-7-(2-(2-(2-methoxyethoxy)ethoxy)ethoxy)-9H-carbazol-3-amine | 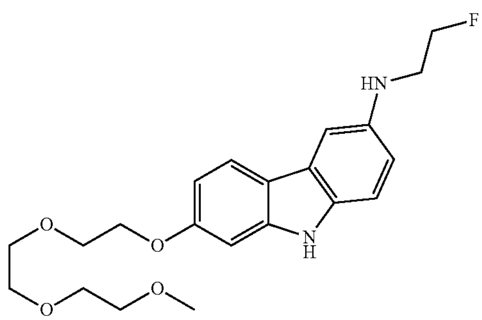 [SMILES: COCCOCCOCCOc1ccc2c(c1)[nH]c1ccc(NCCF)cc12] | $C_{21}H_{27}FN_2O_4$ | 390.45 | |
| 7-(2-fluoroethoxy)-N,N-dimethyl-9H-carbazol-2-amine | 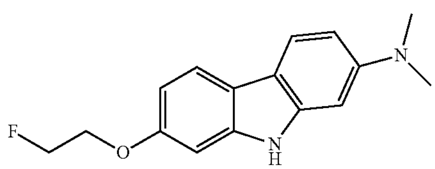 [SMILES: CN(C)c1ccc2c(c1)[nH]c1cc(OCCF)ccc12] | $C_{16}H_{17}FN_2O$ | 272.32 | |
| 7-(2-(2-(2-fluoroethoxy)ethoxy)ethoxy)-N-methyl-9H-carbazol-3-amine | 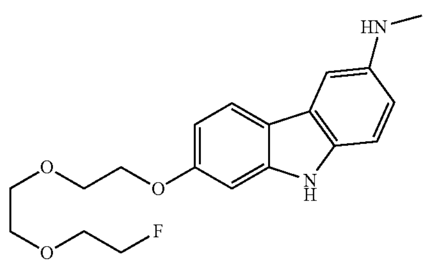 [SMILES: CNc1ccc2[nH]c3cc(OCCOCCOCCF)ccc3c2c1] | $C_{19}H_{23}FN_2O_3$ | 346.40 | CB-008 |
| 1-(3,6-diamino-9H-carbazol-9-yl)-3-(2-(2-(2-fluoroethoxy)ethoxy)ethoxy)propan-1-one | 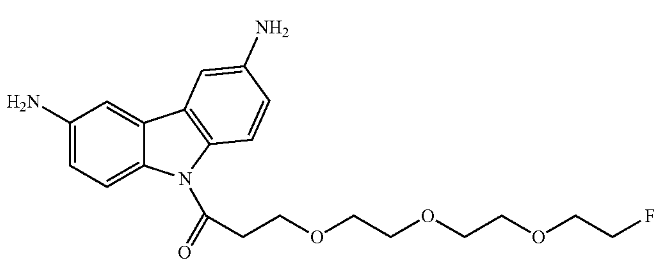 [SMILES: Nc1ccc2c(c1)c1cc(N)ccc1n2C(=O)CCOCCOCCOCCF] | $C_{21}H_{26}FN_3O_4$ | 403.45 | |

TABLE 2-continued

Examples of compounds useful for detecting AD biomarkers in vivo. These compounds may be radiolabeled or be "cold".

| Name | Structure | Chemical Formula | MW | Code |
|---|---|---|---|---|
| N-(2-fluoroethyl)-2-hydroxy-11H-benzo[a]carbazole-3-carboxamide | 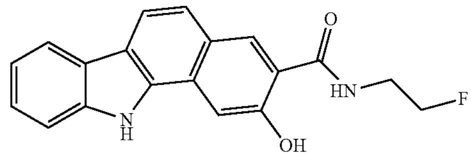 [SMILES: O=C(NCCF)c1cc2ccc3c4ccccc4[nH]c3c2cc1O] | $C_{19}H_{15}FN_2O_2$ | 322.33 | |
| 2-(6-chloro-9H-carbazol-2-yl)-N-(2-fluoroethyl)propanamide | 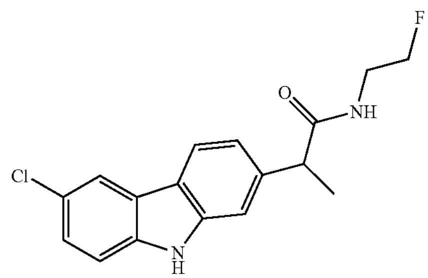 [SMILES: CC(C(=O)NCCF)c1ccc2c(c1)[nH]c1ccc(Cl)cc12] | $C_{17}H_{16}ClFN_2O$ | 318.77 | |
| 2-(6-fluoro-9H-carbazol-2-yl)-N,N-dimethyl-propanamide | 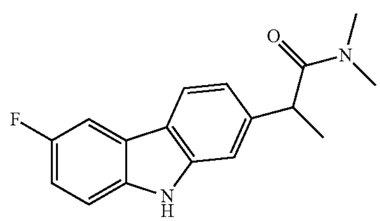 [SMILES: CC(C(=O)N(C)C)c1ccc2c(c1)[nH]c1ccc(F)cc12] | $C_{17}H_{17}FN_2O$ | 284.33 | |
| 2-methoxy-9H-carbazole | 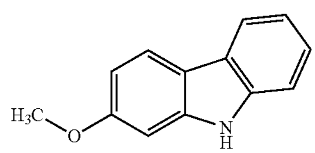 | $C_{13}H_{11}NO$ | 197.23 | |
| 6-iodo-2-methoxy-9H-carbazole | 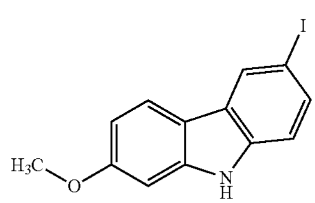 [SMILES: COc1ccc2c(c1)[nH]c1ccc(I)cc12] | $C_{13}H_{10}INO$ | 323.13 | |
| 7-(2-fluoroethoxy)-N,N-dimethyl-9H-carbazol-2-amine | 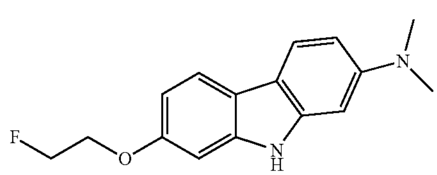 [SMILES: CN(C)c1ccc2c(c1)[nH]c1cc(OCCF)ccc12] | $C_{16}H_{17}FN_2O$ | 272.32 | |
| tert-butyl 2-(2-(2-fluoroethoxy)ethoxy)ethoxy)-9H-carbazole-9-carboxylate | | $C_{23}H_{28}FNO_5$ | 417.47 | CB-005 |
| 2-(2-(2-(2-fluoroethoxy)ethoxy)ethoxy)-9-methyl-9H-carbazole | 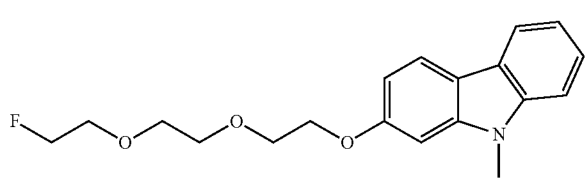 [SMILES: Cn1c2ccccc2c2ccc(OCCOCCOCCF)cc21] | $C_{19}H_{22}FNO_3$ | 331.38 | CB-006 |

TABLE 2-continued

Examples of compounds useful for detecting AD biomarkers in vivo. These compounds may be radiolabeled or be "cold".

| Name | Structure | Chemical Formula | MW | Code |
|---|---|---|---|---|
| 7-(2-(2-(2-fluoroethoxy)ethoxy)ethoxy)-N,N-dimethyl-9H-carbazol-2-amine | 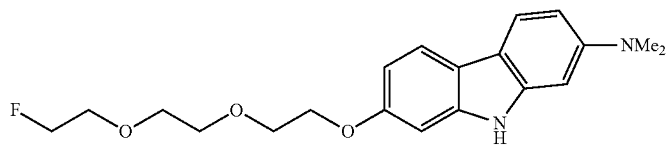 [SMILES: CN(C)c1ccc2c(c1)[nH]c1cc(OCCOCCOCCF)ccc12] | $C_{20}H_{25}FN_2O_3$ | 360.42 | CB-007 |
| N-(7-(2-(2-(2-fluoroethoxy)ethoxy)ethoxy)-9H-carbazol-2-yl)acetamide | 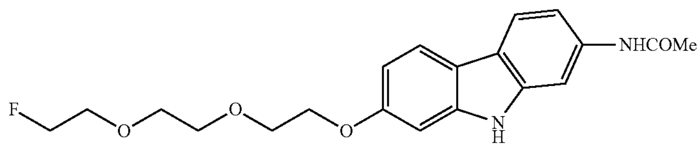 | $C_{20}H_{23}FN_2O_4$ | 374.41 | CB-009 |
| 7-(2-(2-(2-fluoroethoxy)ethoxy)ethoxy)-9H-pyrido[2,3-b]indole | 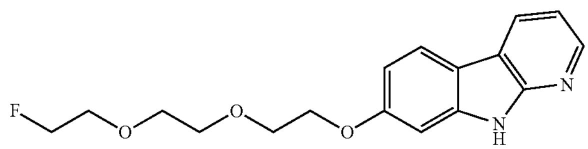 [SMILES: FCCOCCOCCOc1ccc2c(c1)[nH]c1ncccc12] | $C_{17}H_{19}FN_2O_3$ | 318.34 | CB-028 |
| 2-(2-(2-(2-fluoroethoxy)ethoxy)ethoxy)-9H-carbazole | 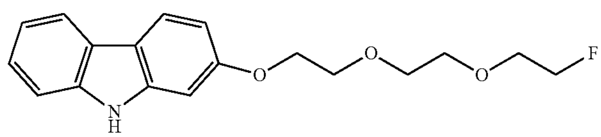 [SMILES: FCCOCCOCCOc1ccc2c(c1)[nH]c1ccccc12] | $C_{18}H_{20}FNO_3$ | 317.35 | CB-003 |
| 7-(2-(2-(2-fluoroethoxy)ethoxy)ethoxy)-N-methyl-9H-carbazol-2-amine | 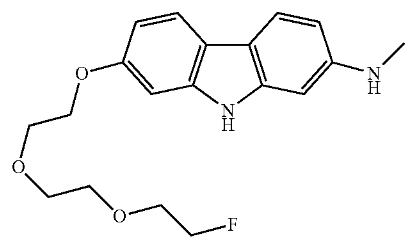 [SMILES: CNc1ccc2c(c1)[nH]c1cc(OCCOCCOCCF)ccc12] | $C_{19}H_{23}FN_2O_3$ | 346.40 | CB-004 |
| N-(7-(2-(2-(2-fluoroethoxy)ethoxy)ethoxy)-9H-carbazol-2-yl)formamide | 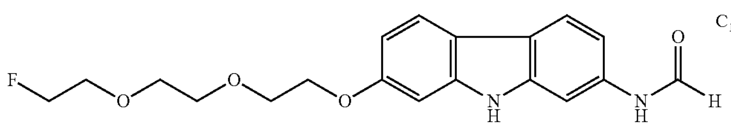 | $C_{19}H_{21}FN_2O_4$ | 360.38 | CB-010 |
| 6-(2-(2-(2-fluoroethoxy)ethoxy)ethoxy)-9-(methoxymethyl)-N,N-dimethyl-9H-carbazol-3-amine | | $C_{22}H_{29}FN_2O_4$ | 404.48 | CB-011 |
| N-(7-(2-fluoroethoxy)-9H-carbazol-2-yl)formamide | 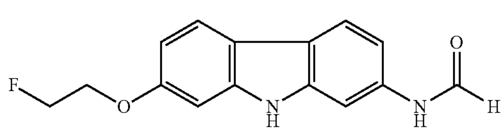 [SMILES: O=CNc1ccc2c(c1)[nH]c1cc(OCCF)ccc12] | $C_{15}H_{13}FN_2O_2$ | 272.27 | CB-012 |
| N-(7-(2-(2-fluoroethoxy)ethoxy)-9H-carbazol-2-yl)formamide | 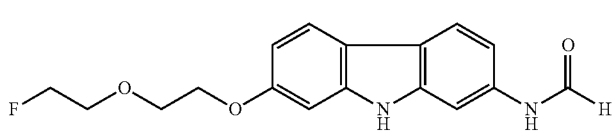 [SMILES: O=CNc1ccc2c(c1)[nH]c1cc(OCCOCCF)ccc12] | $C_{17}H_{17}FN_2O_3$ | 316.33 | CB-024 |

TABLE 2-continued

Examples of compounds useful for detecting AD biomarkers in vivo. These compounds may be radiolabeled or be "cold".

| Name | Structure | Chemical Formula | MW | Code |
|---|---|---|---|---|
| N-(2-fluoroethyl)-6-methoxy-9H-carbazol-3-amine | 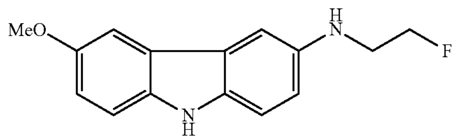 [SMILES: COc1ccc2[nH]c3ccc(NCCF)cc3c2c1] | $C_{15}H_{15}FN_2O$ | 258.29 | CB-013 |
| 7-((4-fluorobutyl)(methyl)amino)-9H-carbazol-2-ol | 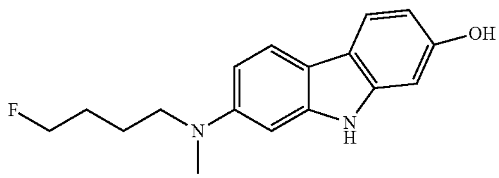 [SMILES: CN(CCCCF)c1ccc2c(c1)[nH]c1cc(O)ccc12] | $C_{17}H_{19}FN_2O$ | 286.34 | CB-014 |
| 7-((2-fluoroethyl)(methyl)amino)-9H-carbazol-2-ol | 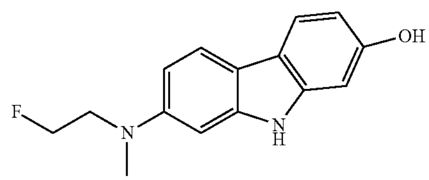 [SMILES: CN(CCF)c1ccc2c(c1)[nH]c1cc(O)ccc12] | $C_{15}H_{15}FN_2O$ | 258.29 | CB-015 |
| 7-(2-fluoroethyl-amino)-9H-carbazol-2-ol | 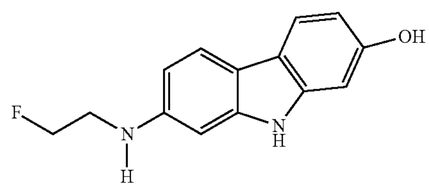 [SMILES: Oc1ccc2c(c1)[nH]c1cc(NCCF)ccc12] | $C_{14}H_{13}FN_2O$ | 244.26 | CB-016 |
| 7-((2-(2-(2-fluoroethoxy)ethoxy)ethyl)(methyl)amino)-9H-carbazol-2-ol | 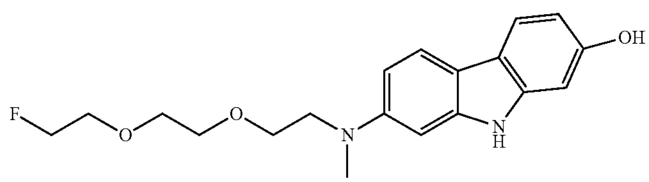 [SMILES: CN(CCOCCOCCF)c1ccc2c(c1)[nH]c1cc(O)ccc12] | $C_{19}H_{23}FN_2O_3$ | 346.40 | CB-019 |
| 7-(2-fluoroethoxy)-N-methyl-9H-carbazol-2-amine | 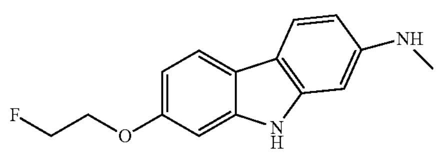 [SMILES: CNc1ccc2c(c1)[nH]c1cc(OCCF)ccc12] | $C_{15}H_{15}FN_2O$ | 258.29 | CB-020 |
| 7-(2-fluoroethoxy)-9H-carbazol-2-ol | 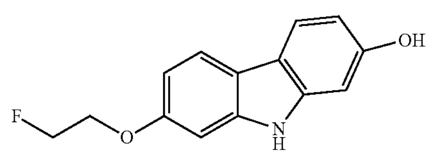 [SMILES: Oc1ccc2c(c1)[nH]c1cc(OCCF)ccc12] | $C_{14}H_{12}FNO_2$ | 245.25 | CB-025 |
| 7-(2-(2-(2-fluoroethoxy)ethoxy)ethoxy)-9H-carbazol-2-ol | 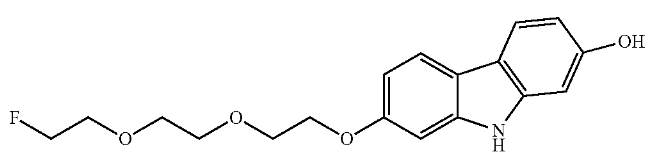 [SMILES: Oc1ccc2c(c1)[nH]c1cc(OCCOCCOCCF)ccc12] | $C_{18}H_{20}FNO_4$ | 333.35 | CB-026 |
| N-(4-(7-amino-9H-carbazol-2-yloxy)phenyl)-2-fluoro-propanamide | 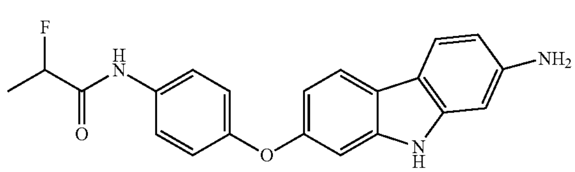 [SMILES: CC(F)C(=O)Nc1ccc(Oc2ccc3c(c2)[nH]c2cc(N)ccc23)cc1] | $C_{21}H_{18}FN_3O_2$ | 363.38 | CB-027 |

TABLE 2-continued

Examples of compounds useful for detecting AD biomarkers in vivo. These compounds may be radiolabeled or be "cold".

| Name | Structure | Chemical Formula | MW | Code |
| --- | --- | --- | --- | --- |
| 1-(2-(2-(2-(2-fluoroethoxy)ethoxy)ethoxy)-9H-carbazol-9-yl)ethanone | 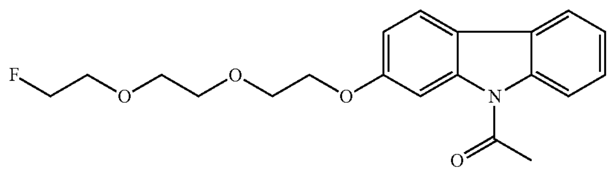 [SMILES: CC(=O)n1c2ccccc2c2ccc(OCCOCCOCCF)cc21] | $C_{20}H_{22}FNO_4$ | 359.39 | CB-017 |
| (2-(2-(2-(2-fluoroethoxy)ethoxy)ethoxy)-9H-carbazol-9-yl)(phenyl)methanone | 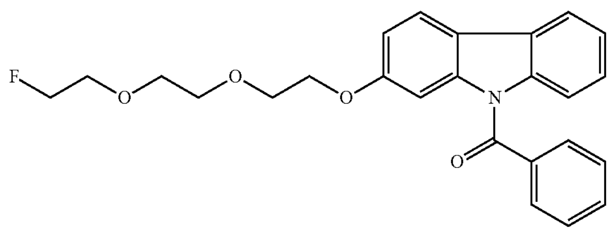 [SMILES: O=C(c1ccccc1)n1c2ccccc2c2ccc(OCCOCCOCCF)cc21] | $C_{25}H_{24}FNO_4$ | 421.46 | CB-021 |
| 2-fluoro-N-(4-(7-(methyl-amino)-9H-carbazol-2-yloxy)phenyl)propanamide | 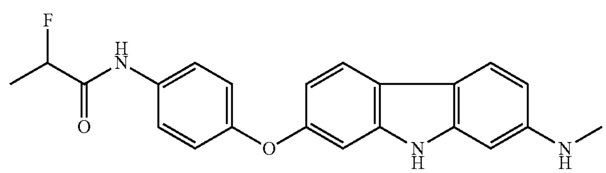 [SMILES: CNc1ccc2c(c1)[nH]c1cc(Oc3ccc(NC(=O)C(C)F)cc3)ccc12] | $C_{22}H_{20}FN_3O_2$ | 377.41 | CB-029 |
| N-(7-(4-fluorobutoxy)-9H-carbazol-2-yl)formamide | 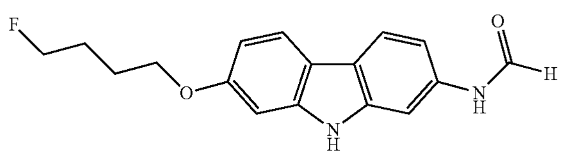 [SMILES: O=CNc1ccc2c(c1)[nH]c1cc(OCCCCF)ccc12] | $C_{17}H_{17}FN_2O_2$ | 300.33 | CB-030 |
| tert-butyl 2-(2-(2-(2-fluoroethoxy)ethoxy)ethoxy)-9H-pyrido[2,3-b]indol-7-ylcarbamate | 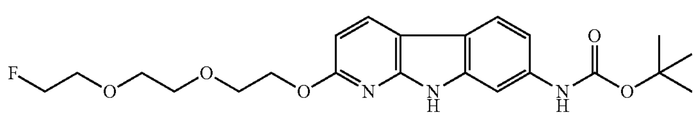 [SMILES: CC(C)(C)OC(=O)Nc1ccc2c(c1)[nH]c1nc(OCCOCCOCCF)ccc12] | $C_{22}H_{28}FN_3O_5$ | 433.47 | CB-031 |
| 2-(2-(2-(2-fluoroethoxy)ethoxy)ethoxy)-9H-pyrido[2,3-b]indol-7-amine | 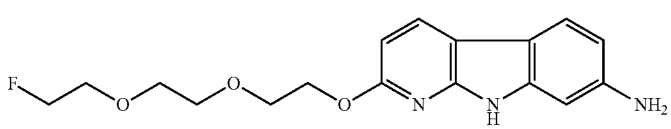 [SMILES: Nc1ccc2c(c1)[nH]c1nc(OCCOCCOCCF)ccc12] | $C_{17}H_{20}FN_3O_3$ | 333.36 | CB-032 |
| 7-(benzyloxy)-N-(2-fluoroethyl)-N-methyl-9H-carbazol-2-amine | 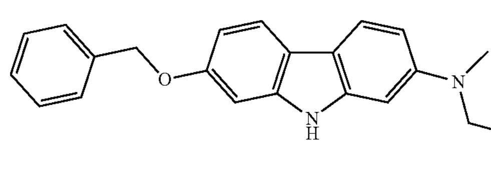 | $C_{22}H_{21}FN_2O$ | 348.41 | CB-033 |
| 2-(2-(2-(2-fluoroethoxy)ethoxy)ethoxy)-N-methyl-9H-pyrido[2,3-b]indol-7-amine | 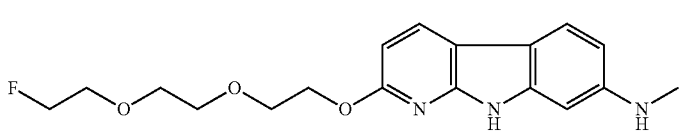 [SMILES: CNc1ccc2c(c1)[nH]c1nc(OCCOCCOCCF)ccc12] | $C_{18}H_{22}FN_3O_3$ | 347.38 | CB-034 |
| 6-bromo-9H-carbazol-2-ol | 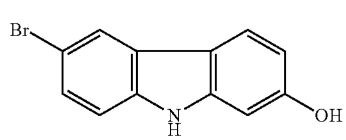 [SMILES: Oc1ccc2c(c1)[nH]c1ccc(Br)cc12] | $C_{12}H_8BrNO$ | 262.10 | |

TABLE 2-continued

Examples of compounds useful for detecting AD biomarkers in vivo. These compounds may be radiolabeled or be "cold".

| Name | Structure | Chemical Formula | MW | Code |
|---|---|---|---|---|
| 6-(2-fluoroethoxy)-3-hydroxy-2-phenylquinolin-4(1H)-one | 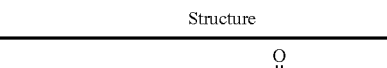 | $C_{17}H_{14}FNO_3$ | 299.30 | |

Other embodiments of the present invention include the following Table 3:

| | ID | | | |
|---|---|---|---|---|
| | T807 | T805 | T703 | T794 |
| | 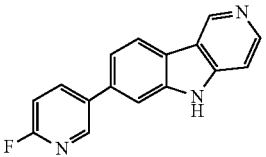 | 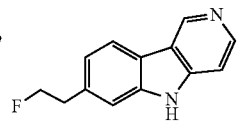 | 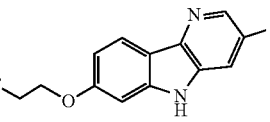 | 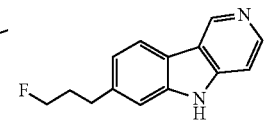 |
| MW | 360.3 | 214.2 | 244.3 | 228.3 |
| CLogP | 3.2 | 2.8 | 3.6 | 3.4 |
| KD (tau) | 15 nM | | 32 nM | 30 nM |
| selectivity (tau/Ab) | 29x | 14x | 16x | 17x |
| GM Intensity (comp. with W372) | 28% | 8% | 6% | 14% |
| background (normal brain 32566) PSL/mm2 | 61 | 49 | 15 | 97 |
| Tx/tau/amyloid correlation | yes | | | yes |
| Brain uptake in vivo | yes (3 rats, 3 mice) | yes (2 rats, 2 mice) | Yes | yes (4 rats, 4 mice) |
| metabolism in vivo | 15, 30 min | 15 min | Yes | 5, 15, 30 min |
| metabolism: one day human hepatocytes | somewhat stable (less polar metabolite) | | | stable |
| PK | yes | yes | yes | yes |
| 45 brain panel | done | | | done |
| double staining | | | | yes |
| AchE activity (IC50) | 6 uM | <50% at 10 uM | | 5 uM |
| MAO inhibition | 0% (1 uM) MAO-A<br>0% (1 uM) MAO-B | 0% (1 uM) MAO-A<br>0% (1 uM) MAO-B | 16% (1 μM) MAO-A<br>0% (1 μM) MAO-B | 19% (1 uM) MAO-A<br>0% (1 uM) MAO-B |
| CNS selectivity panel | | | NET, σ1 | 1 uM Norepinephrine transp. (49%) Dopamine transp.(34%) Glutamate, NMDA (44%) Monoamine transp. (41%) Serotonin 5-HT2c (33%) |
| MDS SDL/quote# | SDL-20, #22673 | | | SDL-18, #22639-1 (5 targets at 2 more concentrations) |

Other embodiments of the present invention include the following Table 4:

| ID | Structure | MW | CLogP | compound dbl staining (100 uM) | KD (tau) | KD (amyloid) |
|---|---|---|---|---|---|---|
| T734 | 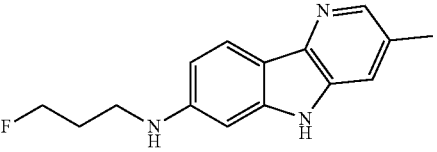 [SMILES: Cc1cnc2c(c1)[nH]c1cc(NCCCF)ccc12] | 257.31 | 3.5 | blue/green. Tau+. Other− | | |
| T733 | 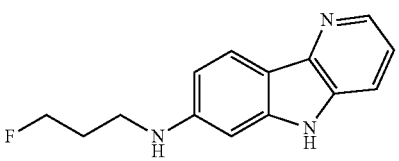 [SMILES: FCCCNc1ccc2c(c1)[nH]c1cccnc12] | 243.3 | 3.0 | blue/green. Tau−. Other− | | |
| T728 | 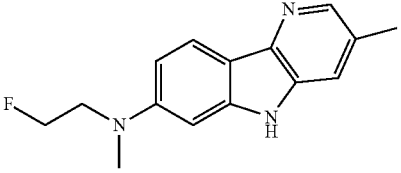 [SMILES: Cc1cnc2c(c1)[nH]c1cc(N(C)CCF)ccc12] | 257.3 | 3.8 | green/blue. Tau+. Other− | | |
| T726 | 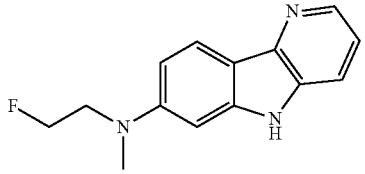 [SMILES: CN(CCF)c1ccc2c(c1)[nH]c1cccnc12] | 243.3 | 3.3 | green/blue. Tau+++. Other+ | | |
| T687 | 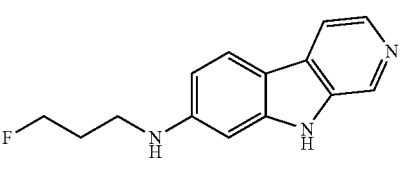 [SMILES: FCCCNc1ccc2c(c1)[nH]c1cnccc12] | 243.3 | 2.8 | blue. Tau++++. Ab++ | | |
| T686 | 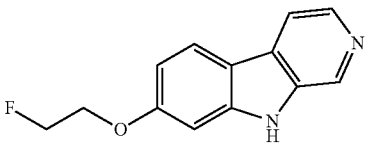 [SMILES: FCCOc1ccc2c(c1)[nH]c1cnccc12] | 230.2 | 2.9 | blue. Tau+. Other+ | | |
| T660 | 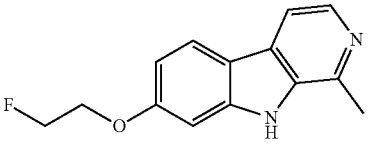 [SMILES: Cc1nccc2c1[nH]c1cc(OCCF)ccc12] | 244.3 | 3.4 | Tau−. Ab+ | | |

It will be understood that the halogen of these carbazole-based compounds, for example, F, may be radioactive or it may be "cold." In particular, it may be $^{18}F$. Other suitable radioactive atoms may include $^{11}C$, $^{13}N$, $^{15}O$, $^{18}F$, $^{61}Cu$, $^{62}Cu$, $^{64}Cu$, $^{67}Cu$, $^{68}Ga$, $^{124}I$, $^{125}I$, $^{131}I$, $^{99}Tc$, $^{75}Br$, $^{153}Gd$ and $^{32}P$.

For example, radiolabeled compounds may include:

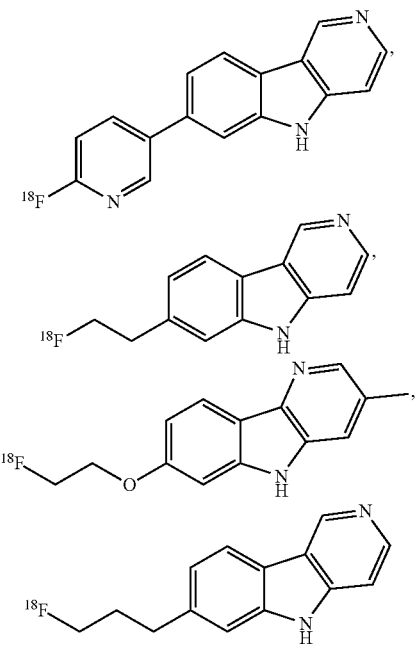

Compounds of the present invention may also be precursors:

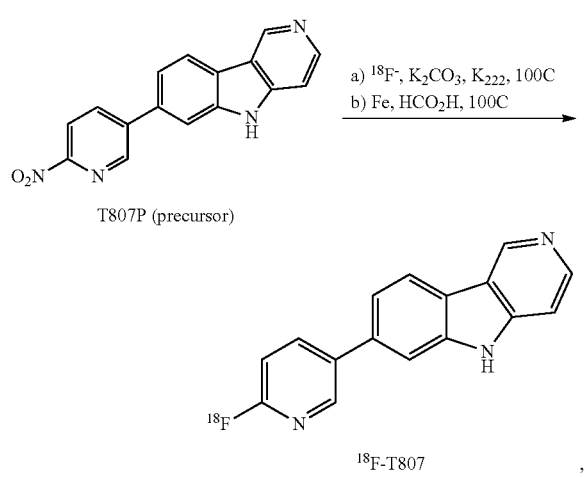

Other precursors may include:

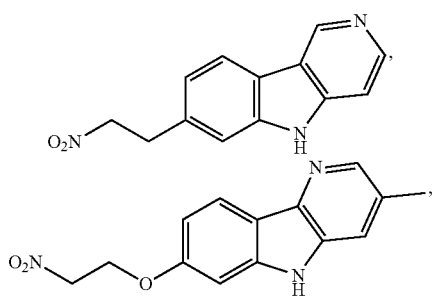

-continued

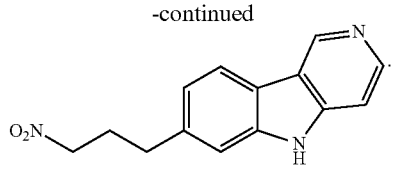

Compounds of the present invention may also be:

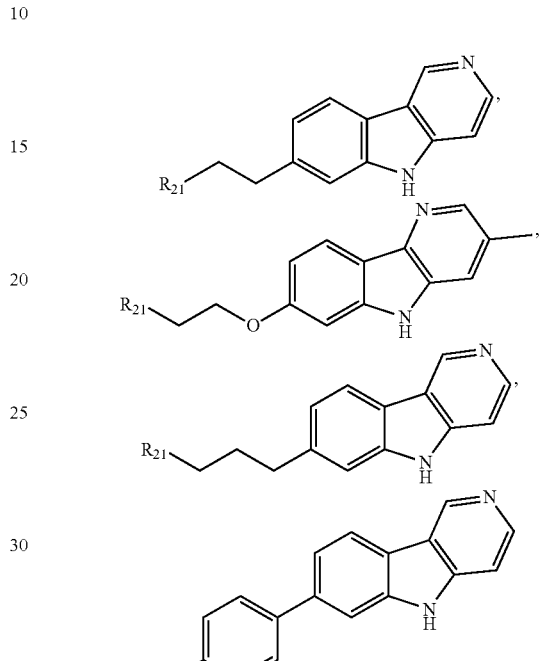

wherein $R_{13}$ is halo or a radionuclide.

When injected intravenously into mice, the Carbazole based compounds; in particular T807, T805 and T794 have shown excellent brain uptake. These compounds also display high binding affinity to tau fibrils. Autoradiography using the present compounds demonstrated labeling of NFTs in AD brain sections. Fluorescence assay data shows the binding ability of these agents to tau aggregates and Aβ fibrils. In neuropathological staining, compounds of the present invention stained amyloid plaques and/or tau aggregates.

In another embodiment, the present invention relates to compounds and compositions which comprise the formulae as disclosed herein, wherein the compound is an amyloid and/or tau protein binding compound. An amyloid and/or tau protein binding compound of the invention may be administered to a patient in amounts suitable for in vivo imaging of amyloid deposits and/or NTFs, and distinguish between neurological tissue with amyloid deposits and/or NTfs and normal neurological tissue.

Aβ compounds are typically evaluated in a competitive binding assay using synthetic Aβ1-42 fibrils ($IC_{50}$s). The situation is more complicated for tau, because there are 6 isoforms of tau potentially present in AD brains as products of alternate splicing of a single tau gene. Most reports in the literature rely therefore on only one recombinant isoform, Tau-441. To add more complexity, the various tau isoforms are hyperphosphorylated in vivo, something that is difficult to mimic in vitro. Furthermore, structural information on these tau fibrils is lacking, making an interpretation of binding of compounds difficult.

Native forms of tau (various isoforms, hyperphosphorylated) and amyloid aggregates are present in brain sections and therefore preferred for compound testing. Using the self-fluorescence of a test compound can give an indication of whether the compound binds to tau tangles/PHFs and/or amyloid plaques. This is further confirmed by immunostaining with Aβ and tau antibodies and overlaying the images. The drawback is that the fluorescent signals cannot be used for quantitation as some compounds might exhibit a stronger fluorescent signal than others and the coexistence of Aβ plaques and tau tangles in AD brains. However, it is possible to "rate" the signal strength qualitatively and distinguish compounds that show binding to these aggregates.

Furthermore, the selectivity can be evaluated in brains containing only Aβ plaques/no tau aggregates, Aβ plaques/ and tau aggregates, and control brains. Unfortunately, there are no AD brains with only tau and no Aβ present. By testing radiolabeled tracers in these brain sections, one can more quantitative evaluate the relative binding strength (signal strength) and selectivity of various test compounds as they all contain the same radioactive tracer. For examples, if a test tracer binds only to tau, and not amyloid, it should show no signal in the Aβ plaques only brain sections. If a compound binds only to amyloid, it should show uptake in both types of brains. The difficulty of identifying and further quantifying selective compounds lies in the relative abundance of amyloid vs. tau, which is difficult to measure.

Amyloid and/or tau protein probes of the invention may be used to detect and quantitate amyloid deposits and/or NTFs in diseases including, but not limited to Mediterranean fever, MuckleWells syndrome, idiopathic myeloma, amyloid polyneuropathy, amyloid cardiomyopathy, systemic senile myloidosis, amyloid polyneuropathy, hereditary cerebral hemorrhage with amyloidosis, Down's syndrome, Scrapie, Creutzfeldt-Jacob disease, Kuru, Gerstamnn-Straussler-Scheinker syndrome, medullary carcinoma of the thyroid, Isolated atrial amyloid, $\beta_2$-microglobulin amyloid in dialysis patients, inclusion body myositis, $\beta_2$-amyloid deposits in muscle wasting disease, chronic traumatic encephalopathy (CTE), and Islets of Langerhans diabetes Type II insulinoma.

In other embodiments of the invention, the labeled compound is introduced into a patient in a detectable quantity and after sufficient time has passed for the compound to become associated with amyloid deposits and/or tau proteins, the labeled compound is detected noninvasively. In another embodiment of the invention, a labeled compound of the Formulas disclosed herein is introduced into a patient, sufficient time is allowed for the compound to become associated with amyloid deposits, and then a sample of tissue from the patient is removed and the labeled compound in the tissue is detected apart from the patient. In another embodiment of the invention, a tissue sample is removed from a patient and a labeled compound of Formula 7, for example, is introduced into the tissue sample. After a sufficient amount of time for the compound to become bound to amyloid deposits and/or tau proteins, the compound is detected.

Synthesis of Ligands and their Labeling Precursors

Halogenation and Radiohalogenation:

As disclosed herein, for a number of different AD ligands, such as flavones, coumarins, carbazoles, quinolinones, chromenones, trisubstituted imidazoles and their derivatives as disclosed herein, the radiolabeled atom, such as a halogen atom, for example, may be readily introduced into the ligand using a number of different methods well known in the art. Accordingly, the radiolabeled compounds of the Formulas 7-8 may be prepared using standard methods known in the art for preparing such radiolabeled compounds having a particular substituent, wherein the compound may be incorporated with a particular radionuclide selected from the group consisting of $^{11}C$, $^{13}N$, $^{15}O$, $^{18}F$, $^{123}I$, $^{124}I$, $^{125}I$, $^{131}I$ and $^{77}Br$.

In one particular example, the halogen may be introduced by a method using a tin for halogen exchange process. For example, a non-radioactive halogen such as iodine, may be replaced by an organo tin compound via a metal, such as a palladium composition, to form the radiolabeling tin precursor, as represented below. This precursor is then subjected to radioactive halogenation via displacement with $Na^{125}I$ source, for example, to afford the radioactive ligand.

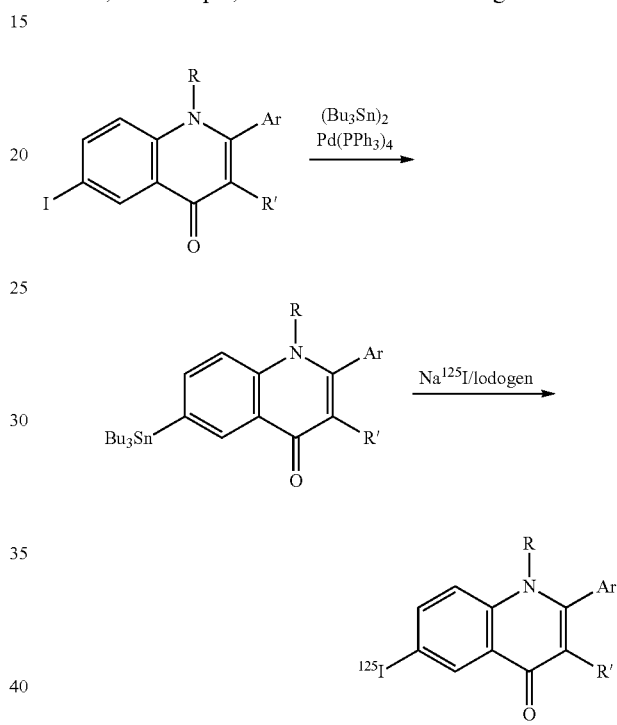

Alternatively, the radio labeled halogen may be readily introduced via direct halogenation. For example, for a ligand comprising an aromatic ring as part of the scaffold, or an aromatic substituent of a ligand, the aromatic ring may be directly iodinated using well-established radioiodination procedure. One such example is represented below using a carbazole ligand.

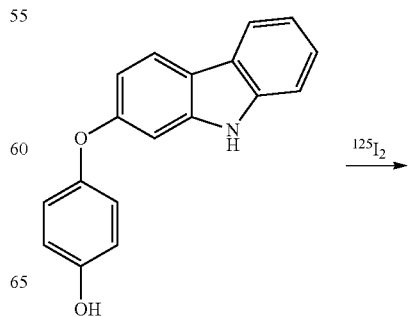

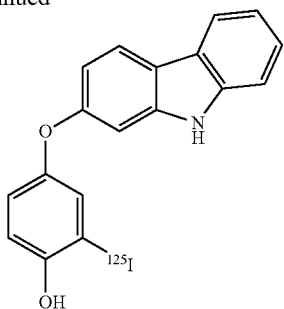

For [11C]-labeled compounds, the labeled compound may be prepared by the alkylation or methylation of a hydroxyl group, such as with [11C]CH$_3$I to provide the corresponding C-11 labeled methoxy derivative. For example, such a process is represented by the reaction of the flavone derivative shown below.

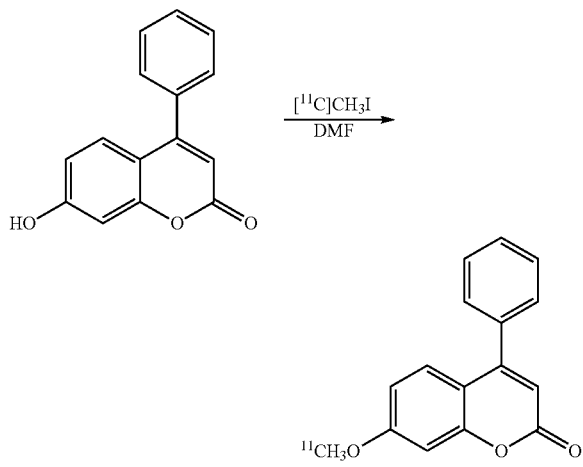

Other methods of preparing radiolabeled ligands are well known in the art. Example of such methods are disclosed in, for example: 1) Jewett, D. M. (1992) A Simple Synthesis of [11C]Methyl Triflate Appl. Radiat. Isot. 43, 1383-1385; 2) Crouzel, C. Langstrom, B., Pike, V. W., and Coenen, H. H. (1987) Recommendations for a practical production of [11C] methyl iodide Appl. Radiat. Isot. Int. J. Appl. Instrum. Part A 38, 601-603; Dannals, R. F., Ravert, H. T.; 3) Wilson, A. A. (1990) Radiochemistry of Tracers for Neurotransmitter Receptor Studies. In: Quantitative Imaging: Neuroreceptors, Neurotransmitters, and Enzymes. (Edited by Frost, J. J. Wagner Jr., H. N. pp. 19-35, Raven Press, New York; 4) Jewett, D. M., Manger, T. J., and Watkins, G. L. (1991) Captive Solvent Methods for Fast Simple Carbon-11 Radioalkylations. In: New Trends in Radiopharmaceutical Synthesis, Quality Assurance and Regulatory Control (Edited by Emran, A. M.) pp. 387-391. Plenum Press, New York; 5) Marazano, C., Maziere, M., Berger, G., and Comar, D. (1977) Synthesis of methyl iodide-11C and formaldehyde-11C Appl. Radiat. Isot. 28, 49-52; 6) Watkins, G., Jewett, D., Mulholland, G., Kitbourn, M., and Toorongian, S. (1988) A Captive Solvent Method for Rapid N—[11C]Methylation of Secondary Amides: Application to the Benzodiazepine, 4'-Chlorodiazepam (RO5-4864) Appl. Radiat. Isot. 39, 441-444; and 7) Wilson, A. A., DaSilva, J. N., and Houle, S. (1996) In vivo evaluation of [11C] and [15F]-labelled cocaine analogues as potential dopamine transporter ligands for positron emission tomography Nucl. Med. Biol. 23, 141-146. The subject matter of all references cited herein are incorporated herein by reference in their entirety.

Synthesis of AD-CB-WZ01013

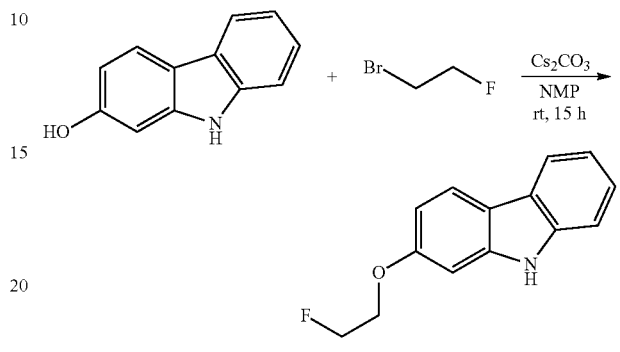

To hydroxycarbazole (73 mg, 0.4 mmol) in 1 mL of NMP was added Cs$_2$CO$_3$ (130 mg, 0.4 mmol) and bromofluoroethane (51 mg, 0.4 mmol). The mixture was stirred at rt for 15 h and diluted with Et$_2$O (50 mL). It was washed with 1 M HCl (30 mL) and water (2×40 mL), dried over MgSO$_4$ and concentrated. The crude product was purified with silica chromatography (4% EtOAc in hexane to 25%) to afford the desired product (36 mg) as an off-white solid.

$^1$H NMR (400 MHz, CDCl$_3$/acetone-d$_6$) δ 9.98 (s, 1H), 7.95 (t, J=8.8 Hz, 2H), 7.40 (d, J=8.0 Hz, 1H), 7.28 (t, J=8 Hz, 1H), 7.13 (t, J=8.0 Hz, 1H), 7.00 (d, J=2 Hz, 1H), 6.83 (dd, J=8.8, 2.0 Hz, 1H), 4.85 (t, J=4 Hz, 1H), 4.73 (t, J=4 Hz, 1H), 4.35 (t, J=4 Hz, 1H), 4.28 (t, J=4 Hz, 1H); MS (ESI) m/z 230 (M+H$^+$).

Synthesis of AD-C-WZ01011

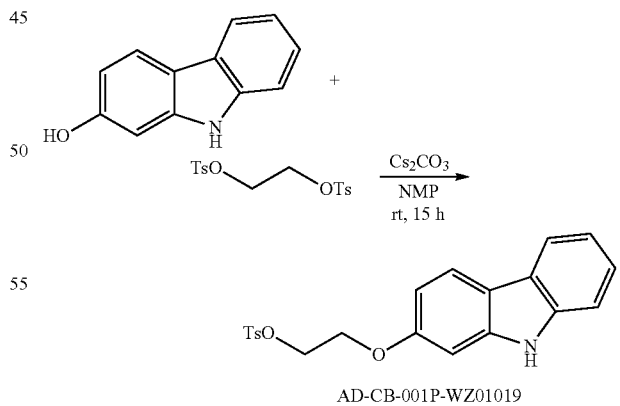

To hydroxycarbazole (183 mg, 1 mmol) in 4 mL of NMP was added Cs$_2$CO$_3$ (326 mg, 1 mmol) and ethylenedi-tosylate (370 mg, 1 mmol). The mixture was stirred at rt for 15 h and diluted with Et$_2$O (80 mL). It was washed with 1 M HCl (50 mL) and water (2×50 mL), dried over MgSO$_4$ and concentrated. The crude product was purified with silica chromatography (50% DCM in hexane to 100% DCM) to afford the desired product (75 mg) as an off-white solid.

$^1$H NMR (400 MHz, acetone-d$_6$) δ 10.21 (s, 1H), 8.00 (d, J=8.0 Hz, 1H), 7.95 (d, J=8.4 Hz, 1H), 7.84 (d, J=8.4 Hz, 2H), 7.45 (m, 3H), 7.30 (t, J=8.0 Hz, 1H), 7.13 (t, J=8.0 Hz, 1H),); 6.98 (s, 1H), 6.73 (d, J=8.4 Hz, 1H), 4.44 (t, J=4.0 Hz, 2H), 4.30 (t, J=4.0 Hz, 2H), 2.42 (s, 3H); MS (ESI) m/z 382 (M+H$^+$), 404 (M+Na$^+$).

Synthesis of 18F-labeled AD-CB-001P-WZ-01019 ([$^{18}$F]2-(2-Fluoro-ethoxy)-9H-carbazole)

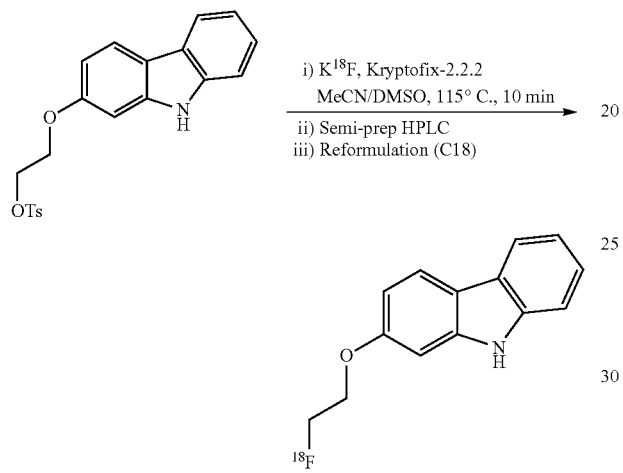

[$^{18}$F]Fluoride (600-900 mCi) as an enriched solution in H$_2$$^{18}$O was delivered to the synthesis module. The [$^{18}$F]fluoride was trapped on an ion-exchange column and then eluted into the reaction vessel using aqueous potassium carbonate (3.0 mg in 0.4 mL H$_2$O). Kryptofix-2.2.2 phase transfer reagent was added (20.0 mg in 1.0 mL MeCN) and the water-acetonitrile azeotrope was evaporated to dryness. Toluene-4-sulfonic acid 2-(9H-carbazol-2-yloxy)-ethyl ester precursor (4 mg in 0.9 mL MeCN/0.1 mL DMSO) was added to the reactor and then the fluorination reaction was heated at 115° C. for 10 min. The crude reaction mixture was then purified by semi-preparative HPLC (Column: Phenomenex Luna C-18, 250 mm×10 mm; Mobile-Phase Gradient 95:5 H$_2$O (+0.05% TFA): MeCN (+0.05% TFA) to 100% MeCN (+0.05% TFA); Flow rate: 5 mL/min).

The peak corresponding to [$^{18}$F]2-(2-fluoro-ethoxy)-9H-carbazole was collected and simultaneously diluted with sterile water (10 mL). The resulting mixture was passed over a C-18 Sep-Pak so that the product was trapped and residual acetonitrile was washed away with further water (10 mL). [$^{18}$F]2-(2-Fluoro-ethoxy)-9H-carbazole was then eluted into the product vial with USP grade ethanol (0.5 mL) and diluted with sterile water (9.5 mL) to provide a final formulation (19-34 mCi in 10 mL) suitable for injection (7.5% decay corrected yield, 100% radiochemical purity).

Figure 3:
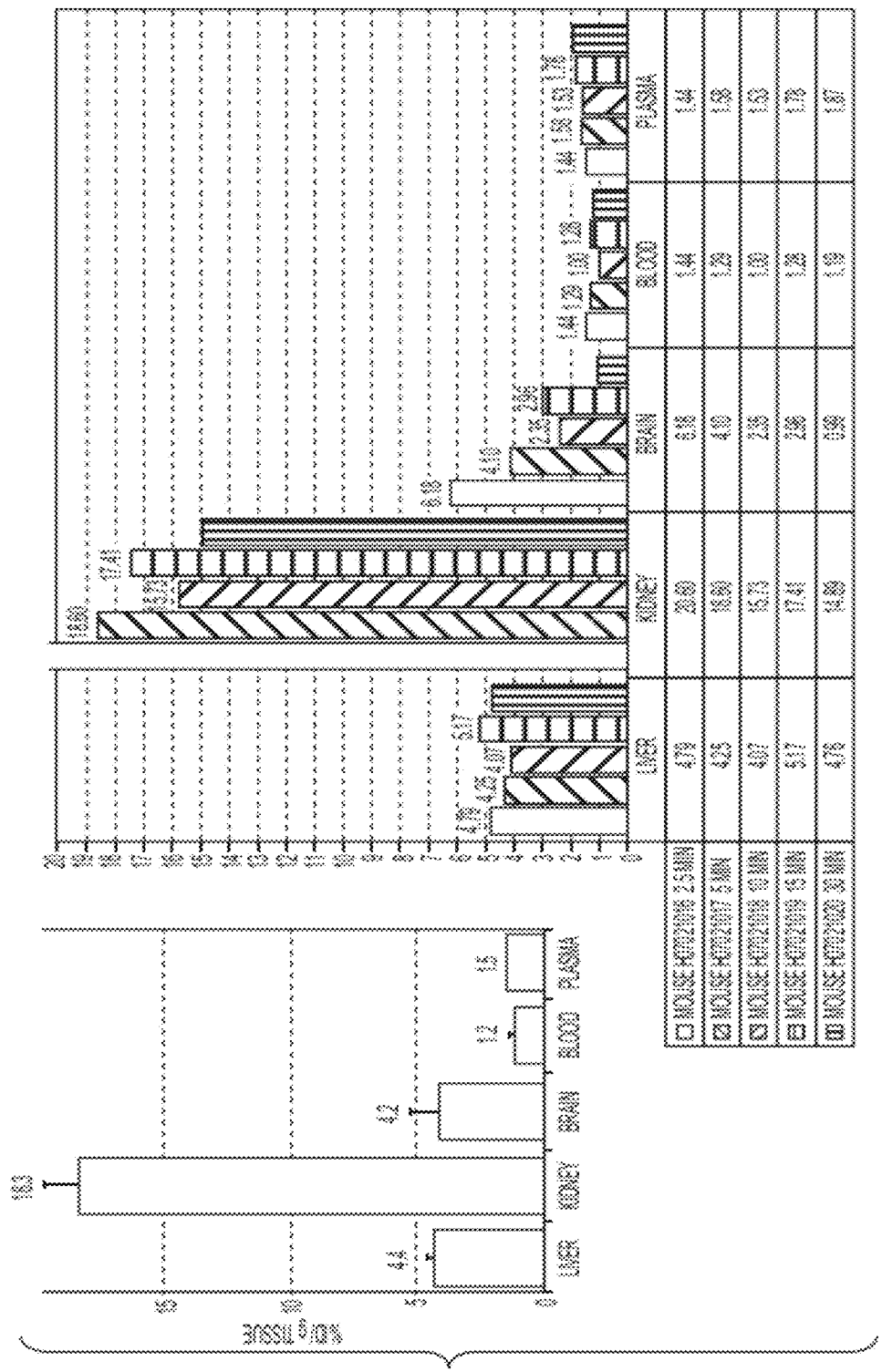
FIG. 3 shows [18F]-T794 PK in mice.

Purity was determined by analytical HPLC equipped with a radioactivity detector and identity was confirmed by comparison with HPLC data for the corresponding unlabeled reference standard (FIG. 3A and FIG. 3B of U.S. Ser. No. 12/372,717).

Synthesis of AD-CB-002P-WZ01031

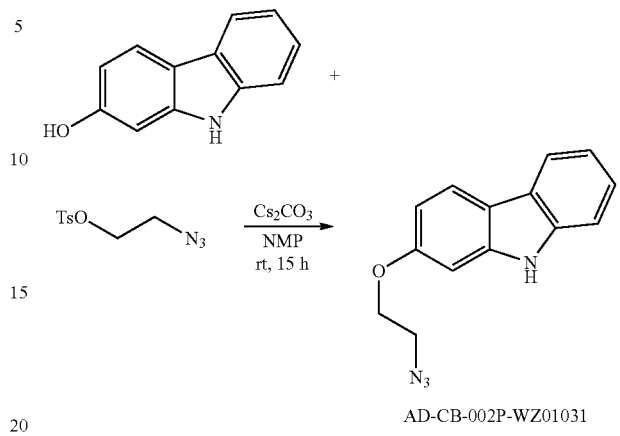

To hydroxycarbazole (92 mg, 0.5 mmol) in 2 mL of NMP was added Cs$_2$CO$_3$ (163 mg, 0.5 mmol) and azido ethyltosylate (121 mg, 0.5 mmol). The mixture was stirred at rt for 15 h and diluted with Et$_2$O (50 mL). It was washed with 0.5 M HCl (50 mL) and water (2×50 mL), dried over MgSO$_4$ and concentrated. The crude product was purified with silica chromatography (80% DCM in hexane to 100% DCM) to afford the desired product (76 mg) as a white solid.

$^1$H NMR (400 MHz, CDCl$_3$/acetone-d$_6$) δ 9.98 (s, 1H), 7.95 (m, 2H), 7.41 (d, J=8.4 Hz, 1H), 7.29 (t, J=8.0 Hz, 1H), 7.14 (t, J=8.0 Hz, 1H),); 7.01 (s, 1H), 6.84 (d, J=8.4 Hz, 1H), 4.28 (t, J=4.8 Hz, 2H), 3.67 (t, J=4.8 Hz, 2H); MS (ESI) m/z 253 (M+H$^+$).

Synthesis of AD-CB-002S-WZ01033

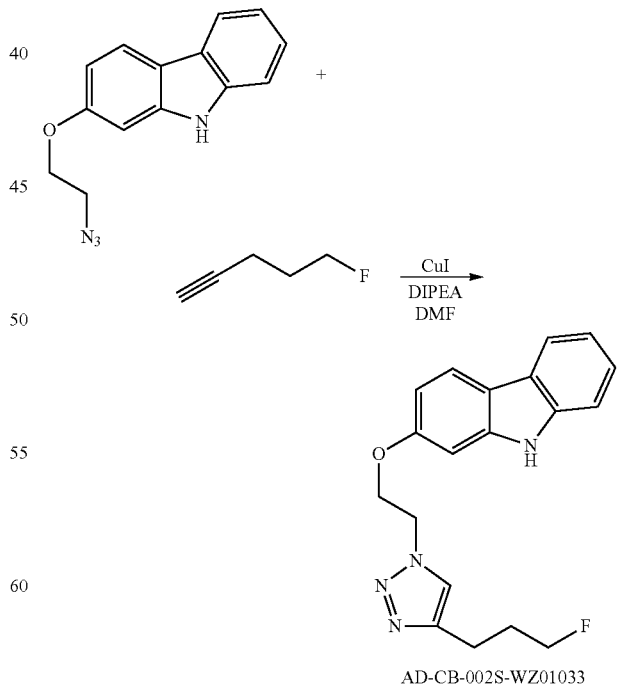

To azido carbazole (32 mg, 0.127 mmol) in 0.5 mL of DMF was added CuI (7.6 mg, 0.04 mmol), DIPEA (16.4 mg, 0.127 mmol), and fluoropentyne (16.4 mg, 0.19 mmol). The reaction mixture was vigorously stirred for 1 h and diluted with EtOAc (30 mL). It was washed with water (50 mL), 0.5 M HCl (30 mL), water (2×50 mL), dried over MgSO₄ and concentrated. The crude product was pre-absorbed on silica (3 g) and loaded on a 4 g silica column and eluted with 30% EtOAc in hexane to 50% to afford the desired compound (20 mg).

¹H NMR (400 MHz, CDCl₃/CD₃OD) δ 7.95 (d, J=7.6 Hz, 1H), 7.91 (d, J=8.4 Hz, 1H), 7.76 (s, 1H), 7.40 (d, J=8.0 Hz, 1H), 7.31 (t, J=7.6 Hz, 1H), 7.14 (t, J=7.6 Hz, 1H), 6.94 (d, J=2.4 Hz, 1H), 6.78 (dd, J=8.8, 2.4 Hz, 1H), 4.83-4.78 (m, 2H), 4.53-4.48 (m, 3H), 4.40 (t, J=6.0 Hz, 1H), 2.85 (t, J=7.6 Hz, 2H), 2.10-1.99 (m, 2H); MS (ESI) m/z 339 (M+H±).

Synthesis of 18F-labeled AD-CB-002S-WZ01033

Preparation of [¹⁸F]5-Fluoro-pent-1-yne

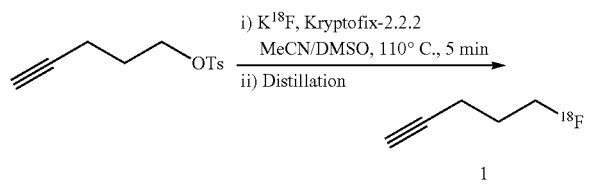

[¹⁸F]Fluoride (600-900 mCi) as an enriched solution in H₂¹⁸O is delivered to the synthesis module. The [¹⁸F]fluoride is trapped on an ion-exchange column and then eluted into the reaction vessel using aqueous potassium carbonate (3.0 mg in 0.4 mL H₂O). Kryptofix-2.2.2 phase transfer reagent is added (20.0 mg in 1.0 mL MeCN) and the water-acetonitrile azeotrope is evaporated to dryness.

Toluene-4-sulfonic acid pent-4-ynyl ester (20 mg in 0.8 mL MeCN) is added to the reactor and the fluorination reaction is heated at 110° C. for 5 min. Following fluorination, the crude reaction mixture is purified by distillation and yields [¹⁸F]5-fluoro-pent-1-yne as a solution in acetonitrile (trapped at −78° C. due to the volatility of the product).

Preparation of Triazole

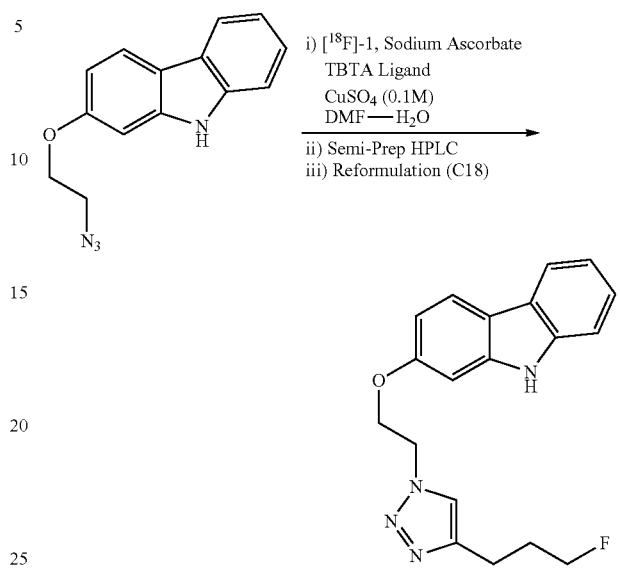

A mixture of azide precursor (5 mg), sodium ascorbate (40 mg), tris-(benzyltriazolylmethyl)amine (TBTA, 25 mg) and aqueous copper sulfate solution (0.1 M, 0.25 mL) in DMF (0.4 mL) and water (0.1 mL) is added to the cooled pentyne solution described above. The reaction mixture is then warmed to rt and stirred for 30 min. After this time, the reaction is purified by semi-preparative HPLC. The peak corresponding to the product is collected and simultaneously diluted with sterile water (10 mL). The resulting mixture is passed over a C-18 Sep-Pak and residual acetonitrile is washed away with additional water (10 mL). The product is eluted into the product vial with USP grade ethanol (0.5 mL) and diluted with sterile water (9.5 mL) providing a final formulation suitable for injection.

Purity is determined by analytical HPLC equipped with a radioactivity detector and identity is confirmed by comparison with HPLC data for the corresponding unlabeled reference standard.

Synthesis of ¹⁸F-labeled CB-003

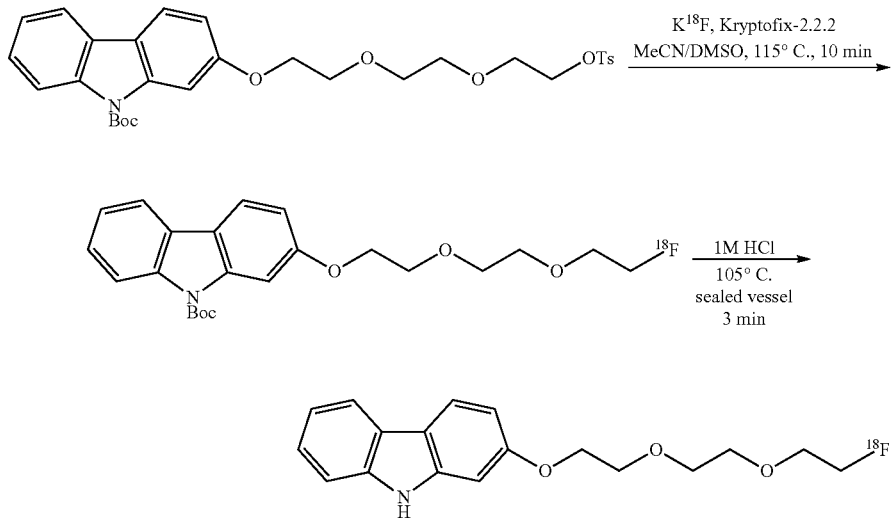

[¹⁸F]Fluoride (600-900 mCi) as an enriched solution in H₂¹⁸O is delivered to the synthesis module. The [¹⁸F]fluoride is trapped on an ion-exchange column and then eluted into the reaction vessel using aqueous potassium carbonate (3.0 mg in 0.4 mL H₂O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture was cooled to 55° C. and most of the acetonitrile was evaporated under vacuum and a stream of argon as before. To the crude Boc-protected product was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 H₂O (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection (31% decay uncorrected yield, 100% radiochemical purity). Purity was determined by analytical HPLC equipped with a radioactivity detector and identity was confirmed by comparison with HPLC data for the corresponding unlabeled reference standard.

Synthesis of ¹⁸F-labeled CB-004

[¹⁸F]Fluoride (600-900 mCi) as an enriched solution in H₂¹⁸O is delivered to the synthesis module. The [¹⁸F]fluoride is trapped on an ion-exchange column and then eluted into the reaction vessel using aqueous potassium carbonate (3.0 mg in 0.4 mL H₂O). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture was cooled to 55° C. and most of the acetonitrile was evaporated under vacuum and a stream of argon as before. To the crude Boc-protected product was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 H₂O (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection (3% decay uncorrected yield, 100% radiochemical purity). Purity was determined by analytical HPLC equipped with a radioactivity detector and identity was confirmed by comparison with HPLC data for the corresponding unlabeled reference standard.

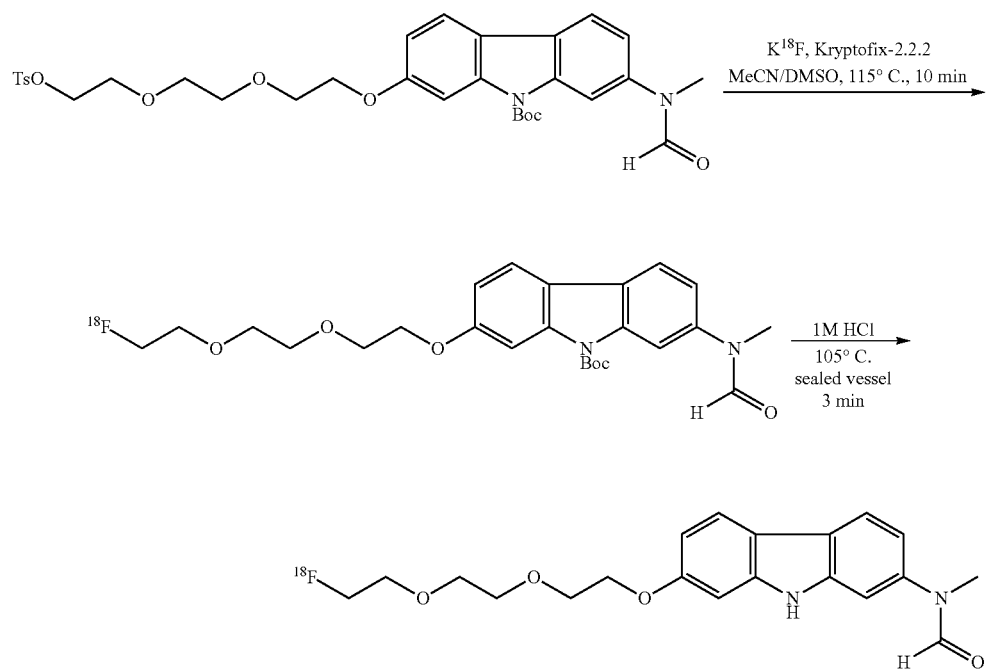

Synthesis of [18F]-labeled CB-007

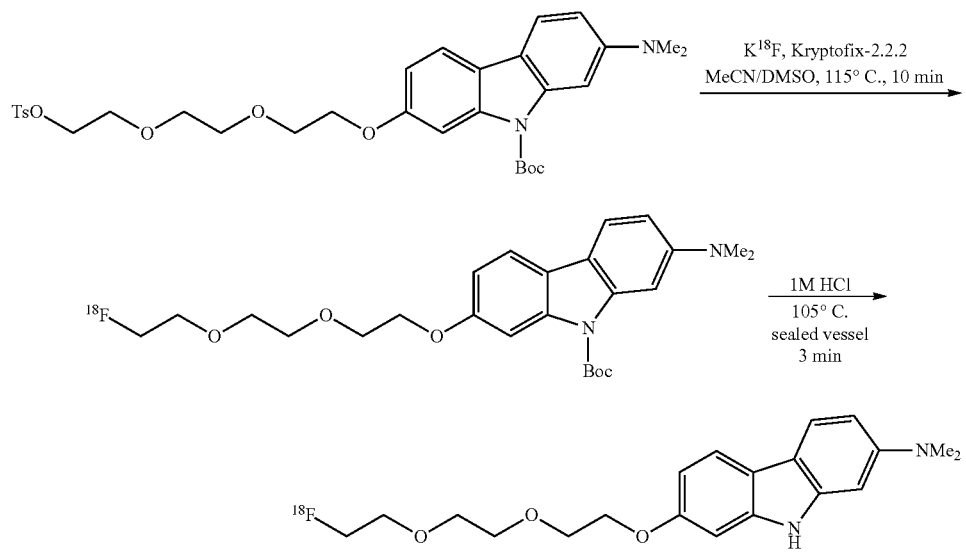

[18F]Fluoride (600-900 mCi) as an enriched solution in $H_2{}^{18}O$ is delivered to the synthesis module. The [18F]fluoride is trapped on an ion-exchange column and then eluted into the reaction vessel using aqueous potassium carbonate (3.0 mg in 0.4 mL $H_2O$). Kryptofix-2.2.2 phase transfer reagent is added (20.0 mg in 1.0 mL MeCN) and the water-acetonitrile azeotrope is evaporated to dryness. The precursor (4 mg in 0.9 mL MeCN/0.1 mL DMSO) is added to the reactor and the fluorination reaction is heated at 115° C. for 10 min. The mixture was cooled to 55° C. and most of the acetonitrile was evaporated under vacuum and a stream of argon as before. To the crude Boc-protected product was added aqueous hydrochloric acid (1.0 M, 1.0 mL), and the mixture was heated to 105° C. for 3 minutes. After cooling to 35° C., aqueous sodium acetate (2.0 M, 0.5 mL) was added with stirring. The crude reaction mixture is then purified by semi-preparative HPLC (Column: Phenomenex Luna C-18, 250 mm×10 mm; Mobile-Phase Gradient 95:5 $H_2O$ (+0.05% TFA): MeCN (+0.05% TFA) to 100% MeCN (+0.05% TFA); Flow rate: 5 mL/min; time=25 min). The peak corresponding to the final product is collected and simultaneously diluted with sterile water (10 mL). The resulting mixture is passed over a C-18 Sep-Pak so that the product is trapped and residual acetonitrile is washed away with further water (10 mL). The product is then eluted into the product vial with USP grade ethanol (0.5 mL) and diluted with sterile water (9.5 mL) providing a final formulation suitable for injection (1.2% decay uncorrected yield, 100% radiochemical purity). Purity was determined by analytical HPLC equipped with a radioactivity detector and identity was confirmed by comparison with HPLC data for the corresponding unlabeled reference standard.

Synthesis of [18F]-labeled CB-012

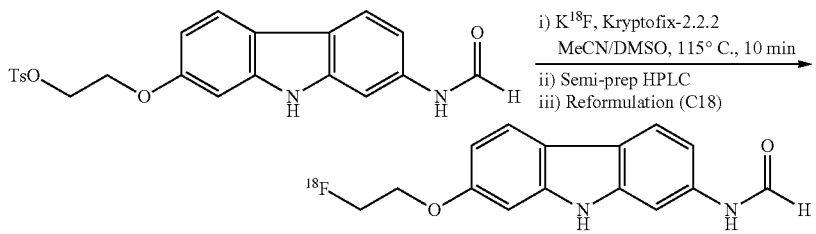

[18F]Fluoride (600-900 mCi) as an enriched solution in $H_2{}^{18}O$ was delivered to the synthesis module. The [18F]fluoride was trapped on an ion-exchange column and then eluted into the reaction vessel using aqueous potassium carbonate (3.0 mg in 0.4 mL $H_2O$). Kryptofix-2.2.2 phase transfer reagent was added (20.0 mg in 1.0 mL MeCN) and the water-acetonitrile azeotrope was evaporated to dryness. Toluene-4-sulfonic acid 2-(9H-carbazol-2-yloxy)-ethyl ester precursor (4 mg in 0.9 mL MeCN/0.1 mL DMSO) was added to the reactor and then the fluorination reaction was heated at 115° C. for 10 min. The crude reaction mixture was then purified by semi-preparative HPLC (Column: Phenomenex Luna C-18, 250 mm×10 mm; Mobile-Phase Gradient 95:5 $H_2O$ (+0.05% TFA): MeCN (+0.05% TFA) to 100% MeCN (+0.05% TFA); Flow rate: 5 mL/min). The peak corresponding to the product was collected and simultaneously diluted with sterile water (10 mL). The resulting mixture was passed over a C-18 Sep-Pak so that the product was trapped and residual acetonitrile was washed away with further water (10 mL). [18F]2-(2-Fluoro-ethoxy)-9H-carbazole was then eluted into the product vial with USP grade ethanol (0.5 mL) and diluted with sterile water (9.5 mL) to provide a final formulation (19-34 mCi in 10 mL) suitable for injection (2% decay uncorrected yield, 100% radiochemical purity). Purity was determined by analytical HPLC equipped with a radio-activity detector and identity was confirmed by comparison with HPLC data for the corresponding unlabeled reference standard.

Assays of Carbazole Derivatives:

From the Biacore assay, two carbazole derivatives displayed promising binding affinities to oligomers/polymers and fibrils (Table 4). The beta-carboline Harmol, a member of the harmala alkaloids, is the urinary metabolite of harmine. The harmala alkaloids are MAO inhibitors and are commonly found in Syrian rue, *Peganum harmala*, and the South American vine *Banisteriopsis caapi*, both of which are purported to possess strong hallucinogenic effects. The beta-carbolenes have a varied effect on the central nervous system including binding to the 5-HT$_2$, 5-HT$_{1a}$, glutamate NMDA and imidazoline receptors; inhibiting MAO-A enzyme and interfering with dopaminergic transmission. And while beta-carbolines are thought to be cytotoxic, they also maintain neuroprotective properties supposedly offering neuroprotection against dopamine and glutamate and, additionally, by scavenging reactive oxygen species. A recent report demonstrated that beta-carboline alkyloids induce a facilitation of short and long term memory in object recognition tasks in mice, although the means by which the alkyloids are exerting their effect is unclear. Moura, D. J., et al., *Effects of b-carboline alkaloids in the object recognition task in mice*. Life Sciences, 2006, 79: p. 2099-2104.

The second active carbazole discovered in the assay is 2-hydroxycarbazole. 2-Hydroxycarbazole has been recently shown to release Ca$^{2+}$ ion from skeletal and cardiac muscle through a distinct pharmacological pathway. The generic carbazole scaffold exists in several therapeutics including the non-steroidal anti-inflammatory carprofen, carazolol (a beta-blocker) and YM-53601 (a squalene synthase inhibitor). Recent work has shown that carbazole derivatives can act as γ-secretase modulators. [Narlawar, R., et al., *N-Substituted carbazolyloxyacetic acids modulate Alzheimer associated g-secretas*. Bioorganic & Medicinal Chemistry Letters, 2007, 17: p. 176-182] In another AD related project, Howlett discovered highly elaborated carbazoles, such as carvedilol, inhibit fibril formation, albeit the binding affinities to the fibrils were not determined. [Howlett, D. R., et al., *Common Structural Features Determine the Effectiveness of Carvedilol, Daunomycin and Rotiletracycline as Inhibitors of Alzheimer b-Amyloid Fibril Formation*. Biochemical Journal, 1999, 343: p. 419-423] Interestingly, an article intending to determine the practicality of using carbazoles as fibril inhibitors based on cell permeability suggests that carbazoles are unlikely to cross the blood brain barrier, as they are PGP substrates, precluding their use as therapeutics for fibril inhibition. [Saengkhae, C., et al., *Ability of Carbazole Salts, Inhibitors of Alzheimer b-Amyloid Fibril Formation, to Cross Cellular Membranes*. European Journal of Pharmacology, 2007, 559: p. 124-131]

Figure 6:
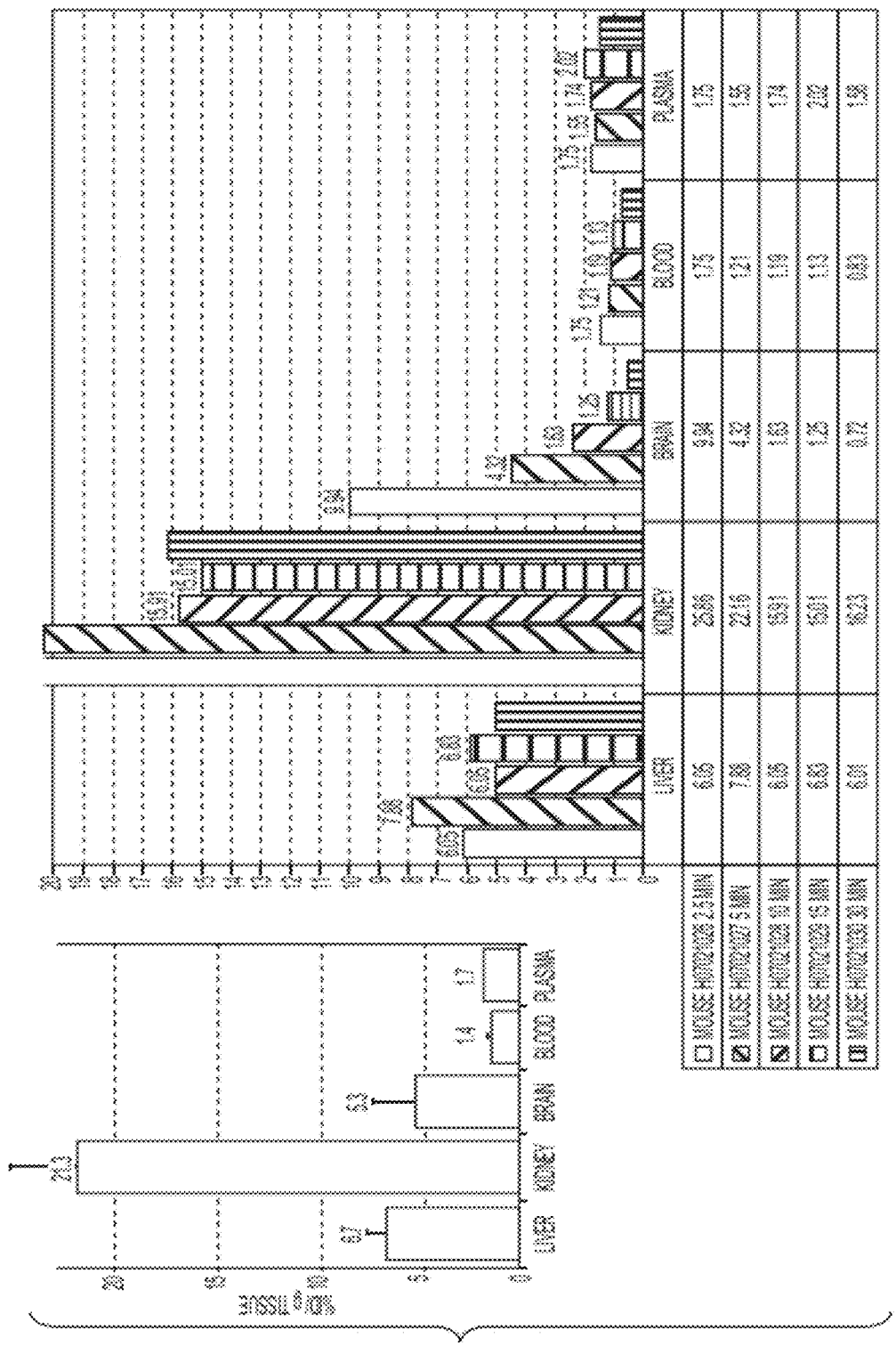
FIG. 6 shows [18F]-T805 PK in mice.

By using an appropriate imaging modality, a tracer's biodistribution pattern becomes instantly visible and accessible. For example, by using $^{18}$F-labeled tracers one can easily quantify a tracer's uptake into, and washout from, the brain using positron emission tomography (PET). Tracers with high uptake and slow washout in normal brains generate low signal to noise ratios. Tracers with high uptake and fast washout in normal brains have high signal to noise rations and are considered ideal. $^{18}$F-labeled carbazoles possess ideal brain imaging properties. For example, an $^{18}$F-labeled carbazole was prepared and administered to a normal, white Sprague-Dawley rat (FIG. 6 of U.S. Ser. No. 12/372,717). Within minutes, the tracer entered into the brain and washed out over several minutes.

Figure 4:
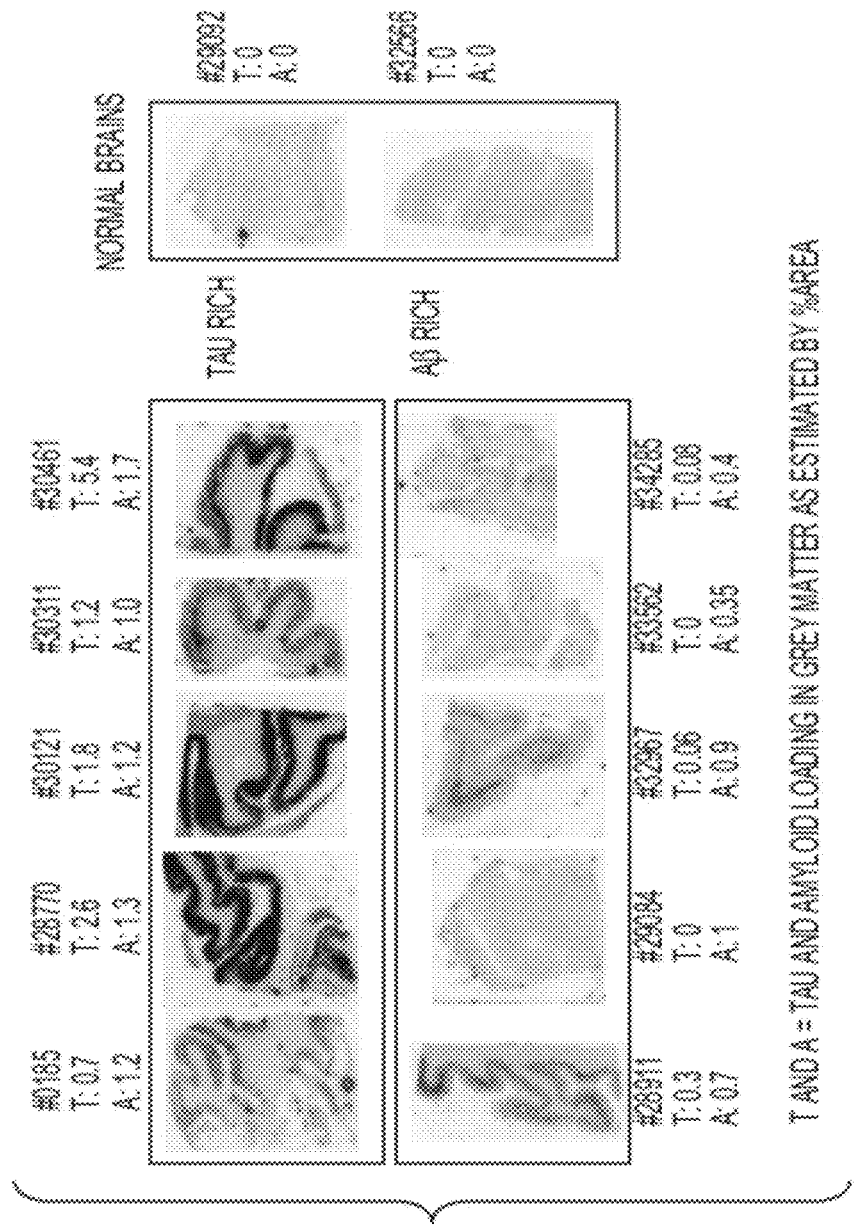
FIG. 4 shows Audoradiography of [18F]-T805.
Figure 5:
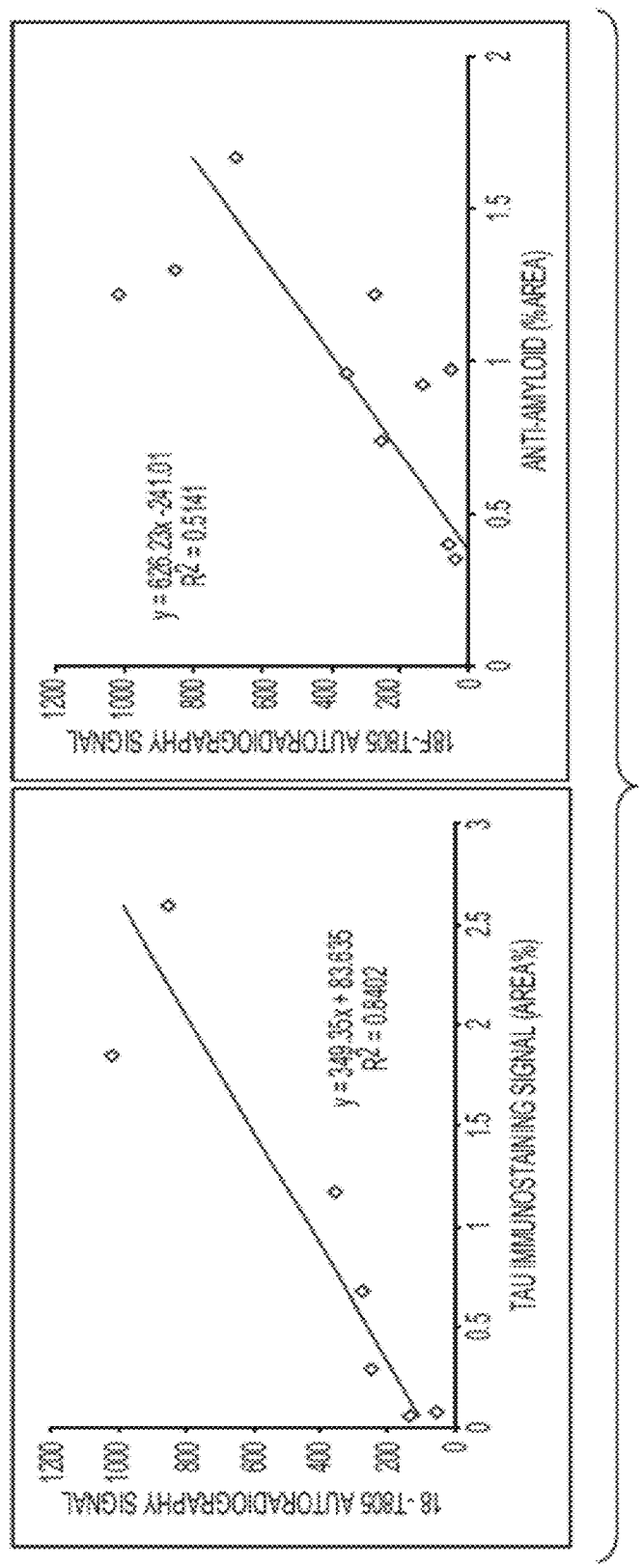
FIG. 5 shows the correlation of [18F]-T805 with Tau and Amyloid loads.

The non-radioactive carbazole also successfully competes off both Thioflavin T and FDDNP in brain tissue sections suggesting that the tracer binds to similar binding sites (FIGS. 4 and 5 of U.S. Ser. No. 12/372,717).

TABLE 4

Carbazole-based hits from the Biacore assay. A "+" sign represents a hit and the increase in "+" signs relates to increasing binding affinity. A "–" sign represents no binding.

| | Binding to oligomers/polymers (Aβ1-42) | Binding to fibrils (Aβ1-42) |
|---|---|---|
| #54: Harmol  | ++ | + |
| #55: 2-Hydroxycarbazole 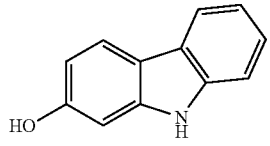 [SMILES: Oc1ccc2c(c1)[nH]c1ccccc12] | +++ | + |
| #73: 7,8-Dihydroxy-4-phenylcoumarin | | |

A list of examples of carbazole-based imaging agents are shown in Table 5. Many of the compounds are either $^{18}$F- or $^{11}$C-labeled.

TABLE 5

Examples of carbazole-based imaging agents. Any of these may include a halogen and/or a radionuclide or may be "cold." The halogen may be replaced with a radionuclide such as $^{18}$F.

| Compound Name | Structure | Formula | Mol. Weight |
|---|---|---|---|
| 2-(2-fluoroethoxy)-9H-carbazole | 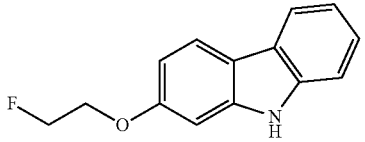 | C$_{14}$H$_{12}$FNO | 229.25 |

TABLE 5-continued

Examples of carbazole-based imaging agents. Any of these may include a halogen and/or a radionuclide
or may be "cold." The halogen may be replaced with a radionuclide such as $^{18}$F.

| Compound Name | Structure | Formula | Mol. Weight |
|---|---|---|---|
| 9-(2-fluoroethyl)-9H-carbazol-2-ol | 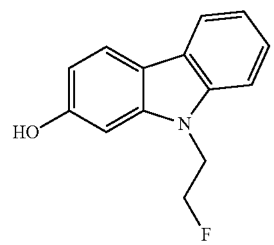 [SMILES: Oc1ccc2c3ccccc3n(CCF)c2c1] | $C_{14}H_{12}FNO$ | 229.25 |
| N-(2-fluoroethyl)-7-(2-(2-(2-methoxyethoxy)ethoxy)ethoxy)-9H-carbazol-3-amine | 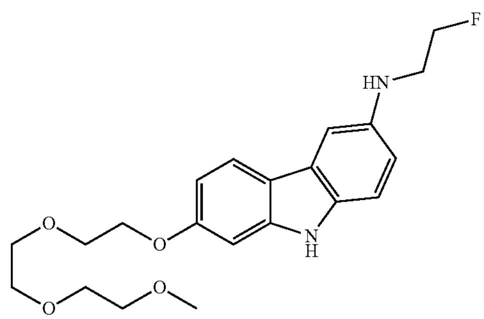 [SMILES: COCCOCCOCCOc1ccc2c(c1)[nH]c1ccc(NCCF)cc12] | $C_{21}H_{27}FN_2O_4$ | 390.45 |
| 7-(2-fluoroethoxy)-N,N-dimethyl-9H-carbazol-2-amine | 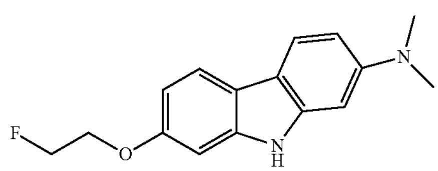 [SMILES: CN(C)c1ccc2c(c1)[nH]c1cc(OCCF)ccc12] | $C_{16}H_{17}FN_2O$ | 272.32 |
| 7-(2-(2-(2-fluoroethoxy)ethoxy)ethoxy)-N-methyl-9H-carbazol-3-amine | 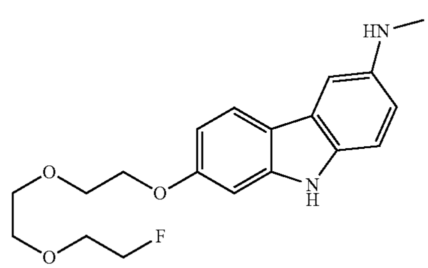 [SMILES: CNc1ccc2[nH]c3cc(OCCOCCOCCF)ccc3c2c1] | $C_{19}H_{23}FN_2O_3$ | 346.40 |
| 1-(3,6-diamino-9H-carbazol-9-yl)-3-(2-(2-(2-fluoroethoxy)ethoxy)ethoxy)propan-1-one | 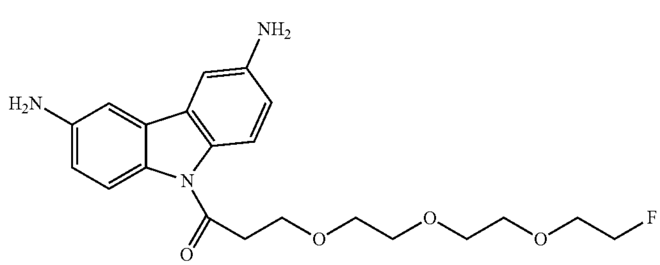 [SMILES: Nc1ccc2c(c1)c1cc(N)ccc1n2C(=O)CCOCCOCCOCCF] | $C_{21}H_{26}FN_3O_4$ | 403.45 |
| N-(2-fluoroethyl)-2-hydroxy-11H-benzo[a]carbazole-3-carboxamide | 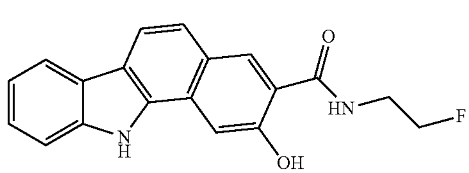 [SMILES: O=C(NCCF)c1cc2ccc3c4ccccc4[nH]c3c2cc1O] | $C_{19}H_{15}FN_2O_2$ | 322.33 |

TABLE 5-continued

Examples of carbazole-based imaging agents. Any of these may include a halogen and/or a radionuclide or may be "cold." The halogen may be replaced with a radionuclide such as $^{18}F$.

| Compound Name | Structure | Formula | Mol. Weight |
|---|---|---|---|
| 2-(6-chloro-9H-carbazol-2-yl)-N-(2-fluoroethyl)propanamide | 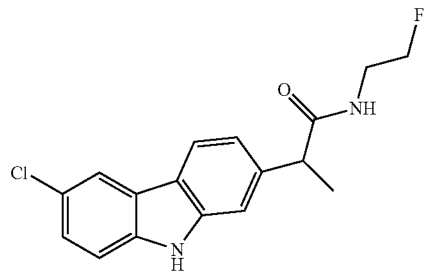 [SMILES: CC(C(=O)NCCF)c1ccc2c(c1)[nH]c1ccc(Cl)cc12] | $C_{17}H_{16}ClFN_2O$ | 318.77 |
| 2-(6-fluoro-9H-carbazol-2-yl)-N,N-dimethylpropanamide | 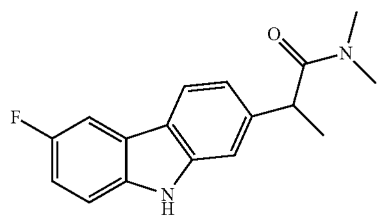 [SMILES: CC(C(=O)N(C)C)c1ccc2c(c1)[nH]c1ccc(F)cc12] | $C_{17}H_{17}FN_2O$ | 284.33 |
| 2-methoxy-9H-carbazole | 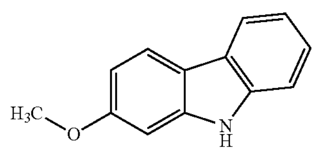 | $C_{13}H_{11}NO$ | 197.23 |
| 6-iodo-2-methoxy-9H-carbazole | 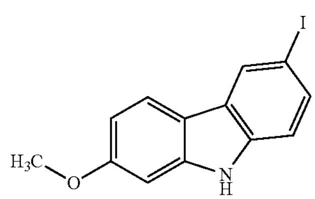 [SMILES: COc1ccc2c(c1)[nH]c1ccc(I)cc12] | $C_{13}H_{10}INO$ | 323.13 |

Detailed Biacore Assay Protocol:

β-Amyloid (Aβ42) Soluble Aggregates (Oligomers/Soluble Polymers).

Biotin-LC-Aβ42 was mixed with Aβ42 at a ratio of 3:2. After dissolving in 1% NH$_4$OH and dH$_2$O, the mixture (40 uM concentration) was incubated in 1×PBS (pH 7.4) buffer at RT for 6-hours to form oligomers/soluble polymers. The free monomer of Aβ42 in the sample was removed using a Microcon centrifugal filter tube with a 10 KDa of MW cutoff. The Biotin-LC-Aβ42 oligomers/polymers were immobilized onto SA chip by streptavidin-biotin capture.

β-Amyloid (Aβ42) Insoluble Aggregates (Fibrils).

Fibrils were prepared according to methods published previously (Agdeppa E D et al. 2001). Briefly, 0.5 mg of Aβ42 (Biotin-LC-Aβ42:Aβ42=1:1) was dissolved in 1 ml of PBS, pH 7.4, and mixed with a magnetic stir bar for 3 d at 37° C., resulting in a visibly cloudy solution. The fibril pellet was collected by centrifugation. The Biotin-LC-Aβ42 fibrils were immobilized onto SA chip by streptavidin-biotin capture.

Screening of Amyloid Binding Compounds with Biacore (Surface Plasmon Resonance Analysis).

Aβ42 oligomers/soluble polymers or fibrils were immobilized on Flow Cell 2 (Fc2) or Flow Cell 3 (Fc3) of the Sensor Chip, with Fc1 serving as the control. Screening compounds at 10 uM concentration was flown through Fc1, Fc2, and Fc3 for 2 minutes at a flow rate of 30 ul/minute. The Flow Cells were then washed with running buffer (1×PBS) for 2 minute, and regenerated with 50 mM of NaOH for 30 seconds. The real time interaction between the screening compound and the amyloid aggregates immobilized on the chip surface was recorded in the sensorgram.

Immunostaining of Brain Sections with Thioflavin T.

Brain samples from donors with Alzheimer disease were paraffin wax infiltrated after fixation. Paraffin blocks with embedded brain samples were mounted onto microtome and sectioned. Sections were then deparaffinized and hydrated, followed by incubation with or without AD-CB-001S-WZ01013. Staining was carried out with 1 uM Thioflavin T. Images were obtained with a fluorescence microscope (FIG. 4 of U.S. Ser. No. 12/372,717).

Immunostaining of Brain Sections with FDDNP.

Brain samples from donors with Alzheimer disease were paraffin wax infiltrated after fixation. Paraffin blocks with embedded brain samples were mounted onto microtome and sectioned. Sections were then deparaffinized and hydrated, followed by incubation with or without AD-CB-001S-WZ01013. Staining was carried out with 1 uM FDDNP. Images were obtained with a fluorescence microscope (FIG. 5 of U.S. Ser. No. 12/372,717).

Imaging Results of AD-CB-001

A white Sprague-Dawley rat was injected via tail vein with ~850 uCi AD-CB-001, formulated in 10% EtOH:water. A dynamic scan was conducted for 30 min on a R4 microPET scanner. The data was reconstructed using 1 min framing. Within minutes, the tracer entered the rat brain and quickly washed out (FIG. 6 of U.S. Ser. No. 12/372,717).

Synthesis of AD-CB-002P-WZ01031

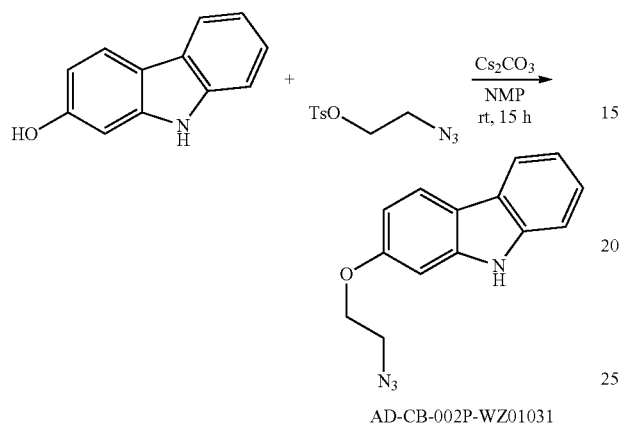

AD-CB-002P-WZ01031

To hydroxycarbazole (92 mg, 0.5 mmol) in 2 mL of NMP was added $Cs_2CO_3$ (163 mg, 0.5 mmol) and ethylazido tosylate (121 mg, 0.5 mmol). The mixture was stirred at rt for 15 h and diluted with $Et_2O$ (50 mL). It was washed with 0.5 M HCl (50 mL) and water (2×50 mL), dried over $MgSO_4$ and concentrated. The crude product was purified with silica chromatography (80% DCM in hexane to 100% DCM) to afford the desired product (76 mg) as a white solid.

$^1$H NMR (400 MHz, $CDCl_3$/acetone-d6) δ 9.98 (s, 1H), 7.95 (m, 2H), 7.41 (d, J=8.4 Hz, 1H), 7.29 (t, J=8.0 Hz, 1H), 7.14 (t, J=8.0 Hz, 1H),); 7.01 (s, 1H), 6.84 (d, J=8.4 Hz, 1H), 4.28 (t, J=4.8 Hz, 2H), 3.67 (t, J=4.8 Hz, 2H); MS (ESI) m/z 253 (M+H$^+$).

Synthesis of AD-CB-002S-WZ01033

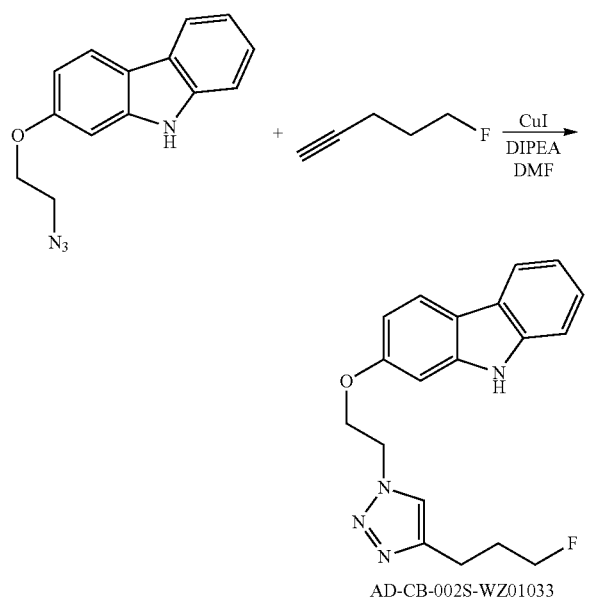

AD-CB-002S-WZ01033

To ethylazido carbazole (32 mg, 0.127 mmol) in 0.5 mL of DMF was added CuI (7.6 mg, 0.04 mmol), DIPEA (16.4 mg, 0.127 mmol), and fluoropentyne (16.4 mg, 0.19 mmol). The reaction mixture was vigorously stirred for 1 h and diluted with EtOAc (30 mL). It was washed with water (50 mL), 0.5 M HCl (30 mL), water (2×50 mL), dried over $MgSO_4$ and concentrated. The crude product was pre-absorbed on silica (3 g) and loaded on a 4 g silica column and eluted with 30% EtOAc in hexane to 50% to afford the desired compound (20 mg).

$^1$H NMR (400 MHz, $CDCl_3$/$CD_3OD$) δ 7.95 (d, J=7.6 Hz, 1H), 7.91 (d, J=8.4 Hz, 1H), 7.76 (s, 1H), 7.40 (d, J=8.0 Hz, 1H), 7.31 (t, J=7.6 Hz, 1H), 7.14 (t, J=7.6 Hz, 1H); 6.94 (d, J=2.4 Hz, 1H), 6.78 (dd, J=8.8, 2.4 Hz, 1H), 4.83-4.78 (m, 2H), 4.53-4.48 (m, 3H), 4.40 (t, J=6.0 Hz, 1H), 2.85 (t, J=7.6 Hz, 2H), 2.10-1.99 (m, 2H); MS (ESI) m/z 339 (M+H$^+$).

Synthesis of 18F-labeled AD-CB-002S-WZ01033

Preparation of Triazole

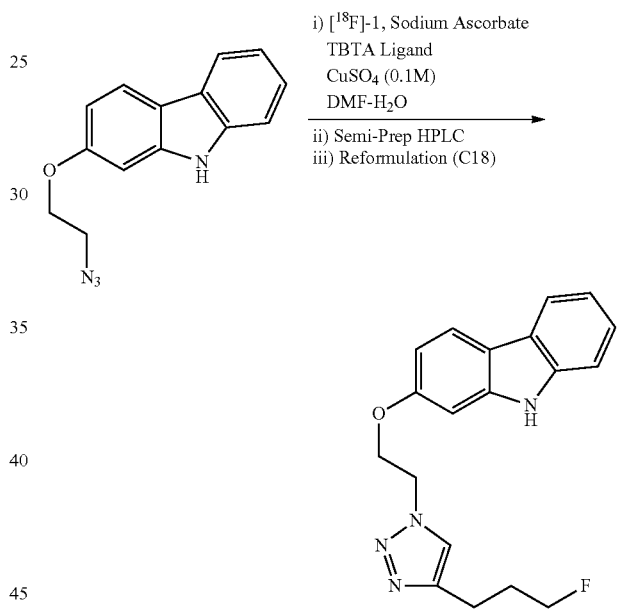

A mixture of azide precursor (5 mg), sodium ascorbate (40 mg), tris-(benzyltriazolylmethyl)amine (TBTA, 25 mg) and aqueous copper sulfate solution (0.1 M, 0.25 mL) in DMF (0.4 mL) and water (0.1 mL) is added to the cooled pentyne solution described above. The reaction mixture is then warmed to rt and stirs for 30 min. After this time, the reaction is purified by semi-preparative HPLC. The peak corresponding to the product is collected and simultaneously diluted with sterile water (10 mL). The resulting mixture is passed over a C-18 Sep-Pak and residual acetonitrile is washed away with additional water (10 mL). The product is eluted into the product vial with USP grade ethanol (0.5 mL) and diluted with sterile water (9.5 mL) providing a final formulation suitable for injection.

Purity is determined by analytical HPLC equipped with a radioactivity detector and identity is confirmed by comparison with HPLC data for the corresponding unlabeled reference standard.

General Procedure for Carbazole N-Boc Protection:

To a round bottomed flask equipped with a magnetic stir bar, rubber septum, and argon inlet containing THF (40 vol)

was placed carbazole (1.0 equiv). To this solution was added NaH (60% dispersion in oil, 3 equiv) at 0° C. and the reaction was allowed to stir at 0° C. for 30 min. To this reaction was added (Boc)$_2$O (1.2 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Procedure for Carbazole N-Methylation:

To a round bottomed flask equipped with a magnetic stir bar, rubber septum, and argon inlet containing THF (50 vol) was placed carbazole (1.0 equiv). To this solution was added NaH (60% dispersion in oil, 3 equiv) at 0° C. and the reaction was allowed to stir at 0° C. for 30 min. To this reaction was added MeOTf (1.0 equiv) at 0° C. and the reaction was allowed to stir for 1 h. After the reaction was complete by LCMS, poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Phenolic Alkylation:

To a round bottomed flask equipped with a magnetic stir bar containing DMF (20 vol) was placed phenol (1 equiv). To this solution was added alkylating agent (1.0 equiv), Cs$_2$CO$_3$ (1.2 equiv) and the reaction was allowed to stir at 60° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Suzuki Coupling Reaction:

To a round bottomed flask equipped with a magnetic stir bar rubber septum, and argon inlet containing toluene:H$_2$O (1:1, 40 vol) was placed chloro compound (1 equiv). To this solution was added boronic acid (1.5 equiv), Pd(PPh$_3$)$_4$ (0.02 equiv), K$_2$CO$_3$ and the reaction was allowed to stir at 110° C. for 16 h. The reaction was then poured into water (25 vol) and extracted into EtOAc (3×20 vol). The combined organic extracts were washed with water (2×25 vol), dried (Na$_2$SO$_4$) and concentrated in vacuo. The residue was purified over silica gel using Hexanes:EtOAc as an eluent to afford the final product.

General Experimental Procedure for Carbazole Formation Using P(OEt)$_3$:

To a round bottomed flask equipped with a magnetic stir bar containing P(OEt)$_3$ (25 vol) was placed biaryl (1 equiv). The reaction was allowed to stir at 150° C. for 16 h. After the reaction was complete, P(OEt)$_3$ was removed in vacuo. The residue was purified over silica gel using Hexanes:EtOAc as the eluent to afford the final compound.

Synthesis of CB1-Nosylate Precursor

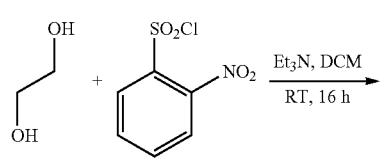

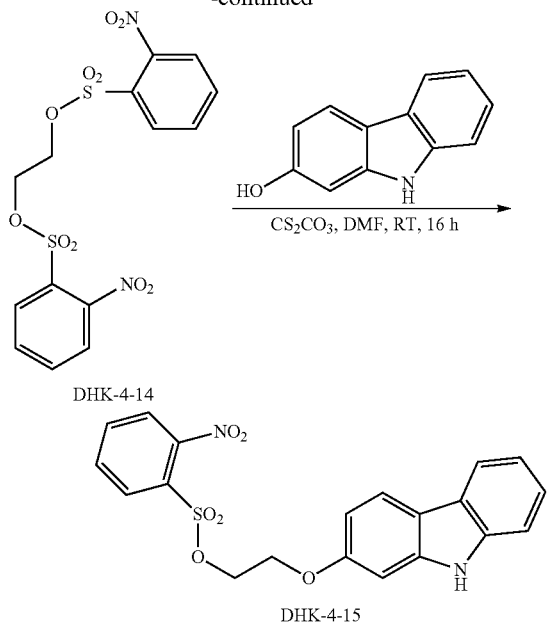

Preparation of ethane-1,2-diyl bis(2-nitrobenzenesulfonate) (DHK-4-14)

To a 50 mL round bottomed flask equipped with a magnetic stir bar containing DCM (10 mL) was placed 1,2-ethanediol (0.25 g, 4.0 mmol). To this solution was added nosyl chloride (1.9 g, 8.5 mmol) and Et$_3$N (0.90 g, 8.9 mmol) at 0° C. and the reaction was allowed to stir at room temperature for 16 h. After the reaction was complete, the white solid was filtered, washed with DCM (100 mL) and dried in vacuo to afford DHK-4-14 (1.3 g, 75%) as a colorless solid.

MS: [M+Na]$^+$: 455.0

Preparation of 2-(9H-carbazol-2-yloxy)ethyl 2-nitrobenzenesulfonate (DHK-4-15)

To a 25 mL round bottomed flask equipped with a magnetic stir bar containing DMF (5 vol) was placed carbazole (0.2 g, 1.1 mmol). To this solution was added the DHK-4-14 (0.52 g, 1.2 mmol), Cs$_2$CO$_3$ (0.43 g, 1.3 mmol) and the reaction was allowed to stir at room temperature for 16 h. The reaction was then poured into water (25 mL) and extracted into EtOAc (4×50 mL). The combined organic extracts were dried (Na$_2$SO$_4$) and concentrated in vacuo. The crude residue was purified by flash chromatography using Hexanes:EtOAc (50:50) on a Combiflash purification system to yield DHK-4-15 as a white solid (0.28 g, 62%). MS: [M+Na]$^+$: 435.0

Synthesis of CB-5

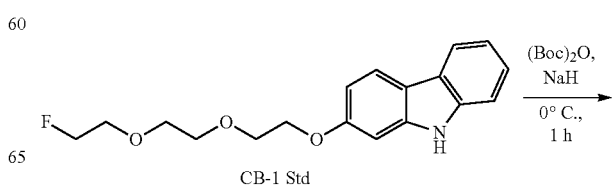

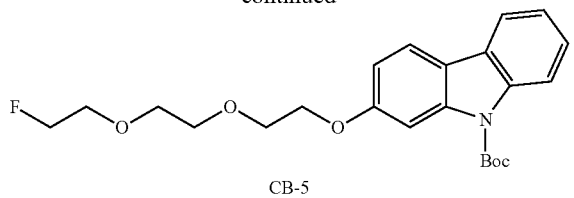
CB-5

Preparation of tert-butyl 2-(2-(2-(2-fluoroethoxy)ethoxy)ethoxy)-9H-carbazole-9-carboxylate: CB-5: DHK-4-27

General experimental procedure for carbazole N-Boc protection was followed. Reaction was performed on a 0.03 g scale. Product eluted out in 30-35% EtOAc:Hexanes mixture in a gradient elution on a Combiflash purification system. Isolated 0.03 g (74%) of CB-5 as a colorless oil. MS: [M+H]$^+$: 418.0

Synthesis of CB-6: DHK-4-28

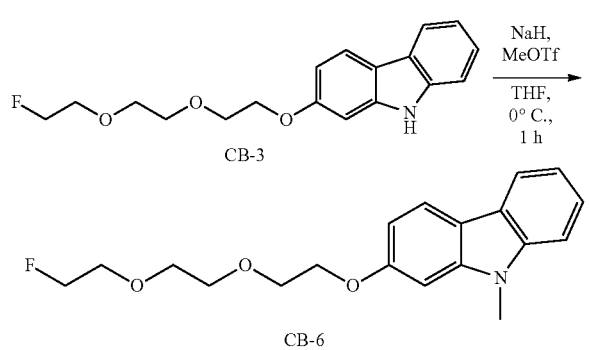

Preparation of 2-(2-(2-(2-fluoroethoxy)ethoxy)ethoxy)-9-methyl-9H-carbazole: CB-6

General experimental procedure for carbazole N-methylation was followed. Reaction was performed on a 0.05 g scale. Product eluted out in 40-45% EtOAc:Hexanes mixture in a gradient elution on a Combiflash purification system. Isolated 0.04 g (78%) of CB-6 as a white solid. MS: [M+H]$^+$: 332.1.

Synthesis of N-Boc-Protected CB-3 Precursor

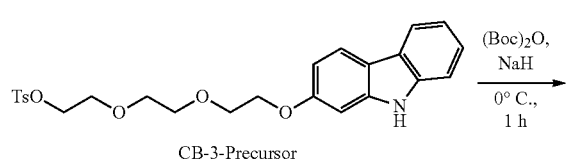
CB-3-Precursor

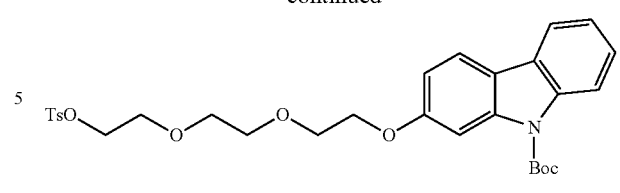
DHK-4-32

Preparation of tert-butyl 2-(2-(2-(2-(tosyloxy)ethoxy)ethoxy)ethoxy)-9H-carbazole-9-carboxylate: DHK-4-32

General experimental procedure for carbazole N-Boc protection was followed. Reaction was performed on a 0.07 g scale. Product eluted out in 40% EtOAc:Hexanes mixture in a gradient elution on a Combiflash purification system. Isolated 0.07 g (82%) of DHK-4-32 as white solid. MS: [M+Na]$^+$: 592.

Synthesis of N-Methyl CB-3 Precursor

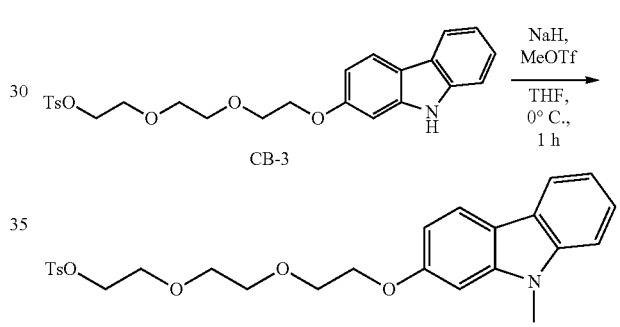
DHK-4-30

Preparation of 2-(2-(2-(9-methyl-9H-carbazol-2-yloxy)ethoxy)ethoxy)ethyl 4-methylbenzenesulfonate: DHK-4-30

General experimental procedure for carbazole N-methylation was followed. Reaction was performed on a 0.075 g scale. Product eluted out in 40% EtOAc:Hexanes mixture in a gradient elution on a Combiflash purification system. Isolated 0.07 g (91%) of DHK-4-30 as a white solid. MS: [M+H]$^+$: 484.2

Synthesis of CB-7 Std

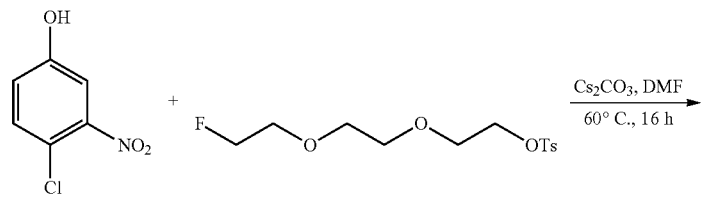

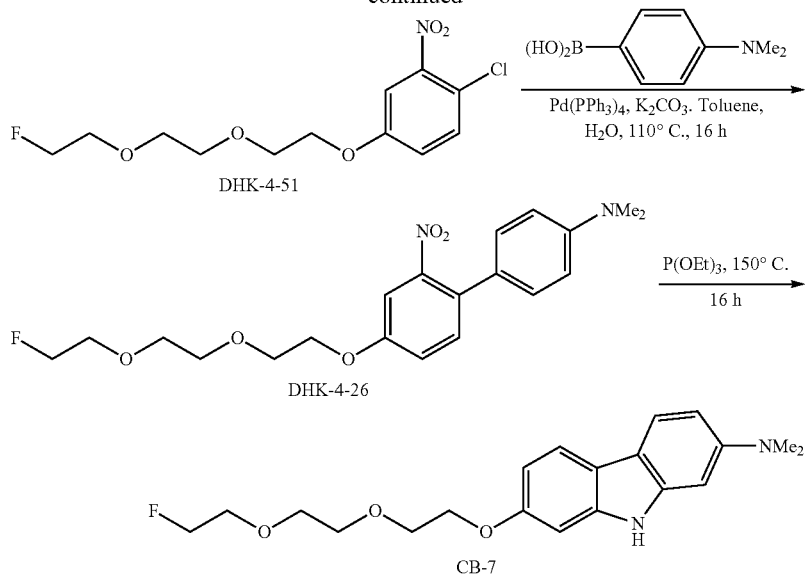

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: $[M+H]^+$: 308.0.

Preparation of 4'-(2-(2-(2-fluoroethoxy)ethoxy)ethoxy)-N,N-dimethyl-2'-nitrobiphenyl-4-amine: DHK-4-26

General experimental procedure for Suzuki coupling reaction was followed. Reaction was performed on a 0.11 g scale. Product eluted out in 50-60% EtOAc:Hexanes mixture in a gradient elution on a Combiflash purification system. Isolated 0.06 g (43%) of DHK-4-26 as yellow oil. MS: $[M+H]^+$: 393.1

Preparation of 7-(2-(2-(2-fluoroethoxy)ethoxy)ethoxy)-N,N-dimethyl-9H-carbazol-2-amine: DHK-4-29: CB-7

General experimental procedure for carbazole formation using $P(OEt)_3$ was followed. Reaction was performed on a 0.06 g scale. Product eluted out in 70-80% EtOAc:Hexanes mixture in a gradient elution on a Combiflash purification system. Isolated 0.03 g (49%) of DHK-4-29 CB-7 as white solid. MS: $[M+H]^+$: 361.1.

Synthesis of CB-9 Std

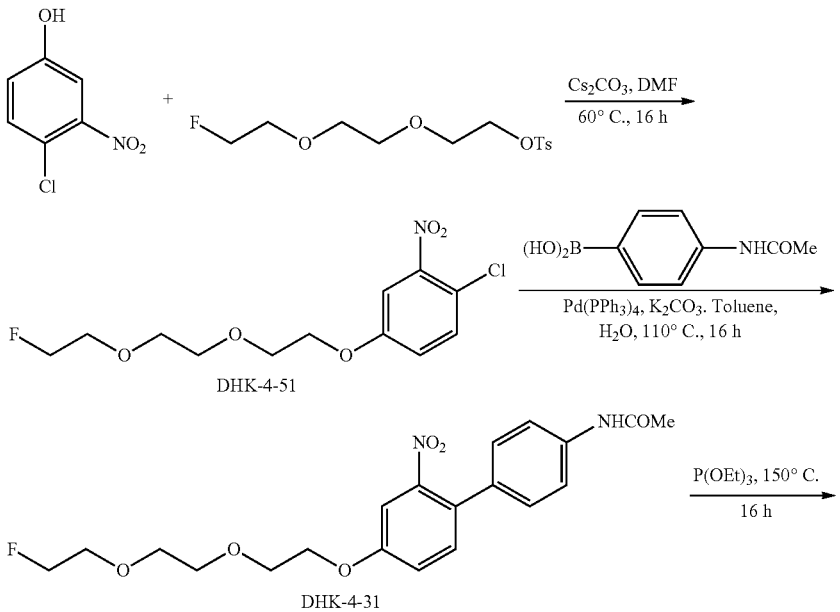

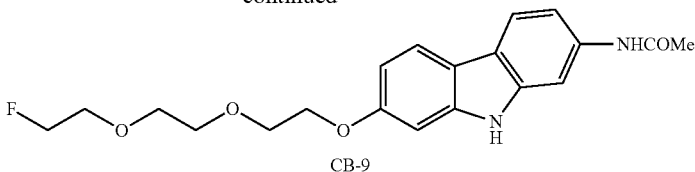

CB-9

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: [M+H]$^+$: 308.0.

Preparation of N-(4'-(2-(2-(2-fluoroethoxy)ethoxy)ethoxy)-2'-nitrobiphenyl-4-yl)acetamide: DHK-4-31

General experimental procedure for Suzuki coupling reaction was followed. Reaction was performed on a 0.11 g scale. Product eluted out in 80-90% EtOAc:Hexanes mixture in a gradient elution on a Combiflash purification system. Isolated 0.14 g (100%) of DHK-4-31 as yellow oil. MS: [M+H]$^+$: 407.0.

Preparation of N-(7-(2-(2-(2-fluoroethoxy)ethoxy)ethoxy)-9H-carbazol-2-yl)acetamide: DHK-4-33: CB-9

General experimental procedure for carbazole formation using P(OEt)$_3$ was followed. Reaction was performed on a 0.15 g scale. Product eluted out in 90% EtOAc:Hexanes mixture in a gradient elution on a Combiflash purification system. Isolated 0.03 g (49%) of CB-9 as white solid. MS: [M+H]$^+$: 375.1.

Synthesis of CB-28 Std

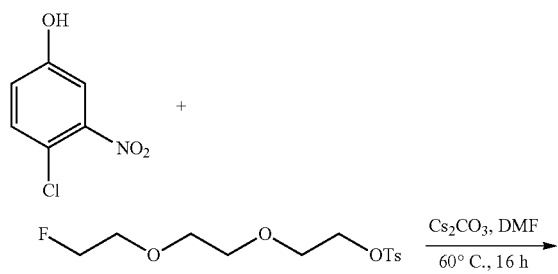

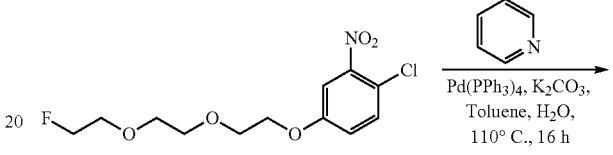

DHK-4-51

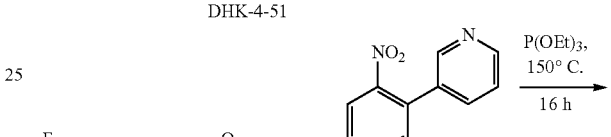

DHK-4-56

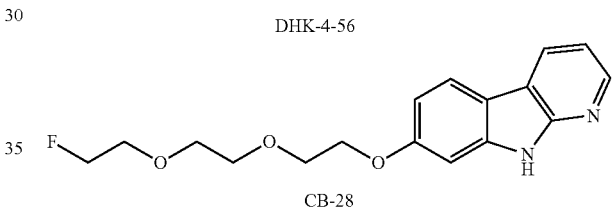

CB-28

Preparation of 1-chloro-4-(2-(2-(2-fluoroethoxy)ethoxy)ethoxy)-2-nitrobenzene: DHK-4-51

General experimental procedure for phenolic alkylation was followed. Reaction was performed on a 0.25 g scale. Product eluted out in 20-30% EtOAc:Hexanes mixture in a gradient elution on a Combiflash purification system. Isolated 0.44 g (99%) of DHK-4-51 as yellow oil. MS: [M+H]$^+$: 308.0.

Preparation of 3-(4-(2-(2-(2-fluoroethoxy)ethoxy)ethoxy)-2-nitrophenyl)pyridine: DHK-4-56

General experimental procedure for Suzuki coupling reaction was followed. Reaction was performed on a 0.095 g scale. Product eluted out in 40-50% EtOAc:Hexanes mixture in a gradient elution on a Combiflash purification system. Isolated 0.01 g (9%) of DHK-4-56 as yellow oil. MS: [M+H]$^+$: 351.1.

Preparation of 7-(2-(2-(2-fluoroethoxy)ethoxy)ethoxy)-9H-pyrido[2,3-b]indole DHK-4-58: CB-28

General experimental procedure for carbazole formation using P(OEt)$_3$ was followed. Reaction was performed on a 0.01 g scale. Product eluted out in 50% EtOAc:Hexanes mixture in a gradient elution on a Combiflash purification system. Isolated 0.002 g (22%) of CB-28 as white solid. MS: [M+H]$^+$: 319

Synthesis of CB-7-Precursor

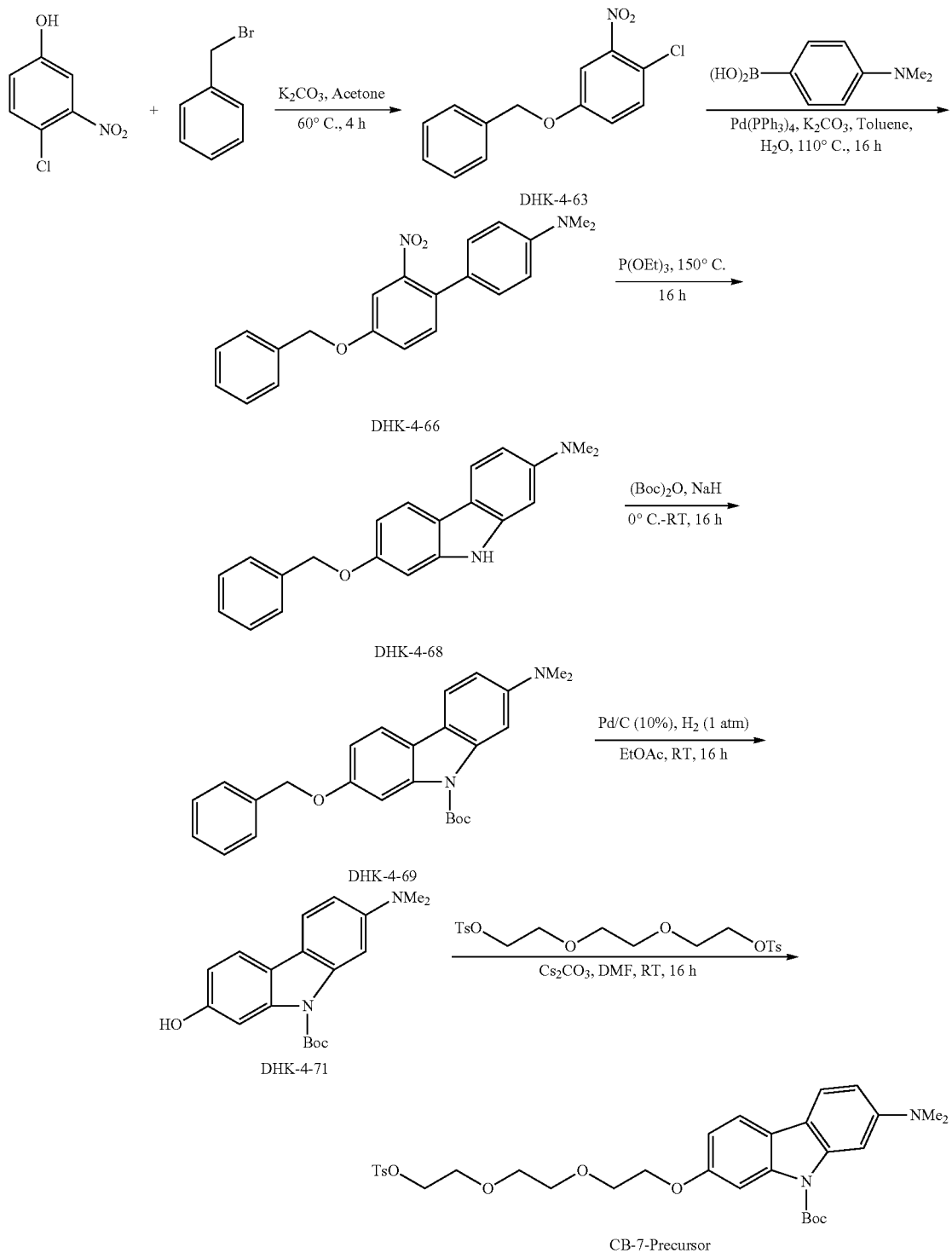

Preparation of 4-(benzyloxy)-1-chloro-2-nitrobenzene: DHK-4-63

General experimental procedure for phenolic alkylation was followed. Reaction was performed on a 1 g scale. $K_2CO_3$ was used as a base and acetone was used as the solvent. Reaction time was 4 h. Product eluted out in 20-30% EtOAc: Hexanes mixture in a gradient elution on a Combiflash purification system. Isolated 1.45 g (95%) of DHK-4-63 as white crystalline solid. MS: $[M+H]^+$: 264.0

Preparation of 3 4'-(benzyloxy)-N,N-dimethyl-2'-nitrobiphenyl-4-amine: DHK-4-66

General experimental procedure for Suzuki coupling reaction was followed. Reaction was performed on a 0.47 g scale. Product eluted out in 20-30% EtOAc:Hexanes mixture in a gradient elution on a Combiflash purification system. Isolated 0.21 g (34%) of DHK-4-66 as orange solid. MS: [M+H]+: 349.1

Preparation of 7-(benzyloxy)-N,N-dimethyl-9H-carbazol-2-amine DHK-4-68

General experimental procedure for carbazole formation using P(OEt)3 was followed. Reaction was performed on a 0.21 g scale. Product eluted out in 20-30% EtOAc:Hexanes mixture in a gradient elution on a Combiflash purification system. Isolated 0.13 g (68%) of DHK-4-68 as white solid. MS: [M+H]+: 317.1

Preparation of tert-butyl 2-(benzyloxy)-7-(dimethylamino)-9H-carbazole-9-carboxylate: DHK-4-69

General experimental procedure for carbazole N-Boc protection was followed. Reaction was performed on a 0.13 g scale. Reaction temperature was carried at room temperature for 16 h. Product eluted out in 10% EtOAc:Hexanes mixture in a gradient elution on a Combiflash purification system. Isolated 0.12 g (70%) of DHK-4-69 as white solid. MS: [M+H]+: 417.2.

Preparation of tert-butyl 2-(dimethylamino)-7-hydroxy-9H-carbazole-9-carboxylate: DHK-4-71

To a 50 mL round bottomed flask equipped with a magnetic stir bar containing EtOAc (50 mL) was placed DHK-4-69 (0.11 g, 0.19 mmol). To this solution was added Pd/C (10%, 20 mg) and the reaction was allowed to stir under H2 (1 atm) at RT for 16 h. After the reaction was complete, the reaction mixture was filtered through celite and the volatiles were removed in vacuo to afford DHK-4-71 (0.09 g, 100%) as white solid.

Preparation of tert-butyl 2-(dimethylamino)-7-(2-(2-(2-(tosyloxy)ethoxy)ethoxy)ethoxy)-9H-carbazole-9-carboxylate: DHK-4-72: CB-7 precursor General experimental procedure for phenolic alkylation was followed. Reaction was performed on a 0.09 g scale. Product eluted out in 45% EtOAc:Hexanes mixture in a gradient elution on a Combiflash purification system. Isolated 0.07 g (41%) of CB-7 precursor as white solid. MS: [M+H]+: 613.2.

Synthesis of AD-CB-003S-WZ0129

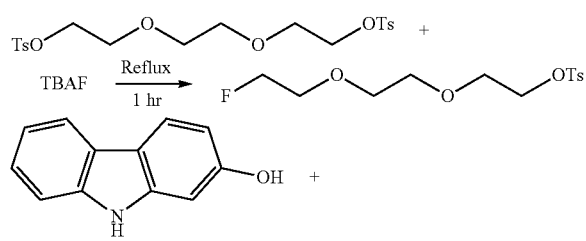
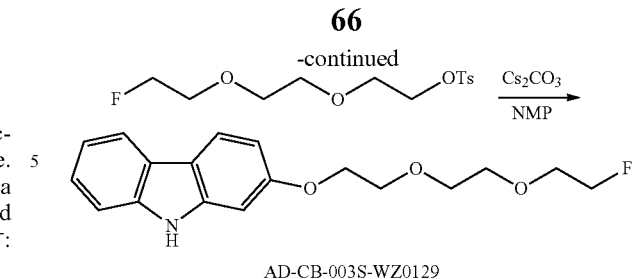

AD-CB-003S-WZ0129

To 2,2'-(ethane-1,2-diylbis(oxy))bis(ethane-2,1-diyl)bis(4-methylbenzenesulfonate) (8.7 g, 19 mmol) was added TBAF (22.8 mL, 1.0 M THF solution, 22.8 mmol). The mixture was heated to reflux for 1 h under Ar atmosphere and cooled to rt and concentrated under reduced pressure. The crude material was purified with silica chromatography (5% to 40% THF in hexane) to afford 2-(2-(2-fluoroethoxy)ethoxy)ethyl 4-methylbenzenesulfonate as a clear oil (2.5 g, 43%). 1H NMR (400 MHz, CDCl3) δ 7.80 (d, J=8.4 Hz, 2H), 7.34 (d, J=8.4 Hz, 2H), 4.61 (m, 1H), 4.49 (m, 1H), 4.16 (m, 2H), 3.75 (m, 1H), 3.71-3.67 (m, 3H), 3.62 (m, 4H); MS (ESI) m/z 307 (M+H+).

To 2-hydroxycarbazole (45 mg, 0.25 mmol) and 2-(2-(2-fluoroethoxy)ethoxy)ethyl 4-methylbenzenesulfonate (82 mg, 0.27 mmol) in 0.5 mL NMP was added Cs2CO3 (82 mg, 0.25 mmol). The mixture was stirred at rt for 15 h under Ar atmosphere and diluted with Et2O (50 mL). It was washed with water (3×50 mL) and dried over MgSO4. Solvent was removed under reduced pressure and the crude product was purified with silica chromatography (5% to 50% EtOAc in hexane) to afford the desired product as white solid (37 mg, 47%). 1H NMR (400 MHz, CDCl3) δ 8.02 (s, 1H), 7.96 (d, J=7.2 Hz, 1H), 7.91 (d, J=8.4 Hz, 1H), 7.38-7.33 (m, 2H), 7.20 (m, 1H), 6.91 (d, J=2.4 Hz, 1H), 6.86 (dd, J=8.8, 2.4 Hz, 1H), 4.63 (m, 1H), 4.51 (m, 1H), 4.21 (m, 2H), 3.90 (m, 2H), 3.80-3.76 (m, 3H), 3.74-3.71 (m, 3H); MS (ESI) m/z 318 (M+H+).

Synthesis of AD-CB-003P-WZ0141

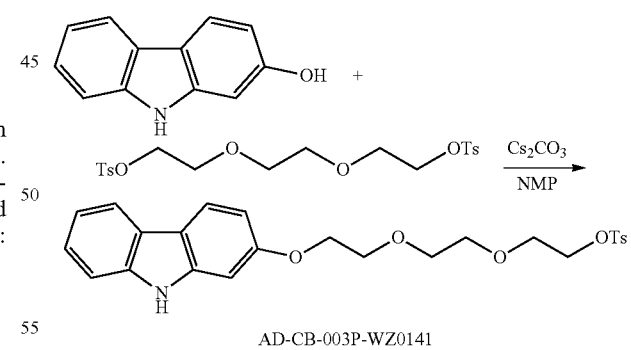

AD-CB-003P-WZ0141

To 2-hydroxycarbazole (183 mg, 1 mmol) and 2-(2-(2-fluoroethoxy)ethoxy)ethyl 4-methylbenzenesulfonate (687 mg, 1.5 mmol) in 5 mL NMP was added Cs2CO3 (326 mg, 1 mmol). The mixture was stirred at rt for 15 h under Ar atmosphere and diluted with Et2O (100 mL). It was washed with water (3×100 mL) and dried over MgSO4. Solvent was removed under reduced pressure and the crude product was purified with silica chromatography (5% to 60% EtOAc in hexane) to afford the desired product as white solid (165 mg, 35%). 1H NMR (400 MHz, CDCl3) δ 8.21 (s, 1H), 7.95 (d, J=7.2 Hz, 1H), 7.91 (d, J=8.4 Hz, 1H), 7.77-7.75 (m, 2H), 7.37-7.30 (m, 2H), 7.28 (s, 1H), 7.25 (m, 1H), (td, J=7.6, 1.2 Hz, 1H), 6.92 (d, J=2.4 Hz, 1H), 6.83 (dd, J=8.8, 2.4 Hz, 1H), 4.15 (m, 4H), 3.84 (m, 2H), 3.69-3.65 (m, 4H), 3.62-3.59 (m, 2H), 2.38 (s, 3H); MS (ESI) m/z 470 (M+H+), 492 (M+Na+).

AD-CB-004S-WZ01165 atmosphere and cooled to rt. It was added EtOAc (100 mL) and washed with brine (80 mL), water (80 mL), and dried over MgSO4. After solvent removal, the residue was chromatographed (hexane/EtOAc) to afford tert-butyl 4'-(benzyloxy)-2'-nitrobiphenyl-4-ylcarbamate as a yellow solid (740 mg, 88%). 1H NMR (400 MHz, CDCl3) δ 7.44-7.34 (m, 8H), (d,

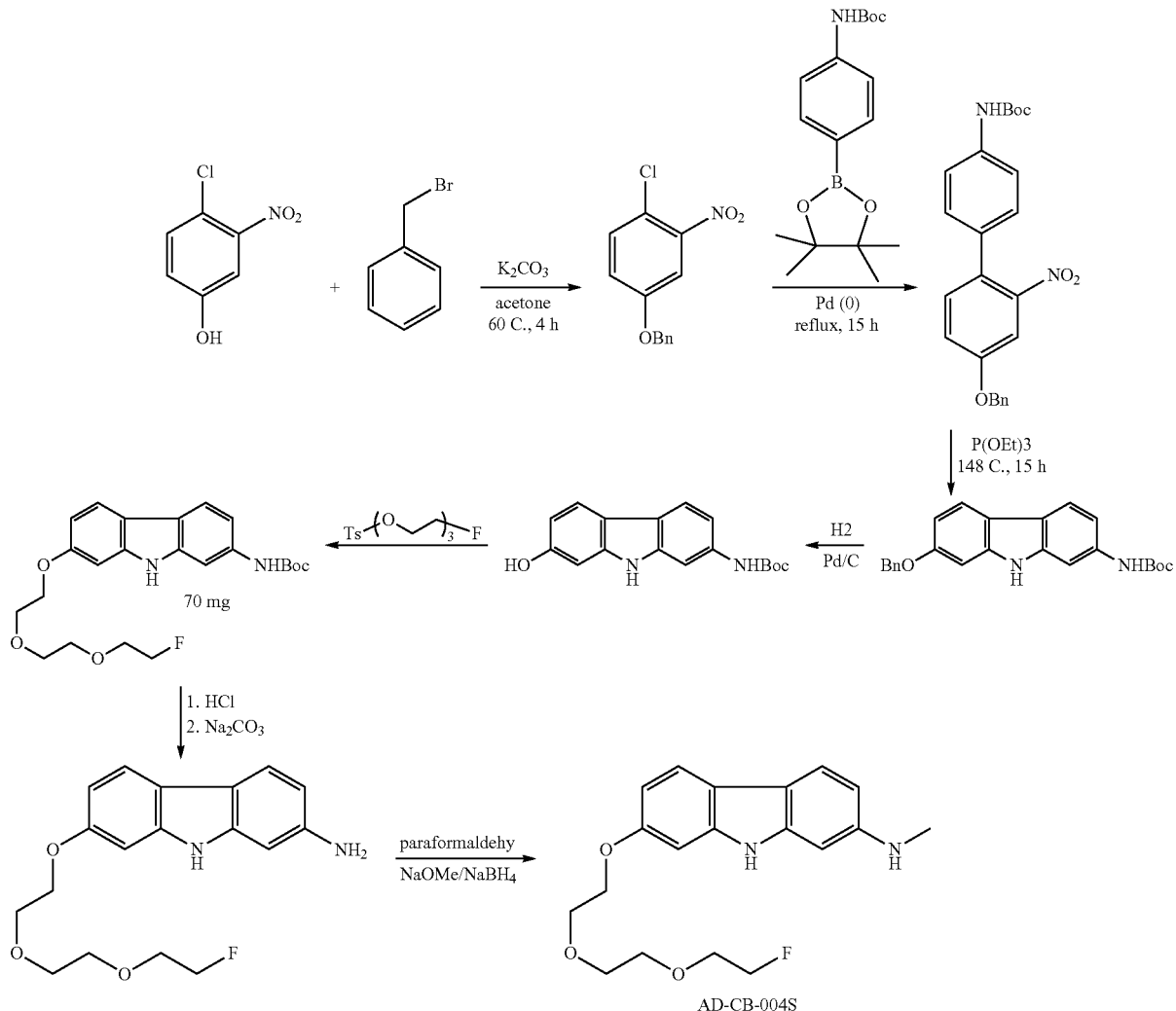

To 4-chloro-3-nitrophenol (1.74 g, 10 mmol) and benzyl bromide (2.05 g, 12 mmol) in 25 mL of acetone was added K2CO3 (2.76 g, 20 mmol). The mixture was heated at 60° C. for 4 h under Ar atmosphere and cooled to rt. It was filtered and the solid was washed with ether (80 mL) and the combined filtrate was concentrated and chromatographed (EtOAc in hexane, 3% to 30% gradient) to afford 4-(benzyloxy)-1-chloro-2-nitrobenzene as a light-yellow solid (2.5 g, 95%). 1H NMR (400 MHz, CDCl3) δ 7.46 (d, J=2.8 Hz, 1H), 7.42-7.34 (m, 5H), 7.11 (dd, J=8.8, 2.8 Hz, 1H), 5.08 (s, 2H); MS (ESI) m/z 264 (M+H+).

To 4-(benzyloxy)-1-chloro-2-nitrobenzene (526 mg, 2 mmol) and tert-butyl 4-(4,4,5,5-tetramethyl-1,3,2-dioxaborolan-2-yl)phenylcarbamate (670 mg, 2.1 mmol) in 12 mL dioxane was added 4 mL of a 1 M Na2CO3 (aq) solution and Tetrakis(triphenylphosphine)palladium (69 mg, 0.06 mmol). The suspension was heated at reflux for 15 h under Ar J=8.4 Hz, 1H), 7.20-7.16 (m, 3H), 6.50 (s, 1H), 5.12 (s, 2H), 1.51 (s, 9H); MS (ESI) m/z 443 (M+Na+).

A suspension of tert-butyl 4'-(benzyloxy)-2'-nitrobiphenyl-4-ylcarbamate (740 mg, 1.67 mmol) in 2 mL of triethyl phosphite was heated at 145° C. for 15 h under Ar atmosphere and cooled to rt. It was added 10 mL of hexane and let sit for 10 min. Solid was collected via filtration and washed with ether/hexane (v:v 1/1, 10 mL) and dried under high vacuum to afford tert-butyl 7-(benzyloxy)-9H-carbazol-2-ylcarbamate as a off-white solid (480 mg, 74%). 1H NMR (400 MHz, CDCl3) δ 7.89 (s, 1H), 7.83-7.78 (m, 3H), 7.46 (d, J=7.2 Hz, 2H), 7.38 (m, 2H), 7.32 (d, J=7.2 Hz, 1H), 6.94 (d, J=2.0 Hz, 1H), 6.88 (dd, J=8.8, 2.4 Hz, 1H), 6.83 (dd, J=8.4, 2.0 Hz, 1H), 6.60 (s, 1H), 5.15 (s, 2H), 1.52 (s, 9H); MS (ESI) m/z 389 (M+H+).

To tert-butyl 7-(benzyloxy)-9H-carbazol-2-ylcarbamate (220 mg, 0.56 mmol) in 50 mL MeOH was added Palladium on activated carbon (80 mg). The mixture was stirred at rt under H2 atmosphere for 3 h. Solid was filtered off and the filtrate was concentrated to afford tert-butyl 7-hydroxy-9H-carbazol-2-ylcarbamate as a brown solid (165 mg, 100%). This material was used directly for the next reaction without purification. MS (ESI) m/z 619 (2M+Na$^+$).

To tert-butyl 7-hydroxy-9H-carbazol-2-ylcarbamate (165 mg, 0.55 mmol) and 2-(2-(2-fluoroethoxy)ethoxy)ethyl 4-methylbenzenesulfonate (202 mg, 0.66 mmol) in 2 mL of NMP was added Cs$_2$CO$_3$ (179 mg, 0.55 mmol). The mixture was stirred at rt for 15 h under Ar atmosphere and diluted with EtOAc (50 mL). It was washed with water (3×50 mL) and dried over MgSO$_4$. After solvent removal, the residue was chromatographed (hexane/EtOAc) to afford tert-butyl 7-(2-(2-(2-fluoroethoxy)ethoxy)ethoxy)-9H-carbazol-2-ylcarbamate as a white solid (130 mg, 55%). $^1$H NMR (400 MHz, CDCl$_3$) δ 7.94 (s, 1H), 7.83-7.79 (m, 3H), 6.91 (d, J=2.0 Hz, 1H), 6.86 (dd, J=8.4, 2.0 Hz, 1H), 6.83 (dd, J=8.8, 2.4 Hz, 1H), 6.63 (s, 1H), 4.64 (m, 1H), 4.51 (m, 1H), 4.21 (m, 2H), 3.91 (m, 2H), 3.81-3.71 (m, 6H), 1.55 (s, 9H); MS (ESI) m/z 433 (M+H$^+$).

To tert-butyl 7-(2-(2-(2-fluoroethoxy)ethoxy)ethoxy)-9H-carbazol-2-ylcarbamate (130 mg, 0.3 mmol) was added 10 mL of a 4 M HCl in dioxane solution. The mixture was stirred at rt for 5 h and concentrated under reduced pressure. The residue was washed with ether (15 mL) and suspended in EtOAc (50 mL). To this suspension was added 10 mL of a NaHCO$_3$ (sat.) and the mixture was stirred for 5 min. The organic layer was dried over MgSO$_4$ and concentrated to afford 7-(2-(2-(2-fluoroethoxy)ethoxy)ethoxy)-9H-carbazol-2-amine as a brown solid (95 mg, 95%). MS (ESI) m/z 333 (M+H$^+$).

A mixture of 7-(2-(2-(2-fluoroethoxy)ethoxy)ethoxy)-9H-carbazol-2-amine (95 mg, 0.28 mmol), paraformaldehyde (43 mg, 1.43 mmol), and NaOMe (492 mg, 25% MeOH solution, 2.3 mmol) in 8 mL of MeOH was heated at reflux for 1.5 h under Ar atmosphere and cooled to rt. To this mixture was added NaBH$_4$ (54 mg, 1.43 mmol) and the mixture was heated at reflux for 2 h. After cooling to rt, the mixture was quenched onto ice. It was extracted with ether (3×30 mL) and the combined organic phase was dried over MgSO$_4$ and concentrated. The crude product was purified with chromatography (hexane/EtOAc) to afford 7-(2-(2-(2-fluoroethoxy)ethoxy)ethoxy)-N-methyl-9H-carbazol-2-amine (AD-CB-003P-WZ0141) as a light-brown solid (55 mg, 56%). $^1$H NMR (400 MHz, CDCl$_3$) δ 7.76 (s, 1H), 7.77 (t, J=8.8 Hz, 2H), 6.78 (dd, J=8.0, 2.0 Hz, 1H), 6.77 (s, 1H), 6.53 (dd, J=8.4, 2.0 Hz, 1H), 6.46 (s, 1H), 4.62 9 m, 1H), 4.50 (m, 1H), 4.13 (t, J=5.2 Hz, 2H), 3.85 (t, J=5.2 Hz, 2H), 3.83 (s, 1H), 3.79-3.67 (m, 6H), 2.87 (s, 3H); MS (ESI) m/z 347 (M+H$^+$).

AD-CB-004 Pa-WZ01179

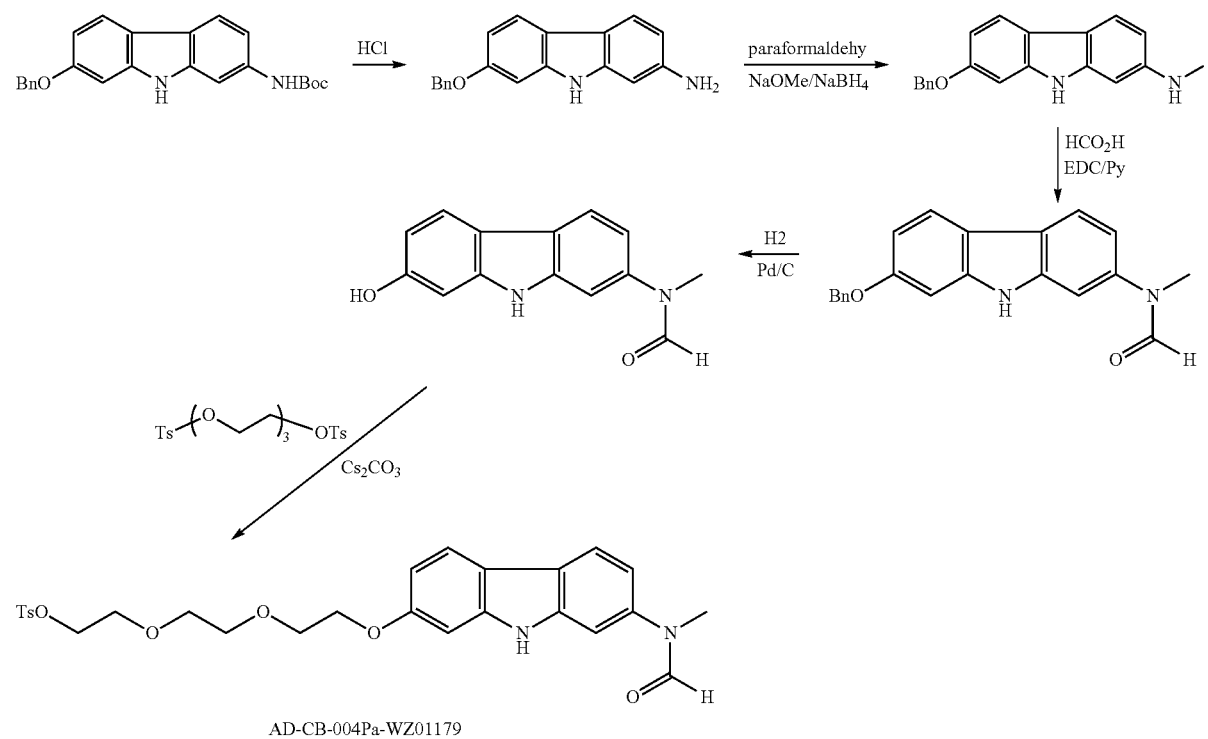

AD-CB-004Pa-WZ01179

To tert-butyl 7-(benzyloxy)-9H-carbazol-2-ylcarbamate (200 mg, 0.51 mmol) was added 10 mL of a 4 M HCl in dioxane solution. The mixture was stirred at rt for 4 h and concentrated under reduced pressure. The residue was washed with ether (15 mL) and suspended in EtOAc (50 mL). To this suspension was added 10 mL of a NaHCO$_3$ (sat.) and the mixture was stirred for 5 min. The organic layer was dried over MgSO$_4$ and concentrated to afford 7-(benzyloxy)-9H-carbazol-2-amine as a brown solid (150 mg, 100%). $^1$H NMR (400 MHz, DMSO-d6) δ 11.33 (s, 1H), 7.99 (d, J=8.4 Hz, 1H), 7.92 (d, J=8.8 Hz, 1H), 7.42 (d, J=6.8 Hz, 2H), 7.34-7.21 (m, 3H), 7.27-7.23 (m, 1H), 7.00-6.97 (m, 2H), 6.81 (dd, J=8.8, 2.4 Hz, 1H), 5.12 (s, 2H); MS (ESI) m/z 289 (M+H$^+$).

A mixture of 7-(benzyloxy)-9H-carbazol-2-amine (150 mg, 0.52 mmol), paraformaldehyde (78 mg, 2.6 mmol), and NaOMe (900 mg, 25% MeOH solution, 4.16 mmol) in 15 mL of MeOH was heated at reflux for 2 h under Ar atmosphere and cooled to rt. To this mixture was added NaBH₄ (98 mg, 2.6 mmol) and the mixture was heated at reflux for 2 h. After cooling to rt, the mixture was quenched onto ice (30 g). It was extracted with EtOAc (3×50 mL) and the combined organic phase was dried over MgSO₄ and concentrated. The crude product was purified with chromatography (hexane/EtOAc) to afford 7-(benzyloxy)-N-methyl-9H-carbazol-2-amine as a light-brown solid (130 mg, 82%). ¹H NMR (400 MHz, acetone-d6) δ 9.78 (s, 1H), 7.72 (d, J=8.4 Hz, 1H), 7.66 (d, J=8.8 Hz, 1H), 7.49 (d, J=7.2 Hz, 2H), 7.37 (m, 2H), 7.32-7.28 (m, 1H), 6.98 (d, J=2.4 Hz, 1H), 6.78 (dd, J=8.4, 2.4 Hz, 1H), 6.56 (d, J=2.0 Hz, 1H), 6.49 (dd, J=8.4, 2.4 Hz, 1H), 5.13 (s, 2H), 4.96 (s, 1H), 2.82 (s, 3H); MS (ESI) m/z 303 (M+H⁺).

To 7-(benzyloxy)-N-methyl-9H-carbazol-2-amine (120 mg, 0.4 mmol), formic acid (55 mg, 1.2 mmol) and DMAP (5 mg, 0.04 mmol) in 3 mL of pyridine was added portionwise EDC (230 mg, 1.2 mmol). The mixture was stirred at rt for 3 h under Ar atmosphere and concentrated under reduced pressure. The residue was diluted with EtOAc (50 mL) and washed with water (2×50 mL), 0.5 M HCl (2×50 mL), and brine (50 mL), and dried over MgSO₄. After solvent removal, the crude product was purified with chromatography (hexane/EtOAc) to afford N-(7-(benzyloxy)-9H-carbazol-2-yl)-N-methylformamide as a white solid (110 mg, 83%). ¹H NMR (400 MHz, acetone-d6) δ 10.34 (s, 1H), 8.49 (s, 1H), 8.02 (d, J=8.4 Hz, 1H), 7.98 (d, J=8.8 Hz, 1H), 7.51 (d, J=7.2 Hz, 2H), 7.39 (m, 2H), 7.34-7.28 (m, 1H), 7.13 (d, J=2.4 Hz, 1H), 7.08 (dd, J=8.4, 2.4 Hz, 1H), 6.91 (dd, J=8.4, 2.4 Hz, 1H), 5.19 (s, 2H), 3.31 (s, 3H); MS (ESI) m/z 331 (M+H⁺).

To N-(7-(benzyloxy)-9H-carbazol-2-yl)-N-methylformamide (110 mg, 0.33 mmol) in 50 mL MeOH was added Palladium on activated carbon (50 mg). The mixture was stirred at rt under H2 atmosphere for 15 h. Solid was filtered off and the filtrate was concentrated to afford N-(7-(hydroxy-9H-carbazol-2-yl)-N-methylformamide as a brown solid (75 mg, 94%). This material was used directly for the next reaction without purification. MS (ESI) m/z 241 (M+H⁺).

To N-(7-hydroxy-9H-carbazol-2-yl)-N-methylformamide (45 mg, 0.187 mmol) and 2-(2-(2-fluoroethoxy)ethoxy)ethyl 4-methylbenzenesulfonate (172 mg, 0.38 mmol) in 0.5 mL NMP was added Cs₂CO₃ (65 mg, 0.2 mmol). The mixture was stirred at rt for 15 h under Ar atmosphere and diluted with EtOAc (50 mL). It was washed with water (2×50 mL), 0.5 M HCl (50 mL) and brine (50 mL), and dried over MgSO₄. Solvent was removed under reduced pressure and the crude product was purified with silica chromatography (hexane/EtOAc) to afford 2-(2-(2-(7-(N-methylformamido)-9H-carbazol-2-yloxy)ethoxy)ethoxy)ethyl 4-methylbenzenesulfonate (AD-CB-004 Pa-WZ01179) as a light-brown oil (48 mg, 48%). ¹H NMR (400 MHz, CDCl₃) δ 8.52 (s, 1H), 8.45 (s, 1H), 7.95 (d, J=8.4 Hz, 1H), 7.90 (d, J=8.8 Hz, 1H), 7.80-7.77 (m, 2H), 7.30 (d, J=8.0 Hz, 2H), 7.17 (d, J=2.4 Hz, 1H), 7.02 (d, J=2.0 Hz, 1H), 7.01 (dd, J=8.0, 2.0 Hz, 1H), 6.89 (dd, J=8.8, 2.4 Hz, 1H), 4.23 (m, 1H), 4.17 (m, 2H), 3.88 (m, 2H), 3.72-3.68 (m, 4H), 3.66-3.61 (m, 2H), 3.39 (s, 3H), 2.41 (s, 3H); MS (ESI) m/z 527 (M+H⁺).

AD-CB-004Pb-WZ01191

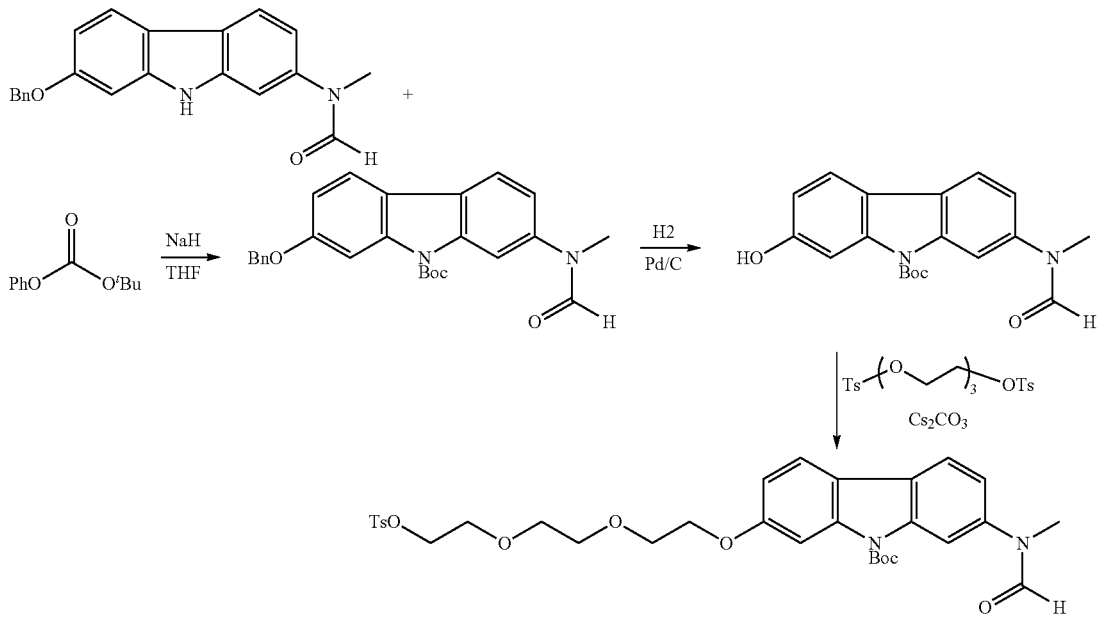

AD-CB-004Pb-WZ01191

To N-(7-(benzyloxy)-9H-carbazol-2-yl)-N-methylformamide (140 mg, 0.42 mmol) in 5 mL dry THF at 0° C. under Ar atmosphere was added NaH (50 mg, 60% in oil, 1.26 mmol) in 4 portions. The mixture was then stirred at rt for 20 min followed by the addition of tert-butyl phenyl carbonate (244 mg, 1.26 mmol) with a syringe. The reaction was allowed to stir at rt for 3 h and quenched onto ice (30 g). The mixture was extracted with EtOAc (2×40 mL) and the combined organic phase was dried over MgSO₄. After solvent removal, the residue was chromatographed to afford tert-butyl 2-(benzyloxy)-7-(N-methylformamido)-9H-carbazole-9-carboxylate as a white solid (120 mg, 66%). ¹H NMR (400 MHz, CDCl₃) δ 8.56 (s, 1H), 8.15 (s, 1H), 7.98 (s, 1H), 7.86 (d, J=8.4 Hz, 1H), 7.83 (d, J=8.4 Hz, 1H), 7.50-7.49 (m, 2H), 7.43-7.39 (m., 2H), 7.37-7.32 (m, 1H), 7.13 (dd, J=8.4, 2.0 Hz, 1H), 7.05 (dd, J=8.8, 2.4 Hz, 1H), 5.18 (s, 2H), 3.41 (s, 3H), 1.75 (s, 9H); MS (ESI) m/z 431 (M+H⁺).

To tert-butyl 2-(benzyloxy)-7-(N-methylformamido)-9H-carbazole-9-carboxylate (120 mg, 0.28 mmol) in 50 mL MeOH was added Palladium on activated carbon (50 mg). The mixture was stirred at rt under H2 atmosphere for 3 h. Solid was filtered off and the filtrate was concentrated to afford tert-butyl 2-hydroxy-7-(N-methylformamido)-9H-carbazole-9-carboxylate as a brown solid (95 mg, 100%). This material was used directly for the next reaction without purification. MS (ESI) m/z 341 (M+H$^+$).

To tert-butyl 2-hydroxy-7-(N-methylformamido)-9H-carbazole-9-carboxylate (65 mg, 0.19 mmol) and 2-(2-(2-fluoroethoxy)ethoxy)ethyl 4-methylbenzenesulfonate (174 mg, 0.38 mmol) in 0.5 mL NMP was added Cs$_2$CO$_3$ (68 mg, 0.21 mmol). The mixture was stirred at rt for 15 h under Ar atmosphere and diluted with EtOAc (80 mL). It was washed with water (3×50 mL), and dried over MgSO$_4$. Solvent was removed under reduced pressure and the crude product was purified with silica chromatography (hexane/EtOAc) to afford tert-butyl 2-(N-methylformamido)-7-(2-(2-(2-(tosyloxy)ethoxy)ethoxy)ethoxy)-9H-carbazole-9-carboxylate (AD-CB-004Pb-WZ01191) as a clear oil (75 mg, 63%). $^1$H NMR (400 MHz, CDCl$_3$) δ 8.56 (s, 1H), 8.14 (s, 1H), 7.89 (s, 1H), 7.87 (d, J=8.0 Hz, 1H), 7.83 (d, J=8.8 Hz, 1H), 7.79 (m, 2H), 7.32 (d, J=8.4 Hz, 2H), 7.15 (dd, J=8.4, 2.0 Hz, 1H), 7.00 (dd, J=8.8, 2.4 Hz, 1H), 4.23 (m, 1H), 3.89 (m, 2H), 3.88 (m, 2H), 3.73-3.68 (m, 4H), 3.66-3.63 (m, 2H), 3.41 (s, 3H), 2.42 (s, 3H), 1.76 (s, 9H); MS (ESI) m/z 527 (M+H$^+$).

AD-CB-010S-WZ01183 suspension was heated at reflux for 15 h under Ar atmosphere and cooled to rt. It was added EtOAc (80 mL) and washed with brine (50 mL), water (2×80 mL), and dried over MgSO$_4$. After solvent removal, the residue was chromatographed (hexane/EtOAc) to afford N-(4'-(benzyloxy)-2'-nitrobiphenyl-4-yl)formamide as a yellow solid (395 mg, 75%). MS (ESI) m/z 349 (M+H$^+$).

A suspension of N-(4'-(benzyloxy)-2'-nitrobiphenyl-4-yl)formamide (350 mg, 1 mmol) in 2 mL of triethyl phosphite was heated at 145 C for 15 h under Ar atmosphere and cooled to rt. It was added 10 mL of hexane and let sit for 10 min. Solid was collected via filtration and washed with ether/hexane (v:v 1/1, 10 mL) and dried under high vacuum to N-(7-(benzyloxy)-9H-carbazol-2-yl)formamide as a light-brown solid (280 mg, 88%). MS (ESI) m/z 317 (M+H$^+$).

To N-(7-(benzyloxy)-9H-carbazol-2-yl)formamide (250 mg, 0.79 mmol) in 50 mL MeOH was added Palladium on activated carbon (60 mg). The mixture was stirred at rt under H2 atmosphere for 15 h. The mixture was concentrated under reduced pressure and dried under high vacuum to afford N-(7-hydroxy-9H-carbazol-2-yl)formamide mixed with the catalyst as a black solid (240 mg). This material was used directly for the next reaction without purification. MS (ESI) m/z 227 (M+H$^+$).

To N-(7-hydroxy-9H-carbazol-2-yl)formamide (30 mg) and 2-(2-(2-fluoroethoxy)ethoxy)ethyl 4-methylbenzenesulfonate (48 mg, 0.156 mmol) in 0.3 mL of NMP was added Cs$_2$CO$_3$ (42 mg, 0.13 mmol). The mixture was stirred at rt for

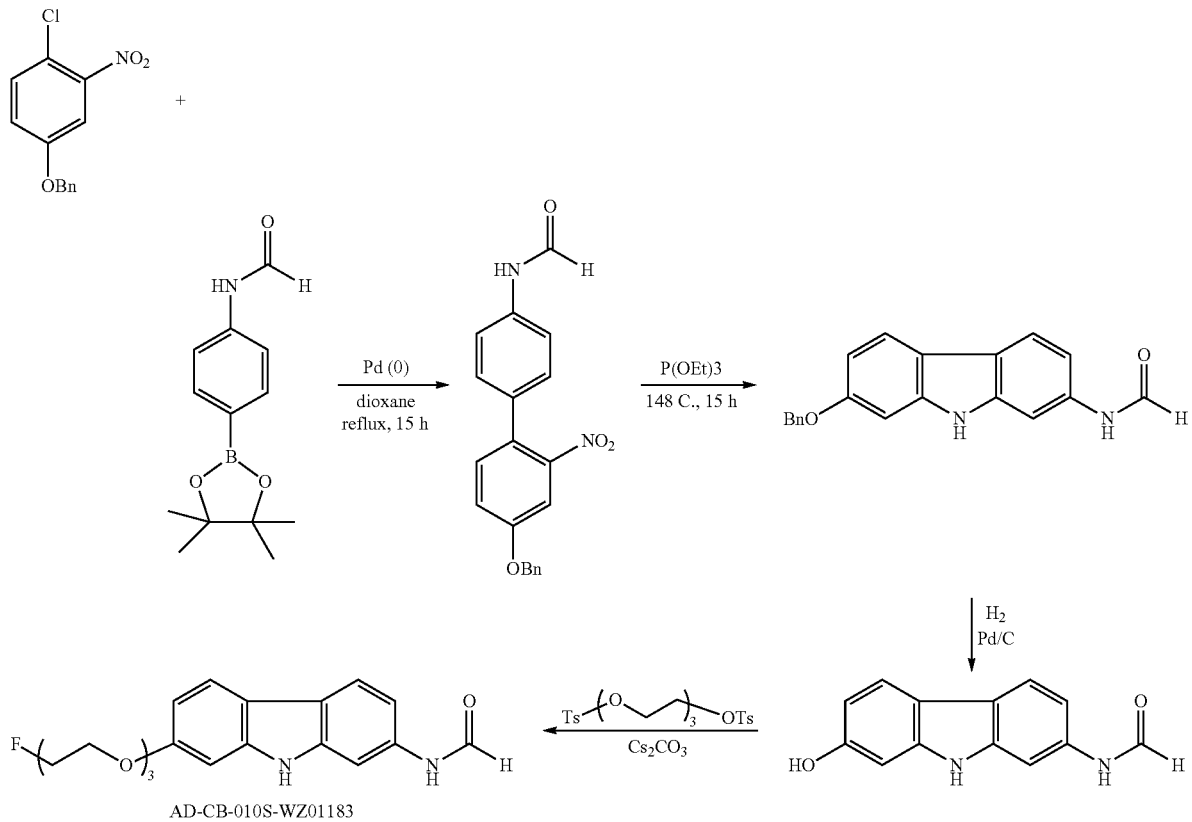

AD-CB-010S-WZ01183

To 4-(benzyloxy)-1-chloro-2-nitrobenzene (394 mg, 1.5 mmol) N-(4-(4,4,5,5-tetramethyl-1,3,2-dioxaborolan-2-yl)phenyl)formamide (370 mg, 1.5 mmol) in 6 mL dioxane was added 3 mL of a 1 M Na$_2$CO$_3$ (aq) solution and Tetrakis(triphenylphosphine)palladium (52 mg, 0.045 mmol). The 15 h under Ar atmosphere and diluted with EtOAc (30 mL). It was washed with water (3×30 mL) and dried over MgSO$_4$. After solvent removal, the residue was chromatographed (hexane/EtOAc) to N-(7-(2-fluoroethoxy)-9H-carbazol-2-yl)formamide (AD-CB-010S-WZ01183) as a white solid (17 mg, 36%). For the major rotomer: $^1$H NMR (400 MHz, acetone-d6) δ 10.10 (s, 1H), 9.28 (s, 1H), 8.39 (d, J=1.6 Hz, 1H), 8.11 (d, J=2.0 Hz, 1H), 7.91 (s, 1H), 7.87 (d, J=8.4, Hz, 2H), 7.17 (dd, J=8.4, 2.0 Hz, 1H), 7.01 (d, J=2.0 Hz, 1H), 6.80 (dd, J=8.4, 2.0 Hz, 1H), 4.58 (m, 1H), 4.46 (m, 1H), 4.21 (m, 2H), 3.88 (m, 2H), 3.77 (m, 1H), 3.73-3.66 (m, 5H); MS (ESI) m/z 361 (M+H$^+$).

AD-CB-012S-WZ01185

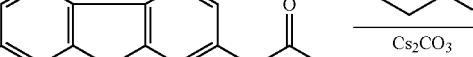

AD-CB-012S-WZ01185

Compound AD-CB-012S-WZ01185 was prepared using the same procedure for the preparation of AD-CB-010S-WZ01183. For the major rotomer: $^1$H NMR (400 MHz, acetone-d6) δ 10.08 (s, 1H), 9.19 (s, 1H), 8.26 (d, J=1.6 Hz, 1H), 8.00 (d, J=2.0 Hz, 1H), 7.84-7.77 (m, 3H), 7.07 (dd, J=8.4, 2.0 Hz, 1H), 6.93 (d, J=2.0 Hz, 1H), 6.69 (dd, J=8.4, 2.0 Hz, 1H), 4.73 (m, 1H), 4.61 (m, 1H), 4.24 (m, 1H), 4.17 (m, 1H); MS (ESI) m/z 273 (M+H$^+$).

AD-CB-024S-WZ02033

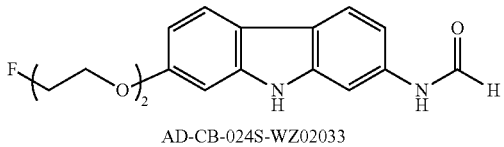

AD-CB-024S-WZ02033

Compound AD-CB-024S-WZ02033 was prepared using the same procedure for the preparation of AD-CB-010S-WZ01183. For the major rotomer: $^1$H NMR (400 MHz, acetone-d6) δ 10.19 (s, 1H), 9.31 (s, 1H), 8.38 (d, J=1.6 Hz, 1H), 8.11 (d, J=2.0 Hz, 1H), 7.88 (d, J=8.2 Hz, 2H), 7.19 (dd, J=8.4, 2.0 Hz, 1H), 7.03 (d, J=2.0 Hz, 1H), 6.79 (dd, J=8.4, 2.0 Hz, 1H), 4.62 (m, 1H), 4.50 (m, 1H), 4.20 (m, 2H), 3.88 (m, 2H), 3.83 (m, 1H), 3.75 (m, 1H); MS (ESI) m/z 317 (M+H$^+$).

AD-CB-013S-WZ-02001

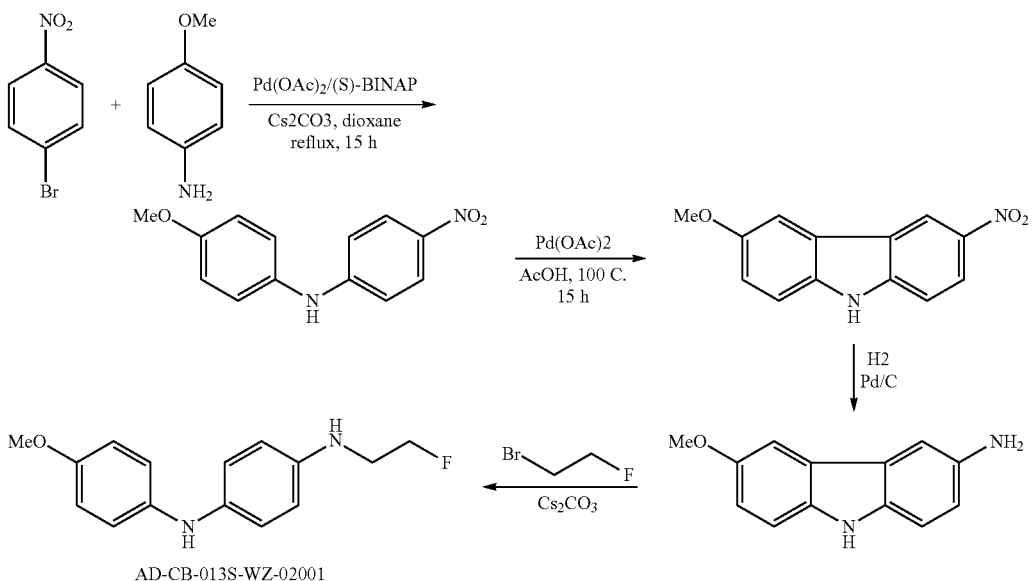

AD-CB-013S-WZ-02001

A mixture of palladium acetate (37 mg, 0.165 mmol) and BINAP (154 mg, 0.248 mmol) in 5 mL dioxane was stirred for 10 min under Ar atmosphere. To this mixture was added 1-bromo-4-nitrobenzene (1.11 g, 5.5 mmol), 4-methoxyaniline (745 mg, 6.07 mmol), CsCO$_3$ (2.5 g, 7.73 mmol), and 10 mL of dioxane. The mixture was heated at reflux for 15 h and cooled and diluted with ether (80 mL). The solid was removed through filtration and the filtrate was concentrated. The residue was chromatographed (hexane/EtOAc) to afford 4-methoxy-N-(4-nitrophenyl)aniline as a yellow solid (786 mg, 58%). MS (ESI) m/z 245 (M+H$^+$).

To 4-methoxy-N-(4-nitrophenyl)aniline (785 mg, 3.2 mmol) in 5 mL of AcOH was added Pd(OAc)2 (1.43 g, 6.4 mmol). The mixture was heated at 100° C. for 15 h under air atmosphere and cooled to rt and concentrated under reduced pressure. The residue was taken up in EtOAc (100 mL) and washed with NaHCO₃ (2×100 mL) and water (100 mL). After solvent removal, the crude was purified with chromatography (hexane/EtOAc) to afford 3-methoxy-6-nitro-9H-carbazole as a orange solid (495 mg, 64%).

¹H NMR (400 MHz, acetone-d6) δ 10.90 (s, 1H), 9.09 (d, J=2.4 Hz, 1H), 8.27 (dd, J=9.2, 2.4 Hz, 1H), 7.96 (d, J=2.4 Hz, 1H), 7.62 (d, J=9.2 Hz, 1H), 7.53 (d, J=8.8 Hz, 1H), 7.14 (dd, J=8.8, 2.8 Hz, 1H), 3.92 (s, 3H); MS (ESI) m/z 243 (M+H⁺).

To 3-methoxy-6-nitro-9H-carbazole (100 mg, 0.41 mmol) in 40 mL MeOH was added Palladium on activated carbon (50 mg). The mixture was stirred at rt under H2 atmosphere for 5 h. Solid was filtered off and the filtrate was concentrated to afford 6-methoxy-9H-carbazol-3-amine as a brown solid (80 mg, 92%). This material was used directly for the next reaction without purification. MS (ESI) m/z 213 (M+H⁺).

To 6-methoxy-9H-carbazol-3-amine (16 mg, 0.075 mmol) and 1-bromo-2-fluoroethane (48 mg, 0.375 mmol) in 0.3 mL of NMP was added Cs₂CO₃ (30 mg, 0.09 mmol). The mixture was stirred at rt for 72 h under Ar atmosphere and diluted with EtOAc (30 mL). It was washed with water (3×30 mL) and dried over MgSO₄. After solvent removal, the residue was purified by reversed-phase HPLC (buffer A: 0.05% aqueous TFA; buffer B: 0.05% TFA in MeCN) to afford a light-brown wax (5 mg, 26%). ¹H NMR (400 MHz, acetone-d6) δ 7.75 (s, 1H), 7.67 (s, 1H), 7.52 (d, J=2.4 Hz, 1H), 7.35 (t, J=9.6 Hz, 2H), 7.14 (d, J=8.0 Hz, 1H), 7.00 (dd, J=8.8, 2.4 Hz, 1H), 4.81 (t, J=5.2 Hz, 1H), 4.69 (t, J=4.8 Hz, 1H), 3.89 (s, 3H); MS (ESI) m/z 259 (M+H⁺).

Synthetic Scheme of CB 14-16, 19 and 20

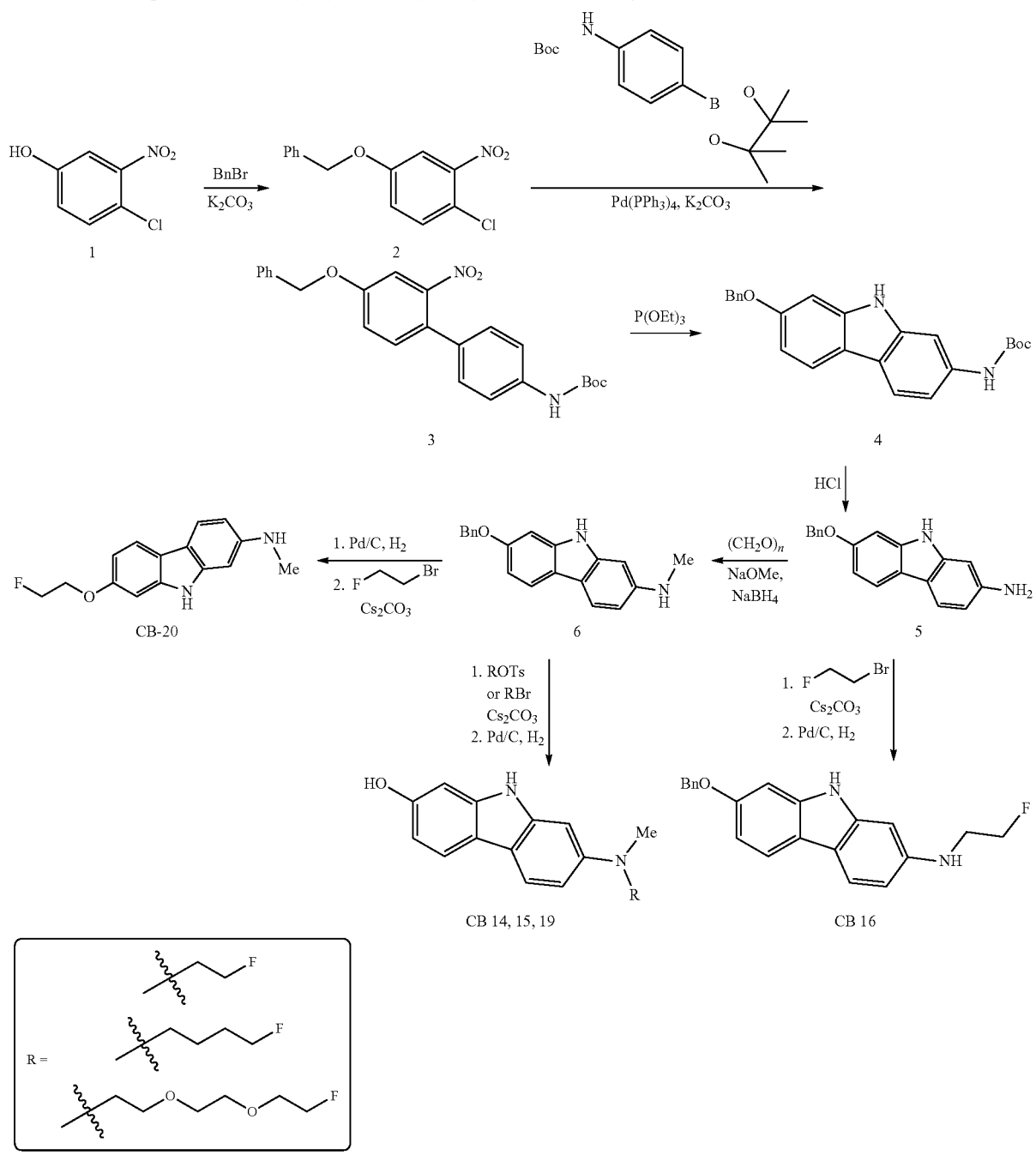

7-((4-fluorobutyl)(methyl)amino)-9H-carbazol-2-ol (CB-14)

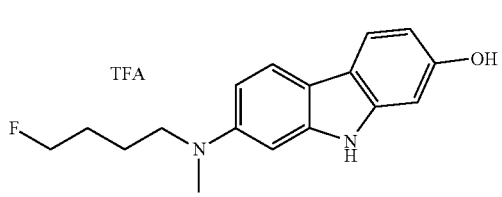 [SMILES: CN(CCCCF)c1ccc2c(c1)[nH]c1cc(O)ccc12]

To a round bottom flask containing Compound 6 (21 mg, 0.073 mmol) in DMF (1 ml), were added cesium carbonate (28.5 mg, 0.087 mmol) and 1-bromo-4-fluorobutane (56.4 mg, 0.364 mmol). The reaction was stirred at rt for 30 min. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (22 mg). The mixture was stirred at rt overnight under hydrogen (1 atm). The reaction was filtered through a celite plug, concentrated in vacuo and purified on HPLC to afford CB-14 (11 mg, 0.029 mmol, 40.3% yield). $^1$H-NMR (400 MHz, CD$_3$OD) δ: 8.74 (d, J=8.4 Hz, 1H), 7.85 (d, J=8.4 Hz, 1H), 7.53 (s, 1H), 7.25 (d, J=8.0 Hz, 1H), 6.85 (s, 1H), 6.73 (d, J=8.4 Hz, 1H), 4.44 (m, 1H), 4.32 (m, 1H), 3.70 (m, 2H), 3.35 (s, 3H), 1.74-1.67 (m, 4H); LRMS for C$_{19}$H$_{19}$F$_4$N$_2$O$_2$+H$^+$, calc'd: 384.1. found: 287.2 (M+H$^+$-TFA).

7-((2-fluoroethyl)(methyl)amino)-9H-carbazol-2-ol (CB-15)

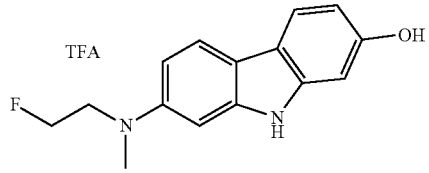 [SMILES: CN(CCF)c1ccc2c(c1)[nH]c1cc(O)ccc12]

To a round bottom flask containing Compound 6 (37 mg, 0.122 mmol) in DMF (0.5 ml), were added cesium carbonate (47.8 mg, 0.147 mmol) and 1-bromo-2-fluoroethane (78 mg, 0.612 mmol). The reaction was stirred at rt for 30 min. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (22 mg). The mixture was stirred at rt overnight under hydrogen (1 atm). The reaction was filtered through a celite plug, concentrated in vacuo and purified on HPLC to afford CB-15 (5 mg, 0.019 mmol, 7.3% yield). $^1$H-NMR (400 MHz, CD$_3$CN) δ: 7.96 (d, J=8.0 Hz, 1H), 7.87 (d, J=8.4 Hz, 1H), 7.31 (d, J=2.0 Hz, 1H), 7.05 (dd, J=8.0 Hz, 2.0 Hz, 1H), 6.90 (d, J=2.0 Hz, 1H), 6.76 (dd, J=8.0 Hz, 2.0 Hz, 1H), 4.86 (m, 1H), 4.74 (m, 1H), 4.60-4.52 (m, 2H), 3.28 (br, 1H), 3.03 (s, 3H); LRMS for C$_{17}$H$_{15}$F$_4$N$_2$O$_2$+H$^+$, calc'd: 356.1. found: 259.2 (M+H$^+$-TFA).

7-(2-fluoroethylamino)-9H-carbazol-2-ol (CB-16)

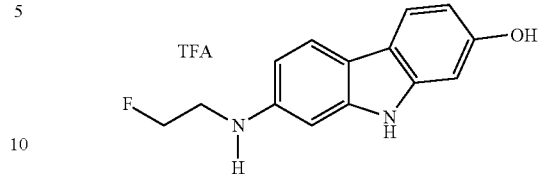

To a round bottom flask containing Compound 5 (21 mg, 0.073 mmol) in DMF (1 ml), were added cesium carbonate (28.5 mg, 0.087 mmol) and 1-bromo-2-fluoroethane (46 mg, 0.36 mmol). The reaction was stirred at rt for 72 hours. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (20 mg). The mixture was stirred at rt overnight under hydrogen (1 atm). The reaction was filtered through a celite plug, concentrated in vacuo and purified on HPLC to afford CB-16 (5 mg, 0.015 mmol, 20% yield). $^1$H-NMR (400 MHz, CD$_3$CN) δ: 9.00 (br, 1H), 7.77-7.73 (m, 2H), 6.82 (s, 1H), 6.81 (s, 1H), 6.72-6.65 (m, 2H), 4.71 (m, 1H), 4.60 (m, 1H), 3.60-3.50 (m, 2H); LRMS for C$_{16}$H$_{13}$F$_4$N$_2$O$_2$±H$^+$, calc'd: 342.3. found: 245.1 (M+H$^+$-TFA).

7-(2-(2-(2-fluoroethoxy)ethoxy)ethyl)(methyl)amino)-9H-carbazol-2-ol (CB-19)

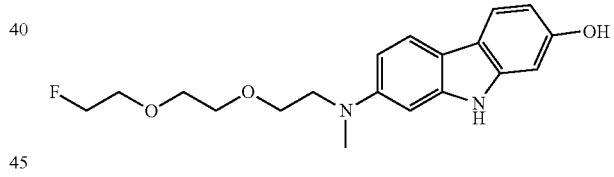

To a round bottom flask containing Compound 6 (41 mg, 0.14 mmol) in DMF (0.5 ml), were added cesium carbonate (53 mg, 0.16 mmol) and 2-(2-(2-fluoroethoxy)ethoxy)ethyl 4-methylbenzenesulfonate (125 mg, 0.407 mmol). The reaction was stirred at rt for 4 weeks. The reaction was work-up with EtOAc (15 mL×3) and water (10 mL). The organic layers were washed with brine (10 mL), dried and concentrated in vacuo. The residue was dissolved in MeOH (10 ml). To the reaction mixture, was added Pd/C (20 mg). The mixture was stirred at rt overnight under hydrogen atmosphere (1 atm). The reaction was filtered through a celite plug, concentrated in vacuo and purified on HPLC to afford CB-19 (7 mg, 0.020 mmol, 14% yield). $^1$H-NMR (400 MHz, CD$_3$CN) δ: 9.43 (br, 1H), 8.07 ((d, J=8.4 Hz, 1H), 7.91 (d, J=8.4 Hz, 1H), 7.58 (d, J=2.4 Hz, 1H), 7.24 (dd, J=8.0 Hz, 2.0 Hz, 1H), 6.93 (d, J=2.0 Hz, 1H), 6.77 (dd, J=8.0 Hz, 2.0 Hz, 1H), 4.59 (m, 1H), 4.52 (m, 1H), 3.74-3.50 (m, 10H), 3.28 (s, 3H); LRMS for C$_{21}$H$_{23}$F$_4$N$_2$O$_4$+Na$^+$, calc'd: 444.2. found: 347.2 (M+H$^+$-TFA).

7-(2-fluoroethoxy)-N-methyl-9H-carbazol-2-amine (CB-20)

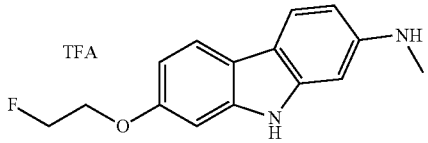 [SMILES: CNc1ccc2c(c1)[nH]c1cc(OCCF)ccc12]

To a round bottom flask containing Compound 6 (90 mg, 0.29 mmol) in MeOH (10 ml), were added Pd/C (20 mg). The reaction was purged with hydrogen and stirred at rt for 2 h under hydrogen atmosphere (1 atm). The reaction was filtered through a celite plug concentrated in vacuo to afford a dark solid (60 mg, 0.28 mmol, 95% yield). To a round bottom flask containing the above dark solid (15 mg, 0.071 mmol) in DMF (0.5 mL), was added cesium carbonate (21 mg, 0.65 mmol) and 2-bromo-1-fluoroethane (8.1 mg, 0.065 mmol). The reaction was stirred at rt overnight. The reaction was concentrated in vacuo via MeCN co-evaporation. The residue was purified on HPLC to afford CB-20 (7.0 mg, 0.027 mmol, 38% yield). $^1$H NMR (400 MHz, CD$_3$CN) δ: 9.52 (br, 1H), 7.91-7.86 (m, 2H), 7.13 (s, 1H), 7.02 (s, 1H), 6.88 (d, J=7.6 Hz, 1H), 6.82 (dd, J=7.6 Hz, J=2.4 Hz 1H), 4.85 (m, 1H), 4.72 (m, 1H), 4.34-4.25 (m, 2H), 2.96 (s, 3H); LRMS for C$_{17}$H$_{15}$N$_2$O$_2$+H$^+$, calc'd: 356.1. found: 259.1 (M+HtTFA).

Synthetic Scheme of CB 25, 26

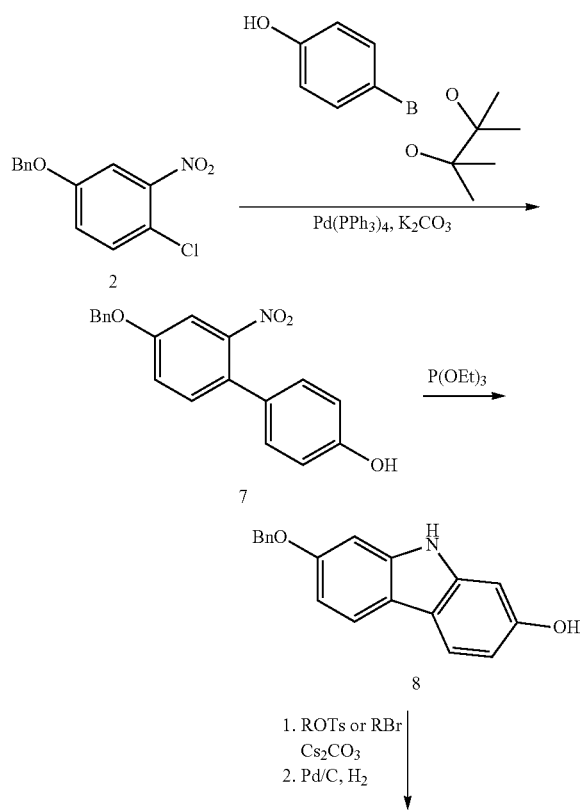

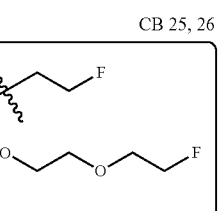

CB 25, 26

4'-(benzyloxy)-2'-nitrobiphenyl-4-ol (Compound 7)

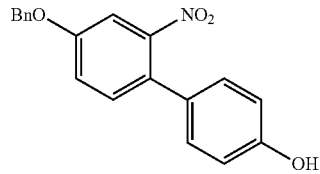 [SMILES: O=[N+]([O-])c1cc(OCc2ccccc2)ccc1-c1ccc(O)cc1]

A round bottom flask charged with Compound 2 (1.96 g, 7.44 mmol), 4-Hydroxyphenylboronic acid pinacol ester (1.56 g, 7.09 mmol), terakis(triphenylphosphine) palladium (0.410 g, 0.354 mmol), were purged with Argon. To the mixture, was added DME (10 ml) and potassium carbonate (1.96 g, 14.2 mmol) in Water (2 ml). The mixture was heated for 60 hours. The reaction was diluted with HCl (1N, 10 mL) and brine (40 mL), then extracted with EtOAc (50 mL×3). The combined organic layer were washed with Brine (50 mL), dried (MgSO4) and concentrated in vacuo. The residue was purified on a silica gel column (EtOAc:Hexanes=1:4) to afford Compound 7 as a yellow solid (2 g, 6.22 mmol, 88% yield). $^1$H-NMR (400 MHz, CDCl$_3$) δ: 7.45-7.33 (m, 7H), 7.37-7.15 (m, 3H), 6.88-6.85 (m, 2H), 5.14 (s, 2H), 5.03 (s, 1H); LRMS for C$_{19}$H$_{15}$NO$_4$+H$^+$, calc'd: 322.1. found: 322.1 (M+H$^+$).

7-(benzyloxy)-9H-carbazol-2-ol (Compound 8)

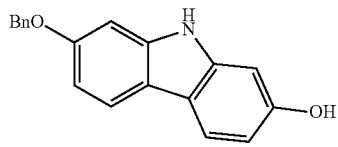 [SMILES: Oc1ccc2c(c1)[nH]c1cc(OCc3ccccc3)ccc12]

To a pressure resistant vial, was added Compound 7 (2.00 g, 6.22 mmol and Triethyl phosphite (6.53 ml, 37.3 mmol. The mixture was heated to 160° C. overnight. The reaction mixture was concentrated in vacuo. The residue was suspended in chloroform (20 mL), solid precipitate formed and was filtered and washed with ether (10 mL×2) to afford Compound 8 (900 mg, 3.11 mmol, 50.0% yield). $^1$H-NMR (400 MHz, DMSO) δ: 10.81 (br, 1H), 9.25 (br, 1H), 7.80 (d, J=8.4 Hz, 1H), 7.72 (d, J=8.4 Hz, 1H), 7.50-7.33 (m, 5H), 6.95 (s, 1H), 6-78-6.76 (m, 2H), 6.56 (dd, J=8.4, 2.0 Hz 1H), 5.16 (s, 2H); LRMS for $C_{19}H_{15}NO_2+H^+$, calc'd: 290.1. found: 290.1 (M+H$^+$).

7-(2-fluoroethoxy)-9H-carbazol-2-ol (CB-25)

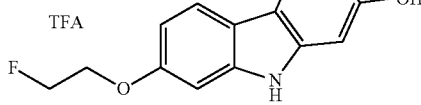

To a round bottom flask containing Compound 8 (50 mg, 0.17 mmol) in DMF (1 ml), was added cesium carbonate (62 mg, 0.19 mmol) and 1-bromo-2-fluoroethane (33 mg, 0.26 mmol). The reaction was stirred at rt for 15 h and then diluted with water (15 mL). White precipitate (50 mg) was collected via filtration and dried in vacu. The solid was dissolved in MeOH (10 mL). To the reaction, was added Pd/C (30 mg) and acetic acid (5 drops). The mixture was stirred under hydrogen (1 atm) atmosphere for 20 h and then filtered through a celite plug, concentrated in vacuo. The residue was purified on HPLC to afford CB-25 (18 mg, 0.053 mmol, 31% yield). $^1$H NMR (400 MHz, CD$_3$CN) δ: 8.99 (br, 1H), 7.72 (d, J=8.4 Hz, 1H), 7.67 (d, J=8.4 Hz, 1H), 6.88 (d, J=2.0 Hz, 1H), 6.76 (d, J=2.0 Hz, 1H), 6.67 (dd, J=8.0 Hz, 2.0 Hz, 1H), 6.58 (dd, J=8.0 Hz, 2.0 Hz, 1H), 4.75-4.74 (m, 1H), 4.63-4.61 (m, 1H), 4.23-4.13 (m, 2H); LRMS for $C_{16}H_{12}F_4NO_3+H^+$, calc'd: 343.1. found: 246.0 (M+H$^+$-TFA).

7-(2-(2-(2-fluoroethoxy)ethoxy)ethoxy)-9H-carbazol-2-ol (CB-26)

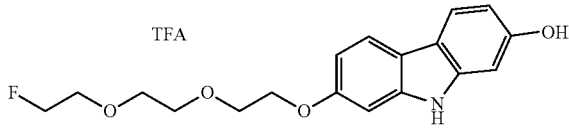 [SMILES: Oc1ccc2c(c1)[nH]c1cc(OCCOCCOCCF)ccc12]

To a round bottom flask containing Compound 8 (50 mg, 0.17 mmol) in DMF (1 ml), was added cesium carbonate (56 mg, 0.17 mmol) and 2-(2-(2-fluoroethoxy)ethoxy)ethyl 4-methylbenzenesulfonate (53 mg, 0.17 mmol). The reaction was stirred at rt for 15 h and then diluted with water (15 mL). White precipitate (72 mg) was collected via filtration and dried in vacou. The solid was dissolved in MeOH (10 mL). To the reaction, was added Pd/C (20 mg) and acetic acid (5 drops). The mixture was stirred under hydrogen (1 atm) atmosphere for 20 h and then filtered through a celite plug and concentrated in vacuo. The residue was purified on HPLC to afford CB-26 (20 mg, 0.046 mmol, 27% yield). $^1$H NMR (400 MHz, CD$_3$CN) δ: 9.03 (br, 1H), 7.81-7.75 (m, 2H), 6.96 (d, J=2.4 Hz, 1H), 6.84 (d, J=2.4 Hz, 1H), 6.76 (dd, J=7.6 Hz, 2.0 Hz, 1H), 6.67 (dd, J=7.6 Hz, 2.0 Hz, 1H), 4.59-4.57 (m, 1H), 4.47-4.45 (m, 1H), 4.17-4.15 (m, 2H), 3.83-3.63 (m, 8H); LRMS for $C_{20}H_{20}NO_5+H^+$, calc'd: 431.1. found: 334.1 (M+H$^+$-TFA).

Synthetic Scheme of CB 27

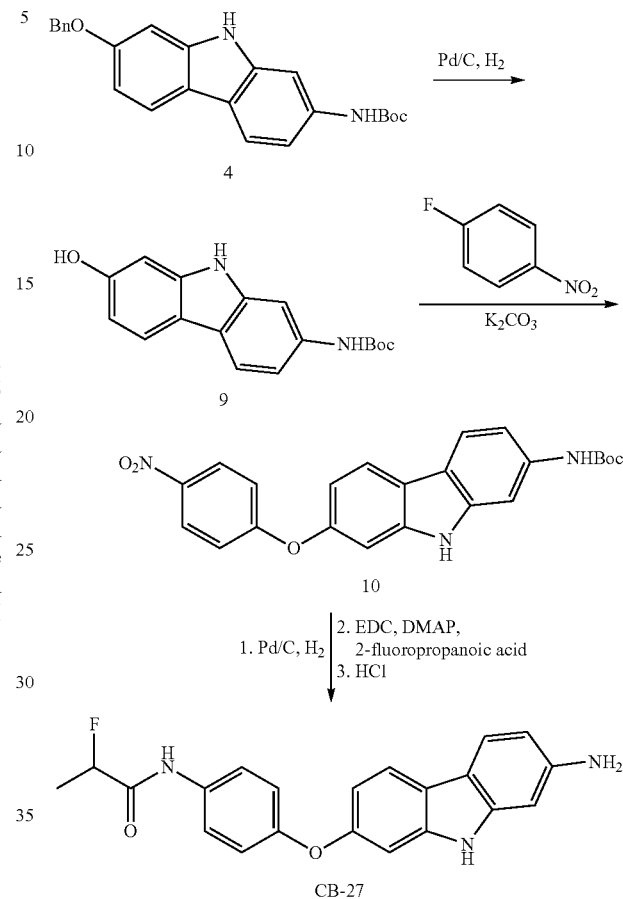

tert-butyl 7-hydroxy-9H-carbazol-2-ylcarbamate (Compound 9)

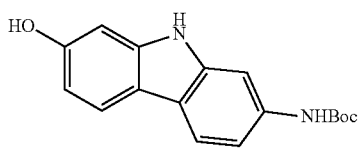 [SMILES: CC(C)(C)OC(=O)Nc1ccc2c(c1)[nH]c1cc(O)ccc12]

To a round bottom flask containing Compound 4 (1.0 g, 2.6 mmol) in MeOH (150 mL), was added palladium on charcoal (400 mg). The flask was purged with hydrogen gas and stirred under hydrogen atmosphere overnight. The reaction mixture was filtered through a celite plug and concentrated to afford Compound 9 as a grey solid (700 mg, 2.34 mmol, 90% yield). $^1$H NMR (400 MHz, (CD$_3$)$_2$CO) δ: 9.99 (br, 1H), 8.41 (br, 1H), 8.24 (s, 1H), 7.86 (s, 1H), 7.81-7.78 (m, 2H), 7.18 (dd, J=8.4 Hz, 2.0 Hz, 1H), 6.90 (d, J=2.0 Hz, 1H), 6.70 (dd, J=8.4 Hz, 2.0 Hz, 1H), 1.51 (s, 9H).

tert-butyl 7-(4-nitrophenoxy)-9H-carbazol-2-ylcarbamate (Compound 10)

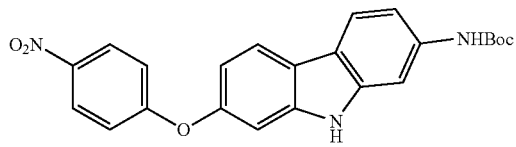 [SMILES: CC(C)(C)OC(=O)Nc1ccc2c(c1)[nH]c1cc(Oc3ccc([N+](=O)[O-])cc3)ccc12]

To a round bottom flask containing Compound 9 (80 mg, 0.268 mmol) in DMF (2 mL) was added potassium carbonate (74.1 mg, 0.536 mmol) and 4-fluoro-nitrobenzene (41.6 mg, 0.295 mmol). The reaction mixture was heated for 20 min at 140° C. After cooling down to rt, the mixture was diluted with water (20 mL) and extracted with EtOAc (20 mL×3). The organic layers were dried, concentrated. The residue was purified on a silica gel column (EtOAc:Hexanes=3:7) to afford Compound 10 as a yellow solid (50 mg, 0.12 mmol, 44% yield). $^1$H NMR (400 MHz, CDCl$_3$) δ: 8.22 (d, J=9.2 Hz, 2H), 8.10 (br, 1H), 8.00-7.90 (m, 3H), 7.12 (s, 1H), 7.06-6.90 (m, 4H), 6.70 (br, 1H), 1.56 (s, 9H); LRMS for $C_{23}H_{21}N_3O_5$+H$^+$, calc'd: 420.2. found: 420.2 (M+H$^+$).

tert-butyl 7-(4-nitrophenoxy)-9H-carbazol-2-ylcarbamate (CB-27)

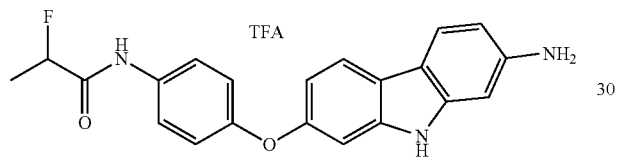

To a round bottom flask containing Compound 10 (35 mg, 0.083 mmol) in MeOH (5 mL), was added palladium on charcoal (10 mg). The flask was purged with hydrogen gas and stirred under hydrogen atmosphere overnight. The reaction mixture was filtered through a silica gel plug and concentrated to afford the amine intermediate (23 mg). To a vial containing 2-fluoropropanoic acid (10.87 mg, 0.118 mmol) in DCM (1 mL), was added EDC (22.64 mg, 0.118 mmol) and DMAP (1 mg). The mixture was stirred at rt for 5 min. The above amine intermediate was dissolved in DCM (1 ml) and added into the reaction vial dropwise. The reaction mixture was stirred at rt from 3 hour. The reaction mixture was then washed with water (3 mL) and concentrated. The residue was redissolved in HCl (4.0 M in dioxane, 5 mL) and stirred overnight. The mixture was concentrated and purified on HPLC to afford CB-27 (12 mg, 0.026 mmol, 31% yield). $^1$H NMR (400 MHz, CD$_3$CN) δ: 9.42 (br, 1H), 8.69 (br, 1H), 7.92 (d, J=8.4 Hz, 1H), 7.87 (d, J=8.4 Hz, 1H), 7.60 (m, 2H), 7.04-7.01 (m, 4H), 6.86 (d, J=8.0 Hz, 1H), 6.84 (d, J=8.0 Hz, 1H), 5.11 (dt, J=49.2, 6.8 Hz, 1H), 1.58 (dd, J=24.8, 6.8 Hz, 3H); LRMS for $C_{23}H_{18}F_4N_3O_3$+H$^+$, calc'd: 460.1. found: 364.1 (M+H$^+$-TFA).

Experimental Section for the Preparation of Carbazole Derivatives

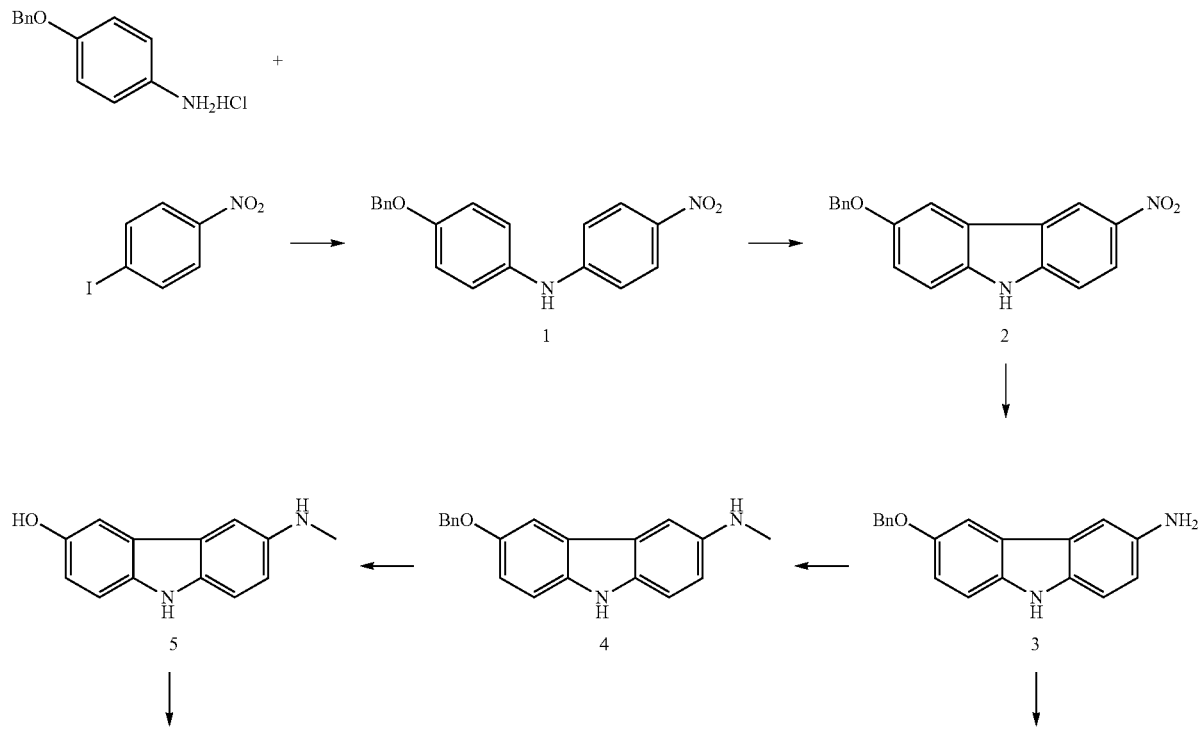

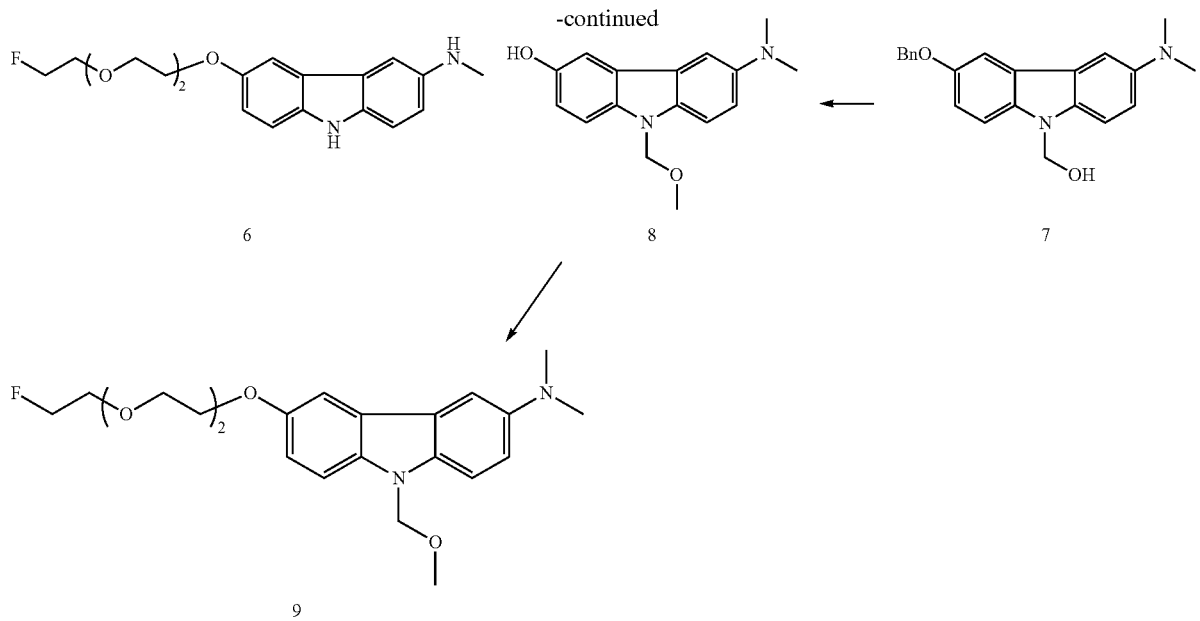

4-(Benzyloxy)-N-(4-nitrophenyl)aniline 1

To a oven dried flask was charged with Pd(OAc)$_2$ (81 mg, 0.36 mmol) and (S)-(−)-BINAP (336 mg, 0.54 mmol), followed by toluene (10 mL). The mixture was stirred under Ar at room temperature for 5 min. To this mixture was added 4-nitroiodobenzene (3.0 g, 12 mmol), 4-benzyloxyaniline hydrochloride (3.39 g, 14.4 mmol), Cs$_2$CO$_3$ (9.8 g, 30 mmol) and toluene (40 mL). The resulting mixture was heated under Ar at 100° C. for 16 hrs, and then cooled to room temperature and poured into H$_2$O (100 mL). The layers were separated. The aqueous layer was extracted with EtOAc (3×20 mL). The combined organic layers were washed with brine (2×20 mL), dried (MgSO$_4$) and filtered. The filtrate was concentrated. The residue was purified via column chromatography (silica gel, 5-40% EtOAc/hexane) to give the desired product as an orange solid (1.2 g, 31%). $^1$H NMR (CDCl$_3$, 400 MHz) δ: 8.09 (d, J=9.2 Hz, 2H), 7.30-7.49 (m, 5H), 7.15 (d, J=9.2 Hz, 2H), 7.01 (d, J=9.2 Hz, 2H), 6.77 (d, J=8.8 Hz, 2H), 6.10 (br s, 1H), 5.09 (s, 2H). MS: m/z=321 (M+H$^+$)$^+$.

3-(Benzyloxy)-9-nitro-9H-carbazole 2

A mixture of 4-(benzyloxy)-N-(4-nitrophenyl)aniline 1 (0.5 g, 1.56 mmol) and Pd(OAc)$_2$ (0.8 g, 3.56 mmol) in acetic acid (20 mL) was refluxed and monitored by TLC. After refluxing for 2 hrs, TLC showed that no starting material was present. It was concentrated in vacuo to remove acetic acid. The residue was diluted with EtOAc (30 mL), washed with H$_2$O (20 mL), sat. NaHCO$_3$ solution (2×20 mL), brine (20 mL), and then dried (MgSO$_4$) and filtered. The filtrate was concentrated in vacuo. The residue was purified via column chromatography (silica gel, 5-40% EtOAc/hexane) to give the desired product 2 as a dark yellow solid (100 mg, 20%). $^1$H NMR (acetone-d$_6$, 400 MHz) δ: 10.92 (br s, 1H), 9.08 (d, J=2.0 Hz, 1H), 8.28 (dd, J=8.8, 2.4 Hz, 1H), 8.07 (d, J=2.4 Hz, 1H), 7.63 (d, J=9.2 Hz, 1H), 7.55 (d, J=8.8 Hz, 3H), 7.40 (t, J=7.2 Hz, 2H), 7.33 (t, J=7.2 Hz, 1H), 7.24 (dd, J=8.8, 2.4 Hz, 1H), 5.26 (s, 2H). MS: m/z=319 (M+H$^+$)$^+$.

3-Amino-6-(benzyloxy)-9H-carbazole 3

To a suspension of 3-(benzyloxy)-9-nitro-9H-carbazole 2 (100 mg, 0.31 mmol) and Cu(OAc)$_2$ (57 mg, 0.31 mmol) in EtOH (20 mL) was added NaBH$_4$ (240 mg, 6.3 mmol). The resulting mixture was stirred at room temperature for 3 hrs, and then concentrated in vacuo. The residue was dissolved in H$_2$O (30 mL), extracted with EtOAc (2×30 mL). The combined organic layers were dried (MgSO$_4$), filtered and concentrated in vacuo to give a solid (90 mg). It was used directly in the next step without any further purification. $^1$H NMR (acetone-d$_6$, 400 MHz) δ: 9.67 (br s, 1H), 7.57 (d, J=2.4 Hz, 1H), 7.52 (d, J=6.8 Hz, 2H), 7.39 (t, J=6.8 Hz, 2H), 7.26-7.33 (m, 3H), 7.19 (d, J=8.8 Hz, 1H), 7.03 (dd, J=8.8, 2.4 Hz, 1H), 6.81 (dd, J=8.8, 2.4 Hz, 1H), 5.17 (s, 2H), 4.24 (br s, 2H). MS: m/z=289 (M+H$^+$)$^+$.

6-(Benzyloxy)-N-methyl-9H-carbazol-3-amine 4

To a suspension of 3-amino-6-(benzyloxy)-9H-carbazole 3 (90 mg, 0.31 mmol) and paraformaldehyde (47 mg, 1.57 mmol) in MeOH (20 mL) was added a solution of NaOMe in MeOH (0.32 mL, 1.56 mmol). The resulting mixture was heated at 80° C. for 1 h, then NaBH$_4$ (59 mg, 1.55 mmol) was added. The resulting mixture was heated at 80° C. for 2 hrs, and then cooled to room temperature. To this solution was added NaOH (1 N, 30 mL). The mixture was then extracted with CH$_2$Cl$_2$ (3×20 mL). The combined organic layers were dried (MgSO$_4$), filtered. The filtrate was concentrated in vacuo to give a brown solid (93 mg, 100%). It was used directly in the next step without any further purification. $^1$H NMR (acetone-d$_6$, 400 MHz) δ: 9.68 (br s, 1H), 7.67 (d, J=2.4 Hz, 1H), 7.53 (d, J=7.6 Hz, 2H), 7.20-7.42 (m, 6H), 7.03 (dd, J=8.8, 2.4 Hz, 1H), 6.79 (dd, J=8.4, 2.4 Hz, 1H), 5.17 (s, 2H), 2.85 (s, 3H). MS: m/z=303 (M+H$^+$)$^+$.

6-(Methylamino)-9H-carbazol-3-ol 5

A mixture of 6-(benzyloxy)-N-methyl-9H-carbazol-3-amine 4 (93 mg, 0.31 mmol), Pd/C (10 mg) and acetic acid (10 drops) in MeOH (10 mL) was hydrogenated at room temperature for 1.5 hrs. It was passed through a short Celite pad. The filtrate was concentrated in vacuo to give the desired product 5 (66 mg). It was used directly in the next step without any further purification. MS: m/z=213 (M+H$^+$)$^+$.

[3-(Benzyloxy)-6-(dimethylamino)-9H-carbazol-9-yl]methanol 7

To a solution of 6-(benzyloxy)-N-methyl-9H-carbazol-3-amine 4 (110 mg, 0.38 mmol) and aqueous formaldehyde solution (37%, 1.0 mL) in acetonitrile (30 mL) was added NaB(OAc)$_3$ (323 mg, 1.52 mmol). The resulting mixture was stirred at room temperature for 6 hrs, and then concentrated. The residue was dissolved in H$_2$O (30 mL), extracted with CH$_2$Cl$_2$ (2×30 mL). The combined organic layers were dried (MgSO$_4$), filtered. The filtrate was concentrated in vacuo to give the desired product (0.12 g). It was used directly in the next step without any further purification. MS: m/z=347 (M+H$^+$)$^+$.

6-(Dimethylamino)-9-(methoxymethyl)-9H-carbazol-3-ol 8

A mixture of [3-(benzyloxy)-6-(dimethylamino)-9H-carbazol-9-yl]methanol 7 (120 mg,), Pd/C (100 mg) and acetic acid (cat. amount) in MeOH (15 mL) was hydrogenated at room temperature for 4 hrs. It was filtered through a short Celite pad. The filtrate was concentrated in vacuo to give the desired product (94 mg, 100%). $^1$H NMR (acetone-d$_6$, 400 MHz) δ: 7.38-7.50 (m, 4H), 7.05 (dd, J=8.8, 2.4 Hz, 1H), 6.97 (dd, J=8.4, 2.4 Hz, 1H), 5.62 (s, 2H), 3.20 (s, 3H), 2.94 (s, 6H). MS: m/z=271 (M+H$^+$)$^+$.

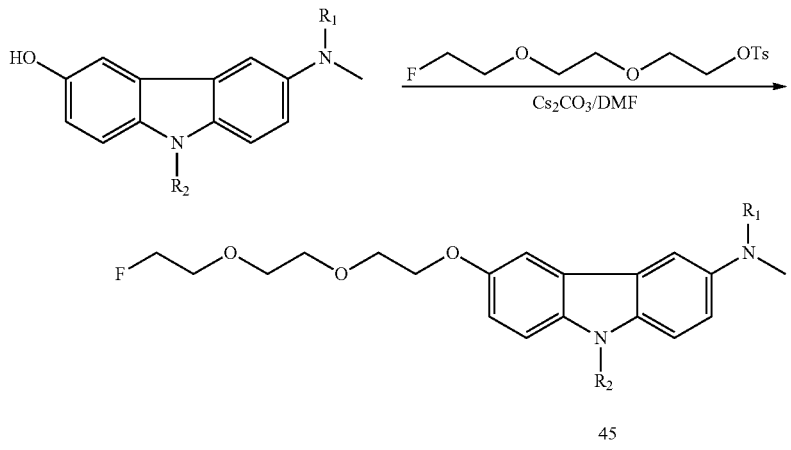

General Procedures for the Preparation of O-Alkylated Carbazole Derivatives:

To a solution of carbazol-3-ol derivatives (1 eq.) and Cs$_2$CO$_3$ (1.5 eq.) in DMF (10 mL) was added a solution of 24242-fluoroethoxy)ethoxy)ethyl-4-methylbenzenesulfonate (1.2 eq.) in DMF (1.0 mL). The resulting mixture was stirred at room temperature overnight, and then concentrated in vacuo. The residue was purified via column chromatography (silica gel, 5-50% EtOAc/hexane) to provide the desired products.

6-(2-(2-(2-Fluoroethoxy)ethoxy)ethoxy)-N-methyl-9H-carbazol-3-amine 6

(3 mg, 5%). $^1$H NMR (acetone-d$_6$, 400 MHz) δ: 7.59 (d, J=2.4 Hz, 1H), 7.28-7.33 (m, 2H), 7.26 (d, J=8.4 Hz, 1H), 6.97 (dd, J=8.8, 2.4 Hz, 1H), 6.85 (dd, J=8.8, 2.0 Hz, 1H), 4.51 (dt, J=48, 4.0 Hz, 2H), 4.19 (t, J=4.4 Hz, 2H), 3.61-3.88 (m, 8H), 3.87 (s, 3H). MS: m/z=347 (M+H$^+$)$^+$.

6-(2-(2-(2-Fluoroethoxy)ethoxy)ethoxy)-9-(methoxymethyl)-N,N-dimethyl-9H-carbazol-3-amine 9

(50 mg, 36%). $^1$H NMR (acetone-d$_6$, 400 MHz) δ: 7.68 (d, J=2.4 Hz, 1H), 7.46-7.52 (m, 3H), 7.04-7.08 (m, 2H), 5.66 (s, 2H), 4.52 (dt, J=48.4, 4.4 Hz, 2H), 4.21 (t, J=4.8 Hz, 2H), 3.63-3.87 (m, 8H). MS: m/z=405 (M+H$^+$)$^+$.

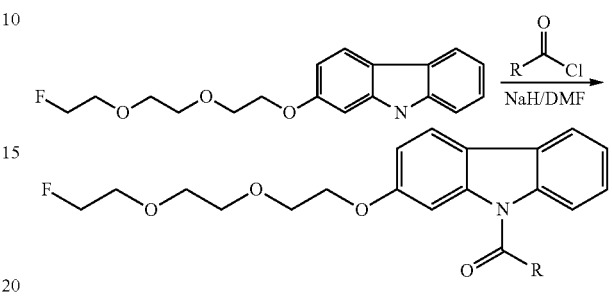

General Procedures for the Preparation of Acylated Carbazole Derivatives:

To a solution of 2-(2-(2-(2-fluoroethoxy)ethoxy)ethoxy)-9H-carbazole (1.0 eq.) in DMF (3.0 mL) was added NaH (excess). After stifling at room temperature for 5 min, an acyl halide (excess) was added. The resulting mixture was stirred at room temperature overnight, and then concentrated in vacuo. The residue was purified via column chromatography (silica gel, 0-40% EtOAc/hexane) to give the desired product.

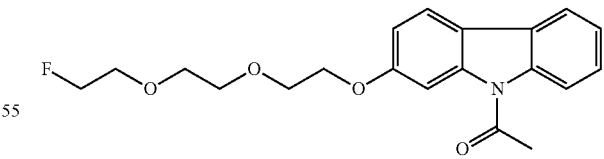

1-(2-(2-(2-(2-Fluoroethoxy)ethoxy)ethoxy)-9H-carbazol-9-yl)ethanone (4 mg, 36%). $^1$H NMR (CDCl$_3$, 400 MHz) δ: 8.21 (d, J=8.0 Hz, 1H), 7.99-8.25 (m, 2H), 7.94 (d, J=2.4 Hz, 1H), 7.36-7.46 (m, 2H), 7.06 (dd, J=8.4, 2.4 Hz, 1H), 4.52 (dt, J=48, 4.4 Hz, 2H), 4.27 (t, J=4.4 Hz, 2H), 3.89 (t, J=8.8 Hz, 2H), 3.64-3.78 (m, 6H), 2.91 (s, 3H). MS: m/z=360 (M+H+)+.

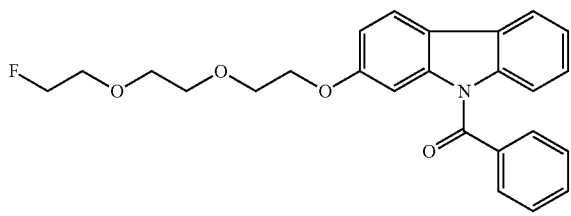 [SMILES: O=C(c1ccccc1)n1c2ccccc2c2ccc(OCCOCCOCCF)cc21]

1-(2-(2-(2-(2-Fluoroethoxy)ethoxy)ethoxy)-9H-carbazol-9-yl)phenylmethanone (51 mg, 78%). $^1$H NMR (CDCl$_3$, 400 MHz) δ: 7.84-7.92 (m, 2H), 7.62-7.74 (m, 3H), 7.53 (t, J=8.0 Hz, 2H), 7.27-7.33 (m, 2H), 7.17-7.23 (m, 1H), 6.99 (dd, J=8.4, 2.4 Hz, 1H), 4.57 (dt, J=47.6, 4.4 Hz, 2H), 4.06 (t, J=4.8 Hz, 2H), 3.70-3.87 (m, 8H). MS: m/z=422 (M+H+)+.

Preparation of 2-(7-formamido-9H-carbazol-2-yloxy)ethyl 4-methylbenzenesulfonate: AD-CB-012P-WZ02039

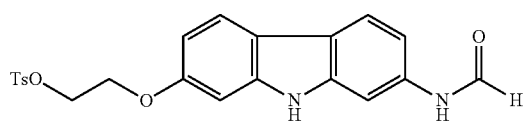 [SMILES: Cc1ccc(S(=O)(=O)OCCOc2ccc3c(c2)[nH]c2cc(NC=O)ccc23)cc1]

Compound 2-(7-formamido-9H-carbazol-2-yloxy)ethyl 4-methylbenzenesulfonate (AD-CB-012P-WZ02039) was prepared using the same procedure for the preparation of AD-CB-012S-WZ01185) from N-(7-hydroxy-9H-carbazol-2-yl)formamide (100 mg) and ethane-1,2-diylbis(4-methylbenzenesulfonate) (325 mg). (white solid, 22 mg, 12%). For the major rotomer: $^1$H NMR (400 MHz, acetone-d6) δ 10.19 (s, 1H), 9.31 (s, 1H), 8.38 (d, J=1.6 Hz, 1H), 8.11 (d, J=2.0 Hz, 1H), 7.90-7.81 (m, 4H), 7.45 (d, J=8.4 Hz, 2H), 7.19 (dd, J=8.4, 2.0 Hz, 1H), 6.95 (d, J=2.0 Hz, 1H), 6.69 (dd, J=8.4, 2.0 Hz, 1H), 4.43-4.41 (m, 2H), 4.29-4.27 (m, 2H); MS (ESI) m/z 425 (M+H+).

Preparation of N-(7-(4-fluorobutoxy)-9H-carbazol-2-yl)formamide: AD-CB-30S-WZ02055

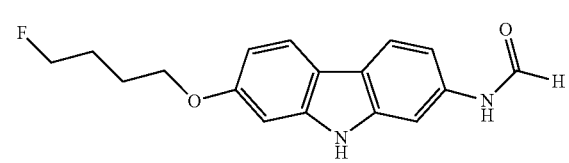 [SMILES: O=CNc1ccc2c(c1)[nH]c1cc(OCCCCF)ccc12]

Compound N-(7-(4-fluorobutoxy)-9H-carbazol-2-yl)formamide (AD-CB-30S-WZ02055) was prepared using the same procedure for the preparation of AD-CB-012S-WZ01185) from N-(7-hydroxy-9H-carbazol-2-yl)formamide (20 mg) and 1-bromo-4-fluorobutane (27 mg). (white solid, 11 mg, 42%). $^1$H NMR (400 MHz, acetone-d6) δ 10.18 (s, 1H), 9.31 (s, 1H), 8.39 (d, J=2.0 Hz, 1H), 8.11 (d, J=2.0 Hz, 1H), 7.95 (d, J=1.6 Hz, 2H), 7.88 (d, J=2.0 Hz, 1H), 7.20 (dd, J=8.4, 2.0 Hz, 1H), 7.03 (d, J=2.4 Hz, 1H), 6.79 (dd, J=8.4, 2.4 Hz, 1H), 4.61 (m, 1H), 4.49 (m, 1H), 4.11 (m, 2H), 1.97-1.88 (m, 4H); MS (ESI) m/z 301 (M+H+).

Preparation of 2-(2-(2-(2-fluoroethoxy)ethoxy)ethoxy)-9H-pyrido[2,3-b]indol-7-amine hydrochloride

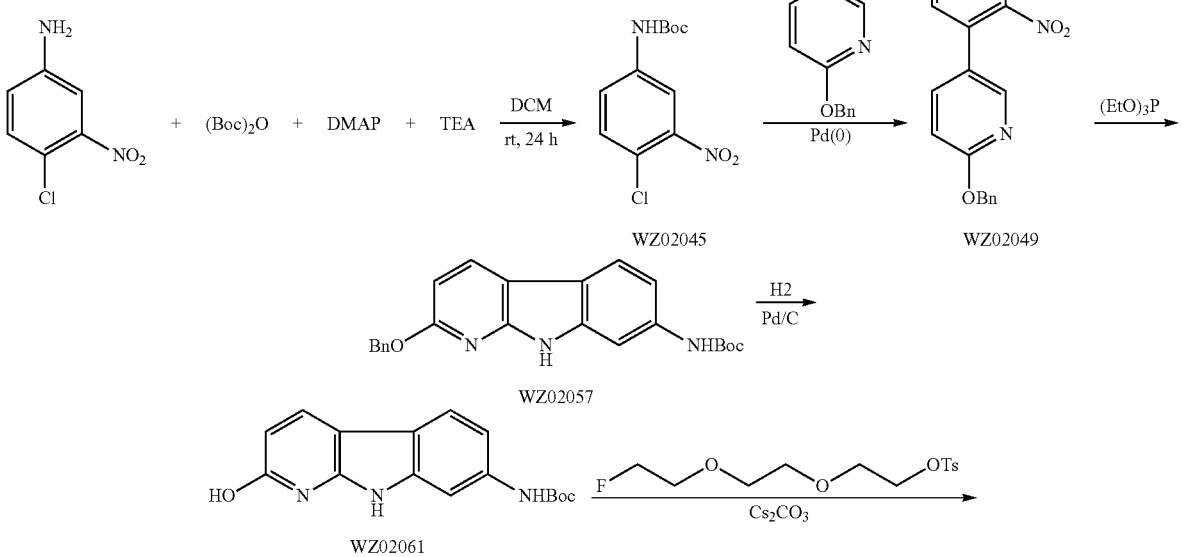

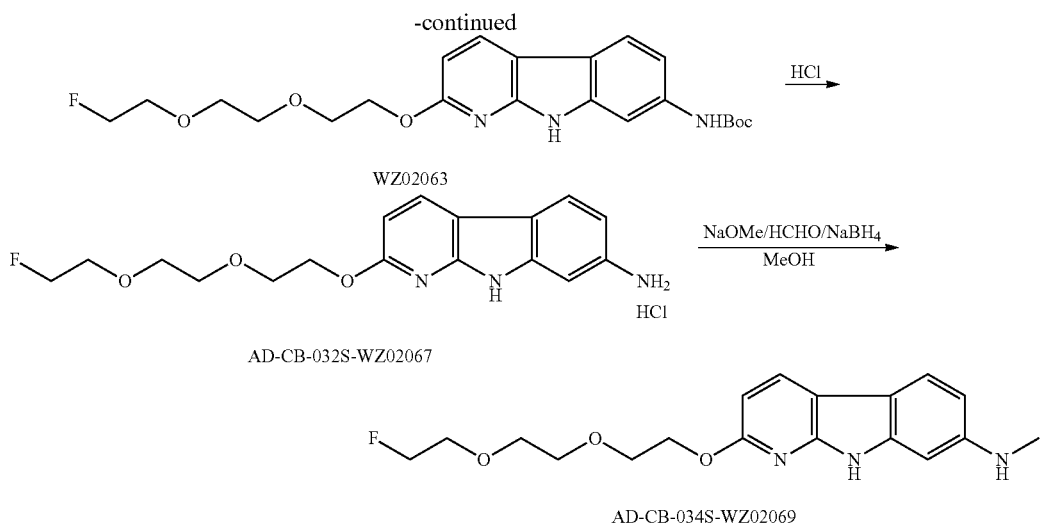

Preparation of WZ02045

To 4-chloro-3-nitroaniline (2.5 g, 14.5 mmol) in 40 mL DCM was added TEA (2.9 g, 29 mmol), DMAP (177 mg, 1.45 mmol), and di-tert-butyl dicarbonate (4.7 g, 21.7 mmol). The mixture was stirred at rt for 24 h and concentrated. The residue was diluted with Et2O (100 mL), washed with brine (100 mL), water (100 mL), 0.5 M HCl (2×100 mL), and brine (100 mL), dried over $MgSO_4$ and concentrated. The crude product was purified by silica chromatography (EtOAc/hexane) to afford tert-butyl 4-chloro-3-nitrophenylcarbamate (WZ02045) as a yellow solid (1.5 g, 38%). MS (ESI) m/z 295 (M+Na$^+$).

Preparation of WZ02049

A mixture of tert-butyl 4-chloro-3-nitrophenylcarbamate (818 mg, 3 mmol), 2-(benzyloxy)-5-(4,4,5,5-tetramethyl-1,3,2-dioxaborolan-2-yl)pyridine (933 mg, 3 mmol), tetrakis (triphenylphosphine)palladium (104 mg, 0.09 mmol), 10 mL of dioxane, and 6 mL of 1 M $Na_2CO_3$ was heated at reflux for 15 h. It was diluted with 50 mL $Et_2O$ and washed with brine (2×50 mL) and dried over $MgSO_4$ and concentrated. The crude product was purified by silica chromatography (EtOAc/hexane) to afford tert-butyl 4-(6-(benzyloxy)pyridin-3-yl)-3-nitrophenylcarbamate (WZ02049) as a yellow wax (1.2 g, 95%). MS (ESI) m/z 444 (M+Na$^+$).

Preparation of WZ02057

A suspension of above compound (800 mg, 1.9 mmol) in 2 mL of triethyl phosphite was heated at 148° C. for 15 h. After cooling, it was concentrated under reduced pressure to remove volatiles. The crude product was purified by silica chromatography (EtOAc/hexane) to afford tert-butyl 2-(benzyloxy)-9H-pyrido[2,3-b]indol-7-ylcarbamate (WZ02057) as a off-white solid (400 mg, 54%). MS (ESI) m/z 390 (M+H$^+$).

Preparation of WZ02061

To above compound (220 mg, 0.56 mmol) dissolved in 80 mL MeOH was added Palladium on activated carbon (80 mg). The mixture was stirred at rt under $H_2$ atmosphere for 15 h. Solid was filtered off and the filtrate was concentrated to afford tert-butyl 2-hydroxy-9H-pyrido[2,3-b]indol-7-ylcarbamate (WZ02061) as a white solid (105 mg, 100%). This material was used directly for the next reaction without purification. MS (ESI) m/z 300 (M+H$^+$).

Preparation of WZ02063

To above compound (50 mg, 0.167 mmol) in 1 mL of NMP was added 2-(2-(2-fluoroethoxy)ethoxy)ethyl 4-methylbenzenesulfonate (76 mg, 0.25 mmol), and $Cs_2CO_3$ (65 mg, 0.2 mmol). The mixture was stirred at rt for 15 h and diluted with Et2O (40 mL), washed with water (3×30 mL), and dried over $MgSO_4$ and concentrated. The crude product was purified by silica chromatography (EtOAc/hexane) to afford tert-butyl 2-(2-(2-(2-fluoroethoxy)ethoxy)ethoxy)-9H-pyrido[2,3-b]indol-7-ylcarbamate (WZ02063) as a clear wax (45 mg, 62%). MS (ESI) m/z 434 (M+H$^+$).

Preparation of AD-CB-032S-WZ02067

The above compound (45 mg, 0.1 mmol) was treated with 2 mL of a 4 M HCl in dioxane solution at rt for 5 h and concentrated under reduced pressure. The residue was washed with ether (5 mL) and dried under high vacuum to afford 2-(2-(2-(2-fluoroethoxy)ethoxy)ethoxy)-9H-pyrido[2,3-b]indol-7-amine hydrochloride (AD-CB-032S-WZ02067) as a light-yellow solid (23 mg, 62%). $^1$H NMR (400 MHz, methanol-d4) δ 8.42 (d, J=8.4 Hz, 1H), 8.12 (d, J=8.4 Hz, 1H), 7.53 (d, J=2.0 Hz, 1H), 7.21 (dd, J=8.4, 2.0 Hz, 1H), 6.77 (d, J=8.4 Hz, 1H), 4.58-4.54 (m 3H), 4.43 (m, 1H), 3.91 (m, 2H), 3.76-3.72 (m, 3H), 3.70-3.66 (m, 3H); MS (ESI) m/z 334 (M+H$^+$).

Preparation of 2-(2-(2-(2-fluoroethoxy)ethoxy)ethoxy)-N-methyl-9H-pyrido[2,3-b]indol-7-amine: AD-CB-034S-WZ02069

Compound AD-CB-034S-WZ02069 was prepared using the same procedure for the preparation of AD-CB-004S from 2-(2-(2-(2-fluoroethoxy)ethoxy)ethoxy)-9H-pyrido[2,3-b] indol-7-amine hydrochloride (AD-CB-032S-WZ02067, 20 mg) (10 mg, 53%). $^1$H NMR (400 MHz, methanol-d4) δ 8.06 (d, J=8.0 Hz, 1H), 7.66 (d, J=8.4 Hz, 1H), 6.65 (d, J=2.0 Hz, 1H), 6.58 (dd, J=8.4, 2.0 Hz, 1H), 6.53 (d, J=8.0 Hz, 1H), 4.58

(m 1H), 4.53-4.45 (m, 3H), 3.88 (m, 2H), 3.76 (m, 1H), 3.73-3.67 (m, 5H), 3.03 (s, 3H); MS (ESI) m/z 348 (M+H$^+$).

Preparation of 6-bromo-9H-carbazol-2-ol: W138

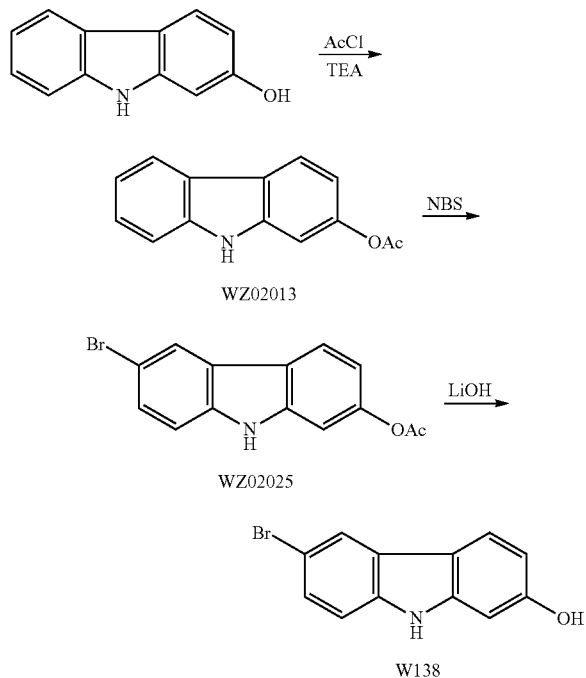

Preparation of WZ02013

To 9H-carbazol-2-ol (915 mg, 5 mmol) in 10 mL DMF and 20 mL DCM was added TEA (1.0 g, 10 mmol), followed by acetyl chloride (589 mg, 7.5 mmol) at 0° C. The reaction mixture was then stirred at rt for 1 h and poured onto ice (50 g). The mixture was extracted with EtOAc (2×60 mL) and combined organic phase was dried over MgSO$_4$ and concentrated. The crude product was purified by silica chromatography to afford 9H-carbazol-2-yl acetate (WZ02013) as an off-white solid (800 mg, 71%). MS (ESI) m/z 348 (M+H$^+$).

Preparation of WZ02025

To a solution of 9H-carbazol-2-yl acetate (500 mg, 2.2 mmol) in DCM (40 mL) was added a solution of NBS in 25 mL of DCM dropwise at rt. The reaction mixture was stirred in the dark for 5 h. It was washed with water (3×50 mL) and dried over MgSO$_4$ and concentrated. The crude product was purified by silica chromatography (EtOAc/hexane) to afford 6-bromo-9H-carbazol-2-yl acetate (WZ02025) as an off-white solid (250 mg, containing 17% dibrominated product). MS (ESI) m/z 305 (M+H$^+$).

Preparation of W138

A suspension of 6-bromo-9H-carbazol-2-yl acetate (200 mg, 0.65 mmol) in 30 mL MeOH and 4 mL of 1.0 M aqueous LiOH was stirred for 5 h. It was neutralized with 1 M HCl and concentrated. The crude product was purified by silica chromatography (EtOAc/hexane) to afford 6-bromo-9H-carbazol-2-ol (W138) as an off-white solid (125 mg, containing 15% dibrominated product). $^1$H NMR (400 MHz, acetone-d6) δ 8.58 (s, 1H), 8.10 (d, J=2.0 Hz, 1H), 1H), 7.92 (d, J=8.8 Hz, 1H), 7.42 (dd, J=8.4, 2.0 Hz, 1H), 7.35 (s, 1H), 7.13 (d, J=8.4 Hz, 1H), 6.92 (d, J=2.0 Hz, 1H), 6.76 (dd, J=8.8, 2.0 Hz, 1H); MS (ESI) m/z 263 (M+H$^+$).

Ex Vivo Competition Assay Using Amyloid (AD Patient's Brain Slice) Autoradiography Staining The carbazole series of AD imaging agents display surprisingly good qualities when compared to previously established results performed by others. Data from prior art suggests that compounds with higher LogP values have higher amyloid affinities, yet these same compounds can also suffer from high non-specific binding, i.e poor brain washout (J. Molecular Neuroscience 2003, 20, 255-260). For the disclosed studies in this application, cLogP values were used in place of LogP values.

Figure 7:
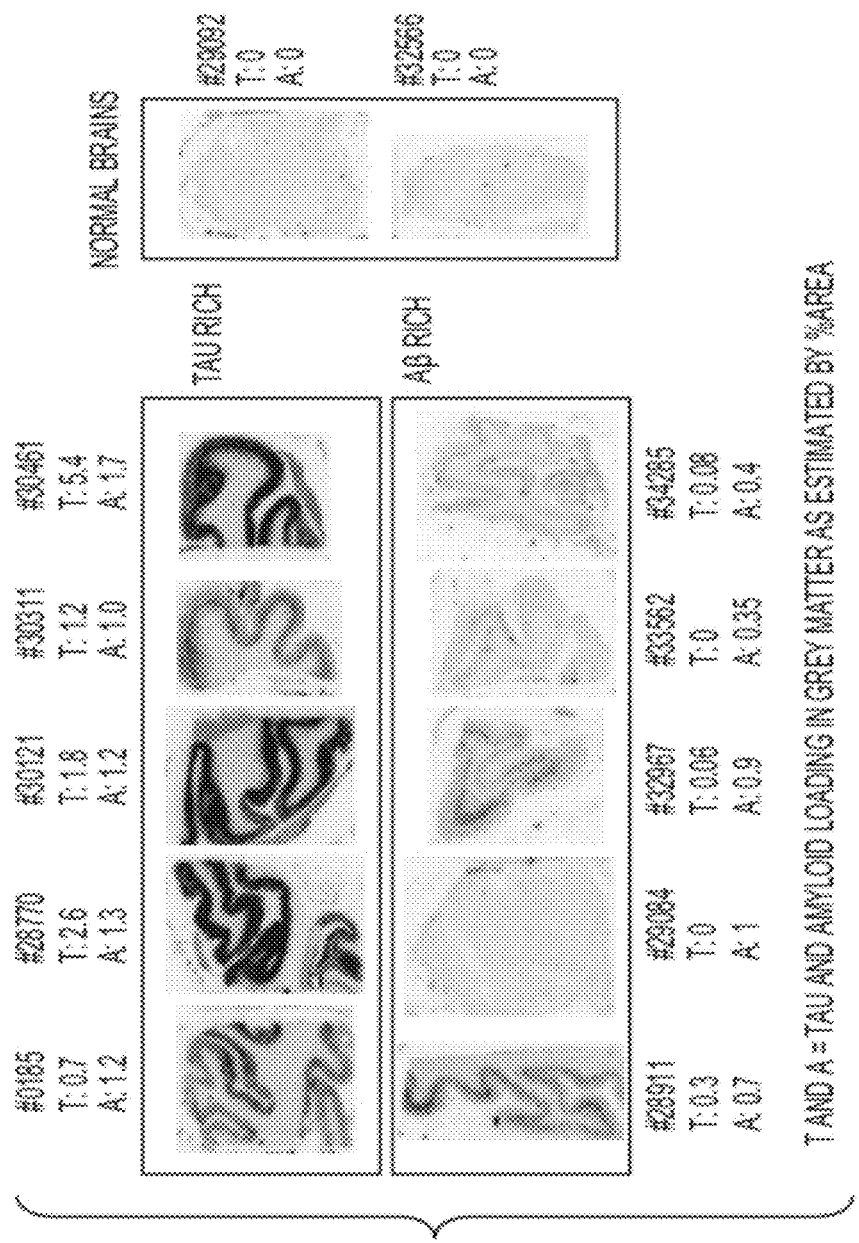
FIG. 7 shows Audoradiography of [18F]-T807.
Figure 8:
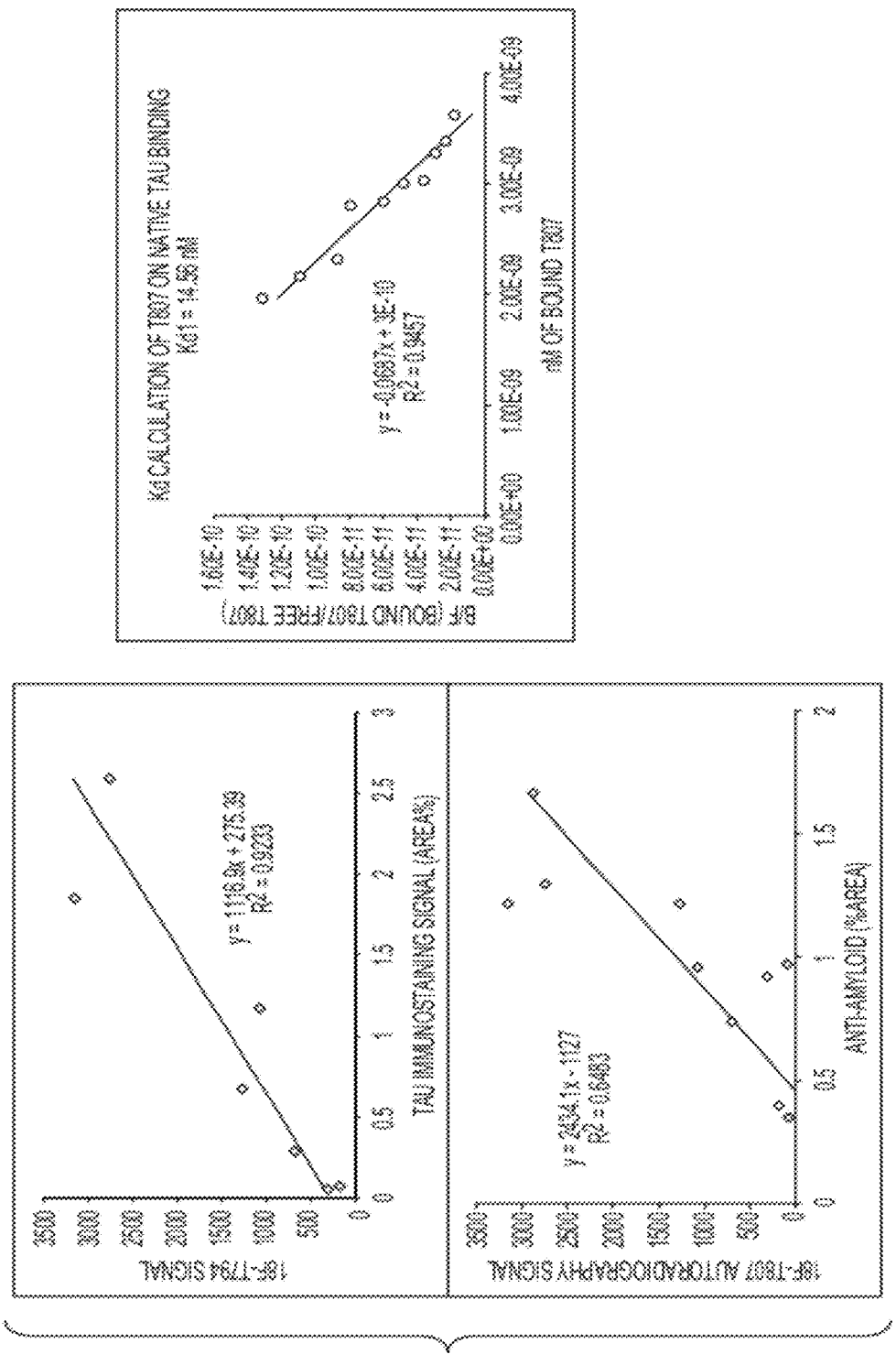
FIG. 8 shows the correlation of [18F]-T807 with Tau and Amyloid loads.
Figure 9:
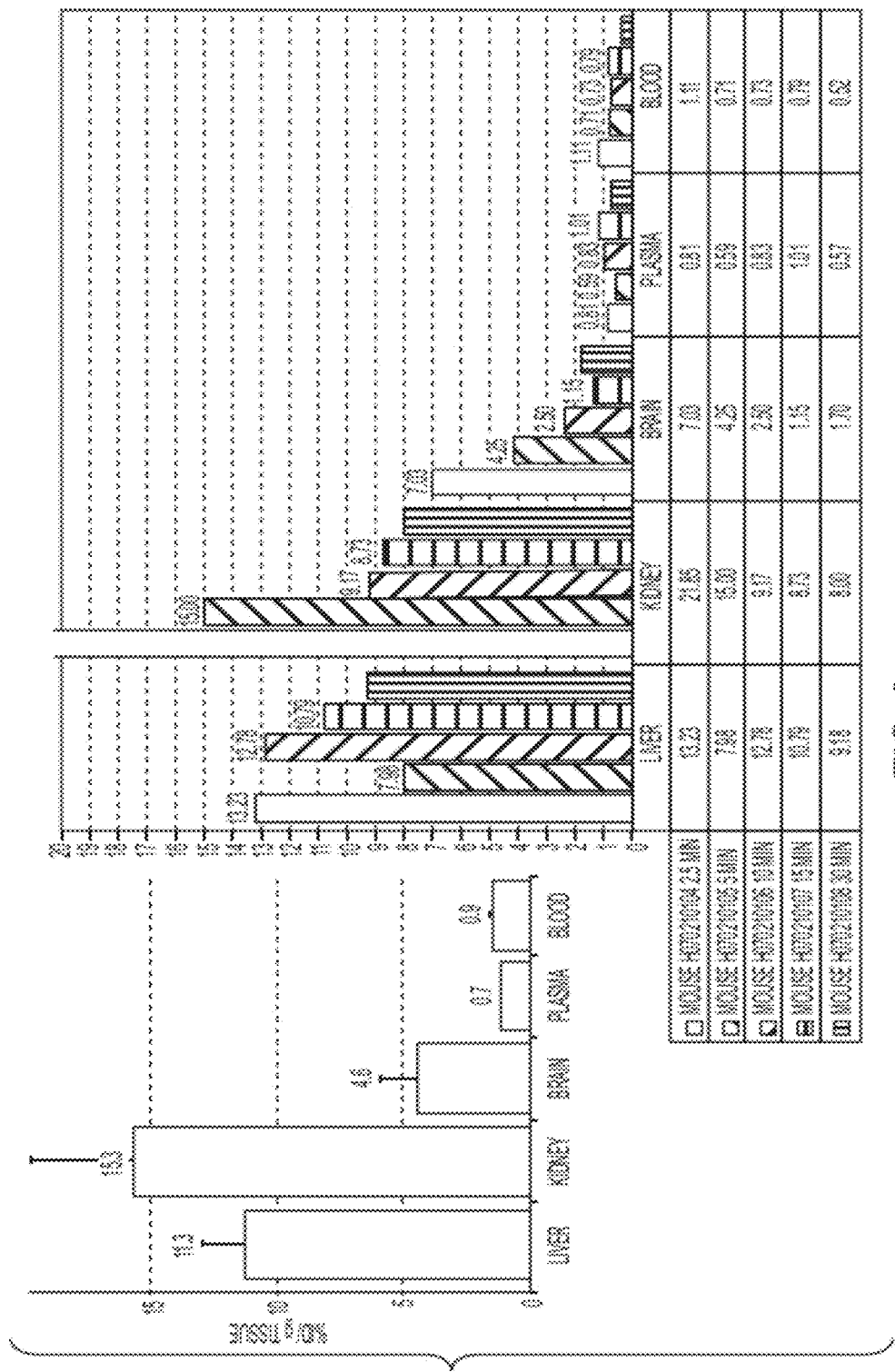
FIG. 9 shows [18F]-T807 PK in mice.

A study was conducted to examine the grey to white matter binding ratios for 4 different tracers: CB-001, CB-003, FDDNP and F-PiB (FIG. 7 and FIG. 8 of U.S. Ser. No. 12/372,717). A known carbazole containing imaging agent, 18F-fluorocarazolol, was not examined in this study because of its relatively low cLogP value (2.77) compared to FDDNP and PiB, and its competing specific uptake into the beta-adrenoceptors. In addition, there is no prior art data suggesting that 18F-fluorocarazolol binds to AD plaques. After the human brain slices from AD patients were incubated with a given tracer for 30 min, the slices were washed with various EtOH:water solutions in an attempt to optimize the grey to white matter ratios (FIG. 9 of U.S. Ser. No. 12/372,717). The results were surprising and unexpected in view of previous work performed by other researchers. CB-001 has a slightly higher cLogP than FDDNP (3.8 vs 3.4) and would be expected to have poorer washout than FDDNP based on these values. However, despite the difference in cLogP values, CB-001 has a lower non-specific binding propensity and displays a much better grey to white matter ratio compared to FDDNP (see section above, "original wash"). More specifically, the white matter binding of FDDNP is several shades darker than CB-001's white matter binding, indicating low non-specific binding of CB-001. In contrast, F-PiB, which has a cLogP value of 3.99, also displays reasonable, binding ratios similar to CB-001, albeit displaying a very weak overall signal. The washing data suggests that the carbazoles are a viable and novel target for imaging AD-related targets due to their unique binding and washout properties.

To expand on these results, CB-003, a tracer with a cLogP value similar to FDDNP, was prepared and tested. Using washing conditions that were far milder than the harsh washing conditions (FIG. 9 of U.S. Ser. No. 12/372,717), CB-003 displayed excellent grey to white matter binding ratios that are far superior to the results taken from FDDNP, PiB and CB-001. These favorable and unique results suggest that CB-003 would have a more favorable brain washout in living systems, leading to more specific uptake and lowered non-specific binding, leading to a clear advantage over FDDNP and PiB imaging.

Summary of Washing Results:

| Name | Structure | cLogP | Grey/white matter binding ratio using harsh FDDNP wash conditions* | Grey/white matter binding ratio using mild wash conditions** |
|---|---|---|---|---|
| CB-001 | 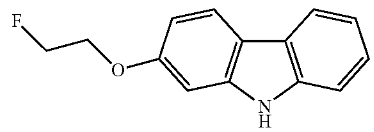 [SMILES: FCCOc1ccc2c(c1)[nH]c1ccccc12] | 3.789 | Excellent | Poor |
| CB-003 | 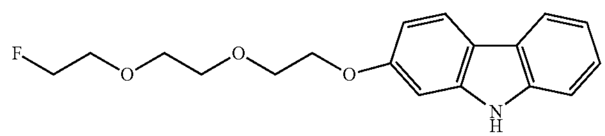 [SMILES: FCCOCCOCCOc1ccc2c(c1)[nH]c1ccccc12] | 3.4032 | N/A | Excellent |

*published FDDNP wash conditions: 30 min incubation of CB-1 or CB-3 tracer, PBS wash (5 min), 70% EtOH:water (1 min), 90% EtOH:water (1 min), 70% EtOH:water (1 min), PBS (5 min). The brain slices were 20 um thick.
**mild wash conditions: 30 min incubation of CB-1 or CB-3 tracer, PBS wash (5 min), 30% EtOH:water (2 min), 40% EtOH:water (2 min), 20% EtOH:water (2 min), PBS (5 min). The brain slices were 20 um thick.

The results demonstrate that 1) PiB blocks [18F]-CB001 staining with increasing concentrations, suggesting the two compounds to compete for the same amyloid binding pockets; 2) PiB appears to block tracer binding with the same strength as cold CB001, suggesting both to have similar binding affinities; 3) FDDNP is much less capable of blocking [18F]-CB001 staining, due to its lower amyloid binding affinity.

This data suggests the following order of (non-specific) white matter binding:
FDDNP>CB001>[18F]-PiB>CB003
IC50 Determination with [18F]-PiB by Ex Vivo Competition Assay Using Autoradiography Staining of a phenolic OH and terminal NH-Me group, which are deemed essential for binding to AD plaques. Despite CB-003 lacking both of these functional groups, it still competes with 18F-PiB for binding sites in human AD brains. Because of the simplicity of its structure, the labeling yields of CB-001 and CB-003 are exceptionally high and better than the labeling yields of 18F-PiB.

Surface Plasmon Resonance (SPR) Assay

An assay was developed using a Biacore instrument that introduced the ligands over gold-surface immobilized target proteins and measured the resultant rates of association and disassociation in order to test various compounds that bind to soluble AD oligomers, polymers and fibrils (FIGS. 12 to 17 of U.S. Ser. No. 12/372,717).

| Compound Code | 1 | 2 | 3 | 4 | 5 | 6 | 7 | 8 | 9 | 10 | 11 | 12 | 13 | Average IC50 | SD | SD % |
|---|---|---|---|---|---|---|---|---|---|---|---|---|---|---|---|---|
| F-PiB | | | | | | 43 | | 43 | 40 | 50 | 55 | 41 | | 45 | 6 | 13 |
| PiB | 80 | 40 | 40 | 48 | 60 | 43 | 50 | | | | | | 280 | 52 | 14 | 28 |
| CB7 | 260 | | 170 | 200 | 290 | | | | | | | | 300 | 244 | 57 | 23 |
| CB4 | 260 | | 350 | 300 | 300 | | | | | | | | 400 | 322 | 54 | 17 |
| CB12 | | | | 610 | 300 | 450 | 390 | | | | | | | 438 | 130 | 30 |
| CB24 | | | | | | 540 | | | | | | | | 540 | | |
| CB1 | 1000 | 480 | | | | | | | | | | | | 740 | 368 | 50 |
| CB10 | | | 900 | | | | | | | | | | | 900 | | |
| CB3 | 1100 | | | | | 900 | | | | | | | 920 | 973 | 110 | 11 |

Figure 10:
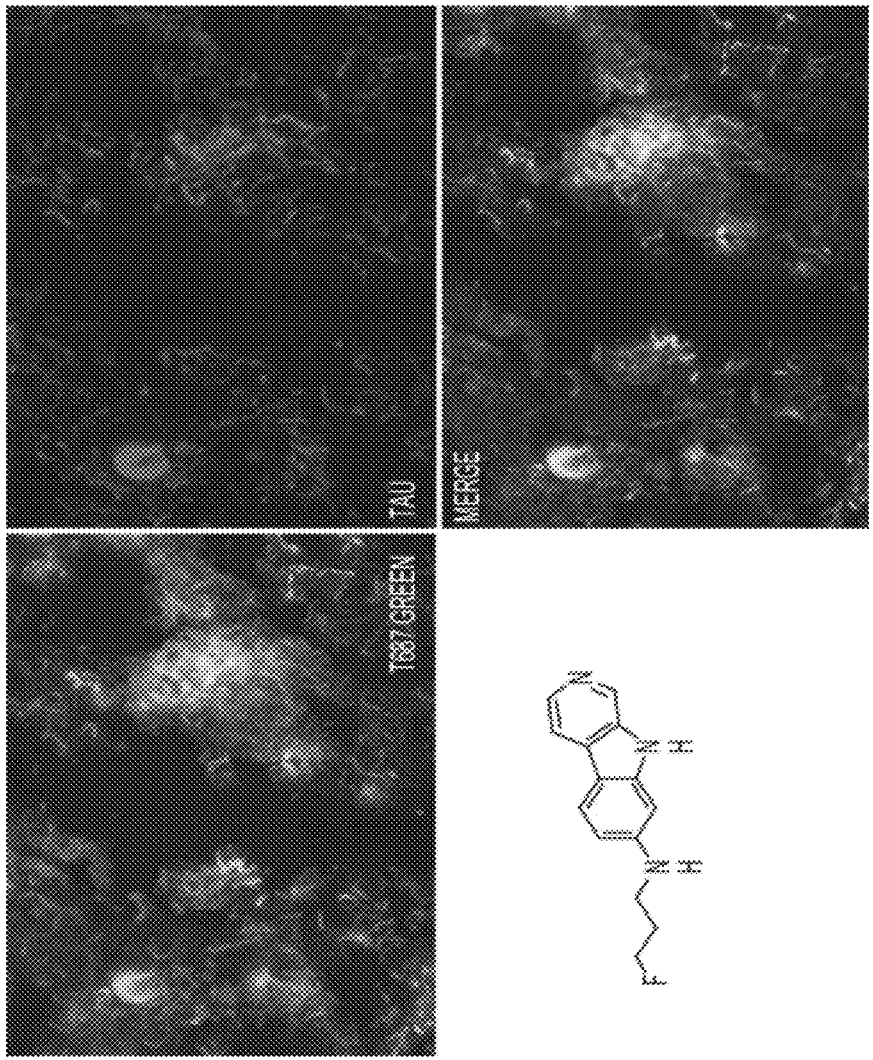
FIG. 10 shows double labeling of compound T687 and PHF-tau IHC staining on human brain section.

To further demonstrate the efficiency of employing these CB-related tracers as AD imaging agents, CB-003 was used to clearly differentiate between a healthy brain and an AD brain (FIG. 10 of U.S. Ser. No. 12/372,717). More specifically, by using the mild wash protocol, the amyloid deposits were clearly visible in the grey matter with little white matter uptake. The results were corroborated by both antibody IHC and thioflaving T amyloid staining, confirming the specificity of uptake. These surprising results demonstrate that this tracer possess the unique quality of rapid washout from white matter and significant high uptake in grey matter that is specific for AD plaques.

Figure 11:
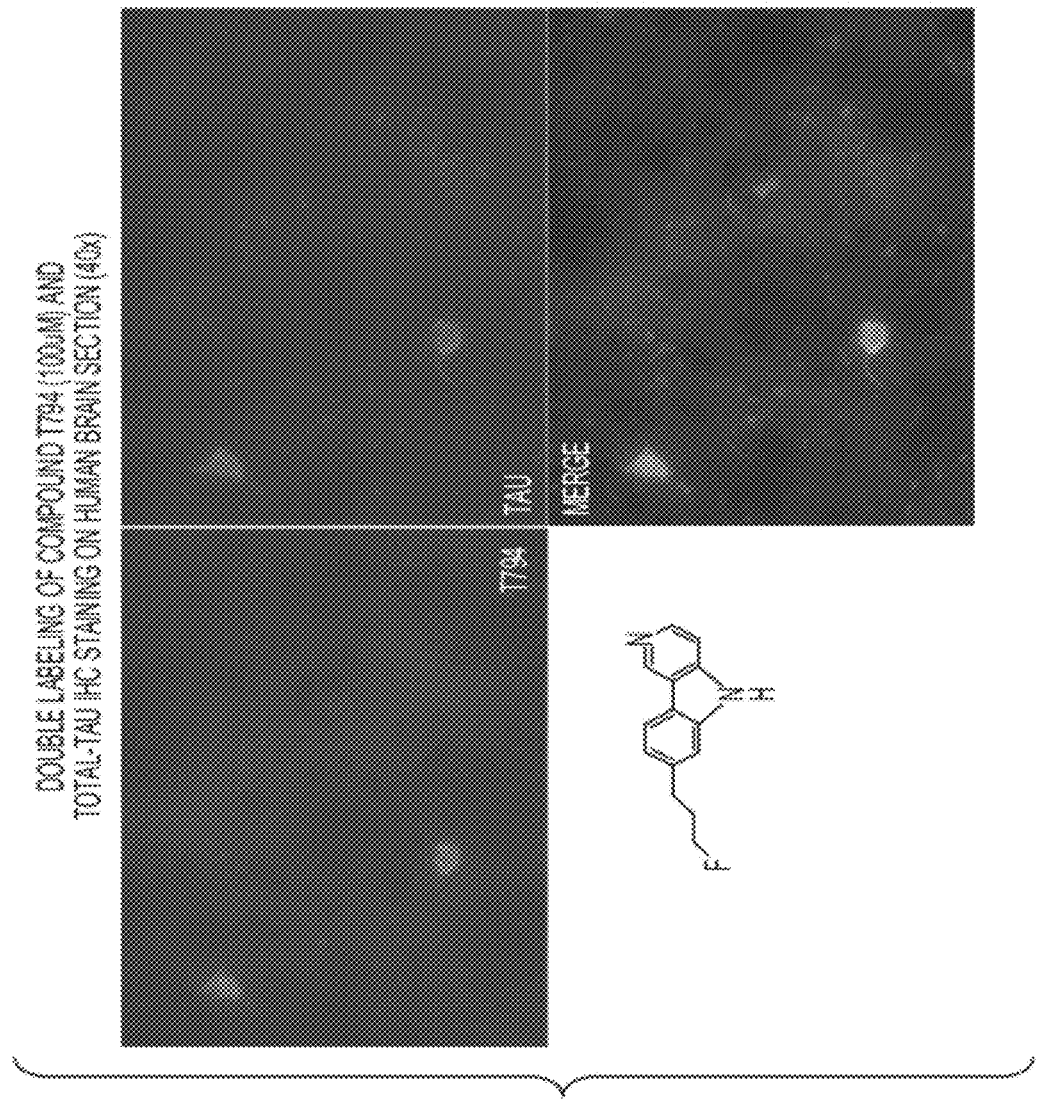
FIG. 11 shows Double labeling of Compound T794 and total-tau IHC Staining on Human Brain Section.
Figure 12:
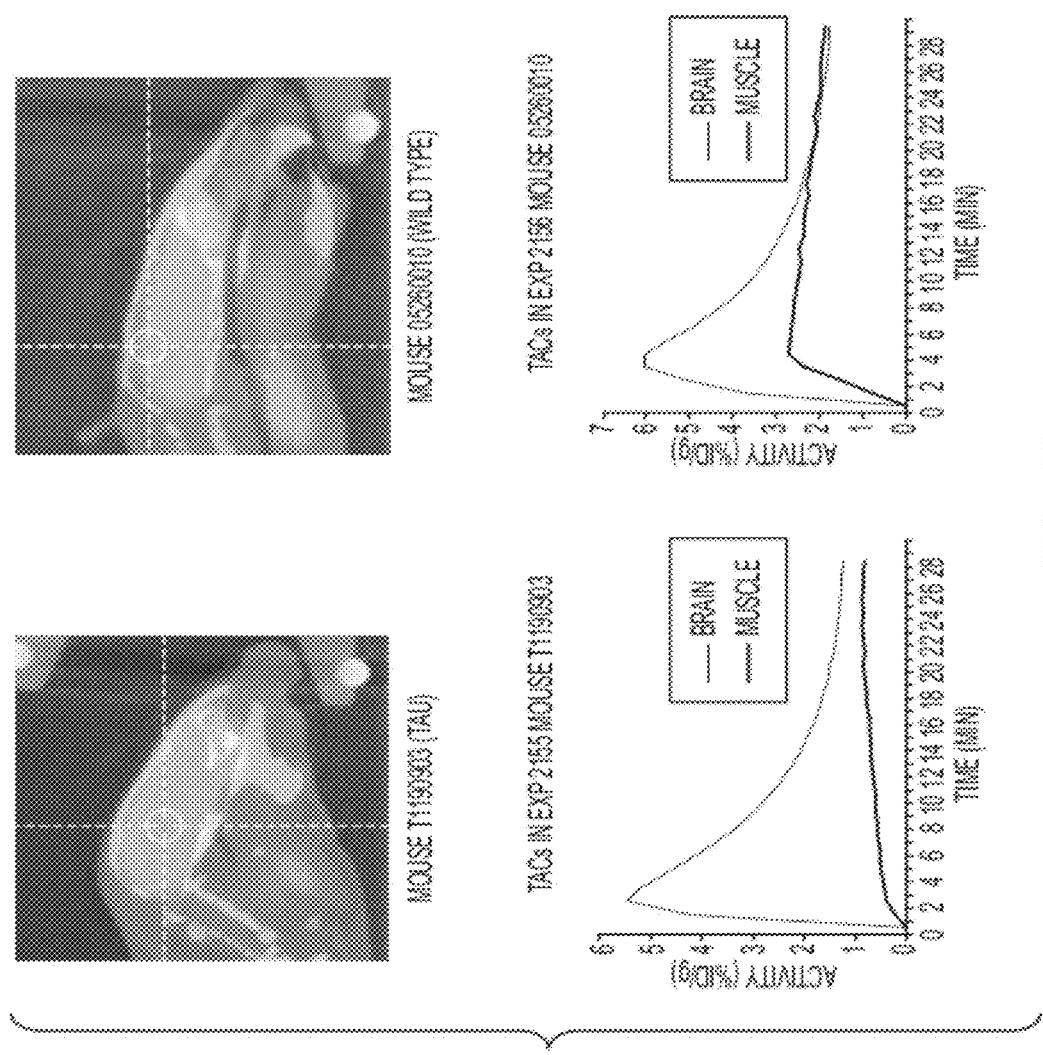
FIG. 12 shows 18F-T805: Brain uptake in mice.
Figure 13:
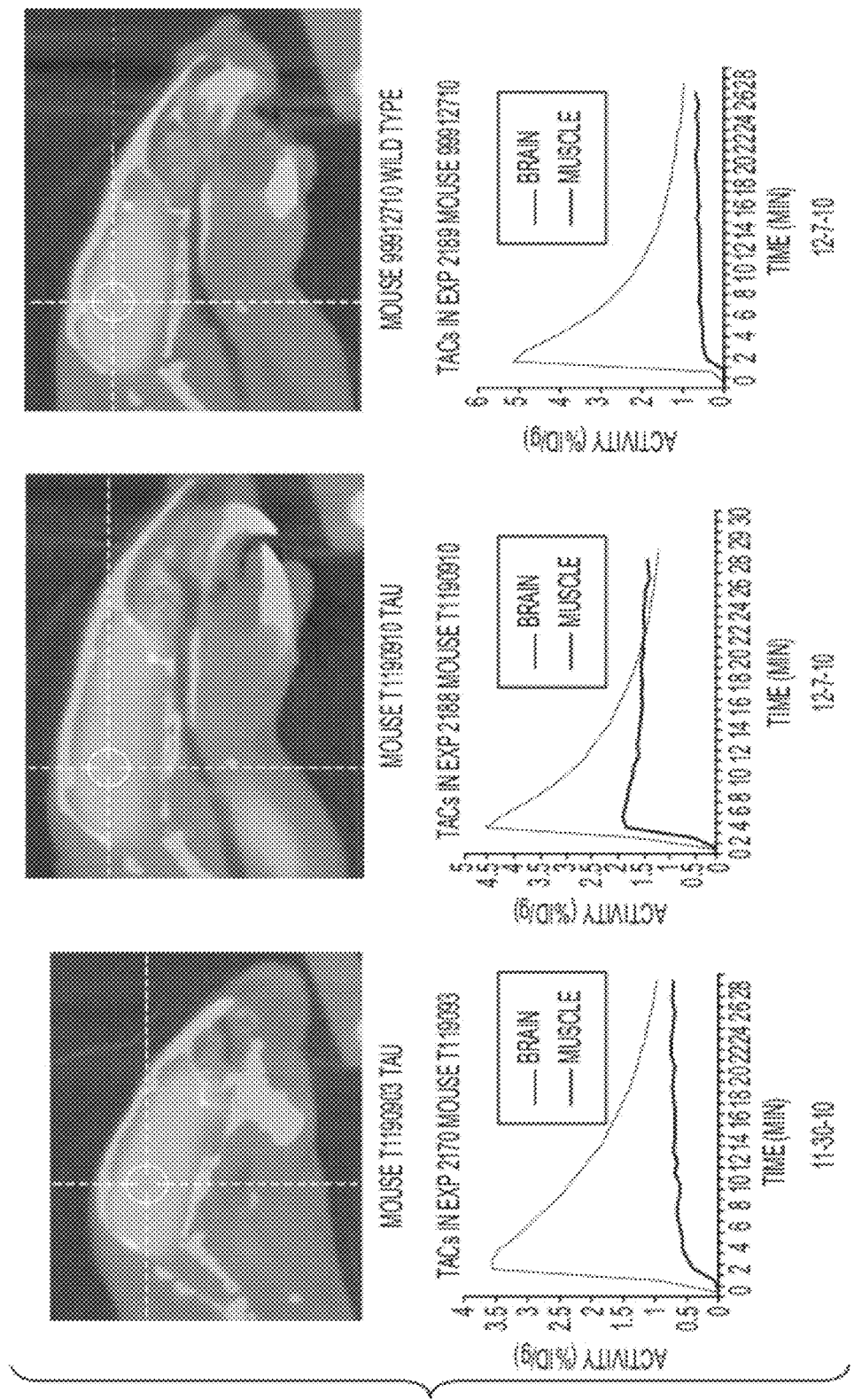
FIG. 13 shows 18F-T807: Brain uptake in mice.
Figure 14:
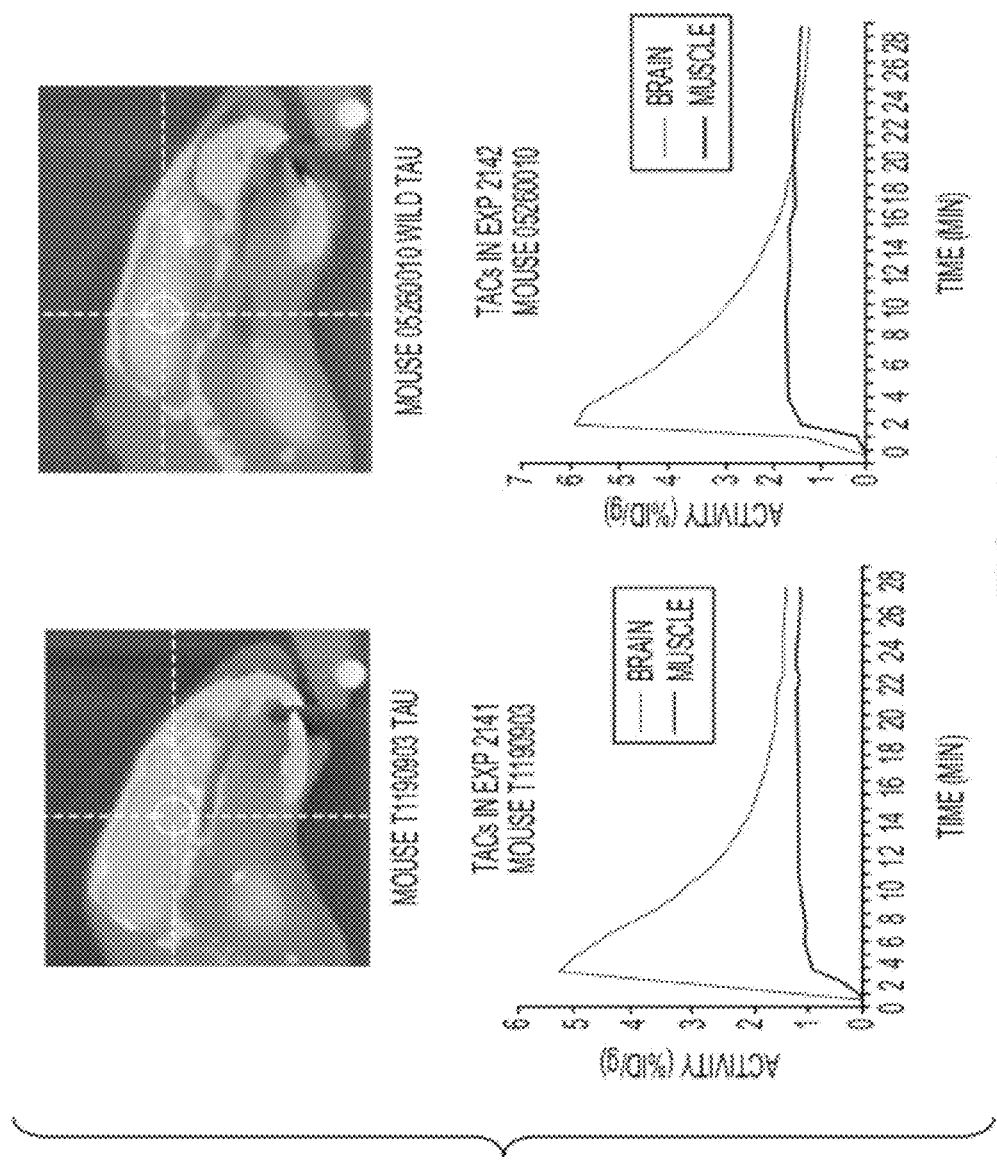
FIG. 14 shows 18F-T794 in WT and Tau mice.

The carbazoles compete directly against 18F-PiB for the same binding sites in human AD brains (FIG. 11 of U.S. Ser. No. 12/372,717). This surprising result could not have been predicted given their dissimilar structures and CB-003's lack The carbazole series also demonstrated a unique and surprising ability to bind favorably and preferentially to insoluble aggregates (9 nM) over soluble aggregates (262 nM) (FIG. 12 and FIG. 13 of U.S. Ser. No. 12/372,717). PiB also binds well to insoluble aggregates (16 nM) but also binds essentially equally as well to soluble aggregates (48 nM) (FIG. 14 and FIG. 15 of U.S. Ser. No. 12/372,717). For imaging applications where it is favorable to distinguish between a tracer's binding to insoluble versus soluble aggregates, CB-003 provides a larger binding ratio of 29:1, whereas PiB only provides a ratio 3:1. Thus, CB-003 may provide more selective binding information relative to PiB. The results indicate that 1) for soluble aggregate binding, PIB>CB3>CB4; and 2) for insoluble aggregate binding, PIB=CB3>CB4.

MicroPET Imaging with [18F]-CB-001 or [18F]-CB-003 in WT and App Mice

The results demonstrate that 1) WT and App mice show statistically significant differences in tracer retention in the brain (FIG. 18A, FIG. 18B and FIG. 19 of U.S. Ser. No. 12/372,717); 2) App mice show up to 25% larger brain/muscle ratios compared to WT mice (FIG. 20 and FIG. 21 of U.S. Ser. No. 12/372,717). The carbazoles display both a surprising high uptake in mice brains (both WT and APP) and sufficiently slow washout such that one can distinguish WT from APP mice (FIG. 22 and FIG. 23 of U.S. Ser. No. 12/372,717). Without being bound by any theory proposed herein, we speculate that the reason behind these results may be that CB-003 possesses a faster washout rate than 18F-PiB, which is consistent with consistent with the staining data: 18F-PiB requires harsher wash conditions in order to give reasonable grey to white matter ratios. The rapid washout of CB-003 is presumably a major factor for its low non-specific binding, yet the washout is slow enough to distinguish WT from APP. This suggests that the carbazoles display a unique combination of excellent washout and retention properties in human AD brains that are not obvious from prior art data. CB-003, being a neutral compound, would also potentially possess greater uptake values versus zwitterionic-based imaging agents such as methylene blue.

7-(3-Fluoropropyl)-3-methyl-5H-pyrido[3,2-b]indole*TFA: T793

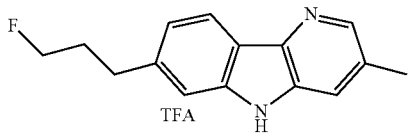 [SMILES: Cc1cnc2c(c1)[nH]c1cc(CCCF)ccc12]

General experimental procedure for carbazole formation was followed. Reaction was performed on a 8.9 mg scale of 2-(4-(3-fluoropropyl)phenyl)-5-methyl-3-nitropyridine. Isolated 3.6 mg (45%) of T793 as a white solid. $^1$H NMR (CD$_3$OD): δ 8.48 (1H, d, J=1.6 Hz), 8.39 (1H, d, J=1.6 Hz), 8.21 (1H, d, J=8.4 Hz), 7.55 (1H, d, J=1.6 Hz), 7.34 (1H, d, J=8.4, 1.6 Hz), 4.52 (1H, t, J=6.0 Hz), 4.40 (1H, t, J=6.0 Hz), 2.97 (2H, t, J=7.6 Hz), 2.68 (3H, s), 2.03-2.15 (2H, m); MS: 243 (M+H$^+$).

7-(2-Fluoroethyl)-5H-pyrido[4,3-b]indole: T805

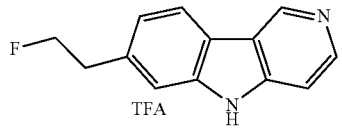 [SMILES: FCCc1ccc2c(c1)[nH]c1ccncc12]

General experimental procedure for carbazole formation was followed. (Same for T794.) Reaction was performed on a 28.5 mg scale of 3-(4-(2-fluoroethyl)phenyl)-4-nitropyridine. Isolated 13.3 mg (54%) of T805 as a white solid. $^1$H NMR (CD$_3$OD): δ 9.14 (1H, d, J=1.2 Hz), 8.31 (1H, d, J=5.6 Hz), 8.07 (1H, dd, J=8.0, 0.8 Hz), 7.40-7.43 (2H, m, overlapped), 7.17 (1H, dd, J=8.0, 1.6 Hz), 4.72 (1H, t, J=6.4 Hz), 4.60 (1H, t, J=6.4 Hz), 3.17 (1H, t, J=6.4 Hz), 3.11 (1H, t, J=6.4 Hz); MS: 215 (M+H$^+$).

7-(2-(2-(2-Fluoroethoxy)ethoxy)ethyl)-5H-pyrido[4,3-b]indole: T813

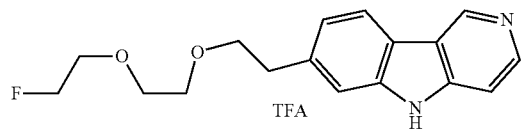 [SMILES: FCCOCCOCCc1ccc2c(c1)[nH]c1ccncc12]

To a solution of tert-butyl 7-(2-hydroxyethyl)-5H-pyrido[4,3-b]indole-5-carboxylate (9.0 mg, 0.0288 mmol) in DMF (1.0 mL) was added NaH (60% in mineral oil, 3.6 mg, 0.09 mmol). The mixture was stirred for 15 min before 2-(2-fluoroethoxy)ethyl 4-methylbenzenesulfonate (23 mg, 0.0878 mmol) was added. The mixture was stirred at room temperature for 1.5 hours. The mixture was diluted with DCM and washed with water twice. The DCM layer was separated and added TFA (10% TFA in DCM). Reaction was stirred at room temperature for 1 hour. The mixture was concentrated and purified by HPLC (acetonitrile/water) to give 4.5 mg (52%) of T813 as a white solid. $^1$H NMR (CD$_3$OD): δ 9.46 (1H, d, J=1.6 Hz), 8.51 (1H, dd, J=6.8, 0.8 Hz), 8.28 (1H, d, J=8.8 Hz), 8.09 (1H, dd, J=6.8, 0.4 Hz), 7.76 (1H, d, J=0.8 Hz), 7.45 (1H, dd, J=8.4, 1.6 Hz), 4.79 (2H, m), 4.36 (1H, m), 4.25 (1H, m), 3.98 (2H, t, J=5.0 Hz), 3.88 (2H, t, J=6.8 Hz), 3.60 (1H, m), 3.53 (1H, m), 3.08 (2H, t, J=6.8 Hz); MS: 303 (M+H$^+$).

Synthesis of T757 and T758

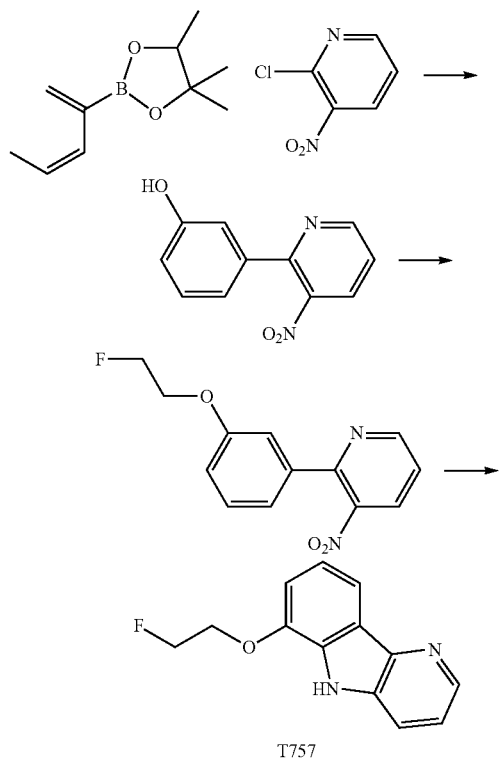

T757

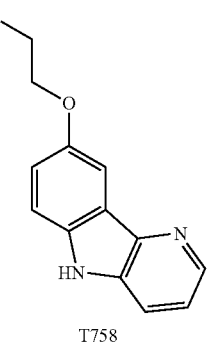

T758

Preparation of 3-(3-nitropyridin-2-yl)phenol

[1,1'-Bis(diphenylphosphino)ferrocnee]dichloropalladium(II), w/DCM (0.039 g, 0.047 mmol) was added to a solution containing 3-(4,4,5,5-tetramethyl-1,3,2-dioxaborolan-2-yl)phenol (0.292 g, 1.325 mmol), 2-chloro-3-nitropyridine (0.15 g, 0.946 mmol), Copper(I) iodide (0.018 g, 0.095 mmol) and Potassium carbonate (0.946 ml, 1.892 mmol). Heated the reaction to 110° C. for 15 mins. Cooled reaction to room temperature. Diluted with water and extracted with ethyl acetate. Combined organics, dried, filtered, concentrated and purified to afford 3-(3-nitropyridin-2-yl)phenol (0.1 g, 0.463 mmol, 48.9% yield).

Preparation of 2-(3-(2-fluoroethoxy)phenyl)-3-nitropyridine

Sodium hydride 60% (0.021 g, 0.925 mmol) was added to a solution containing 3-(3-nitropyridin-2-yl)phenol (0.2 g, 0.925 mmol) and 1-Bromo-2-fluoroethane (0.138 ml, 1.850 mmol) in DMF (Volume: 3.08 ml). The reaction was stirred for 2 hours. Diluted reaction with water and extracted with ethyl acetate. Combined organics, dried, filtered, and purified by ISCO column using 35% ethyl acetate in hexanes to afford 2-(3-(2-fluoroethoxy)phenyl)-3-nitropyridine (0.11 g, 0.419 mmol, 45.3% yield).

Preparation of T757 and T758

2-(3-(2-fluoroethoxy)phenyl)-3-nitropyridine (0.11 g, 0.419 mmol) in Triethyl phosphite (1.100 ml, 6.29 mmol) was heated to 125° C. for 6 hours. Cooled the reaction to room temperature, concentrated, and purified by PREP HPLC to afford T757 (0.005 g, 0.022 mmol, 5.18% yield) MS (ESI, Pos.) m/z: 231.0 [M+H]+ and T758 (0.005 g, 0.022 mmol, 5.18% yield) MS (ESI, Pos.) m/z: 231.0 [M+H]+.

Synthesis of T789

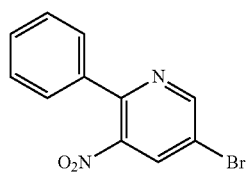

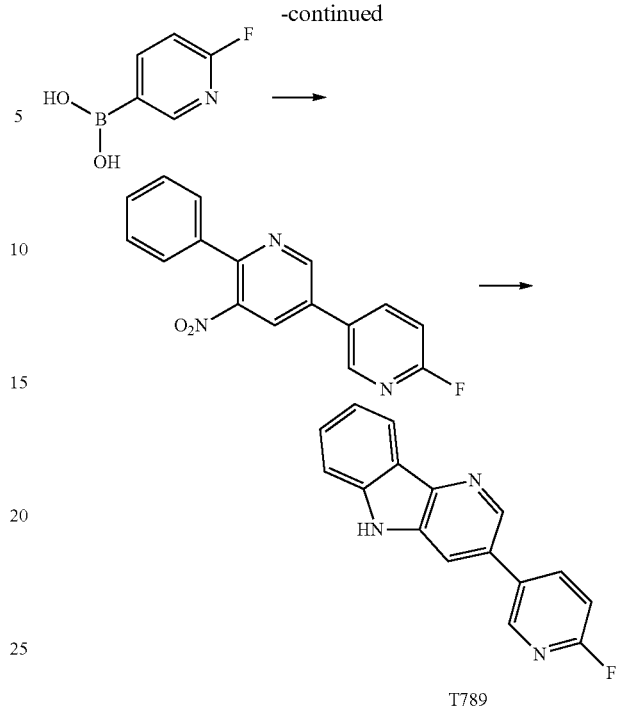

T789

Preparation of 6'-fluoro-5-nitro-6-phenyl-3,3'-bipyridine

[1,1'-Bis(diphenylphosphino)ferrocnee]dichloropalladium(II), w/DCM (7.32 mg, 8.96 µmol) was added to a solution containing 5-bromo-3-nitro-2-phenylpyridine (0.05 g, 0.179 mmol), (6-fluoropyridin-3-yl)boronic acid (0.025 g, 0.179 mmol), Copper(I) iodide (3.41 mg, 0.018 mmol) and Potassium carbonate (0.134 ml, 0.269 mmol) in DMF (Volume: 0.597 ml). Heated the reaction in a microwave at 110° C. for 15 minutes. Let the reaction cool to room temperature. Diluted reaction with water, dried, filtered, concentrated and purified with Combiflash using 0% to 25% ethyl acetate in hexanes to afford 6'-fluoro-5-nitro-6-phenyl-3,3'-bipyridine (0.03 g, 0.102 mmol, 56.7% yield).

Preparation of T789

6'-fluoro-5-nitro-6-phenyl-3,3'-bipyridine (0.03 g, 0.102 mmol) and Triethyl phosphite (1 ml, 5.72 mmol) was heated to 125° C. for 3 hours. Let the reaction cool to room temperature. Concentrated and purified by PREP HPLC to afford T789 (0.002 g, 7.60 µmol, 7.48% yield) MS (ESI, Pos.) m/z: 264.0 [M+H]+.

Synthesis of T810

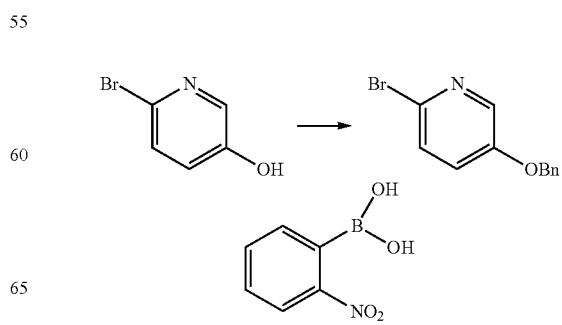

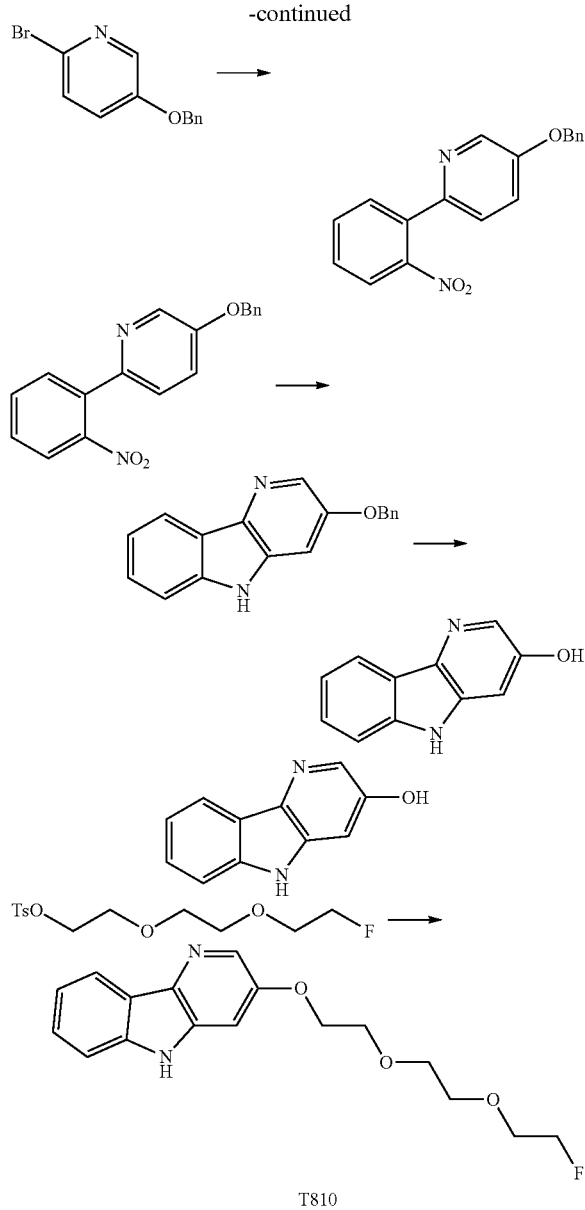

sium carbonate (1.420 ml, 2.84 mmol) in DMF (Volume: 6.31 ml). Let the reaction cool to room temperature. Diluted reaction with water, extracted with ethyl acetate, combined organics, dried, filtered and concentrated. Purified with Combiflash using 15% ethyl acetate in hexanes to afford 5-(benzyloxy)-2-(2-nitrophenyl)pyridine (0.3 g, 0.979 mmol, 51.7% yield).

Preparation of 3-(benzyloxy)-5H-pyrido[3,2-b]indole

Triethyl phosphite (3 ml, 17.15 mmol) and 5-(benzyloxy)-2-(2-nitrophenyl)pyridine (0.3 g, 0.979 mmol) were heated to 125° C. for 4 hours. Let the reaction cool to room temperature. Concentrated and purified with Combiflash column using ethyl acetate followed by 15% methanol in DCM to afford 3-(benzyloxy)-5H-pyrido[3,2-b]indole (0.09 g, 0.328 mmol, 33.5% yield).

Preparation of 5H-pyrido[3,2-b]indol-3-ol 3-(benzyloxy)-5H-pyrido[3,2-b]indole (0.09 g, 0.328 mmol) and Palladium 10% on carbon (0.035 g, 0.033 mmol) in MeOH (Volume: 5 ml) was stirred under hydrogen for 2 hours. Filtered and concentrated to afford 5H-pyrido[3,2-b]indol-3-ol (0.06 g, 0.326 mmol, 99% yield).

Preparation of T810

Sodium hydride 60% (0.019 g, 0.489 mmol) was added to a solution containing 2-(2-(2-fluoroethoxy)ethoxy)ethyl 4-methylbenzenesulfonate (0.100 g, 0.326 mmol), 5H-pyrido[3,2-b]indol-3-ol (0.06 g, 0.326 mmol) in DMF (Volume: 1.086 ml). The reaction was stirred for 2 hours. Concentrated and purified by PREP HPLC to afford T810 (0.006 g, 0.019 mmol, 5.79% yield) MS (ESI, Pos.) m/z: 319.0 [M+H]$^+$.

Preparation of 5-(benzyloxy)-2-bromopyridine

Benzyl bromide (1.367 ml, 11.49 mmol) was added to a solution containing 6-bromopyridin-3-ol (2 g, 11.49 mmol) and Potassium carbonate (2.383 g, 17.24 mmol) in Acetone (Volume: 38.3 ml). Let the reaction stir for 4 hours. Concentrated and purified by Combiflash using 15% ethyl acetate in hexanes to afford 5-(benzyloxy)-2-bromopyridine (2.5 g, 9.47 mmol, 82% yield).

Preparation of 5-(benzyloxy)-2-(2-nitrophenyl)pyridine

[1,1'-Bis(diphenylphosphino)ferrocnee]dichloropalladium(II), w/DCM (0.077 g, 0.095 mmol) was added to a solution containing (2-nitrophenyl)boronic acid (0.316 g, 1.893 mmol), 5-(benzyloxy)-2-bromopyridine (0.5 g, 1.893 mmol), Copper(I) iodide (0.036 g, 0.189 mmol) and Potas-

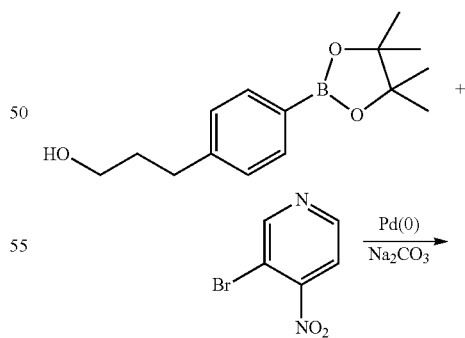

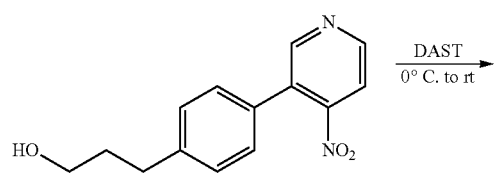

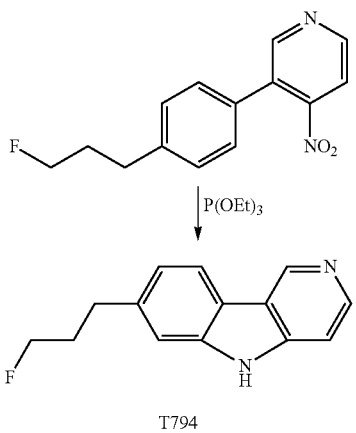

T794

3-(4-(4-Nitropyridin-3-yl)phenyl)propan-1-ol

A mixture of boronic ester (524 mg, 2 mmol), bromide (406 mg, 2 mmol), Pd (0) (116 mg, 0.1 mmol), and Na2CO3 solution (1 M, 4 mL) in 8 mL of dioxane was heated at 90 C for 10 min in a microwave reactor. After cooling to rt, the mixture was extracted with EtOAc (3×20 mL) and the organic phase was dried over MgSO4 and concentrated. The crude product was purified with silica chromatography (EtOAc/hexane, 5% to 90%) to afford the title compound as a yellow oil (412 mg). $^1$H NMR (400 MHz, CDCl$_3$): δ 8.83-8.79 (m, 2H), 7.64 (dd, J=5.2, 0.8 Hz, 1H), 7.38 (d, J=8.4 Hz, 2H), 7.32 (d, J=8.4 Hz, 2H), 3.71 (t, J=6.2 Hz, 2H), 2.79 (t, J=7.6 Hz, 2H), 1.94 (m, 2H); MS (ESI) m/z [M+H]$^+$259.

3-(4-(3-Fluoropropyl)phenyl)-4-nitropyridine

To 3-(4-(4-nitropyridin-3-yl)phenyl)propan-1-ol (60 mg, 0.23 mmol) in 2 mL of dry DCM at 0° C. was added (Diethylamino)sulfur trifluoride (111 mg, 0.69 mmol) dropwise. The reaction was warmed to rt and stirred for 1 h and quenched onto ice (20 g) in saturated Na$_2$CO$_3$ (20 mL). The mixture was extracted with EtOAc (2×30 mL) and the organic phase was dried over MgSO$_4$ and concentrated. The residue was purified by silica chromatography (EtOAc in hexane, 5% to 30%) to afford 3-(4-(3-fluoropropyl)phenyl)-4-nitropyridine as a pale-yellow oil (12 mg, 20%). $^1$H NMR (400 MHz, CDCl$_3$): δ 8.82-8.80 (m, 2H), 7.64 (d, J=5.2, 1H), 7.33-7.27 (m, 2H), 4.55 (t, J=5.6 Hz, 1H), 4.43 (t, J=5.6 Hz, 1H), 2.82 (t, J=7.6 Hz, 2H), 2.12-1.99 (m, 2H); MS (ESI) m/z [M+H]$^+$261.

7-(3-Fluoropropyl)-5H-pyrido[4,3-b]indole

A solution of 3-(4-(3-fluoropropyl)phenyl)-4-nitropyridine (12 mg, 0.046 mmol) in 0.3 mL of triethyl phosphate was heated at 125° C. for 1 h. After cooling to rt, the volatiles were removed under reduced pressure and the residue was purified by silica chromatography (MeOH in DCM, 0% to 10%) to afford a off-white solid. This material was then further purified by reversed phase HPLC to yield 7-(3-fluoropropyl)-5H-pyrido[4,3-b]indole as a white solid (3 mg, 28%). $^1$H NMR (400 MHz, methanol-d4): δ 9.15 (s, 1H), 8.32 (d, J=4.4, 1H), 8.07 (d, J=8.0 Hz, 1H), 7.44 (d, J=6 Hz, 1H), 7.37 (m, 1H), 7.16 (dd, J=8.0, 1.2 Hz, 1H), 4.50 (t, J=6 Hz, 1H), 4.43 (t, J=6 Hz, 1H), 2.90 (t, J=7.6 Hz, 2H), 2.12-1.99 (m, 2H); MS (ESI) m/z [M+H]$^+$229.

2-(5-Fluoropent-1-yn-1-yl)benzo[4,5]imidazo[1,2-a] pyrimidine (T806)

To 5-(benzo[4,5]imidazo[1,2-a]pyrimidin-2-yl)pent-4-yn-1-ol (20 mg, 0.08 mmol) in 1 mL dry DCM at 0° C. was added (Diethylamino)sulfur trifluoride (64 mg, 0.4 mmol) dropwise. The reaction was warmed to rt and stirred for 1 h and quenched onto a mixture of ice (10 g) in saturated Na$_2$CO$_3$ (10 mL). The mixture was extracted with EtOAc (2×10 mL) and the organic phase was dried over MgSO$_4$ and concentrated. The residue was purified by silica chromatography (EtOAc in DCM, 5% to 50%) to afford 2-(5-fluoropent-1-yn-1-yl)benzo [4,5]imidazo[1,2-a]pyrimidine as a yellow oil (3 mg, 15%). $^1$H NMR (400 MHz, CDCl$_3$): δ 8.65 (d, J=6.8 Hz, 1H), 8.03 (d, J=8 Hz, 1H), 7.85 (d, J=8 Hz, 1H), 7.58 (m, 1H), 7.43 (m, 1H), 6.93 (d, J=7.2 Hz, 1H), 4.69 (t, J=5.6 Hz, 1H), 4.57 (t, J=5.6 Hz, 1H), 2.70 (t, J=5.6 Hz, 2H), 2.14-2.00 (m, 2H); MS (ESI) m/z [M+H]$^+$254.

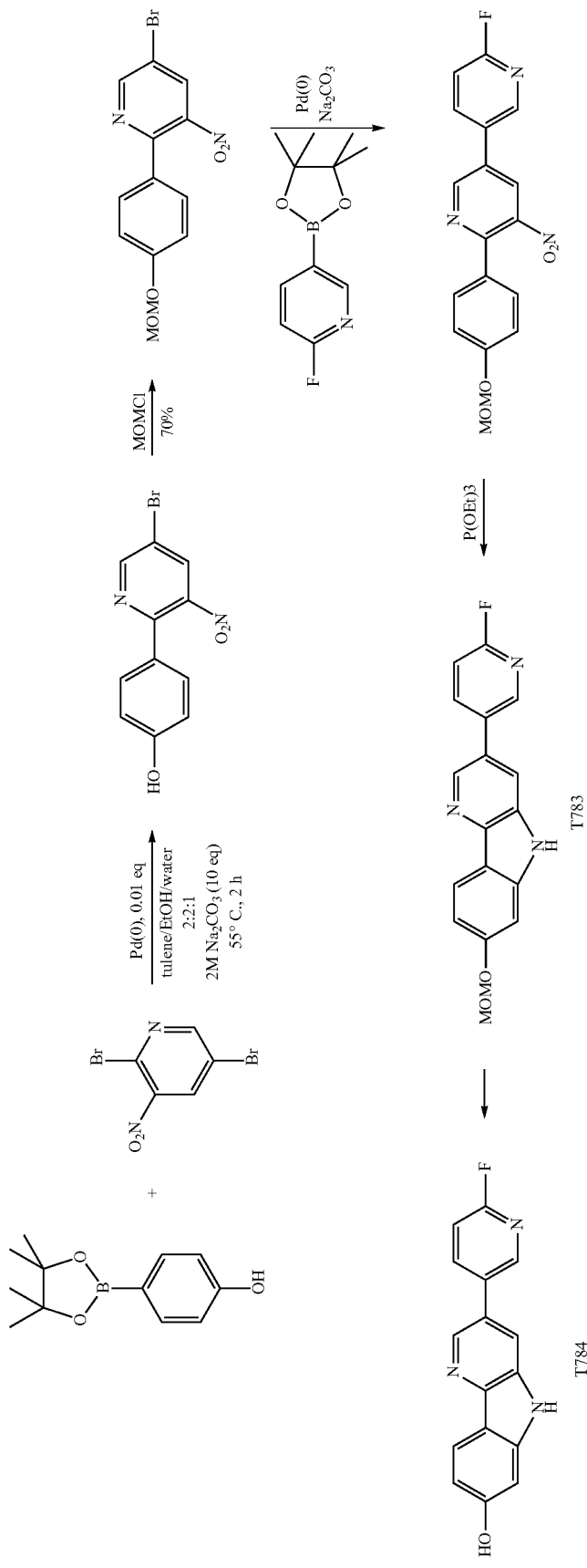

4-(5-Bromo-3-nitropyridin-2-yl)phenol

A mixture of 4-(4,4,5,5-tetramethyl-1,3,2-dioxaborolan-2-yl)phenol (300 mg, 1.36 mmol), 2,5-dibromo-3-nitropyridine (383 mg, 1.36 mmol), tetrakis(triphenylphosphine)palladium (31 mg, 0.027 mmol), $Na_2CO_3$ (4.3 mL, 2 M aqueous), 4.3 mL toluene, and 2.1 mL EtOH was vigorously stirred at 55° C. for 2 h. After cooling to rt, the volatiles were removed under reduced pressure and the residue was purified with silica chromatography (EtOAc in hexane, 5% to 35%) to afford 4-(5-bromo-3-nitropyridin-2-yl)phenol as a yellow wax (285 mg, 71%). MS (ESI) m/z [M+H]$^+$295, 297.

5-Bromo-2-(4-(methoxymethoxy)phenyl)-3-nitropyridine

To a mixture of 4-(5-bromo-3-nitropyridin-2-yl)phenol (280 mg, 0.95 mmol) and DIPEA (360 mmg, 2.85 mmol) in 5 mL of dry DCM at 0° C. was added dropwise chloro(methoxy)methane (210 mg, 1.9 mmol). The reaction was warmed to rt and stirling was continued for 3 h and the diluted with EtOAc (30 mL), washed with water (3×30 mL) and dried over $MgSO_4$. Solvent was removed under reduced pressure and the residue was purified by silica chromatography (EtOAc in hexane, 5% to 35%) to afford 5-bromo-2-(4-(methoxymethoxy)phenyl)-3-nitropyridine as a yellow wax (260 mg, 80%). MS (ESI) m/z [M+H]$^+$339, 341.

6'-Fluoro-6-(4-(methoxymethoxy)phenyl)-5-nitro-3,3'-bipyridine

A mixture of 5-bromo-2-(4-(methoxymethoxy)phenyl)-3-nitropyridine (68 mg, 0.2 mmol), 2-fluoro-5-(4,4,5,5-tetramethyl-1,3,2-dioxaborolan-2-yl)pyridine (45 mg, 0.2 mg), tetrakis(triphenylphosphine)palladium (12 mg, 0.01 mmol), $Na_2CO_3$ (0.5 mL, 1 M aqueous solution) and dioxane (1.5 mL) was heated at 100° C. for 10 min in a microwave reactor. After cooling to rt, the reaction was diluted with EtOAc (20 mL) and washed with brine (20 mL) and water (2×20 mL) and dried over $MgSO_4$. Solvent was removed under reduced pressure and the residue was purified by silica chromatography (EtOAc in hexane, 5% to 40%) to afford 6'-fluoro-6-(4-(methoxymethoxy)phenyl)-5-nitro-3,3'-bipyridine as a yellow solid (48 mg, 67%). MS (ESI) m/z [M+H]$^+$356.

2-Fluoro-5-(4,4,5,5-tetramethyl-1,3,2-dioxaborolan-2-yl)pyridine (T783)

A solution of 6'-fluoro-6-(4-(methoxymethoxy)phenyl)-5-nitro-3,3'-bipyridine (45 mg, 0.12 mmol) in 1 mL of triethyl phosphate was heated at 125° C. for 4 h. After cooling to rt, volatiles was removed under reduced pressure and the residue was purified by silica chromatography (EtOAc in hexane, 10% to 100%) to afford 2-fluoro-5-(4,4,5,5-tetramethyl-1,3,2-dioxaborolan-2-yl)pyridine (T783) as a off-white solid (8 mg, 20%). $^1$H NMR (400 MHz, CDCl$_3$): δ 9.00 (d, J=1.6 Hz, 1H), 8.52 (d, J=1.6 Hz, 1H), 8.24 (d, J=2.4 Hz, 1H), 8.06 (td, J=8.4, 2.8 Hz, 1H), 7.59-7.56 (m, 2H), 5.22 (s, 2H), 3.51 (s, 3H); MS (ESI) m/z [M+H]$^+$324.

3-(6-Fluoropyridin-3-yl)-5H-pyrido[3,2-b]indol-7-ol (T784)

A solution of 2-fluoro-5-(4,4,5,5-tetramethyl-1,3,2-dioxaborolan-2-yl)pyridine (7 mg, 0.02 mmol) in 0.5 mL of HCl (4 M in dioxane) was stirred at rt for 2 h. Volatiles were removed under reduced pressure and the residue was purified by reversed phase HPLC (water/MeCN with TFA buffer) to afford 3-(6-fluoropyridin-3-yl)-5H-pyrido[3,2-b]indol-7-ol (T784) as a white solid (4 mg, 71%). $^1$H NMR (400 MHz, methanol-d4): δ 8.81 (d, J=1.2 Hz, 1H), 8.66 (d, J=2.0 Hz, 1H), 8.64 (d, J=1.2 Hz, 1H), 8.39 (td, J=8.8, 2.8 Hz, 1H), 8.17 (d, J=8.8 Hz, 1H), 7.28 (dd, J=8.8, 2.8 Hz, 1H), 7.02 (d, J=1.6 Hz, 1H), 6.98 (dd, J=8.8, 2.0 Hz, 1H); MS (ESI) m/z [M+H]$^+$ 280.

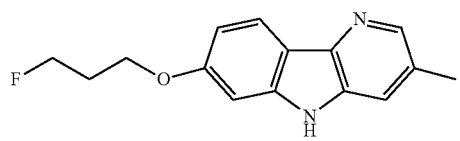

T773

7-(3-Fluoropropoxy)-3-methyl-5H-pyrido[3,2-b]indole (T773)

The title compound was synthesized using the same procedure as for the preparation of 7-(2-fluoroethoxy)-3-methyl-5H-pyrido[3,2-b]indole (T703). 7-(3-Fluoropropoxy)-3-methyl-5H-pyrido[3,2-b]indole (T773) was obtained as a white solid (8 mg, 15%). $^1$H-NMR (400 MHz, CD$_3$OD): δ 8.25 (m, 1H), 8.13 (dd, J=9.2, 0.8 Hz, 1H), 7.66 (m, 1H), 7.06 (d, J=2.0 Hz, 1H), 6.91 (dd, J=8.8, 2.4 Hz, 1H), 4.74 (t, J=6.0 Hz, 1H), 4.62 (t, J=6.0 Hz, 2H), 4.22 (t, J=6.0 Hz, 1H), 2.22 (dp, J=25.2, 6.0 Hz, 1H); MS (ESI) m/z [M+H]$^+$259.

Preparation of Azacarbazole Derivatives as the Tau Tracers

T660, T686, T687, T688, T692, T703, T722, T726, T728, T731, T733, T734, T735, T740, T741, T742, T744, T775, T779, T787, T788, T790, T803, T804, T811

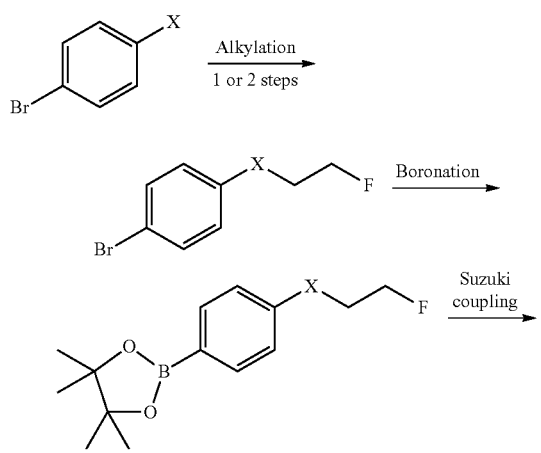

-continued

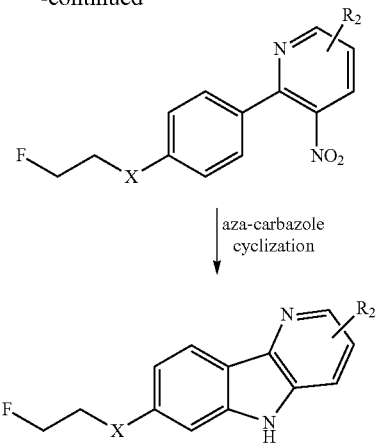

The compound was synthesized via the above scheme using the general procedures of alkylation (or reductive amination), boronation, Suzuki coupling and azacarbazole cyclization.

General Experimental Procedure for Boronation of Arylbromide to Arylboronic Pinacol Ester

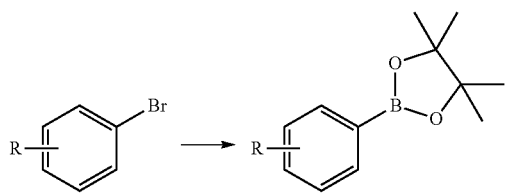

To a microwave vial with a magnetic stir bar, was added the arylbromide starting materials (1 equiv), Pd(dppf)Cl2 (0.05 eq), Potassium acetate (3 eq) and Bis(pinacol)borate (1.2 eq). The solid was dissolved in DMSO (5 vol), sealed and heated to 80° C. in an oil bath for 40-50 hours. The reaction was diluted with brine extracted with ether/hexanes or DCM. The combine organic layers was concentrated, the residue was purified over silica gel using Hexanes:EtOAc or DCM:EtOAc or DCM:MeOH as the eluent to afford boronic ester.

General Experimental Procedure for Cyclization of Aza-Carbazole from Nitro-Substituted Biaryl Precursor:

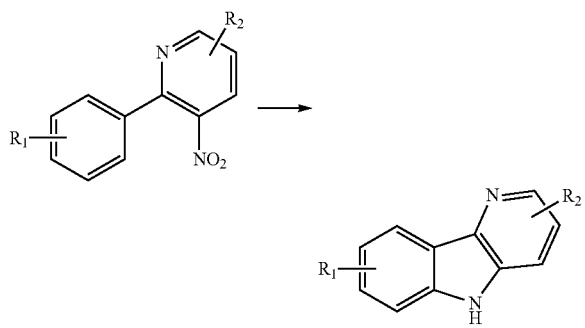

To a microwave vial with a magnetic stir bar, was added the nitro-substituted biaryl precursor aryl/heterocyclic halide (1 equiv), triethyl phosphite (4-8 eq). The suspension was heated at 120-135° C. (depends on the reactivity of the starting material and stability of the product) in an oil bath for 2 hours. The reaction was concentrated under vacuum to remove all the volatiles. The residue was purified over silica gel using Hexanes:EtOAc or DCM:EtOAc or DCM:MeOH as the eluent to afford the aza-carbazoles.

7-(2-fluoroethoxy)-1-methyl-9H-pyrido[3,4-b]indole; T660

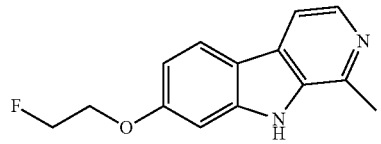 [SMILES: Cc1nccc2c1[nH]c1cc(OCCF)ccc12]

$^1$H-NMR (400 MHz, CD$_3$CN) δ: 10.77 (br, 1H), 8.24-8.16 (m, 3H), 7.15 (s, 1H), 7.08-7.05 (m, 1H), 4.89-4.88 (m, 2H), 4.44-4.35 (m, 2H), 2.95 (s, 3H); LRMS for C$_{14}$H$_{13}$FN$_2$O+H$^+$, calc'd: 245.1. found: 245.1 (M+H$^+$).

7-(2-fluoroethoxy)-9H-pyrido[3,4-b]indole T686

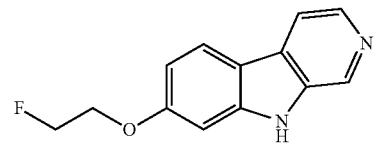 [SMILES: FCCOc1ccc2c(c1)[nH]c1cnccc12]

$^1$H-NMR (400 MHz, CD$_3$OD) δ: 8.97 (s, 1H), 8.51-8.50 (m, 1H), 8.38-8.37 (m, 1H), 8.30-8.28 (m, 1H), 7.21 (s, 1H), 7.10-7.09 (m, 1H), 4.85-4.75 (m, 2H), 4.42-4.35 (m, 2H), LRMS for C$_{13}$H$_{11}$FN$_2$O+H$^+$, calc'd: 231.1. found: 231.1 (M+H$^+$).

N-(3-fluoropropyl)-9H-pyrido[3,4-b]indol-7-amine T687

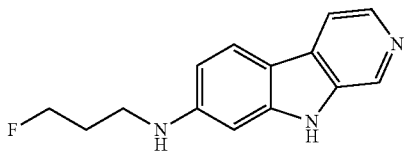 [SMILES: FCCCNc1ccc2c(c1)[nH]c1cnccc12]

$^1$H-NMR (400 MHz, CD$_3$OD) δ: 8.66 (s, 1H), 8.20-8.15 (m, 2H), 7.99-7.97 (m, 1H), 6.80-6.77 (m, 1H), 6.51 (s, 1H), 4.63-4.51 (m, 2H), 3.39-3.35 (m, 2H), 2.08-2.01 (m, 2H); LRMS for C$_{14}$H$_{14}$FN$_3$+H$^+$, calc'd: 244.1. found: 244.1 (M+H$^+$).

7-(2-fluoroethoxy)-5H-pyrido[3,2-b]indole T688

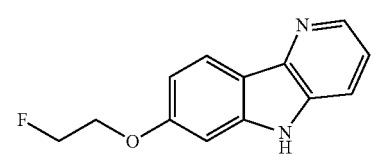 [SMILES: FCCOc1ccc2c(c1)[nH]c1cccnc12]

$^1$H-NMR (400 MHz, CD$_3$OD) δ: 8.52-8.44 (m, 2H), 8.21-8.19 (m, 1H), 7.80-7.78 (m, 1H), 7.17 (s, 1H), 7.10-7.07 (m,

1H), 4.88-4.72 (m, 2H), 4.42-4.33 (m, 2H); LRMS for C$_{13}$H$_{11}$FN$_2$O+Ft, calc'd: 231.1. found: 231.1 (M+H$^+$).

7-(2-fluoroethoxy)-2-methoxy-5H-pyrido[3,2-b]indole T692

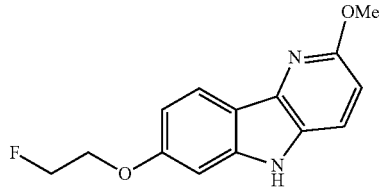 [SMILES: COc1ccc2[nH]c3cc(OCCF)ccc3c2n1]

$^1$H-NMR (400 MHz, CD$_3$OD) δ: 8.24-8.22 (m, 1H), 8.06-8.04 (m, 1H), 7.17-7.15 (m, 1H), 7.06 (s, 1H), 6.97-6.95 (m, 1H), 4.82-4.71 (m, 2H), 4.40-4.29 (m, 2H), 4.15 (s, 3H); LRMS for C$_{14}$H$_{13}$FN$_2$O$_2$+H$^+$, calc'd: 261.1. found: 261.1 (M+H$^+$).

7-(2-fluoroethoxy)-3-methyl-5H-pyrido[3,2-b]indole T703

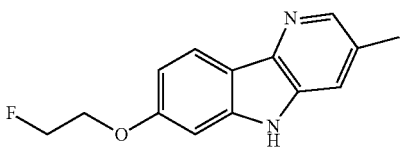 [SMILES: Cc1cnc2c(c1)[nH]c1cc(OCCF)ccc12]

$^1$H-NMR (400 MHz, CD$_3$OD) δ: 8.39 (s, 1H), 8.31 (s, 1H), 8.15 (d, J=9.2 Hz, 1H), 7.15 (s, 1H), 7.08 (d, J=9.2 Hz, 1H), 4.85-4.70 (m, 2H), 4.40-4.32 (m, 2H), 2.64 (s, 3H); LRMS for C$_{14}$H$_{13}$FN$_2$O+H$^+$, calc'd: 245.1. found: 245.1 (M+H$^+$).

N-(2-fluoroethyl)-N-methyl-9H-pyrido[3,4-b]indol-7-amine T722

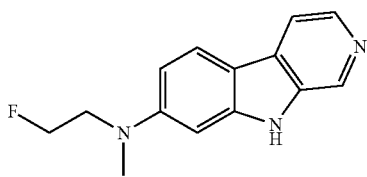 [SMILES: CN(CCF)c1ccc2c(c1)[nH]c1cnccc12]

$^1$H-NMR (400 MHz, CD$_3$OD) δ: 8.71 (s, 1H), 8.26-8.23 (m, 2H), 8.12 (d, J=9.2 Hz, 1H), 7.02 (d, J=9.2 Hz, 1H), 6.78 (s, 1H), 4.72-4.62 (m, 2H), 3.90-3.83 (m, 2H), 3.18 (s, 3H); LRMS for C$_{14}$H$_{14}$FN$_3$+H$^+$, calc'd: 244.1. found: 244.0 (M+H$^+$).

N-(2-fluoroethyl)-N-methyl-5H-pyrido[3,2-b]indol-7-amine T726

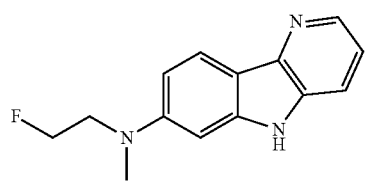 [SMILES: CN(CCF)c1ccc2c(c1)[nH]c1cccnc12]

$^1$H-NMR (400 MHz, CD$_3$OD) δ: 8.29-8.22 (m, 2H), 8.06 (d, J=9.2 Hz, 1H), 7.60 (m, 1H), 7.04 (m, 1H), 6.77 (s, 1H), 4.72-4.60 (m, 2H), 3.90-3.84 (m, 2H), 3.19 (s, 3H); LRMS for C$_{14}$H$_{14}$FN$_3$+H$^+$, calc'd: 244.1. found: 244.1 (M+H$^+$).

N-(2-fluoroethyl)-N,3-dimethyl-5H-pyrido[3,2-b]indol-7-amine T728

$^1$H-NMR (400 MHz, CD$_3$OD) δ: 8.17 (s, 1H), 8.09 (s, 1H), 8.01 (d, J=9.2 Hz, 1H), 6.97 (d, J=9.2 Hz, 1H), 6.75 (s, 1H), 4.83-4.60 (m, 2H), 3.90-3.81 (m, 2H), 3.17 (s, 3H), 2.59 (s, 3H); LRMS for C$_{15}$H$_{16}$FN$_3$+H$^+$, calc'd: 258.1. found: 258.1 (M+H$^+$).

N-(2-fluoroethyl)-2-methoxy-N-methyl-5H-pyrido[3,2-b]indol-7-amine T731

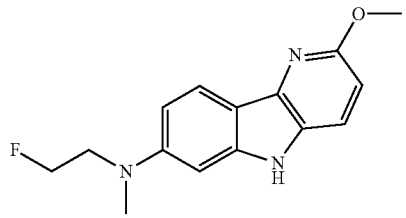 [SMILES: COc1ccc2[nH]c3cc(N(C)CCF)ccc3c2n1]

$^1$H-NMR (400 MHz, CD$_3$OD) δ: 7.95 (d, J=8.8 Hz, 1H), 7.61 (d, J=8.8 Hz, 1H), 6.78-6.65 (m, 3H), 4.67-4.55 (m, 2H), 3.98 (s, 3H), 3.90-3.86 (m, 2H), 3.07 (s, 3H); LRMS for C$_{15}$H$_{16}$FN$_3$O+H$^+$, calc'd: 274.1. found: 274.1 (M+H$^+$).

N-(3-fluoropropyl)-5H-pyrido[3,2-b]indol-7-amine T733

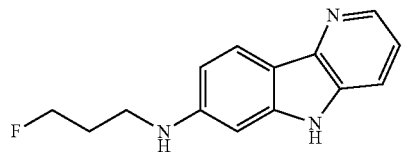 [SMILES: FCCCNc1ccc2c(c1)[nH]c1cccnc12]

$^1$H-NMR (400 MHz, CD$_3$OD) δ: 8.28-8.19 (m, 2H), 7.95 (d, J=9.2 Hz, 1H), 7.58-7.55 (m, 1H), 6.81 (d, J=9.2 Hz, 1H), 6.61 (s, 1H), 4.66-4.52 (m, 2H), 3.42-3.38 (m, 2H), 2.10-2.03 (m, 2H); LRMS for C$_{14}$H$_{14}$FN$_3$+H$^+$, calc'd: 244.1. found: 244.1 (M+H$^+$).

N-(3-fluoropropyl)-3-methyl-5H-pyrido[3,2-b]indol-7-amine T734

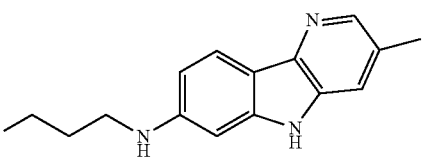

$^1$H-NMR (400 MHz, CD$_3$OD) δ: 8.14 (s, 1H), 8.05 (s, 1H), 7.90 (d, J=9.2 Hz, 1H), 6.76 (d, J=9.2 Hz, 1H), 6.60 (s, 1H), 4.64-4.62 (m, 2H), 3.40-3.35 (m, 2H), 2.59 (s, 3H), 2.10-2.00 (m, 2H); LRMS for $C_{15}H_{16}FN_3+H^+$, calc'd: 258.1. found: 258.1 (M+H$^+$).

N-(3-fluoropropyl)-2-methoxy-5H-pyrido[3,2-b]indol-7-amine T735

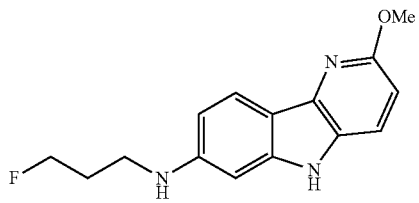 [SMILES: COc1ccc2[nH]c3cc(NCCCF)ccc3c2n1]

$^1$H-NMR (400 MHz, CD$_3$OD) δ: 8.12 (d, J=8.8 Hz, 1H), 7.89 (d, J=9.2 Hz, 1H), 7.03 (d, J=8.8 Hz, 1H), 6.78 (d, J=9.2 Hz, 1H), 6.56 (s, 1H), 4.65-4.52 (m, 2H), 4.16 (s, 3H), 3.37-3.31 (m, 2H), 2.10-2.03 (m, 2H); LRMS for $C_{15}H_{16}FN_3O+H^+$, calc'd: 274.1. found: 274.1 (M+H$^+$).

7-(2-(2-fluoroethoxy)ethoxy)-3-methyl-5H-pyrido[3,2-b]indole T740

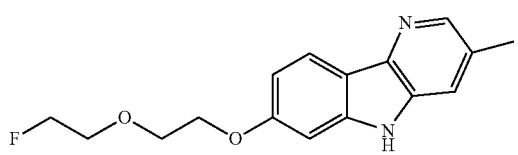 [SMILES: Cc1cnc2c(c1)[nH]c1cc(OCCOCCF)ccc12]

$^1$H-NMR (400 MHz, CD$_3$OD) δ: 8.39 (s, 1H), 8.31 (s, 1H), 8.14 (d, J=9.2 Hz, 1H), 7.16 (s, 1H), 7.05 (d, J=9.2 Hz, 1H), 4.60-4.50 (m, 2H), 4.29-4.28 (m, 2H), 3.95-3.68 (m, 4H), 2.65 (s, 3H); LRMS for $C_{16}H_{17}FN_2O_2+H^+$, calc'd: 289.1. found: 289.1 (M+H$^+$).

7-(4-(2-fluoroethoxy)phenyl)-5H-pyrido[3,2-b]indole T741

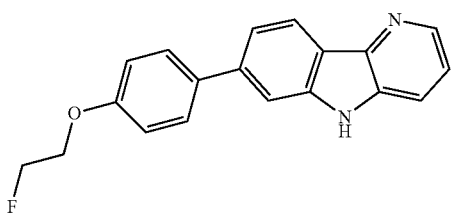 [SMILES: FCCOc1ccc(-c2ccc3c(c2)[nH]c2cccnc23)cc1]

$^1$H-NMR (400 MHz, CD$_3$OD) δ: 8.60-8.35 (m, 3H), 7.86-7.70 (m, 5H), 7.08 (d, J=8.8 Hz, 2H), 4.80-4.69 (m, 2H), 4.35-4.11 (m, 2H); LRMS for $C_{19}H_{15}FN_2O+H^+$, calc'd: 307.1. found: 307.1 (M+H$^+$).

7-(6-fluoropyridin-3-yl)-5H-pyrido[3,2-b]indole T742

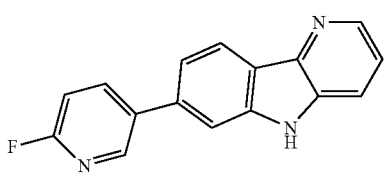 [SMILES: Fc1ccc(-c2ccc3c(c2)[nH]c2cccnc23)cn1]

$^1$H-NMR (400 MHz, CD$_3$OD) δ: 8.68-8.34 (m, 5H), 7.98 (s, 1H), 7.93-7.89 (m, 1H), 7.75-7.73 (m, 1H), 7.23-7.21 (m, 1H); LRMS for $C_{16}H_{10}FN_3+H^+$, calc'd: 264.1. found: 264.1 (M+H$^+$).

N-(2-fluoroethyl)-N-methyl-4-(3-methyl-5H-pyrido[3,2-b]indol-7-yl)aniline T744

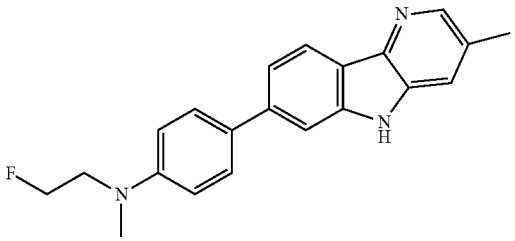 [SMILES: Cc1cnc2c(c1)[nH]c1cc(-c3ccc(N(C)CCF)cc3)ccc12]

$^1$H-NMR (400 MHz, CD$_3$OD) δ: 8.47 (s, 1H), 8.39 (s, 1H), 8.28 (d, J=8.4 Hz, 1H), 7.84 (s, 1H), 7.73-7.67 (m, 3H), 6.91 (d, J=8.4 Hz, 2H), 4.69-4.57 (m, 2H), 3.80-3.70 (m, 2H), 3.10 (s, 3H), 2.70 (s, 3H) LRMS for $C_{21}H_{20}FN_3+H^+$, calc'd: 334.2. found: 334.2 (M+H$^+$).

7-(4-fluoropiperidin-1-yl)-3-methyl-5H-pyrido[3,2-b]indole TFA salt; T775

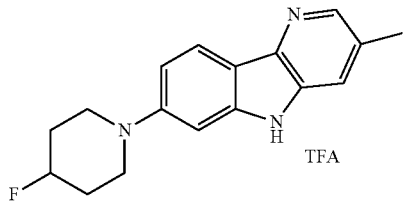 [SMILES: Cc1cnc2c(c1)[nH]c1cc(N3CCC(F)CC3)ccc12]

$^1$H-NMR (400 MHz, CD$_3$OD) δ: 8.26 (s, 1H), 8.17 (s, 1H), 8.06 (d, J=8.8 Hz, 1H), 7.20 (d, J=9.2 Hz, 1H), 7.01 (s, 1H), 4.95-4.90 (m, 1H), 3.70-3.50 (m, 4H), 2.62 (s, 3H), 2.15-1.90 (m, 4H); LRMS for $C_{19}H_{18}F_4N_3O+H^+$, calc'd: 381.1. found: 284.2 (M+H-TFA$^+$).

7-(3-fluoropropoxy)-5H-pyrido[4,3-b]indole T779

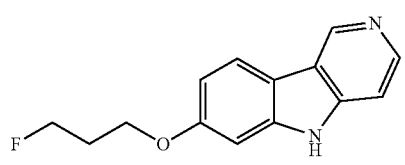 [SMILES: FCCCOc1ccc2c(c1)[nH]c1ccncc12]

$^1$H-NMR (400 MHz, CD$_3$OD) δ: 9.38 (s, 1H), 8.47-8.45 (m, 1H), 8.23-8.21 (m, 1H), 7.89-7.87 (m, 1H), 7.25 (s, 1H), 7.14-7.11 (m, 1H), 4.75-4.60 (m, 2H), 3.32-3.30 (m, 2H), 2.30-2.10 (m, 2H) LRMS for $C_{14}H_{13}FN_2O+H^+$, calc'd: 245.1. found: 245.1 (M+H$^+$).

4-(7-(3-fluoropropoxy)-5H-pyrido[3,2-b]indol-3-yl) aniline T787

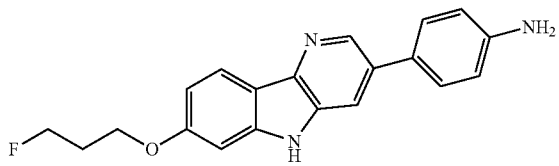 [SMILES: Nc1ccc(-c2cnc3c(c2)[nH]c2cc(OCCCF)ccc23)cc1]

¹H-NMR (400 MHz, CD₃OD) δ: 8.79 (s, 1H), 8.64 (s, 1H), 8.23 (d, J=8.8 Hz, 1H), 7.85-7.82 (m, 2H), 7.31-7.28 (m, 2H), 7.21 (m, 1H), 7.11-7.09 (m, 1H), 5.48, (s, 2H), 4.87-4.61 (m, 2H), 4.31-4.29 (m, 2H), 2.30-2.04 (m, 2H); LRMS for C₂₀H₁₈FN₃O+H⁺, calc'd: 336.1. found: 336.1 (M+H⁺).

(E)-7-(3-fluoropropoxy)-3-(prop-1-enyl)-5H-pyrido [3,2-b]indole T788

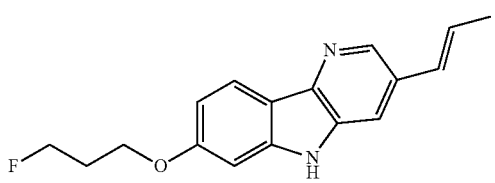 [SMILES: C/C=C/c1cnc2c(c1)[nH]c1cc(OCCCF)ccc12]

¹H-NMR (400 MHz, CD₃OD) δ: 8.30 (s, 1H), 8.07 (d, J=8.8 Hz, 1H), 7.78 (s, 1H), 7.00 (s, 1H), 6.89-6.86 (m, 1H), 6.61-6.40 (m, 2H), 4.73-4.58 (m, 2H), 4.22-4.20 (m, 2H), 2.24-2.08 (m, 2H); LRMS for C₁₇H₁₇FN₂O+H⁺, calc'd: 285.1. found: 285.1 (M+H⁺).

3-cyclopropyl-7-(3-fluoropropoxy)-5H-pyrido[3,2-b] indole T790

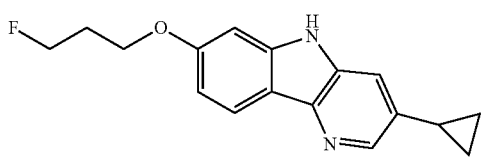 [SMILES: FCCCOc1ccc2c(c1)[nH]c1cc(C3CC3)cnc12]

¹H-NMR (400 MHz, CD₃OD) δ: 8.20 (s, 1H), 8.08-8.06 (m, 1H), 7.43 (m, 1H), 7.00 (s, 1H), 6.88-6.86 (m, 1H), 4.74-4.61 (m, 2H), 4.22-4.19 (m, 2H), 2.24-2.18 (m, 2H), 1.30 (m, 1H), 1.10-1.07 (m, 2H), 0.82-0.80 (m, 2H); LRMS for C₁₇H₁₇FN₂O+H⁺, calc'd: 285.1. found: 285.1 (M+H⁺).

7-(2-(2-(2-fluoroethoxy)ethoxy)ethoxy)-5H-pyrido [4,3-b]indole T803

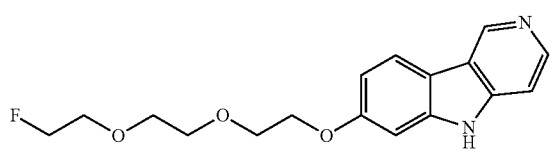 [SMILES: FCCOCCOCCOc1ccc2c(c1)[nH]c1ccncc12]

¹H-NMR (400 MHz, CD₃OD) δ: 9.35 (s, 1H), 8.45-8.43 (m, 1H), 8.20-8.18 (m, 1H), 7.86-7.84 (m, 1H), 7.22 (s, 1H), 7.12-7.09 (m, 1H), 4.54-4.42 (m, 2H), 4.26-4.25 (m, 2H), 3.92-3.90 (m, 2H), 3.74-3.70 (m, 6H); LRMS for C₁₇H₁₉FN₂O₃+H⁺, calc'd: 319.4. found: 319.4 (M+H⁺).

7-(2-(2-fluoroethoxy)ethoxy)-5H-pyrido[4,3-b]indole T804

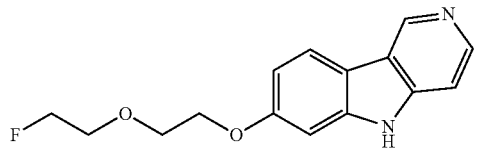 [SMILES: FCCOCCOc1ccc2c(c1)[nH]c1ccncc12]

¹H-NMR (400 MHz, CD₃OD) δ: 9.09 (s, 1H), 8.28-8.27 (m, 1H), 8.04-8.02 (m, 1H), 7.43-7.41 (m, 1H), 7.07 (s, 1H), 6.96-6.93 (m, 1H), 4.60-4.50 (m, 2H), 4.24-4.22 (m, 2H), 3.92-3.79 (m, 4H); LRMS for C₁₅H₁FN₂O₂+H⁺, calc'd: 275.1. found: 275.1 (M+H⁺).

7-((2-(2-fluoroethoxy)ethoxy)methyl)-5H-pyrido[4, 3-b]indole T811

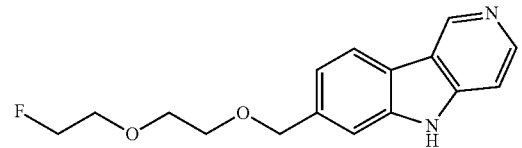 [SMILES: FCCOCCOCc1ccc2c(c1)[nH]c1ccncc12]

¹H-NMR (400 MHz, CD₃OD) δ: 9.50 (s, 1H), 8.51-8.49 (m, 1H), 8.31-8.29 (m, 1H), 7.92-7.90 (m, 1H), 7.75 (s, 1H), 7.50-7.48 (m, 1H), 4.78 (s, 2H), 4.59-4.45 (m, 2H), 3.79-3.73 (m, 6H); LRMS for C₁₆H₁₇FN₂O₂+H⁺, calc'd: 289.1. found: 289.1 (M+H⁺).

7-(6-Fluoropyridine-3-yl)-5-methyl-H-pyrido[4,3-b] indole TFA salt (AS-5357-55, T-820)

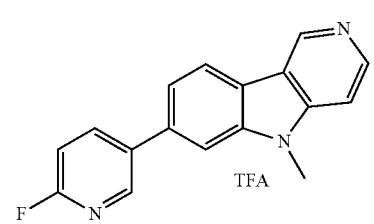 [SMILES: Cn1c2ccncc2c2ccc(-c3ccc(F)nc3)cc21]

T-807 0.010 g was alkylated with dimethylacetone (2 eq) in DMF and Cs₂CO₃ (0.5 eq) at 160° C. for 3 hrs. The residue was purified by HPLC using ACN—H₂O with 0.05% TFA. T-820 isolated as off white solid 0.006 g (72%); ¹H NMR (400 MHz, CD₃OD): δ 9.58 (s, 1H), 8.64 (d, J=2.4 Hz, 1H), 8.61 (dd, J=6.8 and 0.8 Hz), 8.49 (dd, J=8.4 and 0.8 Hz, 1H), 8.38 (qd, J=8.0 and 2.4 Hz, 1H), 8.15 (d, J=0.8 Hz, 1H), 8.11

(d, J=6.8 Hz, 1H), 7.85 (d, J=8.0 and 1.2 Hz, 1H), 7.23 (dd, J=8.4 and 2.8 Hz, 1H), 4.16 (s, 3H); MS (ESI): 278.1 [+H+, Free base].

7-(6-Fluoropyridine-3-yl)-5H-pyrido[4,3-b]indole (AS-5357-18, T-807)

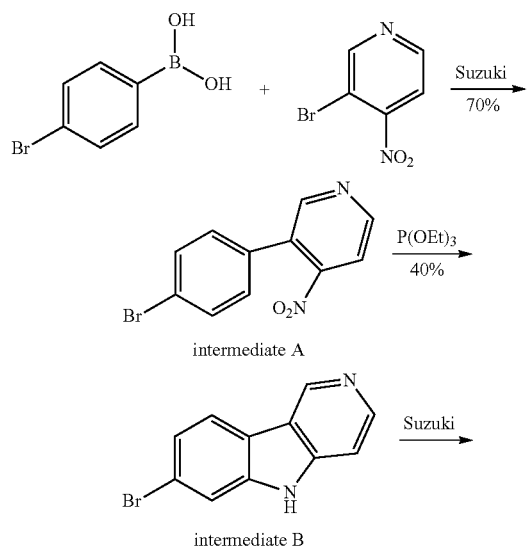

8-Fluoro-7-(2-fluoroethoxy)-3-methyl-5H-pyrido[3,2-b]indole TFA salt (AS-5357-14-1, T-801 and 6-fluoro-7-(2-fluoroethoxy)-3-methyl-5H-pyrido[3,2-b]indole TFA salt AS-5357-14-2, T-801)

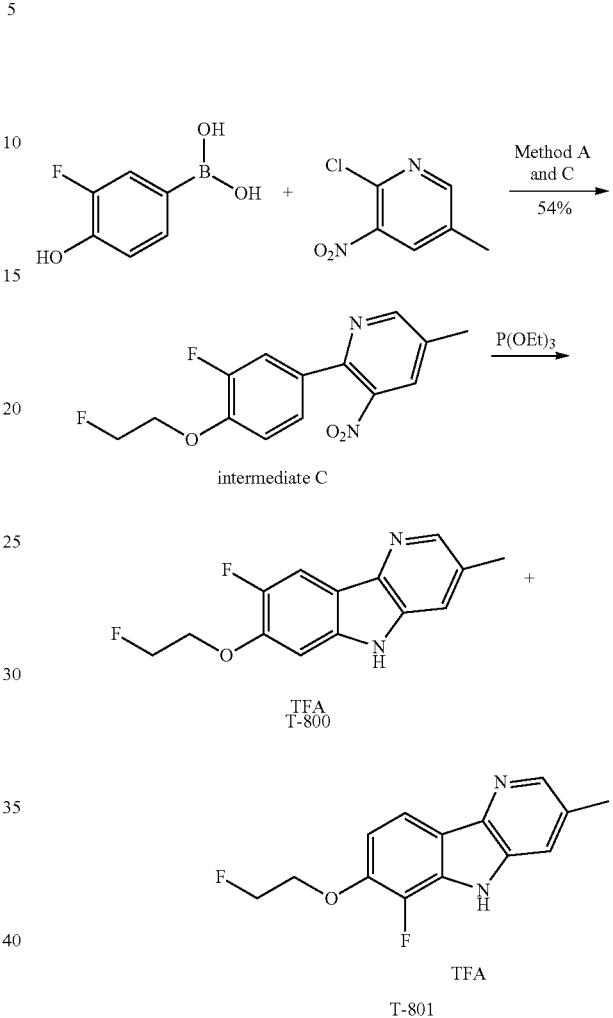

General experimental procedure for Suzuki coupling (Method A) was followed to prepare intermediate A. Reaction was performed on a 0.6 g scale. Product eluted out in hexane-EtOAc on a Combiflash purification system, isolated 0.600 g (72%) of intermediate A as light yellow solid; MS (ESI): 277 and 279 (M+) and (M+2H+). Intermediate A 0.6 g was cyclized using general method carbazole synthesis (Method CC) afforded carbazole B. Carbazole B eluted with DCM-MeOH on a Combiflash purification system isolated 0.21 g (40%) as light brown color solid; $^1$H NMR (400 MHz, DMSO-$d_6$): δ 11.9 (s, 1H), 9.36 (d, J=0.88 Hz, 1H), 8.45 (d, J=0.8 Hz, 1H), 8.20 (d, J=8.4 Hz, 1H), 7.76 (d, J=0.8 Hz, 1H), 7.43 (d, J=2.0 Hz, 1H), 7.41 (d, J=1.6 Hz, 1H); MS (ESI): 247 [M+] and 249 [M+2H+]. Carbazole B was further used for Suzuki coupling (Method A). Reaction was performed on a 0.1 g scale. Product T-807 eluted with DCM-MeOH on a Combiflash purification system, isolated 0.056 g as off white solid (56%) which was further purified by HPLC using ACN—H$_2$O with 0.05% TFA; $^1$H NMR (400 MHz, DMSO-$d_6$): δ 11.81 (s, 1H), 9.34 (s, 1H), 8.61 (dd, J=1.6 and 0.8 Hz, 1H), 8.41-8.30 (m, 3H), 7.80 (dd, J=4.0 and 0.4 Hz, 1H), 7.57 (dd, J=8.4 and 1.6 Hz, 1H), 7.46 (dd, J=6.4 and 0.8 Hz, 1H), 7.29 (dd, J=8.4 and 2.8 Hz, 1H); MS (ESI): 264.3 [M+H+, Free base].

General experimental procedure for Suzuki coupling (Method A) followed by O-alkylation (Method C) was followed to prepare the intermediate C. Reaction was performed on a 0.172 g scale. Intermediate C eluted out in Hexane-EtOAc on a Combiflash purification system, isolated 0.158 g (54% in two steps) as off white solid; MS (ESI): 295.25 (M+H+). Intermediate C 0.030 g was cyclized using general experimental process for carbazole synthesis (Method CC) afforded carbazole mixtures. Product T-800 (0.015 g, 42%) and T-801 (0.006 g, 16%) was purified by HPLC using ACN—H$_2$O with 0.05% TFA; $^1$H NMR (400 MHz, CD$_3$OD) (T-800): δ 8.44 (dd, J=1.6 and 0.8 Hz, 1H), 8.29 (br s, 1H), 7.95 (d, J=10.4 Hz, 1H), 7.32 (d, J=6.8 Hz, 1H), 4.89-4.85 (m, 1H), 4.77-4.75 (m, 1H), 4.49-4.48 (m, 1H), 4.42-4.40 (m, 1H), 2.64 (s, 3H); MS (ESI): 263.20 [M+H+, Free base].

$^1$H NMR (400 MHz, CD$_3$OD) T-801: δ 8.44 (d, J=0.8 Hz, 1H), 8.24 (br s, 1H), 8.01 (dd, J=8.8 and 1.2 Hz, 1H), 7.25 (dd, J=8.8 and 7.2 Hz, 1H), 4.85-4.83 (m, 1H), 4.73-4.71 (m, 1H), 4.52-4.50 (m, 1H), 4.45-4.43 (m, 1H), 2.64 (s, 3H); MS (ESI): 263.20 [M+H+, Free base].

8-Fluoro-7-methoxy-3-methyl-5H-pyrido[3,2-b]indole TFA salt (AS-5357-12, T-799)

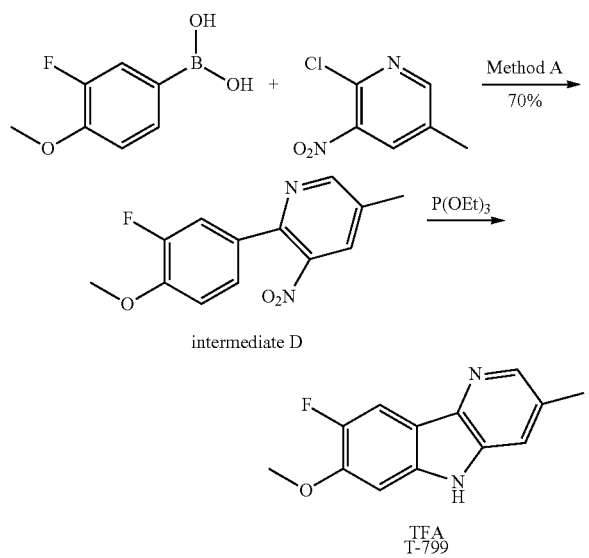

General experimental procedure for Suzuki coupling (Method A) was followed to prepare the intermediate D. Reaction was performed on a 0.172 g scale. Product eluted out in Hexane-EtOAc on a Combiflash purification system, isolated 0.185 g (70%) of intermediate D as light yellow color solid; $^1$H NMR (400 MHz, CDCl$_3$): δ 8.63 (dd, J=1.6 and 0.8 Hz, 1H), 7.88 (dd, J=1.6 and 0.8 Hz, 1H), 7.34 (dd, J=11.6 and 2.0 Hz, 1H), 7.23-7.21 (m, 1H), 6.99 (t, J=8.4 Hz, 1H), 3.92 (s, 3H); MS (ESI): 263.10 [M+H$^+$]. Intermediate D 0.027 g was cyclized using general experimental process for carbazole synthesis (Method CC) afforded carbazole mixtures, which was purified by HPLC using ACN—H$_2$O with 0.05% TFA afforded T-999 as a off white solid (0.002 g, 6%); $^1$H NMR (400 MHz, CD$_3$OD): δ 8.19 (dd, J=1.6 and 0.8 Hz, 1H), 7.84 (d, J=10.8 Hz, 1H), 7.64 (dd, J=1.6 and 0.8 Hz, 1H), 7.12 (d, J=6.8 Hz, 1H), 3.96 (s, 3H), 2.49 (s, 3H); MS (ESI): 231.10 [M+H$^+$, Free base].

7-Fluoro-3-methyl-5H-pyrrolo[2,3-b:4,5-b']dipyridineTert-butyl-(AS-5357-3, T-782)

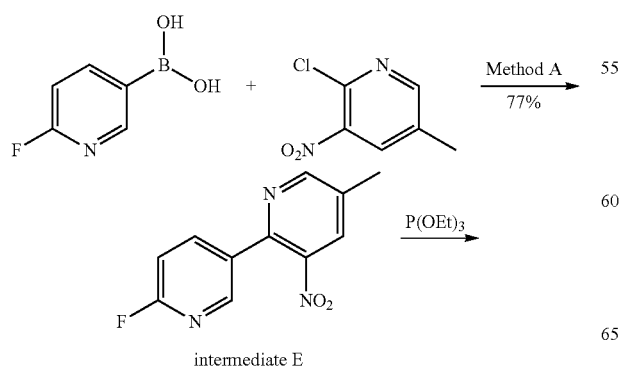

General experimental procedure for Suzuki coupling (Method A) was followed to prepare the intermediate E. Reaction was performed on a 0.172 g scale. and intermediate E was eluted out in DCM-EtOAc on a Combiflash purification system as a off white solid 0.180 g (77%); $^1$H NMR (400 MHz, CDCl$_3$) of intermediate E: δ 8.70 (dd, J=1.2 and 0.8 Hz, 1H), 8.39 (m, 1H), 8.05 (dd, J=2.0 and 0.8 Hz, 1H), 7.93 (m, 1H), 7.00 (dd, J=8.8 and 3.6 Hz, 1H), 2.50 (s, 3H); LC-MS (ESI): 234.1 [M+H$^+$]. Intermediate E 0.048 g was cyclized using general experimental process (Method cc) afforded solid of T-782 which was collected by filtration 0.012 g (29%); $^1$H NMR (400 MHz, CD$_3$OD): δ 8.63 (t, J=8.0 Hz, 1H), 8.34 (m, 1H), 7.76 (dd, J=1.6 and 0.8 Hz, 1H), 6.91 (dd, J=8.4 and 0.8 Hz, 1H), 2.53 (s, 3H); LC-MS (ESI): 202.1 [M+H$^+$].

2-Fluoro-7-methoxy-5H-pyrido[3,2-b]indole (AS-5332-192-1, T-781)

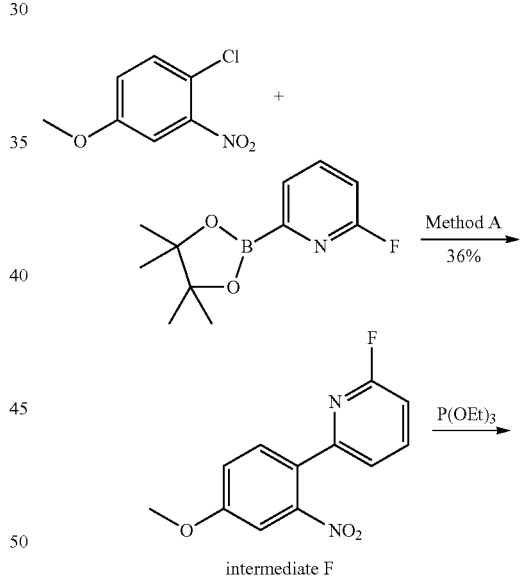

General experimental procedure for Suzuki coupling (method A) was followed to prepare the intermediate F. Intermediate F eluted out in 12% EtOAc:Hexanes mixture in a gradient elution on a Combiflash purification system. Isolated 0.048 g (36%) as light yellow color solid; LC-MS (ESI): 249.1 [M+H$^+$]. Intermediate F was cyclized using general experimental procedure for carbazole synthesis (Method cc). Reaction was performed on a 0.048 g scale. T-781 was eluted out in 15% DCM-EtOAc on a Combiflash purification system as a light yellow color solid (0.003 g, 5%); $^1$H NMR (400 MHz, CDCl$_3$): δ 8.12 (dt, J=8.4 and 0.8 Hz, 1H), 8.02 (br s, 1H), 7.71 (dd, J=8.4 and 6.8 Hz, 1H), 6.92 (d, J=2.4 Hz, 1H), 6.90-6.89 (m, 1H), 6.86 (dd, J=8.8 and 2.0 Hz, 1H), 3.89 (s, 3H); LC-MS (ESI): 217.2 [M+H$^+$].

7-(2-(2-(2-Fluoroethoxy)ethoxy)ethoxy)-3-methyl-5H-pyrrolo[2,3b:4,5-b']dipyridine TFA salt (AS-5357-10, T-795)

General experimental procedure (Method D) for N-alkylation of T-782 with K$_2$CO$_3$ as a base and MW heating at 180° C. for 20 min was used. Reaction was performed on 0.020 g scale. After work-up crude residue 0.032 (90%) was used for DAST reaction (Method). Reaction performed on 0.010 g scale. After work-up product T-795 was purified by HPLC using ACN and H$_2$O with 0.05% TFA as a white solid 0.002 mg (12%); $^1$H NMR (400 MHz, CDCl$_3$): δ 8.45 (d, J=8.0 Hz, 1H), 8.45 (t, J=0.8 Hz, 1H), 8.30 (br s, 1H), 6.89 (d, J=8.8 Hz, 1H), 4.64-4.61 (m, 2H), 4.54-4.52 (m, 1H), 4.42-4.40 (m, 1H), 3.91-3.89 (m, 2H), 3.74-3.64 (m, 6H), 2.64 (s, 3H); LC-MS (ESI): 334.1 [M+H$^+$, Free base].

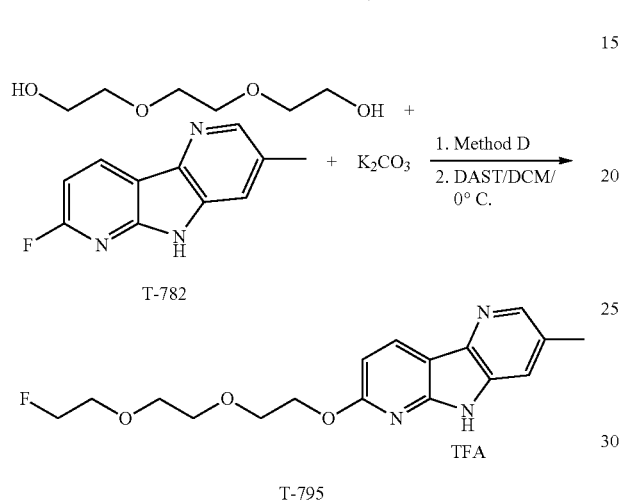

3-(4-(4-Nitropyridin-3-yl)phenyl)propan-1-ol

A mixture of boronic ester (524 mg, 2 mmol), bromide (406 mg, 2 mmol), Pd (0) (116 mg, 0.1 mmol), and Na2CO3 solution (1 M, 4 mL) in 8 mL of dioxane was heated at 90 C for 10 min in a microwave reactor. After cooling to rt, the mixture was extracted with EtOAc (3×20 mL) and the organic phase was dried over MgSO4 and concentrated. The crude product was purified with silica chromatography (EtOAc/hexane, 5% to 90%) to afford the title compound as a yellow oil (412 mg). $^1$H NMR (400 MHz, CDCl$_3$): δ 8.83-8.79 (m, 2H), 7.64 (dd, J=5.2, 0.8 Hz, 1H), 7.38 (d, J=8.4 Hz, 2H), 7.32 (d, J=8.4 Hz, 2H), 3.71 (t, J=6.2 Hz, 2H), 2.79 (t, J=7.6 Hz, 2H), 1.94 (m, 2H); MS (ESI) m/z [M+H]$^+$259.

3-(4-(3-Fluoropropyl)phenyl)-4-nitropyridine

To 3-(4-(4-nitropyridin-3-yl)phenyl)propan-1-ol (60 mg, 0.23 mmol) in 2 mL of dry DCM at 0° C. was added (Diethylamino)sulfur trifluoride (111 mg, 0.69 mmol) dropwise. The reaction was warmed to rt and stirred for 1 h and quenched onto ice (20 g) in saturated Na$_2$CO$_3$ (20 mL). The mixture was extracted with EtOAc (2×30 mL) and the organic phase was dried over MgSO$_4$ and concentrated. The residue was purified by silica chromatography (EtOAc in hexane, 5% to 30%) to afford 3-(4-(3-fluoropropyl)phenyl)-4-nitropyridine as a pale-yellow oil (12 mg, 20%). $^1$H NMR (400 MHz, CDCl$_3$): δ 8.82-8.80 (m, 2H), 7.64 (d, J=5.2, 1H), 7.33-7.27 (m, 2H), 4.55 (t, J=5.6 Hz, 1H), 4.43 (t, J=5.6 Hz, 1H), 2.82 (t, J=7.6 Hz, 2H), 2.12-1.99 (m, 2H); MS (ESI) m/z [M+H]$^+$261.

7-(3-Fluoropropyl)-5H-pyrido[4,3-b]indole

A solution of 3-(4-(3-fluoropropyl)phenyl)-4-nitropyridine (12 mg, 0.046 mmol) in 0.3 mL of triethyl phosphate was heated at 125° C. for 1 h. After cooling to rt, the volatiles were removed under reduced pressure and the residue was purified by silica chromatography (MeOH in DCM, 0% to 10%) to afford a off-white solid. This material was then further purified by reversed phase HPLC to yield 7-(3-fluoropropyl)-5H-pyrido[4,3-b]indole as a white solid (3 mg, 28%). $^1$H NMR (400 MHz, methanol-d4): δ 9.15 (s, 1H), 8.32 (d, J=4.4, 1H), 8.07 (d, J=8.0 Hz, 1H), 7.44 (d, J=6 Hz, 1H), 7.37 (m, 1H), 7.16 (dd, J=8.0, 1.2 Hz, 1H), 4.50 (t, J=6 Hz, 1H), 4.43 (t, J=6 Hz, 1H), 2.90 (t, J=7.6 Hz, 2H), 2.12-1.99 (m, 2H); MS (ESI) m/z [M+H]$^+$229.

Having thus descried in detail advantageous embodiments of the present invention, it is to be understood that the invention defined by the above paragraphs is not to be limited to particular details set forth in the above description as many apparent variations thereof are possible without departing from the spirit or scope of the present invention.

We claim:

1. A compound that is:

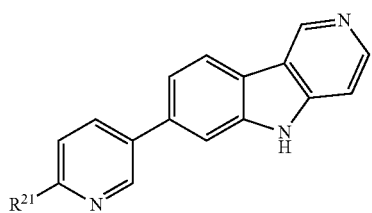

or pharmaceutically acceptable salts thereof,
wherein R$^{21}$ is selected from the group consisting of F, Cl, Br, I, $^{18}$F, $^{77}$Br, $^{123}$I, $^{124}$I, $^{125}$I, $^{131}$I, and NO$_2$.

2. A compound which is:
7-(6-Nitropyridine-3-yl)-5H-pyrido[4,3-b]indole;
or pharmaceutically acceptable salts thereof.

3. A compound that is 7-[6-($^{18}$F)fluoropyridin-3-yl]-5H-pyrido[4,3-b]indole:

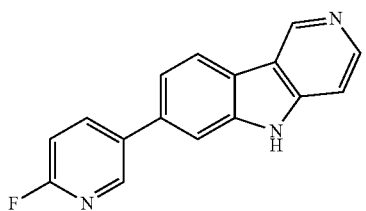 [SMILES: Fc1ccc(-c2ccc3c(c2)[nH]c2ccncc23)cn1]

or a pharmaceutically acceptable salt thereof.

4. A compound that is 7-[6-fluoropyridin-3-yl]-5H-pyrido[4,3-b]indole:

or a pharmaceutically acceptable salt thereof.

5. A process for the preparation of 7-[6-($^{18}$F)fluoropyridin-3-yl]-5H-pyrido[4,3-b]indole, comprising reacting 7-(6-nitropyridine-3-yl)-5H-pyrido[4,3-b]indole with anhydrous [F-18]fluoride ion.

* * * * *

UNITED STATES PATENT AND TRADEMARK OFFICE
CERTIFICATE OF CORRECTION

PATENT NO.       : 8,932,557 B2
APPLICATION NO.  : 13/477095
DATED            : January 13, 2015
INVENTOR(S)      : Chen et al.

It is certified that error appears in the above-identified patent and that said Letters Patent is hereby corrected as shown below:

On the Title Page

First Page, Column 2 Item (57), (Abstract), Line 1: Delete "here in" and insert -- herein --, therefor.

Item (56)

Page 2, Column 1 (Other Publications), Line 12: Delete "meth ylchromene" and insert -- methylchromene --, therefor.

Page 2, Column 1 (Other Publications), Line 34: Delete "Tetrahenron" and insert -- Tetrahedron --, therefor.

Page 2, Column 1 (Other Publications), Line 36: Delete ""Radiolebeled" and insert -- "Radiolabeled --, therefor.

Page 2, Column 1 (Other Publications), Line 46: Delete "Isotops," and insert -- Isotopes, --, therefor.

Page 2, Column 2 (Other Publications), Line 5: Delete "fluoropropy1)" and insert -- fluoropropyl), --, therefor.

Page 2, Column 2 (Other Publications), Line 9: Delete "Lipohilic" and insert -- Lipophilic --, therefor.

Page 2, Column 2 (Other Publications), Line 9: Delete "Fluoralkyl-2lnitroimidazoles" and insert -- Fluoroalkyl-2-nitroimidazoles --, therefor.

Page 2, Column 2 (Other Publications), Line 15: Delete "Radiophaarmaceuticlas," and insert -- Radiopharmaceuticals, --, therefor.

Signed and Sealed this
Twenty-first Day of April, 2015

Michelle K. Lee
*Director of the United States Patent and Trademark Office*

CERTIFICATE OF CORRECTION (continued)
U.S. Pat. No. 8,932,557 B2

Page 2, Column 2 (Other Publications), Line 29: Delete ""Preparatoin" and insert -- "Preparation --, therefor.

Page 3, Column 1 (Other Publications), Line 9: Delete "benzimidaloses";" and insert -- benzimidazoles"; --, therefor.

Page 3, Column 2 (Other Publications), Line 21: Delete "Iodo" and insert -- Iodo --, therefor.

Page 3, Column 2 (Other Publications), Line 53: Delete "Rotiletracycline" and insert -- Rolitetracycline --, therefor.

Page 3, Column 2 (Other Publications), Line 69: Delete "Pyrimidio" and insert -- Pyrimido --, therefor.

Page 4, Column 1 (Other Publications), Line 9: Delete "(9CI)" and insert -- (9Cl) --, therefor.

Page 4, Column 1 (Other Publications), Line 14: Delete "indo1" and insert -- indol --, therefor.

Page 4, Column 2 (Other Publications), Line 11: Delete "assat" and insert -- assay --, therefor.

Page 4, Column 2 (Other Publications), Line 13: Delete "cytotocity,"" and insert -- cytotoxicity," --, therefor.

Page 4, Column 2 (Other Publications), Line 20: Delete "Radiopharmacueticals" and insert -- Radiopharmaceuticals --, therefor.

UNITED STATES PATENT AND TRADEMARK OFFICE

(12)  CERTIFICATE EXTENDING PATENT TERM
UNDER 35 U.S.C. § 156

| | | | |
|---|---|---|---|
| (68) | PATENT NO. | : | 8,932,557 |
| (45) | ISSUED | : | January 13, 2015 |
| (75) | INVENTOR | : | Chen et al. |
| (73) | PATENT OWNER | : | Eli Lilly and Company |
| (95) | PRODUCT | : | TAUVID® (flortaucipir F-18) |

This is to certify that an application under 35 U.S.C. § 156 has been filed in the United States Patent and Trademark Office, requesting extension of the term of U.S. Patent No. 8,932,557 based upon the regulatory review of the product TAUVID® (flortaucipir F-18) by the Food and Drug Administration. According to United States Patent and Trademark Office records, the original expiration date of the patent as of the date of issuance of this certificate is May 19, 2029. Because it appears that the requirements of the law have been met, this certificate extends the term of the patent for the period of

(94)  1,103 days subject to the payment of maintenance fees as provided by law, with all rights pertaining thereto as provided by 35 U.S.C. § 156.

I have caused the seal of the United States Patent and Trademark Office to be affixed this 18th day of October 2023.

*Kathi Vidal*

Katherine K. Vidal
Under Secretary of Commerce for Intellectual Property and
Director of the United States Patent and Trademark Office

(12) SUPPLEMENTAL EXAMINATION CERTIFICATE

United States Patent
Chen et al.

(10) Number: US 8,932,557 F1
(45) Certificate Issued: Feb. 11, 2020

Control No.: 96/000,312

Filing Date: Jan. 14, 2020

Primary Examiner: Dwayne C. Jones

No substantial new question of patentability is raised in the request for supplemental examination. See the Reasons for Substantial New Question of Patentability Determination in the file of this proceeding.

(56) Items of Information

U.S. PATENT DOCUMENTS

US 2011/0091382 A1    4/2011    Kolb et al.

FOREIGN PATENT DOCUMENTS

WO 2009/102498    A1    8/2009

OTHER DOCUMENTS

Amendment dated 02/25/2011, filed during the prosecution history of US Patent Application No. 12/372,717.

Amendment dated 11/29/2011, filed during the prosecution history of US Patent Application No. 12/372,717.

Amendment dated 05/16/2012, filed during the prosecution history of US Patent Application No. 12/372,717.